US009856284B2

(12) United States Patent
Kuldipkumar et al.

(10) Patent No.: US 9,856,284 B2
(45) Date of Patent: Jan. 2, 2018

(54) SOLID FORMS OF A THIOPHOSPHORAMIDATE NUCLEOTIDE PRODRUG

(71) Applicant: Alios BioPharma, Inc., South San Francisco, CA (US)

(72) Inventors: Anuj K Kuldipkumar, Medford, MA (US); Ales Medek, Winchester, MA (US); Lori Ann Ferris, Medford, MA (US); Praveen Mudunuri, Waltham, MA (US); Young Chun Jung, Lexington, MA (US); David Richard Willcox, Wellesley, MA (US); Michael Waldo, Grafton, MA (US); William Aloysius Nugent, Manomet, MA (US)

(73) Assignee: Alios BioPharma, Inc., South San Francisco, CA (US)

( * ) Notice: Subject to any disclaimer, the term of this patent is extended or adjusted under 35 U.S.C. 154(b) by 0 days.

(21) Appl. No.: 15/210,509

(22) Filed: Jul. 14, 2016

(65) Prior Publication Data

US 2016/0318969 A1    Nov. 3, 2016

Related U.S. Application Data

(63) Continuation of application No. 14/578,883, filed on Dec. 22, 2014, now Pat. No. 9,394,330, which is a continuation of application No. 13/794,380, filed on Mar. 11, 2013, now Pat. No. 8,916,538.

(60) Provisional application No. 61/613,972, filed on Mar. 21, 2012.

(51) Int. Cl.
| | | |
|---|---|---|
| A61K 31/70 | (2006.01) | |
| A01N 43/04 | (2006.01) | |
| C07H 19/10 | (2006.01) | |
| C07H 19/06 | (2006.01) | |
| A61K 31/7072 | (2006.01) | |
| A61K 45/06 | (2006.01) | |
| A61K 31/7056 | (2006.01) | |
| A61K 31/7064 | (2006.01) | |
| A61K 31/706 | (2006.01) | |
| A61K 31/7068 | (2006.01) | |
| A61K 38/00 | (2006.01) | |

(52) U.S. Cl.
CPC ......... *C07H 19/10* (2013.01); *A61K 31/7056* (2013.01); *A61K 31/7072* (2013.01); *A61K 45/06* (2013.01); *C07H 19/06* (2013.01); *A61K 31/706* (2013.01); *A61K 31/7064* (2013.01); *A61K 31/7068* (2013.01); *A61K 38/00* (2013.01); *C07B 2200/13* (2013.01)

(58) Field of Classification Search
None
See application file for complete search history.

(56) References Cited

U.S. PATENT DOCUMENTS

| | | |
|---|---|---|
| 2,844,579 A | 7/1958 | Turner et al. |
| 3,180,859 A | 4/1965 | Hoedsema |
| 3,431,252 A | 3/1969 | Walton |
| 3,816,399 A | 6/1974 | Shaw et al. |
| 3,872,084 A | 3/1975 | Jones et al. |
| 3,872,098 A | 3/1975 | Jones et al. |
| 4,093,714 A | 6/1978 | Tolman et al. |
| 4,808,614 A | 2/1989 | Hertel |
| 5,378,825 A | 1/1995 | Cook et al. |
| 5,432,272 A | 7/1995 | Benner |
| 5,552,311 A | 9/1996 | Sorscher et al. |
| 5,578,718 A | 11/1996 | Cook et al. |
| 5,580,967 A | 12/1996 | Joyce |
| 5,602,240 A | 2/1997 | DeMesmaeker et al. |
| 5,610,289 A | 3/1997 | Cook et al. |
| 5,616,488 A | 4/1997 | Sullivan et al. |
| 5,620,676 A | 4/1997 | Jacobson et al. |
| 5,625,056 A | 4/1997 | Genieser et al. |
| 5,631,359 A | 5/1997 | Chowrira et al. |
| 5,631,360 A | 5/1997 | Usman et al. |
| 5,639,647 A | 6/1997 | Usman et al. |
| 5,646,128 A | 7/1997 | Firestein et al. |
| 5,658,780 A | 8/1997 | Stinchcomb et al. |
| 5,677,437 A | 10/1997 | Teng et al. |
| 5,681,940 A | 10/1997 | Wang et al. |
| 5,686,599 A | 11/1997 | Tracz |

(Continued)

FOREIGN PATENT DOCUMENTS

| | | |
|---|---|---|
| CA | 2252144 | 4/2000 |
| CN | 1290707 | 12/2001 |

(Continued)

OTHER PUBLICATIONS

Office Action dated Jul. 22, 2016 in ROC (Taiwan) Patent Application No. 102110127, filed Mar. 21, 2013.

(Continued)

*Primary Examiner* — Patrick Lewis
(74) *Attorney, Agent, or Firm* — Knobbe, Martens, Olson & Bear, LLP

(57) ABSTRACT

The present application relates to solid state forms, for example, crystalline forms of 2'-C-methyluridine-5'-(O-phenyl-N-(S)-1-(isopropoxycarbonyl)ethyl)thiophosphoramidate, pharmaceutical compositions that can include one or more solid forms of 2'-C-methyluridine-5'-(O-phenyl-N-(S)-1-(isopropoxycarbonyl)ethyl)thiophosphoramidate, and methods of treating or ameliorating diseases and/or conditions with one or more solid forms of 2'-C-methyluridine-5'-(O-phenyl-N-(S)-1-(isopropoxycarbonyl)ethyl)thiophosphoramidate. Also disclosed herein are methods of treating diseases and/or conditions with one or more solid forms of 2'-C-methyluridine-5'-(O-phenyl-N-(S)-1-(isopropoxycarbonyl)ethyl)thiophosphoramidate in combination with one or more other agents.

20 Claims, 40 Drawing Sheets

(56) References Cited

U.S. PATENT DOCUMENTS

| | | |
|---|---|---|
| 5,693,532 A | 12/1997 | McSwiggen et al. |
| 5,714,383 A | 2/1998 | Thompson |
| 5,721,350 A | 2/1998 | Chattopadhyaya |
| 5,728,684 A | 3/1998 | Cheng et al. |
| 5,744,595 A | 4/1998 | Srivastava et al. |
| 5,767,097 A | 6/1998 | Tam |
| 5,783,425 A | 7/1998 | Dudycz et al. |
| 5,804,683 A | 9/1998 | Usman et al. |
| 5,807,718 A | 9/1998 | Joyce et al. |
| 5,811,300 A | 9/1998 | Sullivan et al. |
| 5,831,071 A | 11/1998 | Usman et al. |
| 5,837,542 A | 11/1998 | Grimm et al. |
| 5,837,855 A | 11/1998 | Chowrira et al. |
| 5,871,918 A | 2/1999 | Thorp et al. |
| 5,892,024 A | 4/1999 | Chaturvedula et al. |
| 5,902,880 A | 5/1999 | Thompson |
| 5,952,478 A | 9/1999 | Baxter et al. |
| 5,965,721 A | 10/1999 | Cook et al. |
| 5,968,745 A | 10/1999 | Thorp et al. |
| 5,977,343 A | 11/1999 | Tracz |
| 5,985,621 A | 11/1999 | Usman et al. |
| 6,004,939 A | 12/1999 | Chen et al. |
| 6,017,896 A | 1/2000 | Sorscher et al. |
| 6,022,962 A | 2/2000 | Chowrira et al. |
| 6,030,957 A | 2/2000 | Uckun et al. |
| 6,063,566 A | 5/2000 | Joyce |
| 6,063,628 A | 5/2000 | Loeb et al. |
| 6,087,482 A | 7/2000 | Teng et al. |
| 6,130,326 A | 10/2000 | Ramasamy et al. |
| 6,132,971 A | 10/2000 | Thorp et al. |
| 6,156,501 A | 12/2000 | McGall et al. |
| 6,191,266 B1 | 2/2001 | Wang |
| 6,232,463 B1 | 5/2001 | Cook et al. |
| 6,326,174 B1 | 12/2001 | Joyce et al. |
| 6,353,098 B1 | 3/2002 | Usman et al. |
| 6,361,951 B1 | 3/2002 | Thorp et al. |
| 6,365,374 B1 | 4/2002 | Usman et al. |
| 6,437,117 B1 | 8/2002 | Usman et al. |
| 6,440,705 B1 | 8/2002 | Stanton, Jr. et al. |
| 6,455,513 B1 | 9/2002 | McGuigan et al. |
| 6,458,945 B1 | 10/2002 | Stanton, Jr. et al. |
| 6,469,158 B1 | 10/2002 | Usman et al. |
| 6,482,932 B1 | 11/2002 | Beigelman et al. |
| 6,491,905 B1 | 12/2002 | Sorscher et al. |
| 6,495,677 B1 | 12/2002 | Ramasamy et al. |
| 6,503,890 B1 | 1/2003 | Uckun |
| 6,528,640 B1 | 3/2003 | Beigelman et al. |
| 6,552,183 B1 | 4/2003 | Ramasamy et al. |
| 6,566,059 B1 | 5/2003 | Stanton, Jr. et al. |
| 6,569,630 B1 | 5/2003 | Vivekananda et al. |
| 6,573,248 B2 | 6/2003 | Ramasamy et al. |
| 6,582,923 B2 | 6/2003 | Stanton, Jr. et al. |
| 6,589,941 B1 | 7/2003 | Fahrig et al. |
| 6,596,700 B2 | 7/2003 | Sommadossi et al. |
| 6,617,438 B1 | 9/2003 | Beigelman et al. |
| 6,642,206 B2 | 11/2003 | Ramasamy et al. |
| 6,649,750 B1 | 11/2003 | Capaldi et al. |
| 6,649,751 B2 | 11/2003 | Usman et al. |
| 6,670,461 B1 | 12/2003 | Wengel et al. |
| 6,677,314 B2 | 1/2004 | Klecker et al. |
| 6,677,315 B2 | 1/2004 | Klecker et al. |
| 6,682,715 B2 | 1/2004 | Klecker et al. |
| 6,683,045 B2 | 1/2004 | Klecker et al. |
| 6,703,374 B1 | 3/2004 | Klecker et al. |
| 6,753,309 B2 | 6/2004 | Klecker et al. |
| 6,777,395 B2 | 8/2004 | Bhat et al. |
| 6,784,161 B2 | 8/2004 | Ismaili et al. |
| 6,787,526 B1 | 9/2004 | Bryant et al. |
| 6,794,499 B2 | 9/2004 | Wengel et al. |
| 6,812,219 B2 | 11/2004 | LaColla et al. |
| 6,815,542 B2 | 11/2004 | Hong et al. |
| 6,831,069 B2 | 12/2004 | Tam et al. |
| 6,875,752 B2 | 4/2005 | Aszodi et al. |
| 6,887,707 B2 | 5/2005 | Loeb et al. |
| 6,914,054 B2 | 7/2005 | Sommadossi et al. |
| 6,958,318 B2 | 10/2005 | Sorscher et al. |
| 6,974,865 B2 | 12/2005 | Cook et al. |
| 6,995,148 B2 | 2/2006 | Jones et al. |
| 7,018,989 B2 | 3/2006 | McGuigan et al. |
| 7,034,133 B2 | 4/2006 | Wengel et al. |
| 7,037,718 B2 | 5/2006 | Ealick et al. |
| 7,041,817 B2 | 5/2006 | Usman et al. |
| 7,049,068 B2 | 5/2006 | Thorp et al. |
| 7,064,114 B2 | 6/2006 | Yiv et al. |
| 7,081,449 B2 | 7/2006 | Pietrzkowski et al. |
| 7,091,315 B1 | 8/2006 | Ruben et al. |
| 7,094,768 B2 | 8/2006 | Roberts et al. |
| 7,101,861 B2 | 9/2006 | Sommadossi et al. |
| 7,105,493 B2 | 9/2006 | Sommadossi et al. |
| 7,105,499 B2 | 9/2006 | Carroll et al. |
| 7,112,406 B2 | 9/2006 | Behlke et al. |
| 7,125,855 B2 | 10/2006 | Bhat et al. |
| 7,138,501 B2 | 11/2006 | Ruben et al. |
| 7,141,574 B2 | 11/2006 | Beaulieu et al. |
| 7,141,665 B1 | 11/2006 | Joyce et al. |
| 7,148,206 B2 | 12/2006 | Sommadossi et al. |
| 7,151,089 B2 | 12/2006 | Roberts et al. |
| 7,157,441 B2 | 1/2007 | Sommadossi et al. |
| 7,163,929 B2 | 1/2007 | Sommadossi et al. |
| 7,169,766 B2 | 1/2007 | Sommadossi et al. |
| 7,192,936 B2 | 3/2007 | LaColla et al. |
| 7,202,224 B2 | 4/2007 | Eldrup et al. |
| 7,235,649 B2 | 6/2007 | Gewirth et al. |
| 7,268,119 B2 | 9/2007 | Cook et al. |
| 7,285,658 B2 | 10/2007 | Cook et al. |
| 7,335,648 B2 | 2/2008 | Plourde, Jr. et al. |
| 7,339,054 B2 | 3/2008 | Xu et al. |
| 7,351,841 B2 | 4/2008 | Owada et al. |
| 7,365,057 B2 | 4/2008 | LaColla et al. |
| 7,368,438 B2 | 5/2008 | Plourde, Jr. et al. |
| 7,378,402 B2 | 5/2008 | Martin |
| 7,384,924 B2 | 6/2008 | LaColla et al. |
| 7,407,965 B2 | 8/2008 | Chen et al. |
| 7,427,636 B2 | 9/2008 | Cannizzaro et al. |
| 7,429,565 B2 | 9/2008 | Boojamra et al. |
| 7,432,261 B2 | 10/2008 | Cannizzaro et al. |
| 7,452,901 B2 | 11/2008 | Boojamra et al. |
| 7,470,724 B2 | 12/2008 | Cannizzaro et al. |
| 7,547,704 B2 | 6/2009 | LaColla et al. |
| 7,582,618 B2 | 9/2009 | Sommadossi et al. |
| 7,598,230 B2 | 10/2009 | Cook et al. |
| 7,598,373 B2 | 10/2009 | Storer et al. |
| 7,608,597 B2 | 10/2009 | Sommadossi et al. |
| 7,608,599 B2 | 10/2009 | Klumpp et al. |
| 7,608,600 B2 | 10/2009 | Storer et al. |
| 7,625,875 B2 | 12/2009 | Gosselin et al. |
| 7,629,328 B2 | 12/2009 | Roberts et al. |
| 7,635,689 B2 | 12/2009 | LaColla et al. |
| 7,645,747 B2 | 1/2010 | Boojamra et al. |
| 7,713,941 B2 | 5/2010 | Cook et al. |
| 7,718,790 B2 | 5/2010 | Stuyver et al. |
| 7,749,983 B2 | 7/2010 | Hostetler et al. |
| 7,953,557 B2 | 5/2011 | Johnson et al. |
| 8,772,474 B2 | 7/2014 | Beigelman et al. |
| 8,871,737 B2 | 10/2014 | Smith et al. |
| 2001/0011075 A1 | 8/2001 | Townsend et al. |
| 2002/0132237 A1 | 9/2002 | Algate et al. |
| 2002/0150922 A1 | 10/2002 | Stolk et al. |
| 2003/0004122 A1 | 1/2003 | Beigelman et al. |
| 2003/0008841 A1 | 1/2003 | DeVos et al. |
| 2003/0073144 A1 | 4/2003 | Benson et al. |
| 2003/0144489 A1 | 7/2003 | Burgin et al. |
| 2003/0166064 A1 | 9/2003 | King et al. |
| 2003/0170891 A1 | 9/2003 | McSwiggen |
| 2003/0207271 A1 | 11/2003 | Holwitt |
| 2004/0009491 A1 | 1/2004 | Birse |
| 2004/0023265 A1 | 2/2004 | Vivekananda et al. |
| 2004/0023266 A1 | 2/2004 | Vivekananda et al. |
| 2004/0063658 A1 | 4/2004 | Roberts et al. |
| 2004/0077585 A1 | 4/2004 | Peterson et al. |
| 2004/0127436 A1 | 7/2004 | Daifuku et al. |
| 2004/0171028 A1 | 9/2004 | Baker et al. |
| 2004/0171032 A1 | 9/2004 | Baker et al. |
| 2004/0229839 A1 | 11/2004 | Babu et al. |

(56) References Cited

U.S. PATENT DOCUMENTS

| | | |
|---|---|---|
| 2004/0259934 A1 | 12/2004 | Olsen et al. |
| 2005/0031588 A1 | 2/2005 | Sommadossi et al. |
| 2005/0032067 A1 | 2/2005 | Prakash et al. |
| 2005/0042632 A1 | 2/2005 | Radka |
| 2005/0042647 A1 | 2/2005 | Baker et al. |
| 2005/0186568 A1 | 8/2005 | Bandman et al. |
| 2005/0203044 A1 | 9/2005 | Zinnen |
| 2005/0214901 A1 | 9/2005 | Ealick et al. |
| 2005/0233358 A1 | 10/2005 | Thorp et al. |
| 2005/0239733 A1 | 10/2005 | Jurk et al. |
| 2005/0245463 A1 | 11/2005 | Pham et al. |
| 2005/0256073 A1 | 11/2005 | Lipford |
| 2005/0261237 A1 | 11/2005 | Boojamra et al. |
| 2006/0003952 A1 | 1/2006 | Ravikumar et al. |
| 2006/0014689 A1 | 1/2006 | Vesely |
| 2006/0058254 A1 | 3/2006 | Dina et al. |
| 2006/0074035 A1 | 4/2006 | Hong et al. |
| 2006/0094678 A1 | 5/2006 | Vornlocher et al. |
| 2006/0100166 A1 | 5/2006 | DeKoning et al. |
| 2006/0105976 A1 | 5/2006 | Soutschek et al. |
| 2006/0121086 A1 | 6/2006 | Boyer et al. |
| 2006/0122146 A1 | 6/2006 | Chun et al. |
| 2006/0142238 A1 | 6/2006 | McGuigan |
| 2006/0193869 A1 | 8/2006 | Barrat et al. |
| 2006/0217330 A1 | 9/2006 | Hartmann et al. |
| 2006/0229265 A1 | 10/2006 | Milburn et al. |
| 2006/0240462 A1 | 10/2006 | Todd et al. |
| 2006/0264404 A1 | 11/2006 | Boojamra et al. |
| 2006/0269517 A1 | 11/2006 | Blatt et al. |
| 2006/0287260 A1 | 12/2006 | Manoharan et al. |
| 2007/0027116 A1 | 2/2007 | Cho et al. |
| 2007/0032448 A1 | 2/2007 | Hong et al. |
| 2007/0037773 A1 | 2/2007 | Sommadossi et al. |
| 2007/0042350 A1 | 2/2007 | Li et al. |
| 2007/0066552 A1 | 3/2007 | Clarke et al. |
| 2007/0093446 A1 | 4/2007 | Douglass, III et al. |
| 2007/0105122 A1 | 5/2007 | Ota et al. |
| 2007/0105806 A1 | 5/2007 | Sah et al. |
| 2007/0123544 A1 | 5/2007 | Plourde, Jr. et al. |
| 2007/0135372 A1 | 6/2007 | MacLachlan et al. |
| 2007/0196824 A1 | 8/2007 | Stuyver et al. |
| 2007/0197463 A1 | 8/2007 | Chun et al. |
| 2007/0207973 A1 | 9/2007 | Daifukuet et al. |
| 2007/0213292 A1 | 9/2007 | Stoffel et al. |
| 2007/0219365 A1 | 9/2007 | Joyce et al. |
| 2007/0231810 A1 | 10/2007 | Todd et al. |
| 2007/0238099 A1 | 10/2007 | Cohen et al. |
| 2007/0238678 A1 | 10/2007 | Barrat et al. |
| 2007/0258921 A1 | 11/2007 | Dalko |
| 2007/0259832 A1 | 11/2007 | Cook et al. |
| 2007/0265224 A1 | 11/2007 | Cook et al. |
| 2007/0275912 A1 | 11/2007 | Bhat et al. |
| 2007/0281899 A1 | 12/2007 | Bumcrot et al. |
| 2007/0299068 A1 | 12/2007 | Karp et al. |
| 2008/0009462 A1 | 1/2008 | Hostetler et al. |
| 2008/0015161 A1 | 1/2008 | Vornlocher et al. |
| 2008/0026362 A1 | 1/2008 | Ho et al. |
| 2008/0027068 A1 | 1/2008 | Owada et al. |
| 2008/0064753 A1 | 3/2008 | Palladino et al. |
| 2008/0070935 A1 | 3/2008 | Huang et al. |
| 2008/0152621 A1 | 6/2008 | Johansson et al. |
| 2008/0161246 A1 | 7/2008 | Klein et al. |
| 2008/0161324 A1 | 7/2008 | Johansen et al. |
| 2008/0199870 A1 | 8/2008 | Guenther et al. |
| 2008/0200423 A1 | 8/2008 | Cook et al. |
| 2008/0207542 A1 | 8/2008 | McSwiggen et al. |
| 2008/0207554 A1 | 8/2008 | Beigelman et al. |
| 2008/0261913 A1 | 10/2008 | Sommadossi et al. |
| 2008/0286230 A1 | 11/2008 | Sommadossi et al. |
| 2008/0293665 A1 | 11/2008 | Undheim et al. |
| 2009/0131372 A1 | 5/2009 | Chen et al. |
| 2009/0169504 A1 | 7/2009 | Sommadossi et al. |
| 2009/0176732 A1 | 7/2009 | Beigelman et al. |
| 2009/0181921 A1 | 7/2009 | Blatt et al. |
| 2009/0220950 A1 | 9/2009 | Stuyver et al. |
| 2009/0221684 A1 | 9/2009 | Grinstaff et al. |
| 2009/0227543 A1 | 9/2009 | Cannizzaro et al. |
| 2009/0233872 A1 | 9/2009 | Ariga et al. |
| 2009/0238790 A2 | 9/2009 | Sommadossi et al. |
| 2009/0247488 A1 | 10/2009 | Cannizzaro et al. |
| 2009/0275535 A1 | 11/2009 | Boojamra et al. |
| 2009/0280084 A1 | 11/2009 | Schinazi et al. |
| 2009/0280086 A1 | 11/2009 | Sommadossi et al. |
| 2009/0318380 A1 | 12/2009 | Sofia et al. |
| 2010/0016251 A1 | 1/2010 | Sofia et al. |
| 2010/0022467 A1 | 1/2010 | Boojamra et al. |
| 2010/0035835 A1 | 2/2010 | Narjes et al. |
| 2010/0081628 A1 | 4/2010 | Du et al. |
| 2010/0093656 A1 | 4/2010 | Adelfinskaya et al. |
| 2010/0137237 A1 | 6/2010 | Undheim et al. |
| 2010/0137576 A1 | 6/2010 | Stec et al. |
| 2010/0152128 A1 | 6/2010 | Attenni et al. |
| 2010/0249068 A1 | 9/2010 | Beigelman et al. |
| 2010/0297079 A1 | 11/2010 | Almond et al. |
| 2010/0305060 A1 | 12/2010 | Hecker et al. |
| 2010/0311684 A1 | 12/2010 | Cook et al. |
| 2010/0331397 A1 | 12/2010 | Beigelman et al. |
| 2011/0015383 A1 | 1/2011 | Stec et al. |
| 2012/0070411 A1 | 3/2012 | Beigelman et al. |
| 2012/0070415 A1 | 3/2012 | Beigelman et al. |
| 2012/0071434 A1 | 3/2012 | Smith et al. |
| 2012/0108533 A1 | 5/2012 | Herdewijn et al. |
| 2012/0165286 A1 | 6/2012 | Beigelman et al. |
| 2013/0017171 A1 | 1/2013 | Sommadossi et al. |
| 2013/0149283 A1 | 6/2013 | Sommadossi et al. |
| 2013/0164261 A1 | 6/2013 | Wang et al. |
| 2013/0165400 A1 | 6/2013 | Beigelman et al. |
| 2013/0252920 A1 | 9/2013 | Blatt et al. |
| 2013/0253181 A1 | 9/2013 | Serebryany et al. |
| 2013/0281687 A1 | 10/2013 | Serebryany et al. |
| 2013/0315862 A1 | 11/2013 | Sommadossi et al. |
| 2013/0315863 A1 | 11/2013 | Sommadossi et al. |
| 2014/0179627 A1 | 6/2014 | Beigelman et al. |
| 2014/0179910 A1 | 6/2014 | Beigelman et al. |
| 2014/0303108 A1 | 10/2014 | Beigelman et al. |
| 2014/0303113 A1 | 10/2014 | Krop et al. |
| 2015/0005251 A1 | 1/2015 | Dyatkina et al. |
| 2015/0011497 A1 | 1/2015 | Beigelman et al. |
| 2015/0038451 A1 | 2/2015 | Smith et al. |
| 2015/0051167 A1 | 2/2015 | Wang et al. |
| 2015/0105341 A1 | 4/2015 | Beigelman et al. |
| 2015/0141363 A1 | 5/2015 | Wang et al. |
| 2015/0175647 A1 | 6/2015 | Kuldipkumar et al. |
| 2015/0183819 A1 | 7/2015 | Beigelman et al. |
| 2015/0315228 A1 | 11/2015 | Beigelman et al. |
| 2015/0366887 A1 | 12/2015 | Blatt et al. |
| 2015/0366888 A1 | 12/2015 | Blatt et al. |
| 2015/0368286 A1 | 12/2015 | Serebryany et al. |
| 2016/0016987 A1 | 1/2016 | Beigelman et al. |
| 2016/0022724 A1 | 1/2016 | Chanda et al. |
| 2016/0024136 A1 | 1/2016 | Beigelman et al. |
| 2016/0039858 A1 | 2/2016 | Beigelman et al. |
| 2016/0039861 A1 | 2/2016 | Smith et al. |
| 2016/0115190 A1 | 4/2016 | Serebryany et al. |
| 2016/0176910 A1 | 6/2016 | Wang et al. |
| 2016/0176911 A1 | 6/2016 | Beigelman et al. |
| 2016/0264610 A1 | 9/2016 | Beigelman et al. |

FOREIGN PATENT DOCUMENTS

| | | |
|---|---|---|
| CN | 1337401 | 2/2002 |
| CN | 1343673 | 4/2002 |
| CN | 101108870 | 1/2008 |
| CN | 103209987 A | 7/2013 |
| DE | 3824110 | 1/1990 |
| DE | 279247 A1 | 5/1990 |
| DE | 4341161 | 6/1995 |
| EP | 0547008 | 6/1993 |
| EP | 0629633 | 12/1994 |
| EP | 0799834 | 10/1997 |
| EP | 0742287 | 1/2006 |
| GB | 1209654 | 10/1970 |

(56) References Cited

FOREIGN PATENT DOCUMENTS

| | | |
|---|---|---|
| GB | 1319303 | 6/1973 |
| GB | 2136425 | 9/1984 |
| JP | 04-046124 | 2/1992 |
| JP | 06-228186 | 8/1994 |
| JP | 2006-248949 | 9/2006 |
| JP | 2006-248975 | 9/2006 |
| NZ | 216172 | 8/1989 |
| NZ | 224189 | 9/1991 |
| NZ | 226844 | 10/1991 |
| NZ | 231444 | 9/1992 |
| NZ | 505531 | 7/2001 |
| PL | 144471 | 5/1988 |
| WO | WO 84/04748 | 12/1984 |
| WO | WO 88/03147 | 5/1988 |
| WO | WO 9117159 | 11/1991 |
| WO | WO 92/12718 | 8/1992 |
| WO | WO 92/20822 | 11/1992 |
| WO | WO 94/17803 | 8/1994 |
| WO | WO 94/22890 | 10/1994 |
| WO | WO 95/18139 | 7/1995 |
| WO | WO 96/07666 | 3/1996 |
| WO | WO 96/23506 | 8/1996 |
| WO | WO 96/29336 | 9/1996 |
| WO | WO 96/30383 | 10/1996 |
| WO | WO 97/26270 | 7/1997 |
| WO | WO 98/00434 | 1/1998 |
| WO | WO 99/10365 | 3/1999 |
| WO | WO 99/46362 | 9/1999 |
| WO | WO 99/55857 | 11/1999 |
| WO | WO 00/00501 | 1/2000 |
| WO | WO 00/14263 | 3/2000 |
| WO | WO 00/56366 | 9/2000 |
| WO | WO 01/27114 | 4/2001 |
| WO | WO 01/49701 | 7/2001 |
| WO | WO 01/68663 | 9/2001 |
| WO | WO 01/72779 | 10/2001 |
| WO | WO 01/90121 | 11/2001 |
| WO | WO 02/03997 | 1/2002 |
| WO | WO 02/22660 | 3/2002 |
| WO | WO 0218369 | 3/2002 |
| WO | WO 02/26930 | 4/2002 |
| WO | WO 02/29103 | 4/2002 |
| WO | WO 02/069903 | 9/2002 |
| WO | WO 02/088385 | 11/2002 |
| WO | WO 02/090526 | 11/2002 |
| WO | WO 02092006 | 11/2002 |
| WO | WO 02/096927 | 12/2002 |
| WO | WO 02/097031 | 12/2002 |
| WO | WO 02/100415 | 12/2002 |
| WO | WO 03/016475 | 2/2003 |
| WO | WO 03/016497 | 2/2003 |
| WO | WO 03/016572 | 2/2003 |
| WO | WO 03/019189 | 3/2003 |
| WO | WO 03/029271 | 4/2003 |
| WO | WO 03/031419 | 4/2003 |
| WO | WO 03/035012 | 5/2003 |
| WO | WO 03/038052 | 5/2003 |
| WO | WO 03/039348 | 5/2003 |
| WO | WO 03/039523 | 5/2003 |
| WO | WO 03/042357 | 5/2003 |
| WO | WO 03/051896 | 6/2003 |
| WO | WO 03/054152 | 7/2003 |
| WO | WO 03/054219 | 7/2003 |
| WO | WO 03/062257 | 7/2003 |
| WO | WO 03/062376 | 7/2003 |
| WO | WO 03/062379 | 7/2003 |
| WO | WO 03/062385 | 7/2003 |
| WO | WO 03/062391 | 7/2003 |
| WO | WO 03/063688 | 8/2003 |
| WO | WO 03/072602 | 9/2003 |
| WO | WO 03-072729 | 9/2003 |
| WO | WO 03/072757 | 9/2003 |
| WO | WO 03/076586 | 9/2003 |
| WO | WO 03/077875 | 9/2003 |
| WO | WO 03/083082 | 10/2003 |
| WO | WO 03/083084 | 10/2003 |
| WO | WO 03/083085 | 10/2003 |
| WO | WO 03/087300 | 10/2003 |
| WO | WO 03/090674 | 11/2003 |
| WO | WO 03/093439 | 11/2003 |
| WO | WO 03/094848 | 11/2003 |
| WO | WO 2004/001008 | 12/2003 |
| WO | WO 2004/003000 | 1/2004 |
| WO | WO 2004/003162 | 1/2004 |
| WO | WO 2004/009797 | 1/2004 |
| WO | WO 2004/026890 | 4/2004 |
| WO | WO 2004/028454 | 4/2004 |
| WO | WO 2004/041924 | 5/2004 |
| WO | WO 2004/050899 | 6/2004 |
| WO | WO 2004/080466 | 9/2004 |
| WO | WO 2004/106356 | 12/2004 |
| WO | WO 2005/003766 | 1/2005 |
| WO | WO 2005/010150 | 2/2005 |
| WO | WO 2005/020885 | 3/2005 |
| WO | WO 2005/039552 | 5/2005 |
| WO | WO 2005/040174 | 5/2005 |
| WO | WO 2005/047255 | 5/2005 |
| WO | WO 2005/077966 | 8/2005 |
| WO | WO 2005/123755 | 12/2005 |
| WO | WO 2006/034373 | 3/2006 |
| WO | WO 2006/038865 | 4/2006 |
| WO | WO 2006/062240 | 6/2006 |
| WO | WO 2006/066080 | 6/2006 |
| WO | WO 2006/094347 | 9/2006 |
| WO | WO 2006/105440 | 10/2006 |
| WO | WO 2006/106169 | 10/2006 |
| WO | WO 2006/116512 | 11/2006 |
| WO | WO 2006/119507 | 11/2006 |
| WO | WO 2006/121820 | 11/2006 |
| WO | WO 2007/006544 | 1/2007 |
| WO | WO 2007/020018 | 2/2007 |
| WO | WO 2007/027248 | 3/2007 |
| WO | WO 2007/028051 | 3/2007 |
| WO | WO 2007/056191 | 5/2007 |
| WO | WO 2007/089731 | 8/2007 |
| WO | WO 2007/149554 | 12/2007 |
| WO | WO 2008/033432 | 3/2008 |
| WO | WO 2008033466 | 3/2008 |
| WO | WO 2008/039267 | 4/2008 |
| WO | WO 2008/052770 | 5/2008 |
| WO | WO 2008/073661 | 6/2008 |
| WO | WO 2008/083949 | 7/2008 |
| WO | WO 2008/101157 | 8/2008 |
| WO | WO 2008/103276 | 8/2008 |
| WO | WO 2008/104408 | 9/2008 |
| WO | WO 2008/106803 | 9/2008 |
| WO | WO 2009/005382 | 1/2009 |
| WO | WO 2009/073506 | 6/2009 |
| WO | WO 2009/127230 | 10/2009 |
| WO | WO 2009146123 | 12/2009 |
| WO | WO 2010/019954 | 2/2010 |
| WO | WO 2010/020786 | 2/2010 |
| WO | WO 2010030858 | 3/2010 |
| WO | WO 2010/048552 | 4/2010 |
| WO | WO 2010/091386 | 8/2010 |
| WO | WO 2010/108140 | 9/2010 |
| WO | WO 2011/005860 | 1/2011 |
| WO | WO 2011094489 | 8/2011 |
| WO | WO 2011/156757 | 12/2011 |
| WO | WO 2012/040126 | 3/2012 |
| WO | WO 2012/040127 | 3/2012 |
| WO | WO 2012/088155 | 6/2012 |
| WO | WO 2012/142085 | 10/2012 |
| WO | WO 2013/016490 | 1/2013 |
| WO | WO 2013/142124 | 9/2013 |
| WO | WO 2013/142159 | 9/2013 |
| WO | WO 2013/142525 | 9/2013 |
| WO | WO 2014/100498 | 6/2014 |
| WO | WO 2014/134251 | 9/2014 |
| WO | WO 2014/164533 | 10/2014 |

(56) References Cited

FOREIGN PATENT DOCUMENTS

| | | |
|---|---|---|
| WO | WO 2014/209983 | 12/2014 |
| WO | WO 2016/022464 | 2/2016 |

OTHER PUBLICATIONS

Aivazashvili, et al., "Utilization of 5'-C-methylnucleoside triphosphates in RNA synthesis reaction catalyzed by *Escherichia coli* RNA-polymerase," Moledulyarnaya Biologiya (Moscow), 1987, vol. 21, Issue 4, pp. 1080-1091.
Aspelund, et al., "5-Isopropyl- and 5-propyl-1-methyl-3-phynyldialuric acids," Acta Acad. Aboensis, Math. & Phys., 1958, vol. 21, Issue 11, pp. 3-11.
Author Unknown, "IUPAC-IUB Commission on Biochemical Nomenclature," Biochemistry, 1972, vol. 11, pp. 942-944.
Bajwa, et al., "Thymidine nucleoside 3', 5'-cyclic phosphoramidites and phosphites—configuration at phosphorus in trivalent and pentavalent cyclic nucleotides by phosphorus-31 and carbon-13 NMR," Tetrahedron Letters, 1978, vol. 5, pp. 421-424.
Baker, et al., "Synthesis of potential anticancer agents. VI. Use of the O-benzoyl blocking group from synthesis of 6-chloropurine nucleosides," Journal of Organic Chemistry, 1957, vol. 22, pp. 954-959.
Baker, et al., "Synthesis of potential anticancer agents. VII. Nucleosides derived from L-rhamnofuranose," Journal of Organic Chemistry, 1957, vol. 22, pp. 959-966.
Baker, et al., "Synthesis of potential anticancer agents. VII. Nucleosides derived from L-rhamnofuranose," Journal of Organic Chemistry, 1957, vol. 22, pp. 966-971.
Baraniak, et al., "Deoxyribonucleoside cyclic 3', 5'-phosphorofluoridates phosphorus," Sulfur Silicon Relat. Elem., 1996, vol. 111, p. 80.
Baraniak, et al., "Ribonucleoside cyclic 3', 5'-phosphoramidates: Synthesis, stereochemistry, and conversion into ribonucleoside cyclic 3;, 5;-phosphorothioates and -[18O] phosphates," Journal of the Chemical Society, Perkin Transactions 1: Organic and Bio-Organic Chemistry, 1987, vol. 8, pp. 1645-1656.
Baraniak, et al., "Synthesis of adenosine cyclic 3', 5'-phosphorofuoridate (cAMP-F)," Tetrahedron Letters, 1995, vol. 36, Issue 44, Elsevier, pp. 8119-8122.
Beaulieu, et al., "Inhibitors of the HCV NS5B polymerase: New hope for the treatment of hepatitis C infections," Curr. Opin. Invest. Drugs. 2004, vol. 5, Issue 8, pp. 838-850.
Beigelman, et al., Synthesis of 5'-C-methyl-D-alto- & L-talo-ribonucleoside 3'-O-phosphoramidites & their incorporation into hammerhead ribozymes,: Nucleosides & Necleotides, 1995,vol. 14, Issue 5, pp. 901-906.
Bennett, et al., "Designer gene therapy using an *Escherichia coli* purine nucleoside phosphorylase/prodrug system," Chemistry & Biology, 2003, vol. 10, Issue 12, pp. 1173-1181.
Bergstrom, "Nucleoside phosphorylation and related modifications," Current Protocols in Nucleic Acid Chemistry, Chapter 1, John Wiley & Sons, 2008, Suppl. 33, pp. 13.0.1-13.0.2.
Billich, et al., "Synthesis, conformation and enzymatic properties of 1- (.beta.-D-allofuranosyl) uracil and some derivatives," Nucleic Acids Research, 1983, vol. 11, Issue 21, pp. 7611-7624.
Bindal, et al., "The relationship of vasodilator activity of adenosine analogs with molecular connectivity and van der Weals volume," Arzneimittel-Forschung, 1980, vol. 30, Issue 6, pp. 924-928.
Bothelho, et al., "Inhibition of cAMP-dependent protein kinase by adenosine cyclic 3', 5'phosphorodithioate, a second cAMP antagonist," Journal of Biological Chemistry, 1988, vol. 263, Issue 11, pp. 5301-5305.
Bottka, et al., "Evidence for the stereoelectronic control of the acid hydrolysis of adenosine cyclic 3', 5'-phosphoramidate diastereoisomers," Nucleosides & Nucleotides, 1989, vol. 8, Issue 7, pp. 1217-1229.
Bruns, "Adenosine receptor activation in human fibroblasts: nucleoside agonists and antagonists," Canadian Journal of Physiology and Pharmacology, 1980, vol. 58, Issue 6, pp. 673-691.

Bundgaard, "Design of prodrugs," Elsevier Science Publishers B.V., 1985, Table of Contents only.
Cahard, et al., "Aryloxy phosphoramidate triesters as pro-tides," Mini-Reviews in Medicinal Chemistry, 2004, vol. 4, pp. 371-381.
Cappuccino, et al., "Growth inhibition of Clostridium feseri by carcinostatic purine and pyrimidine analogs. I. Effect of medium on growth inhibition," Cancer Research, 1964, vol. 24, pp. 1243-1248.
Carey, "Sulfonate Esters as Substrates in Nucleophilic Substitution Reactions," Organic Chemistry, 2nd ed., McGraw Hill, Inc., New York, 1992, pp. 328-331.
Carroll, et al., "Inhibition of hepatitis C virus RNA replication by 2'-modified nucleoside analogs," Journal of Biological Chemistry, 2003, vol. 278, Issue 14, pp. 11979-11984.
Carroll, S S. et al., "Nucleoside Analog Inhibitors of Hepatitis C Virus Replication, Infectious Disorders," Drug Targets, 2006, vol. 6, pp. 17-29.
CAS Reg. No. 18883-94-8, STNEasy, Entry Date Nov. 16, 1984, (https://stneasy.cas.org), retrieved on Oct. 23, 2013.
CAS Reg. No. 71738-02-8, STNEasy, Entry Date Nov. 16, 1984, (https://stneasy.cas.org), retrieved on Oct. 23, 2013.
CAS Reg. No. 80875-87-2, STNEasy, Entry Date Nov. 16, 1984, (https://stneasy.cas.org), retrieved on Oct. 23, 2013.
CAS RN 486446-48-4, STNEasy, Entry Date Feb. 6, 2003, https://stneasy.cas.org, retrieved on Nov. 17, 2011, one page.
Cass, et al., "Mediated transport of nucleosides by human erythrocytes. Specificity toward purine nucleosides as permeants," Biochemica et Biophysica Acta, Biomembranes, 1973, vol. 291, Issue, 3, pp. 734-746.
Chidgeavadze, et al., "5'-C- and 3'-C-Methyl-2'-deoxynucleoside 5'-triphosphates and their substrate properties in DNA-polymerase-catalyzed DNA synthesis reactions," Soviet Journal of Bioorganic Chemistry (a translation of Bioorganicheskaya Khimiya), 1992, vol. 17, Issue 5, pp. 389-395.
Chidgeavadze, et al., "Synthesis and substrate properties of C-methyl-2'-deoxynucleoside 5'triphosphates in DNA synthesis reactions catalyzed by DNA polymerases," Bioorganicheskaya Khimiya, 1991, vol. 17, Issue 5, pp. 678-684.
Cullis, "The stereospecific conversion of p-chiral dialkyl phosphorothioates into 18O-phosphates," Tetrahedron Letters, 1983, vol. 24, Issue 50, pp. 5677-5680.
Cusack, et al., "Simple syntheses of glycofuranosylamines derived from D-xylose, D-mannose, and L-rhamnose, intermediates in the preparation of some N-glycofuranosyl uracils," Chemical Communications, 1971, vol. 4, pp. 190-191.
David, et al., "Synthesis of the two epimeric 5'-methylcytidines, their 5'phosphates and [5-3H]-5'-pyrophosphates, and the two 5'-methyldeoxycytidines. A novel cytosine anhydronucleoside with two oxygen bridges between the base and the sugar," Journal of the Chemical Society, Perkins Transactions 1: Organic and Bio-Organic Chemistry, 1982, vol. 2, pp. 385-393.
De Vroom, et al., "Synthesis of ribonucleoside 3', 5'-cyclic phosphorothioates using a modified hydroxybenzotriazole phosphotriester approach," Recueil des Travaux Chimiques des Pays-Bas, 1987, vol. 106, Issue 11, pp. 577-580.
De Zwart, et al., "A functional screening of adenosine analogs at the adenosine A2B receptor: A search for potent agonists," Nucleosides & Nucleotides, 1998, vol. 17, Issue 6, pp. 969-985.
Del Vecchio, et al., "Small molecule and biologic inhibitors of hepatitis C virus: A symbiotic approach," Mini-Reviews in Medicinal Chemistry, Nov. 2006, vol. 6, Issue 11, pp. 1263-1268.
Deval, et al., "Pyrophosphorolytic excision of nonobligate chain terminators by hepatitis C virus NS5B polymerase," Antimicrobial Agents and Chemotherapy, Aug. 2007, vol. 51, Issue 8, pp. 2920-2928.
Dutartre, et al., "General catalytic deficiency of hepatitis C virus RNA polymerase with an S282T mutation and mutually exclusive resistance towards 2'-modified nucleotide analogues," Antimicro. Agts. Chemother., 2006, vol. 50, Issue 12, pp. 4161-4169.
Dzhavadova, et al., "The molecular and crystal structure of 1-(2,6-dideoxy-.alpha.-L-lyxo-hexofuranosyl) thymine," Bioorganiocheskaya Khimiya, 1989, vol. 15, Issue 7, pp. 976-982.

(56) References Cited

OTHER PUBLICATIONS

Dzhavadova, et al., "The molecular and crystal structures of 1-(6-deoxy-.beta.-D-allofuranosyl) cytosine and 1-(6-deoxy-.alpha.-L-talofuranosyl) cytosine," Kristallografiya, 1988, vol. 33, Issue 6, pp. 1408-1414.
Eliahu, S., et al., "A Novel Insulin Secretagogue Based on a Dinucleoside Polyphosphate Scaffold," Journal of Medicinal Chemistry, 2010, vol. 53, No. 6, pp. 2472-2481.
Eppacher, et al., "Synthesis and incorporation of C(5')-ethynylated uracil-derived phosphoramidites into RNA," Helvetica Chimica Acta, 2004, vol. 87, pp. 3004-3020.
Estrada, et al., "In silico studies toward the discovery of new anti-HIV nucleoside compounds with the use of TOPS-MODE and 2D/3D connectivity indices. 1. Pyrimidyl derivatives," Journal of Chemical Information and Computer Sciences, 2002, vol. 42, pp. 1194-1203.
Feldwisch, et al., "Purification &characterization of a cAMP-binding protein of *Volvox carteri* f. nagariensis iyengar," European Journal of Biochemistry, 1995, vol. 228, Issue 2, pp. 480-489.
Ferrini, et al., "Free amino acids in the egg of Ciona intestinalis during some development stages," Ricerca Scientifica, Parte 2: Rendiconti, Sezione B: Biologica, 1964, vol. 5, Issue 3, pp. 213-220.
Fingl, et al., "The Pharmacological Basis of Therapeutics," 5th ed., MacMillan Publishing Co., Inc., 1975, Chapter 1, General Principles, pp. 1-46.
Fischer, B., et al., "2-Thioether 5'-o-(1-Thiotriphosphate)adenosine Derivatives as New Insulin Secretagogues Acting through P2Y-Receptors," Journal of Medicinal Chemistry, 1999, vol. 42, No. 18, pp. 3636-3646.
Follmann, et al., "Adenine nucleosides in solution. Stabilization of the anti-conformation by C-5' substituents," European Journal of Biochemistry, 1974, vol. 47, Issue 1, pp. 187-197.
Follmann, et al., "Adenine nucleosides in solution: Circular dichroism studies and base conformation," European Journal of Biochemistry, 1975, vol. 58, Issue 1, pp. 31-41.
Follmann, et al., "Novel nucleosides derived from 5'-C-methyl adenosine," Eur. Biophys. Congr., Proc., 1st, 1971, vol. 1, pp. 285-287.
Gangjee, et al., "Vasodilator activity of adenosine analogs," Journal of Pharmaceutical Sciences, 1978, vol. 67, Issue 1, pp. 121-123.
Gardner, Andrew F., et al., "Comparative Kinetics of Nucleotide Analog Incorporation by Vent DNA Polymerase," J. Bio. Chem., 2004, vol. 279, No. 12, pp. 11834-11842.
Gemcitabine, The Merck Index (15th Ed. 2013), p. 809.
Gimisis, et al., "Tuning the reactivity of O-tert-butyldimethylsilylimidazolyl aminals towards organolithium reagents," Synlet, 2003, vol. 10, pp. 1451-1454.
Girardet, et al., "Synthesis and cytotoxicity of 4-amino-5-oxopyrido [2, 3-d] pyrimidine nucleosides," Journal of Medicinal Chemistry, 2000, vol. 43, Issue 20, pp. 3704-3713.
Gonzalez, et al., "A radial distribution function approach to predict A2B agonist effect of adenosine analogues," Bioorganic & Medicinal Chemistry, 2005, vol. 13, Issue 3, pp. 601-608.
Gopanakrishnan, et al., "A virtual screening approach for thymidine monophosphate kinase inhibitors as antitubercular agents based on docking and pharmacophore models," Journal of Chemical Information and Modeling, 2005, vol. 4, pp. 1101-1108.
Grant, et al., "Binding specificities of adenosine amonohydrolase from calf intestinal mucosa with dialdehydes derived from hexofuranosyladenine nuclio sides," Journal of Medicinal Chemistry, 1980, vol. 23, Issue 1, pp. 39-42.
Grant, et al., "Hexofuranosyladenine nucleosides as substrates and inhibitors of calf intestinal adenosine deaminase," Journal of Medicinal Chemistry, 1979, vol. 22, Issue 8, pp. 1016-1018.
Greene, et al., "Protective Groups in Organic Synthesis," 3.Ed., John Wiley & Sons, 1999, Cover and contents pages.
Gunic et al., "Synthesis & Cytotoxicity of 4'C- and 5'-C-substituted toyocamycins," Bioorganic & Medicinal Chemistry, 2001, vol. 9, Issue 1, pp. 163-170.

Gurskaya, et al., "X-ray crystallographic studies of nucleoside analogs. I. The crystal structure of 1-(6-deoxy-.beta.-D-allofuranosyl) cytosine, C10H15N3O5," Crystal structure Communications, 1982, vol. 11, Issue 4, pp. 1245-1252.
Gwack, Yousang, et al., "DNA Helicase Activity of th eHepatitis C Virus Nonstructural Protein 3," European Journal of Biochemistry, 1997, vol. 250, No. 1, pp. 47-54.
Hai, et al., "Species- or isozyme-specific enzyme inhibitors. 7. Selective effects in inhibitions of rat adenylate kinase isozymes by adenosine 5'-phosphate derivatives," Journal of Medicinal Chemistry, 1982, vol. 25, Issue 7 pp. 806-812.
Hai, et al., "Species- or isozyme-specific enzyme inhibitors. 9. Selective effects in inhibitions of rat pyruvate kinase isozymes by adenosine 5'-diphosphate derivatives," Journal of Medicinal Chemistry, 1982, vol. 25, Issue 10, pp. 1184-1188.
Hampton, et al., "Interactions of epimeric 5'-C-methyl and 5'-C-carbamyl derivatives of adenosine monophosphate with adenosine monophosphate utilizing enzymes," Biochemistry, 1973, vol. 12, Issue 17, pp. 3328-3332.
Hampton, et al., "Substrate properties of cycloadenosines with adenosine aminohydrolase as evidence for the conformation of enzyme-bound adenosine," Biochemistry, 1972, vol. 11, Issue 25, pp. 4736-4739.
Hayakawa, et al., "A strategy for the stereoselective preparation of thymidine phosphorothioates with the (R) or the (S) configuration at the stereogenic oligodeoxyribonucleotides with stereochemically pure phosphate/phosphorothioate chimeric backbones," European Journal of Organic Chemistry, 2006, vol. 17, pp. 3834-3844.
Hayatshahi, et al., "QSARs and activity predicting models for competitive inhibitors of adenosine deaminase," FEBS Letters, 2007, vol. 581, Issue 3, pp. 506-514.
Hebert, et al., "Structural features of the noncatalytic cGMP binding sites of frog photoreceptor phosphodiesterase using cGMP analogs," Journal of Biological Chemistry, 1998, vol. 273, Issue 10, pp. 5557-5565.
Heinemann, et al., "Comparison of the cellular pharmacokinetics and toxicity of 2'.2'-difluorodeoxycytidine and 1-.beta.-D-arabinofuranosylcytosine," Cancer Research, 1988, vol. 48, pp. 4024-41031.
Henderson, et al., "Inhibitors of adenine phosphoribosyltransferase," Cancer Chemotherapy Reports Supplement, 1968, vol. 1, Issue 2, pp. 363-373.
Henderson, et al., "Mechanisms of inhibition of adenine phosphoribosyltransferase by adenine nucleosides and nucleotides," Canadian Journal of Biochemistry, 1970, vol. 48, Issue 5, pp. 573-579.
Hiebl, et al., "Side-chain derivatives of biologically active nucleosides. Part 1. Side-chain analogs of 3'azido-3'-deoxythymidine (AZT)," Journal of Medicinal Chemistry, 1992, vol. 35, Issue 16, pp. 3016-3023.
Hiebl, et al., "Side-chain derivatives of biologically active nucleosides. Part 2. Synthesis and anti-HIV activity of 5'-C-methyl derivatives of 3'-fluroro-3'-deoxythymidine," Antiviral Chemistry and Chemotherapy, 1996, vol. 7, Issue 3, pp. 173-177.
Higuchi, et al., "Pro-drugs as novel drug delivery systems," A.C.S. Symposium Series, American Chemical Society, 1975, vol. 14, pp. 155-182.
Hillaire-Buys, D., et al., "Pharmacological Evaluation and Chemical Stability of 2-benzylthieoether-5'-O-(1-thiotriphosphate)-Adenosine, a New Insulin Secretagogue Acting Through P2Y Receptors," Drug Development Research, 2001, vol. 53, No. 1, pp. 33-43.
Hong, J.A., et al., "Identification of Critical Ligand Binding Determinants in Mycrobacterium tuberculosis Adenosine-5'-phosphosulfate Reductase," Journal of Medicinal Chemistry, 2009, vol. 52, No. 17, pp. 5485-5495.
Howgate, et al., "Conversion of 2'3'-O-isopropylideneadenosine into 9-(6-deoxy-.beta.-D-allofuranosyl)- and 9-(6-deoxy-.alpha.L-talofuranosyl) adenines," Carbohydrate Research, 1972, vol. 2, pp. 309-315.
Hrdlicka, et al., "Synthesis and biological evaluation of branched and conformationally restricted analogs of the anticancer compound

(56) References Cited

OTHER PUBLICATIONS

3'C-ethynyluridine (EUrd) and 3'-C-ethynylcytidine (ECyd)," Bioorganic & Medicinal Chemistry, 2005, vol. 13, No. 7, pp. 2597-2621.

Hrebabecky, et al., "Synthesis of 1-(3-azido-2,3-dideoxy-.beta.-D-allofuranosyl)thymine, 1-(2,3-dideoxy-.beta.-D-allofuranosyl)thymine, and 1-(2,3-dideoxy-.beta.-D-erythro-hex-2-enofuranosyl)thymine," Carbohydrate Research, 1991, vol. 216, pp. 179-186.

Huang, et al., "Recent development of therapeutics for chronic HCV infection," Antiviral Research, 2006, vol. 71, Issue 2 & 3, pp. 351-362.

Hung, et al., "A New Nonhydrolyzable Reactive cGMP Analogue, (Rp)-Guanosine-3',5'-cyclic-S-(4-bromo-2,3-dioxobutyl) monophosphorothioate Which Targets the cGMP Binding Site of Human Platelet PDE3A," Bioorganic Chemistry, 2008, vol. 36, Issue 3, Elsevier Inc., pp. 141-147.

Hung, et al., "A nonhydrolyzable reactive cAMP analogue, (Sp)-8-[4-bromo-2,3-dioxobutyl)thio]adenosine 3',5'-cyclic S-(methyl) monophosphorothioate, irreversibly inactivates human platelet cGMP-inhibited cAMP phosphodiesterase at micromolar concentrations," Biochemistry, 2002, vol. 41, Issue 9, pp. 2962-2969.

Hung, et al., "New insights from the structure-function analysis of the catalytic region of human platelet phosphodiesterase 3A: A role for the unique 44-amino acid insert," Journal of Biological Chemistry, 2006, vol. 281, Issue 39, pp. 29236-29244.

Hung, et al., A New Nonhydrolyzable Reactive cAMP Analogue, (Sp)—adenosine-3',5'-cyclic-S-(4-bromo-2,3-dioxobutyl) monophosphorothioate irreversibly inactivates Human Platelet cGMP-inhibited cAMP phosphodiesterase, Bioorganic Chemistry, 2002, vol. 30, Issue 1, pp. 16-31.

Iimori, et al., "2'-C-, 3'-C-, and 5'-C-Methylsangivamycins: Conformational lock with the methyl group," Tetrahedron Letters, 1991, vol. 32, Issue 49, pp. 7273-7276.

Iimori, et al., "A study on conformationally restricted sangivamycins and their inhibitory abilities of protein kinases," Nucleic Acids Symposium Series, 1992, vol. 27, pp. 169-170.

Jacobson, et al., "Structure-activity relationships of 9-alkyladenine and ribose-modified adenosine derivatives at rat A3 adenosine receptors," Journal of Medicinal Chemistry, 1995, vol. 38, Issue 10, pp. 1720-1735.

Kappler, et al., "Isozyme-specific enzyme inhibitors. 10. Adenosine 5'-triphosphate derivates as substrates or inhibitors of mithionine adenosyltransferases of rat normal and hepatoma tissues," Journal of Medicinal Chemistry, 1986, vol. 29, Issue 3, pp. 318-322.

Kappler, et al., "Species- or isozyme-selective enzyme inhibitors. 8. Synthesis of disubstituted two-substrate condensation products as inhibitors of rat adenylate kinases," Journal of Medicinal Chemistry, 2005, vol. 25, Issue 10, pp. 1179-1184.

Karpeiskii, et al., "Conformational analogs of nucleotides. V. Synthesis of 5'-C-methylnucleosides from 6-deoxy-D-allose," Bioorganicheskaya Khimiya, 1979, vol. 5, No. 6, pp. 895-905.

Karpeiskii, et al., "Conformational analogs of nucleotides. V. Synthesis of 5'-C-methylnucleosides from 6-deoxy-D-allose," Soviet Journal of Bioorganic Chemistry (a translation of Bioorganicheskaya Khimiya), 1979, vol. 5, No. 1, pp. 672-680.

Karpeiskii, et al., "Study of substrate specificity of nuclease S1 from Aspergillus oryzae in the hydrolysis of low molecular weight substrates," Bioorganicheskaya Khimiya, 1982, vol. 8, No. 3, pp. 386-395.

Karpeiskii, et al., "Study of substrate specificity of nuclease S1 from Aspergillus oryzae in the hydrolysis of low molecular weight substrates," Soviet Journal of Bioorganic Chemistry (a translation of Bioorganicheskaya Khimiya), 1983, vol. 8, No. 3, pp. 196-204.

Karpeiskii, et al., "Synthesis of 5'-mono-, di- and triphosphates of 5'-C-methyluridines," Bioorganicheskaya Khimiya, 1982, vol. 8, No. 7, pp. 933-939.

Karpeiskii, et al., "Synthesis of 5'-mono-, di- and triphosphates of 5'-C-methyluridines," Soviet Journal of Bioorganic Chemistry (a translation of Bioorganicheskaya Khimiya), 1983, vol. 8, No. 7, pp. 498-504.

Karpeisky, et al., "Synthesis of 5'-C-methyluridines (D-allo and L-talo), 5'-mono-, di- and triphosphates, and dinucleoside phosphates on their basis," Nucleic Acids Symposium Series, 1981, Issue 9, pp. 157-160.

Kett, et al., "Heterocyclic derivatives of sugars: An NMR study of the formation of 1-glycosyl-3, 5-dimethyl-1H-pyrazoles from hydrazones," Carbohydrate Research, 1997, vol. 299, Issue 3, pp. 129-141.

Kim, et al., "The effect of thalidomide and its derivatives on thyroxine-induced metamorphosis of tadpole," Canadian Journal of Biochemistry and Physiology, 1965, vol. 43, Issue 6, pp. 769-779.

Kiuru, et al., "Synthesis and enzymatic deprotiection of biodegradably protected dinucleoside-2, 5'-monophosphates: 3-(acetylosy)-2,2bis(ethoxycarbonyl)propyl phosphoester of 3'-O-(acyloymethyl)adenylyl-2, 5'-adenosines," Chemistry and Biodiversity, 2011, vol. 8, Issue 2, pp. 266-286.

Klumpp, et al., "The novel nucleoside analog R1479 (4'-azidocytidine) is a potent inhibitor of N55B-dependent RNA synthesis and hepatitis C virus replication in cell culture," Journal of Biological Chemistry, 2006, vol. 281, Issue 7, pp. 3793-3799.

Krakowiak, et al., "Stereochemistry of rHint1 hydrolase assisted cleavage of P-N. bond in nucleoside 5'-O-phosphoramidothioates," Chemical Communications, 2007, vol. 21, pp. 2163-2165.

Lamivudine, The Merck Index (15th Ed. 2013), p. 994.

Lau, et al., "Synthesis and evaluation of antiviral activity of L-acosamine and L-ristosamine nucleosides of furonose configuration," Acta Chemica Scandinavica, 1991, Issue 6, pp. 616-620.

Lee, Choongho, "Discovery of Hepatitis C Virus NS5A Inhibitors as a New Class of Anti-HCV Therapy," Arch. Pharm. Res., 2001, vol. 34, No. 9, pp. 1403-1407.

Leisvouri, et al., Chemical and enzymatic stability of amino acid derived phosphoramides of Biomolecular Chemistry, 2010, vol. 8, Issue 9, pp. 2131-3141.

Lepage, et al., "Metabolism of purine nucleoside analogs," Cancer Research, 1965, vol. 25, pp. 46-52.

Lerner, "9-(6-Deoxyhexofuranosyl) adenine nucleosides. Further studies on the acetolysis of hexofuranosides," Journal of Organic Chemistry, 1978, vol. 43, Issue 5, pp. 962-965.

Lerner, "9-.alpha.-L-Rhamnofuranosyladenine. An improved synthesis of a 6-deoxyhexofuranosyl nucleoside," Nucleic Acid Chem., 1991, vol. 4, pp. 274-280.

Lerner, "Adenine nucleosides derived from 6-deoxyhexofuranoses," Journal of Organic Chemistry, 1976, vol. 41, Issue 2, pp. 306-310.

Lerner, "Interconversions of hexofuranosyl nucleosides. IV. Synthesis of nucleosides derived from 6-deoxy-L-glucose," Journal of Organic Chemistry, 1972, vol. 26, Issue 37, pp. 4386-4391.

Lerner, "Interconversions of hexofuranosyl nucleosides. V. Synthesis and reexamination of the structure of 9-(6-deoxy-.alpha.-L-mannofuranosyl) adenine," Journal of Organic Chemistry, 1973, vol. 21, pp. 3704-3938.

Lerner, "Preparation of nucleosides via isopropylidene sugar derivatives. V. Coupling reactions using the titanium tetrachloride method," Carbohydrate Research, 1970, vol. 14, Issue 3, pp. 297-303.

Lerner, "Synthesis of 9-.alpha.-D-rhamofuranosyladenine," Carbohydrate Research, 1974, vol. 38, pp. 328-332.

Lerner, et al., "Preparation and antileukemic screening of some new 6'-deoxyhexopyranosyladenine nucleosides," Journal of Medical Chemistry, 1987, vol. 30, Issue 8, pp. 1521-1525.

Lesiak, et al., "A new approach to syntheses of organic phosphoroselenoates and phosphorodiselenoates. Proof of absolute configuration assignment in diastereomers of cTMPS [thymidine cyclic 3',5'-phosphorothioates]," Polish Journal of Chemistry, 1979, vol. 53, Issue 10, pp. 2041-2050.

Lesnikowski, et al., "A simple procedure for synthesis of diastereoisomers of thymidine cyclic 31,5'-phosphate derivatives," Nucleic Acids Symposium Series, 1987, vol. 18, pp. 273-276.

(56) References Cited

OTHER PUBLICATIONS

Lesnikowski, et al., "Some aspects of the electron impact induced fragmentation of diastereoisomeric thymidine cyclic 3',5'-phosphoranilidothioates," Organic Mass Spectrometry, 1980, vol. 15, Issue 9, pp. 454-455.

Letters to the Editor from various doctors, Severe Toxicity of Fialuridine, New England Journal of Medicine, 1996, vol. 334, pp. 1135-1138.

Lin, C. et al., "Synthesis of Dinucleotide Thiophosphoramidates as Anti-HIV New Prodrugs," Synthesis, 2003, No. 13, pp. 1989-1994.

Lin, et al., "Novel 3',5'-cyclic nucleotide analog: Adenosine 3',5'-cyclic boranomonophosphate," Organic Letters, 2001, vol. 6, pp. 795-797.

Long, et al., "Structure-activity relationship for adenosine kinase from mycobacterium tuberculosis. II. Modifications to the ribofuranosyl moiety," Biochemical Pharmacology, 2008, vol. 75, Issue 8, pp. 1588-1600.

Malmsjo, Malin, et al., "Characterization of Contractile P2 Receptors in Human Coronary Arteries by Use of the Stable Pyrimidine Uridine 5'-O-Thiodisphospgate and Uridine 5'-O-3-Thiotriphosphate," J. Pharmacology and Experimental Therapeutics, 2000, vol. 293, No. 3, pp. 755-760.

Markiewicz, et al., "The reaction of 1,3-dichloro-1,1,3,3-tetraisopropyldisiloxane with cytosine arabinoside and 1-(6-deoxy-.alpha.-L-talofuranosyl) uracil," Collection of Czechoslovak Chemical Communications, 1980, vol. 45, Issue 6, pp. 1860-1865.

Marx, et al., "Synthesis of 4'-C-acylated thymidines," Helvetica Chimica Acta, 1996, vol. 79, Issue 7, pp. 1980-1994.

McGuigan, et al., "Phosphate prodrugs derived from N-acetyglucosamine have enhanced chondroprotective activity in explant cultures and represent a new lead in antiosteoarthritis drug discovery," Journal of Medicinal Chemistry, 2008, vol. 51, Issue 18, pp. 5807-5812.

McKenzie, et al., "Characteristics of the relaxant response of adenosine and its analogs in intestinal smooth muscle," European Journal of Pharmacology, 1977, vol. 41, Issue 2, pp. 183-192.

McKenzie, et al., "Effects of adenosine and related compounds on adenylate cyclase and cyclic AMP levels in smooth muscle," European Journal of Pharmacology, 1977, vol. 41, Issue 2, pp. 193-203.

McKenzie, et al., "Hepatic failure and lactic acidosis due to fialuridine (FIAU), an investigational nucleoside analogue for chronic hepatitis B," New England Journal of Medicine, 1995, vol. 333, pp. 1099-1105.

McMurry, "The Leaving Group," Organic Chemistry, 5th ed., Brooks/Cole, Pacific Grove, CA, 2000, Chapter 11.5, pp. 398-408.

McOmie, "Protective Groups in Organic Chemistry," Plenum Press, 1973, Cover and contents pages only.

Miao, et al., "A stepwise one pot synthesis of alkyl thiophosphoramidate derivatives of nucleosides," Synthetic Communications, 2002, vol. 32, Issue 8, pp. 1159-1167.

Miao, et al., "One pot synthesis of aryl thiophosphoramidate derivatives of AZT," Synthetic Communications, 2002, vol. 32, Issue 21, pp. 3301-3309.

Miao, et al., "One pot synthesis of nucleoside 5'-thiophosphoramidate," Synthetic Communications, 2002, vol. 32, Issue 7, pp. 1069-1076.

Mikhailov, et al., "Conformational analogs of nucleotides. Synthesis of 5'C-methyl nucleosides," Sint. Issled. Biol. Soedin., Tezisy Dokl. Konf. Molodykh Uch., 1978, vol. 6, pp. 38-39.

Mikhailov, et al., "Conformational features of 5'-C-methylnudeosides," Soviet Journal of Bioorganic Chemistry (a translation of Bioorganicheskaya Khimiya), 1990, vol. 15, Issue 7, pp. 532-538.

Mikhailov, et al., "Conformational peculiarities of 5'-C-methylnudeosides," Bioorganicheskaya Khimiya, 1989, vol. 15, Issue 7, pp. 969-975.

Misiura, et al., "Synthesis, chemical and enzymatic reactivity, and toxicity of dithymidylyl-3',5'-phosphorofluoride and -phosphorothiofluoridate," Bioorganic & Medicinal Chemistry, 2001, vol. 9, Issue 6, pp. 1525-1532.

Murai, et al., "A synthesis and an x-ray analysis of 2'-C-, 3'-C-, and 5'-C-methylsangivamycins," Heterocycles, 1992, vol. 33, Issue 1, pp. 391-404.

Myers, et al., "Synthetic studies of the tunicamycin antibiotics. Preparation of (+)-tunicaminyluracil, (+)-tunicamycin-V, and 5'-epi-tunicamycin-V," Journal of the American Chemical Society, 1994, vol. 116, Issue 11, pp. 4697-4718.

Nelson, et al., "Synthesis and antitumor activity of 7- and 9-(6'-deoxy-.alpha.-L-talofuranosyl)-hypoxathine and 9-(6'- deoxy-.alpha.-L-talofuranosyl)-6-thiopurine," Journal of Medicinal Chemistry, 1983, vol. 26, Issue 10, pp. 1527-1530.

Nelson, et al., "Synthesis of hypoxanthine, guanine, and 6-thiopurine nucleosides of 6-deoxy-D-allofuranose," Journal of Medicinal Chemistry, 1983, vol. 26, Issue 7, pp. 1071-1074.

Nelson, et al., "Synthesis of methyl 3,5-di-O-benzoyl-2,6-dideoxy-.beta.-L-lyxo-hexofuranoside, a nucleoside precursor," Carbohydrate Research, 1983, vol. 124, Issue 1, pp. 161-165.

Nutt, et al., "Branched-chain sugar nucleosides. II. 5',5'-Di-C-methyladenosine," Journal of Medicinal Chemistry, 1968, vol. 11, Issue 1, pp. 151-153.

Oivanen, et al., "Hydrolysis of isomeric cytidyl-(3',5')-5'-C-methyluridines by acids, bases and metal ions: Steric effects in the hydrolysis of the phosphodiester bonds of RNA," Acta Chemica Scandinavica, 1995, vol. 49, Issue 4, pp. 307-310.

Ora, et al., "Biodegradable protections for nucleoside 5'-monophosphates: Comparative study on the removal of O-acetyl and O-acetyloxymethyl protected 3-hydroxy-2,2-bis(ethoxycarbonyl)propyl groups," Journal of Organic Chemistry, 2009, vol. 74, Issue 14, pp. 4992-5001.

Ora, et al., "Hydrolytic stability of nucleoside phosphotriesters derived from bis(hydroxymethyl)-1,3-dicarbonyl compounds and their congeners: Towards a novel prodrug strategy for antisense oligonucleotides," Journal Chem. Soc. Perkin Trans. 2, 2001, vol. 6, pp. 881-885.

Padyukova, et al., "Synthesis of 5'-derivatives of thymidine," Soviet Journal of Bioorganic Chemistry (a translation of Bioorganicheskaya Khimiya), 1991, vol. 16, Issue 5, pp. 370-375.

Padyukova, et al., "Synthesis of dinucleoside phosphates containing 5'-O-bonded 1-(6-deoxy-.beta.-D-allofuranosyl) uracil and 1-(6-deoxy-.alpha.-L-talofuranosyl) uracil," Collection of Czechoslavak Chemical Communications, 1980, vol. 45, Issue 9, pp. 2550-2557.

Padyukova, et al., "Synthesis of thymidine 5'-derivatives," Bioorganicheskaya Khimiya, 1990, vol. 16, Issue 5, pp. 668-673.

Panova, et al., "Substrate specificity of *Escherichia coli* thymidine phosphorylase," Biochemistry, 2007, vol. 72, Issue 1, pp. 21-28.

Parker, et al., "Design and evaluation of 5'-modified nucleoside analogs as prodrugs for an *E. coli* purine nucleoside phosphorylase mutant," Nucleosides Nucleotides and Nucleic Acids, 2005, vol. 24, Issues May 6, 2007, pp. 387-392.

Pockros, Paul J., "Drugs in Development for Chronic Hepatitis C: A Promising Future," Expert Opin. Biol. Ther., 2001, vol. 11, No. 12, pp. 1611-1622.

Poijarvi, et al., "2,2-bis(ethoxycarbonyl)- and 2-(alkylaminocarbonyl)-2-cyano-substituted 3(pivaloyloxy)propyl groups as biodegradable phosphate protections of oligonucleotides," Bioconjugate Chem., 2005, vol. 16, pp. 1564-1571.

Poijarvi, et al., "Towards nucleotide prodrugs derived fro m2,2-bis(hydroxymethyl)malonate and its congeners: Hydrolytic cleavage of 2-cyano-2-(hydroxymethyl)-3-methoxy-3-oxopropyl and 3(alkylamino)-2-cyano-2-(hydroxymethyl)-3-oxopropyl protections from the internucleosidic phosphodiester and phosphorothioate linkages," Helv. Chim. Acta., 2002, vol. 85, pp. 1859-1876.

Poijarvi, et al., "Towards oligonucleotide prodrugs: 2,2-bis(ethoxycarbonyl) and 2-(alkylaminocarbonyl)-2-cyano substituted 3-(pivaloyloxy)propyl groups as biodegradable protecting groups for internucleosidic phosphoromonothioate linkages," Lett. Org. Chem., 2004, vol. 1, pp. 183-188.

Prakash, et al., "Synthesis and evaluation of S-acyl-2-thioethyl esters of modified nucleoside 5'monophosphates as inhibitors of hepatitis C virus RNA replication," Journal of Medicinal Chemistry, 2005,; vol. 48, Issue 4, pp. 1199-1210.

(56) References Cited

OTHER PUBLICATIONS

Pravdina, et al., "Inhibition by nucleoside 5'triphosphate analogs of RNA synthesis catalyzed by RNA polymerase of influenza a virus," Molekulyamaya Genetika, Mikrobiologiya I Virusologiya, 1990, vol. 11, pp. 22-25.
Ranganathan, et al., "Model analogs of nucleoside 3',5'-cyclic phosphates, I. 5'-mono- and dimethyl analogs of adenosine 3',5'-cyclic phosphate," Journal of Organic Chemistry, 1974, vol. 39, Issue 3, pp. 290-298.
Reimer, et al., "Inhibition of hepatitis B virus DNA polymerase by thymidine triphosphae analogs in vitro," Antiviral Chemistry and Chemotherapy, 1991, vol. 2, Issue 4, pp. 249-253.
Reist, et al., "Potential anticancer agents. IV. Synthesis of nucleosides derived from 6-deoxy-D-allofuranose," Journal of the American Chemical Society, 1958, vol. 80, pp. 3962-3966.
Reist, et al., "Potential anticancer agents. LXXVII. Synthesis of nucleosides of purine-6-thiol (6mercaptopurine) containing "fraudulent" sugars," Journal of Organic Chemistry, 1962, vol. 27, pp. 3279-3283.
Reist, et al., "Potential anticancer agents. VIII. Synthesis of nucleosides derived from L-talofuranose," Journal of the American Chemical Society, 1958, vol. 80, pp. 5775-5779.
Reist, et al., "Potential anticancer agents. X. Synthesis of nucleosides derived from 6-deoxy-D-glucofuranose," Journal of Organic Chemistry, 1958, vol. 23, pp. 1753-1757.
Reist, et al., "Potential anticancer agents. XI. Synthesis of nucleosides derived from 6-deoxy-L-idofuranose," Journal of Organic Chemistry, 1958, vol. 23, pp. 1757-1760.
Roche, "Bioreversible carriers in drug design: Theory and application," Pergamon Press: New York, 1987, pp. 14-21.
Saha, et al., "5'-methyl-DNA—A new oligonucleotide analog: Synthesis and biochemical properties," Journal of Organic Chemistry, 1995, vol. 60, Issue 4, pp. 788-789.
Sakai, et al., "Isolation from nocardioides sp. strain CT16, purificaiton, and characterization of a deoxycytidine deaminase extremely thermostable in the presence of D,L-dithiothreitol," Biosci. Biotechnol. Biochem., 2002, vol. 66, Issue 8, pp. 1646-1651.
Scott, et al., "Mapping ligand interactions with the hyperpolarization activated cyclic nucleotide modulated (HCN) ion channel binding domain using a soluble construct," Biochemistry, 2007, vol. 46, Issue 33, pp. 9417-9431.
Secrist, et al., "Gene therapy of cancer: Activation of nucleoside prodrugs with *E. coli* purine nucleoside phosphorylase," Nucleosides & Nucleotides, 1999, vol. 18, Issue 4 & 5, pp. 745-757.
Shaw, et al., "Mass spectrometry of nucleic acid components. Analogs of adenosine," Journal of the American Chemical Society, 1970, vol. 92, Issue 8, pp. 2510-2522.
Sheid, et al., "Enzymatic formation of potential anticancer and antiviral inosine analogs," Experientia, 1996, vol. 52, ' Issue 9, pp. 878-881.
Shigeura, et al., "Structrual basis for phosphorylation of adenosine congeners," Nature, 1967, vol. 215, Issue 5099, pp. 419-420.
Shuto, et al., "Stereo- and regioselective introduction of 1- or 2-hydroxyethyl group via intramolecular radical cyclization reaction with a novel silicon-containing tether. An efficient synthesis of 4'.alpha.-branched 2'-deoxyadenosines," Journal of Organic Chemistry, 1998, vol. 63, Issue 3, pp. 746-754.
Smith, et al., "The design, synthesis, and antiviral activity of monofluoro and difluoro analogues of 4'-azidocytidine and against hepatitis C virus replication: The discovery of 4'-azido-2'-deoxy-2'-fluorocytidine and 4'-azido-2'-dideoxy-2',2'-difluorocytidine," Journal of Medicinal Chemistry, 2009, vol. 52, pp. 2971-2978.
Sopchik, et al., "Facile preparation of the individual diastereoisomers of thymidine 3',5'-cyclic phosphorothioate (cTMPS)," Tetrahedron Letters, 1981, vol. 22, Issue 4, pp. 307-310.
Spormann, et al., "Synthesis and photoreaction of 4'-pivaloyl guanosides," Synthesis, 2001, vol. 14, pp. 2156-2164.
Srivastava, et al., "Enantiomeric forms of 9-(5,6-dideoxy-.alpha.-D-arabino-hex-5-enofuranosyl) adenine and preparation of 9-(6-deoxy-.beta.D-galactofuranosyl) adenine. Further results with the acetolysis of hexofuranosides," Tetrahedron, 1978, vol. 34, Issue 17, pp. 2627-2631.
Stanton, G. John, et al., "Interferon Review," Invest. Radiol., 1987, vol. 22, No. 3, pp. 259-273.
Streitwieser, et al., "Introduction to Organic Chemistry," 2nd ed., MacMillan Publishing Co., Inc., New York, NY, 1981, pp. 169-171.
Sun, et al., "Effects of cGMP, cAMP and two other cAMP derivatives on the transcription system of isolated rat liver nuclei," Shengwu Huaxue Zazhi, 1987, vol. 3, Issue 5, pp. 455-461.
Tian, et al., "Synthesis of 8-chloroadenosine 3',5'-cyclophosphotriesters and phosphoramidates," Progress in Natural Science, 1994, vol. 4, Issue 6, pp. 726-731.
Tomassini, et al., "Inhibitory effect of 2'-substituted nucleosides on hepatitis C virus replication correlates with metabolic properties in replicon cells," Antimicrobial Agents and Chemotherapy, 2005, vol. 49, Issue 5, pp. 2050-2058.
Tomei, et al., "HCV antiviral resistance: the impact of in vitro studies on the development of antiviral agents targeting the viral NS5B polymerase," Antiviral Chemistry and Chemotherapy, 2005, vol. 16, Issue 4, pp. 225-245.
Trafelet, et al., "Synthesis of (5'S)-5'-C-alkyl-2'-deoxynucleosides," Helvetica Chimica Acta, 2001, vol. 84, Issue 1, pp. 87-105.
Tunitskaya, et al., "Substrate properties of C'-methyl UTP derivatives in T7 RNA polymerase reactions. Evidence for N-type NTP conformation," FEBS Letters, 1997, vol. 400, Issue 3, pp. 263-266.
Ueno, et al., "Nucleosides and nucleotides. 174. Synthesis of oligodexynucleotides containing 4'-C-[2[[N-(2aminoethyl)carbamoyl]oxy]ethyl]thymidine and their thermal stability and nuclease-resistance properties," Journal of Organic Chemistry, 1998, vol. 63, Issue 5, pp. 1660-1667.
Venkatachalam, et al., "A comparative study of the hydrolysis pathways of substituted aryl phosphoramidate versus aryl thiophosphoramidate derivatives of stavudine," European Journal of Medicinal Chemistry, 2004, vol. 39, pp. 665-683.
Vilar, et al., "Probabilistic neural network model for the in silico evaluation of anti-HIV activity and mechanism of action," Journal of Medicinal Chemistry, 2006, vol. 49, Issue 3, pp. 1118-1124.
Walczak, et al., "Synthesis of 1-(3-(1,2,4-triazol-1-y1)-2,3,6-trideoxy-L-arabino-hexofuranosyl) uracils via an .alpha., .beta.-unsaturated aldehydohexose," Monatshefte fur Chemie, 1992, vol. 123, Issue 4, pp. 349-354.
Wang, et al., "Study on the structure-activity relationship of new anti-HIV nucleoside derivatives based on the Suport Vector Machine method," QSAR & Conbinatorial Science, 2007, vol. 26, Issue 2, pp. 161-172.
Wang, et al., "Synthesis and cytokine modulation properties of pyrrolo [2,3-d]-4-pyrimidone nucleosides," Journal of Medicinal Chemistry, 2000, vol. 43, Issue 13, pp. 2566-2574.
Wu, et al., "The cyclophosphorylation of adenosine," Huaxue Xuebao, 1986, vol. 44, Issue 6, pp. 635-638.
Yakovlev, et al., "Stereoelectronic effects in Rnase-catalyzed reactions of dinucleoside phosphate cleavage," FEBS Letters, 1985, vol. 179, Issue 2, pp. 217-220.
Yakovlev, et al., "Stereoelectronic effects in the enzymatic cleavage of dinucleoside phosphates by Rnases," Bioorganicheskaya Khimiya, 1985, vol. 11, Issue 2, pp. 205-210.
Yakovlev, et al., "Stereoelectronic effects in the reactions involved in the enzymatic cleavage of dinucleoside phosphates by Rnases," Soviet Journal of Bioorganic Chemistry (a translation of Bioorganicheskaya Khimiya), 1985, vol. 11, Issue 2, pp. 107-112.
Zhong, Weidong, et al., "Dinucleotide analogues as novel inhibitors of RNA-dependent RNA polymerase of hepatitis C virus," Antimicrobial Agents and Chemotherapy, Aug. 1, 2003, American Society of Microbiology, US vol. 47, No. 8, pp. 2674-2681.
Zinchenko, et al., "2'-, 3'-, and 5'-methyl derivatives of uridine in the reaction of microbiological transglycosylation," Dodlady Adademii Nauk SSR, 1987, vol. 297, Issue 3, pp. 731-734.
Zinchenko, et al., "Substrate specificity of uridine and purine nucleoside phosphorylases of *Escherichia coli* whole cells," Biopolimery I Kletka, 1988, vol. 4, Issue 6, pp. 298-302.

(56) References Cited

OTHER PUBLICATIONS

Zinchenko, et al., "Substrate specificity of uridine and purine nucleoside phosphorylases of the whole cells of *Escherichia coli*," Nucleic Acids Symposium Series, 1987, vol. 18, Issue 7, pp. 137-140.
International Search Report and Written Opinion, dated Nov. 17, 2011, for International Application No. PCT/US2011/052220, filed Sep. 19, 2011, 13 pages.
Written Opinion dated Sep. 19, 2012, for International Application No. PCT/US2011/052220, filed Sep. 19, 2011, 6 pages.
International Preliminary Report on Patentability, dated Dec. 12, 2012, for International Application No. PCT/US2011/052220, filed Sep. 19, 2011, 37 pages.
International Search Report, dated May 24, 2013, for International Application No. PCT/US2013/030267, filed Mar. 11, 2013, 4 pages.
International Preliminary Report on Patentablility dated Sep. 23, 2014 for International Application No. PCT/US2013/030267, filed Mar. 11, 2013, 7 pages.
Written Opinion dated May 24, 2013, for International Application No. PCT/US2013/030267, filed Mar. 11, 2013, 6 pages.
Office Action dated Feb. 19, 2014 in U.S. Appl. No. 13/794,380, filed Mar. 11, 2013.
Office Action dated Oct. 23, 2015 in Chinese Patent Application No. 201380025218.6, filed Mar. 11, 2013.
First Examination Report dated Jun. 15, 2015 in New Zealand Patent Application No. 631601, filed Mar. 11, 2013.
Office Action dated Oct. 23, 2015 in U.S. Appl. No. 14/578,883, filed Dec. 22, 2014.
Office Action dated Jun. 22, 2016 in Chinese Patent Application No. 201380025218.6, filed Mar. 11, 2013.

Figure 1: X-Ray Powder Diffraction (XRPD) pattern/spectrum of Form A

Figure 3: Solid State Nuclear Magnetic Resonance (ssNMR) Spectrum of Form A

Figure 4: X-Ray Powder Diffraction (XRPD) pattern/spectrum of Form B

Figure 5: Solid State Nuclear Magnetic Resonance (ssNMR) Spectrum of Form B

Figure 6: X-Ray Powder Diffraction (XRPD) pattern/spectrum of Form C

Figure 7: Solid State Nuclear Magnetic Resonance (ssNMR) Spectrum of Form C

Figure 8: X-Ray Powder Diffraction (XRPD) pattern/spectrum of Form D

Figure 9: Solid State Nuclear Magnetic Resonance (ssNMR) Spectrum of Form D

Figure 10: X-Ray Powder Diffraction (XRPD) pattern/spectrum of a mixture of Form A and Form E Figure 11: Solid State Nuclear Magnetic Resonance (ssNMR) Spectrum of a mixture of Form A and Form E Figure 12: X-Ray Powder Diffraction (XRPD) pattern/spectrum of a mixture of Form A and Form F Figure 13: Solid State Nuclear Magnetic Resonance (ssNMR) Spectrum of a mixture of Form A and Form F Figure 14: X-Ray Powder Diffraction (XRPD) pattern/spectrum of Form G Figure 15: Solid State Nuclear Magnetic Resonance (ssNMR) Spectrum of Form G Figure 16: X-Ray Powder Diffraction (XRPD) pattern/spectrum of Form H Figure 17: Solid State Nuclear Magnetic Resonance (ssNMR) Spectrum of Form H Figure 18: X-Ray Powder Diffraction (XRPD) pattern/spectrum of Form I Figure 19: Solid State Nuclear Magnetic Resonance (ssNMR) Spectrum of Form I Figure 20: X-Ray Powder Diffraction (XRPD) pattern/spectrum of Form J Figure 22: Solid State Nuclear Magnetic Resonance (ssNMR) Spectrum of Form J Figure 23: X-Ray Powder Diffraction (XRPD) pattern/spectrum of Form K Figure 24: Solid State Nuclear Magnetic Resonance (ssNMR) Spectrum of Form K Figure 25: X-Ray Powder Diffraction (XRPD) pattern/spectrum of Form L Figure 26: Solid State Nuclear Magnetic Resonance (ssNMR) Spectrum of Form L Figure 27: X-Ray Powder Diffraction (XRPD) pattern/spectrum of Form M Figure 28: Solid State Nuclear Magnetic Resonance (ssNMR) Spectrum of Form M Figure 29: X-Ray Powder Diffraction (XRPD) pattern/spectrum of Form N Figure 30: Solid State Nuclear Magnetic Resonance (ssNMR) Spectrum of Form N Figure 31: X-Ray Powder Diffraction (XRPD) pattern/spectrum of Amorphous Form O

| # | Name | Structure |
|---|---|---|
| 1007 | GS-9256 | |
| 1008 | GS-9451 | |
| 1009 | IDX-320 | |
| 1010 | ACH-1625 | |
| 1011 | ACH-2684 | |
| 1012 | TMC-435<br>TMC-435350 | (structure shown) |

| # | Name | Structure |
|---|---|---|
| 1013 | Danoprevir<br>ITMN-191<br>RG7227<br>RO5190591 | (structure shown) |
| 1014 | MK-7009<br>Vaniprevir | (structure shown) |
| 1015 | PHX1766 | |

Figure 32 (cont.)

| # | Name | Structure |
|---|---|---|
| 1019 | PSI-352938 GS-938 | (structure shown) |
| 1020 | 4'-azidouridine and its prodrugs | (structure shown) |
| 1021 | PSI-661 | |
| 1022 | GS-6620 | |
| 1023 | TMC649128 | |

| # | Name | Structure |
|---|---|---|
| 1016 | RG7128 Mericitabine | (structure shown) |
| 1017 | PSI-7851 | (structure shown) |
| 1018 | PSI-7977 GS-7977, Sofosbuvir | (structure shown) |

Figure 32 (cont.)

| # | Name | Structure |
|---|---|---|
| 1024 | NM283 | (structure shown: cytidine analog with Me, OH, ValO substituents) |
| 1025 | BCX5191 | |
| 1026 | IDX19368 | |
| 1027 | IDX19370 | |
| 1028 | ABT-333 | |
| 1029 | ANA-598 Setrobuvir | (structure shown) |
| 1030 | VX-222<br>S1480<br>VCH-222 | (structure shown) |
| 1031 | HCV-796 | (structure shown) |
| 1032 | BI-207127 | |

Figure 32 (cont.)

| # | Name | Structure |
|---|---|---|
| 1033 | GS-9190 | (structure shown) |
| 1034 | Filibuvir PF-00868554 | (structure shown) |
| 1035 | VX-497 | (structure shown) |
| 1036 | ABT-072 | |
| 1037 | MK-3281 | |
| 1038 | TMC647055 | |
| 1039 | BMS-791325 | |
| 1040 | PPI-383 | |
| 1041 | GS9669 | |

| # | Name | Structure |
|---|---|---|
| 1042 | BMS-790052 BMS052 S1482 Daclatasvir | (structure shown) |
| 1043 | PPI-461 | |
| 1044 | ACH-2928 | |
| 1045 | GS-5885 | |
| 1046 | BMS-824393 | |
| 1047 | ABT 267 | |
| 1048 | ACH-3102 | |
| 1049 | AZD-7295 | |
| 1050 | IDX719 | |
| 1051 | PPI-668 | |
| 1052 | MK8742 | |
| 1053 | GSK2336805 GSK805 | |
| 1054 | Debio-025 Alisporivir | |
| 1055 | MIR-122 | |

| # | Name | Structure |
|---|---|---|
| 1056 | clemizole | |
| 1057 | ITX 5061 | |
| 1058 | BIT225 | |
| 1059 | NIM811 | |
| 1060 | SCY-635 | |
| 1061 | Nitazoxanide | 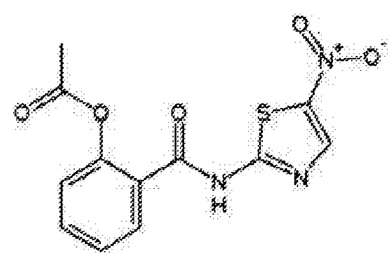 |

| # | Name | Structure |
|---|---|---|
| 1062 | Miravirsen | |
| 1063 | Celgosivir | 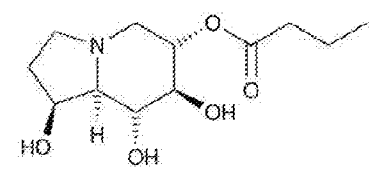 |
| 1064 | GS9620 | |
| 1065 | Ribavirin | 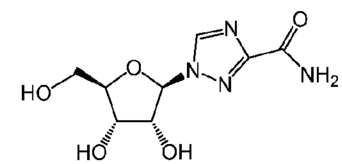 |
| 1066 | GS-5816 | |

Figure 33: Compounds of Formula (BB)

| # | Structure |
|---|---|
| 8000 | (structure with $B^{BB1}$, $R^{BB2}$–$R^{BB8}$, $X^{BB}$, $R^{BB1}$) |
| 8001 | (structure) |
| 8002 | (structure) |
| 8003 | (structure) |
| 8004 | (structure) |
| 8005 | (structure) |
| 8006 | (structure) |

Figure 33: Compounds of Formula (BB) Continued

| # | Structure |
|---|---|
| 8010 | 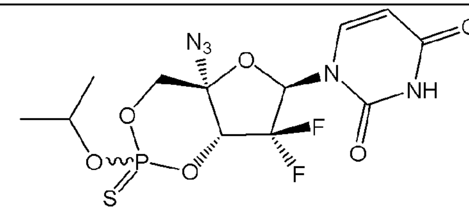 |
| 8011 | 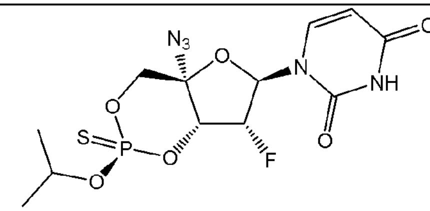 |
| 8012 | 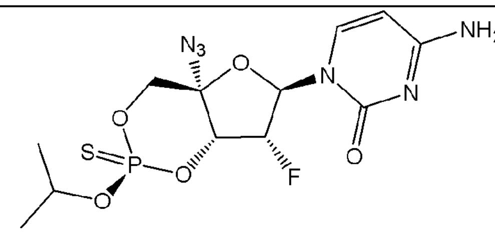 |

| # | Structure |
|---|---|
| 8007 | 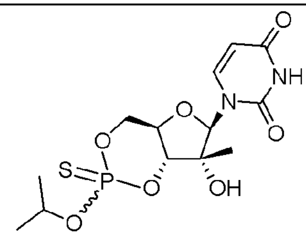 |
| 8008 | 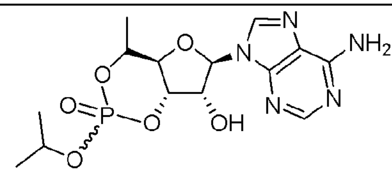 |
| 8009 | 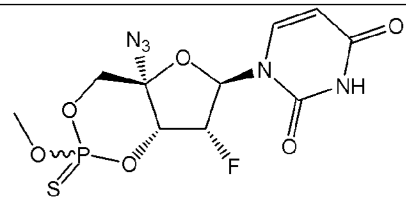 |

Figure 34: Formula (DD)
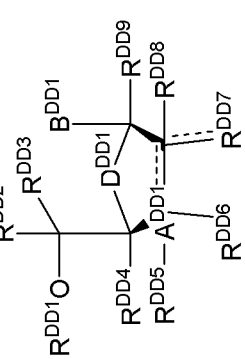

SOLID FORMS OF A THIOPHOSPHORAMIDATE NUCLEOTIDE PRODRUG

CROSS-REFERENCE TO RELATED APPLICATION

This application is a continuation of U.S. application Ser. No. 14/578,883, filed Dec. 22, 2014, (now U.S. Pat. No. 9,394,330) which is a continuation of U.S. application Ser. No. 13/794,380, filed Mar. 11, 2013, (now U.S. Pat. No. 8,916,538), which claims the benefit of priority under 35 U.S.C. 119(e) to U.S. provisional application No. 61/613,972, filed Mar. 21, 2012; all of which are incorporated herein by reference in their entirety, including any drawings.

TECHNICAL FIELD

The present application relates to solid state forms, for example, crystalline forms of 2'-C-methyluridine-5'-(O-phenyl-N—(S)-1-(isopropoxycarbonyl)ethyl)thiophosphoramidate, pharmaceutical compositions that can include one or more solid forms of 2'-C-methyluridine-5'-(O-phenyl-N—(S)-1-(isopropoxycarbonyl)ethyl)thiophosphoramidate, and methods of treating or ameliorating diseases and/or conditions with one or more solid forms of 2'-C-methyluridine-5'-(O-phenyl-N—(S)-1-(isopropoxycarbonyl)ethyl)thiophosphoramidate. Also disclosed herein are methods of treating diseases and/or conditions with one or more solid forms of 2'-C-methyluridine-5'-(O-phenyl-N—(S)-1-(isopropoxycarbonyl)ethyl)thiophosphoramidate in combination with one or more other agents.

BACKGROUND

Nucleoside analogs are a class of compounds that have been shown to exert antiviral and anticancer activity both in vitro and in vivo, and thus, have been the subject of widespread research for the treatment of viral infections and cancer. Nucleoside analogs are usually therapeutically inactive compounds that are converted by host or viral enzymes to their respective active anti-metabolites, which, in turn, may inhibit polymerases involved in viral or cell proliferation. The activation occurs by a variety of mechanisms, such as the addition of one or more phosphate groups and, or in combination with, other metabolic processes.

SUMMARY

Some embodiments disclosed herein generally relate to solid forms of 2'-C-methyluridine-5'-(O-phenyl-N—(S)-1-(isopropoxycarbonyl)ethyl)thiophosphoramidate (hereinafter "Compound 1") which has the structure below:

Compound 1

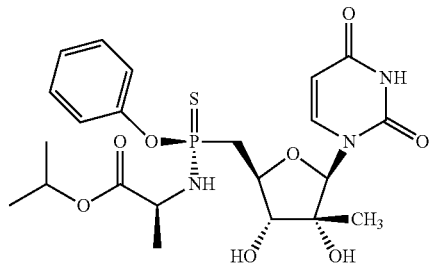

In some embodiments, Compound 1 can be 2'-C-methyluridine-5'-(O-phenyl-N—(S)-1-(isopropoxycarbonyl)ethyl)thiophosphoramidate characterized as Form A.

In some embodiments, Compound 1 can be 2'-C-methyluridine-5'-(O-phenyl-N—(S)-1-(isopropoxycarbonyl)ethyl)thiophosphoramidate characterized as Form B.

In some embodiments, Compound 1 can be 2'-C-methyluridine-5'-(O-phenyl-N—(S)-1-(isopropoxycarbonyl)ethyl)thiophosphoramidate characterized as Form C.

In some embodiments, Compound 1 can be 2'-C-methyluridine-5'-(O-phenyl-N—(S)-1-(isopropoxycarbonyl)ethyl)thiophosphoramidate characterized as Form D.

In some embodiments, Compound 1 can be 2'-C-methyluridine-5'-(O-phenyl-N—(S)-1-(isopropoxycarbonyl)ethyl)thiophosphoramidate characterized as Form E.

In some embodiments, Compound 1 can be 2'-C-methyluridine-5'-(O-phenyl-N—(S)-1-(isopropoxycarbonyl)ethyl)thiophosphoramidate characterized as Form F.

In some embodiments, Compound 1 can be 2'-C-methyluridine-5'-(O-phenyl-N—(S)-1-(isopropoxycarbonyl)ethyl)thiophosphoramidate characterized as Form G.

In some embodiments, Compound 1 can be 2'-C-methyluridine-5'-(O-phenyl-N—(S)-1-(isopropoxycarbonyl)ethyl)thiophosphoramidate characterized as Form H.

In some embodiments, Compound 1 can be 2'-C-methyluridine-5'-(O-phenyl-N—(S)-1-(isopropoxycarbonyl)ethyl)thiophosphoramidate characterized as Form I.

In some embodiments, Compound 1 can be 2'-C-methyluridine-5'-(O-phenyl-N—(S)-1-(isopropoxycarbonyl)ethyl)thiophosphoramidate characterized as Form J.

In some embodiments, Compound 1 can be 2'-C-methyluridine-5'-(O-phenyl-N—(S)-1-(isopropoxycarbonyl)ethyl)thiophosphoramidate characterized as Form K.

In some embodiments, Compound 1 can be 2'-C-methyluridine-5'-(O-phenyl-N—(S)-1-(isopropoxycarbonyl)ethyl)thiophosphoramidate characterized as Form L.

In some embodiments, Compound 1 can be 2'-C-methyluridine-5'-(O-phenyl-N—(S)-1-(isopropoxycarbonyl)ethyl)thiophosphoramidate characterized as Form M.

In some embodiments, Compound 1 can be 2'-C-methyluridine-5'-(O-phenyl-N—(S)-1-(isopropoxycarbonyl)ethyl)thiophosphoramidate characterized as Form N.

In some embodiments, Compound 1 can be 2'-C-methyluridine-5'-(O-phenyl-N—(S)-1-(isopropoxycarbonyl)ethyl)thiophosphoramidate characterized as Amorphous Form O.

Some embodiments disclosed herein generally relate to a process for producing Form A that can include:
a) contacting Compound 1 with a first amount of ethyl acetate to form a mixture;
b) heating the mixture until the solids are dissolved;
c) cooling the mixture to allow precipitation of a solid;
d) optionally adding a second amount of ethyl acetate and repeating steps a, b and c; and
e) isolating Form A from said mixture.

Some embodiments disclosed herein generally relate to a process for producing Form J that can include:
a) contacting Amorphous Form O with ethanol to form a mixture; and
b) isolating Form J from said mixture.

Some embodiments disclosed herein generally relate to a process for producing a solvated solid form of Compound 1 that can include:
a) contacting Compound 1 with a solvent to form a mixture; and
b) isolating the solvated solid form of Compound 1 from said mixture.

Some embodiments disclosed herein generally relate to a method of ameliorating or treating a viral infection (for example, a HCV infection) in a subject, said method can include administering to said subject an effective amount of one or more solid forms of Compound 1 as described herein.

Some embodiments disclosed herein relate to a pharmaceutical composition that can include one or more solid forms of Compound 1 as described herein.

Some embodiments disclosed herein generally relate to a pharmaceutical composition that can include one or more solid forms of Compound 1, and one or more additional agent(s).

Some embodiments disclosed herein relate to a method of ameliorating and/or treating a HCV infection that can include administering to a subject identified as suffering from the HCV infection an effective amount of a compound described herein or a pharmaceutically acceptable salt thereof (for example, one or more solid forms of Compound 1, or a pharmaceutically acceptable salt thereof), or a pharmaceutical composition that includes one or more solid forms of Compound 1 as described herein, or a pharmaceutically acceptable salt thereof, in combination with an agent selected from an interferon, ribavirin, a HCV protease inhibitor, a HCV polymerase inhibitor, a NS5A inhibitor, an other antiviral compound, a compound of Formula (BB) and a compound of Formula (DD), or a pharmaceutically acceptable salt of any of the foregoing.

BRIEF DESCRIPTION OF THE DRAWINGS

FIG. 33 shows examples of Compounds of Formula (BB).
FIG. 34 shows the generic Formula (DD).

DETAILED DESCRIPTION

Definitions

Figure 1:
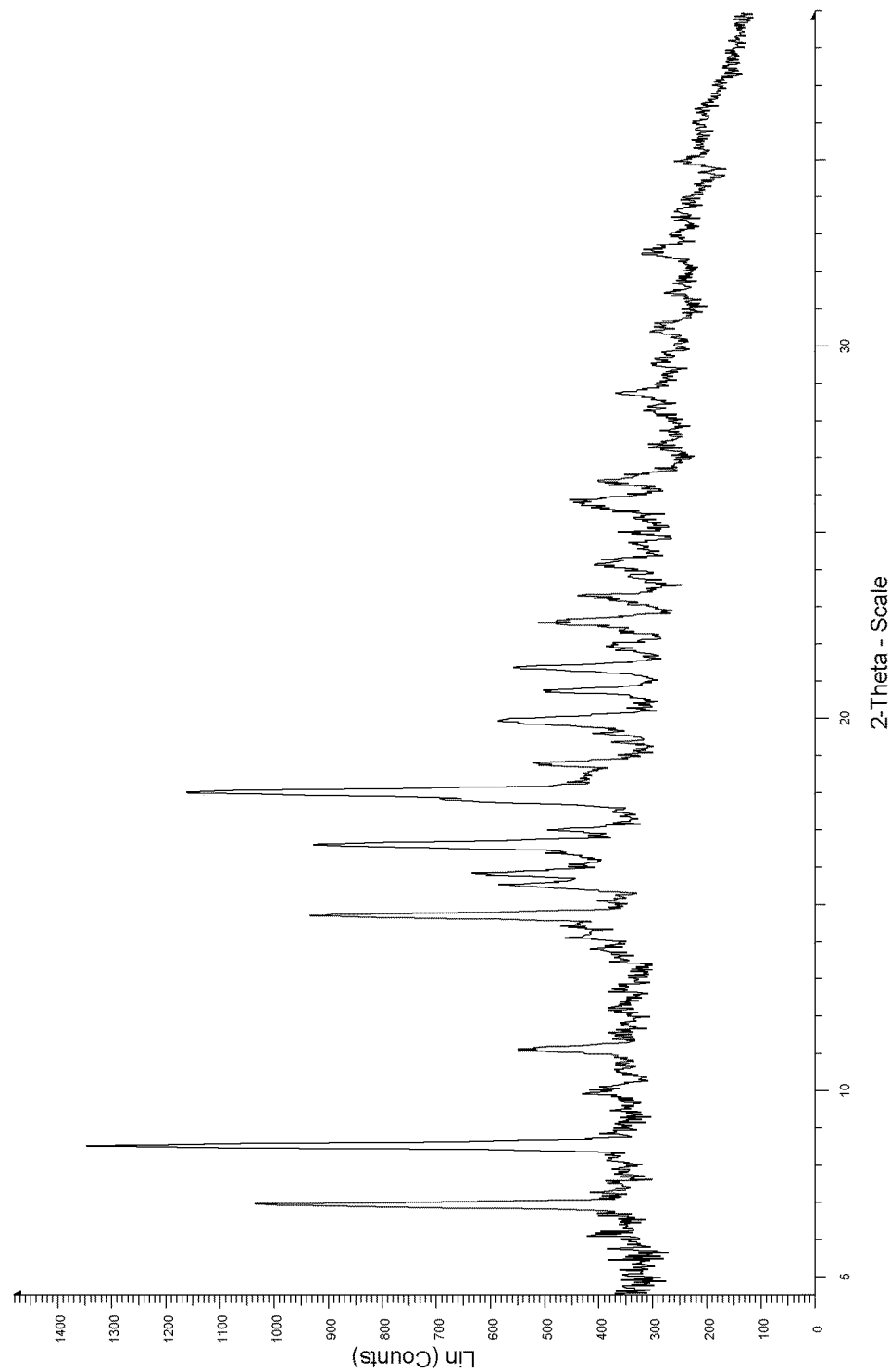
FIG. 1 is an XRPD spectrum of Form A.

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used herein, the following definitions shall apply unless otherwise indicated.

The term "crystalline" refers to a substance that has its atoms, molecules or ions packed in a regularly ordered three-dimensional pattern. The term "substantially crystalline" refers to a substance where a substantial portion of the substance is crystalline. For example, substantially crystalline materials can have more than about 85% crystallinity (e.g., more than about 90% crystallinity, more than about 95% crystallinity, or more than about 99% crystallinity).

The chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "nucleoside" refers to a compound composed of an optionally substituted pentose moiety or modified pentose moiety attached to a heterocyclic base or tautomer thereof via a N-glycosidic bond, such as attached via the 9-position of a purine-base or the 1-position of a pyrimidine-base. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers. In some instances, the nucleoside can be a nucleoside analog drug.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

As used herein, the term "room temperature" refers to a temperature in the range of about 20° C. to about 25° C., such as a temperature in the range of about 21° C. to about 23° C.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof. Unless otherwise stated, all tautomeric forms of Compound 1 are intended to be included.

Likewise, it is understood that, in any compound described, all tautomeric forms are also intended to be included. For example all tautomers of phosphate groups are intended to be included. Furthermore, all tautomers of heterocyclic bases known in the art are intended to be included, including tautomers of natural and non-natural purine-bases and pyrimidine-bases.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Example Embodiments of Compound 1

All XRPD spectra provided herein are measured on a degrees 2-Theta scale, and all $^{13}$C solid state NMR's are referenced to adamantane at 29.5 ppm.

Form A

In some embodiments, Compound 1 can be 2'-C-methyluridine-5'-(O-phenyl-N—(S)-1-(isopropoxycarbonyl)ethyl)thiophosphoramidate characterized as Form A.

In some embodiments, Form A can be characterized by one or more peaks in an X-ray powder diffraction pattern, wherein the one or more peaks is selected from a peak in the range of from about 6.8 to about 7.2 degrees, a peak in the range of from about 8.3 to about 8.7 degrees, a peak in the range of from about 15.6 to about 16.0 degrees, a peak in the range of from about 21.2 to about 21.6 degrees, a peak in the range of from about 21.8 to about 22.2 degrees, a peak in the range of from about 22.4 to about 22.8 degrees, and a peak in the range of from about 23.1 to about 23.5 degrees.

In some embodiments, Form A can be characterized by one or more peaks in an X-ray powder diffraction pattern, wherein the one or more peaks is selected from a peak in the range of from about 6.8 to about 7.2 degrees, a peak in the range of from about 8.3 to about 8.7 degrees, a peak in the range of from about 15.6 to about 16.0 degrees and a peak in the range of from about 21.2 to about 21.6 degrees.

In some embodiments, Form A can be characterized by one or more peaks in an X-ray powder diffraction pattern, wherein the one or more peaks is selected from a peak at about 7.0 degrees, a peak at about 8.5 degrees, a peak at about 15.8 degrees, a peak at about 21.4 degrees, a peak at about 22.0 degrees, a peak at about 22.6 degrees, and a peak at about 23.3 degrees.

In some embodiments, Form A can be characterized by a peak at about 8.5 degrees, a peak at about 15.8 degrees, and a peak at about 21.4 degrees in an X-ray powder diffraction pattern.

In some embodiments, Form A can be characterized by a peak at about 8.5 degrees, a peak at about 15.8 degrees, a peak at about 21.4 degrees, a peak at about 22.0 degrees, a peak at about 22.6 degrees, and a peak at about 23.3 degrees in an X-ray powder diffraction pattern.

In some embodiments, Form A can be characterized by a peak at about 7.0 degrees, a peak at about 8.5 degrees, a peak at about 15.8 degrees, and a peak at about 21.4 degrees in an X-ray powder diffraction pattern.

In some embodiments, Form A can be characterized by a peak at about 7.0 degrees, a peak at about 8.5 degrees, a peak at about 15.8 degrees, a peak at about 21.4 degrees, a peak at about 22.0 degrees, a peak at about 22.6 degrees, and a peak at about 23.3 degrees in an X-ray powder diffraction pattern.

In some embodiments, Form A can exhibit an X-ray powder diffraction pattern as shown in FIG. 1.

In some embodiments, Form A can be characterized by one or more peaks in an X-ray powder diffraction pattern selected from the table below.

| No. | 2-Theta ° | Intensity % |
|---|---|---|
| 1 | 7.0* | 91.8 |
| 2 | 8.5* | 100.0 |
| 3 | 10.0 | 70.0 |
| 4 | 11.0 | 73.4 |
| 5 | 14.7 | 90.3 |
| 6 | 15.5 | 76.7 |
| 7 | 15.8* | 79.6 |
| 8 | 16.6 | 90.9 |
| 9 | 17.8 | 81.1 |
| 10 | 18.0 | 99.2 |
| 11 | 18.8 | 72.2 |
| 12 | 19.9 | 76.1 |
| 13 | 20.8 | 73.5 |
| 14 | 21.4* | 77.0 |
| 15 | 22.0** | 68.9 |
| 16 | 22.6** | 73.0 |
| 17 | 23.3** | 68.8 |
| 18 | 25.8 | 71.7 |
| 19 | 28.7 | 67.4 |

Figure 2:
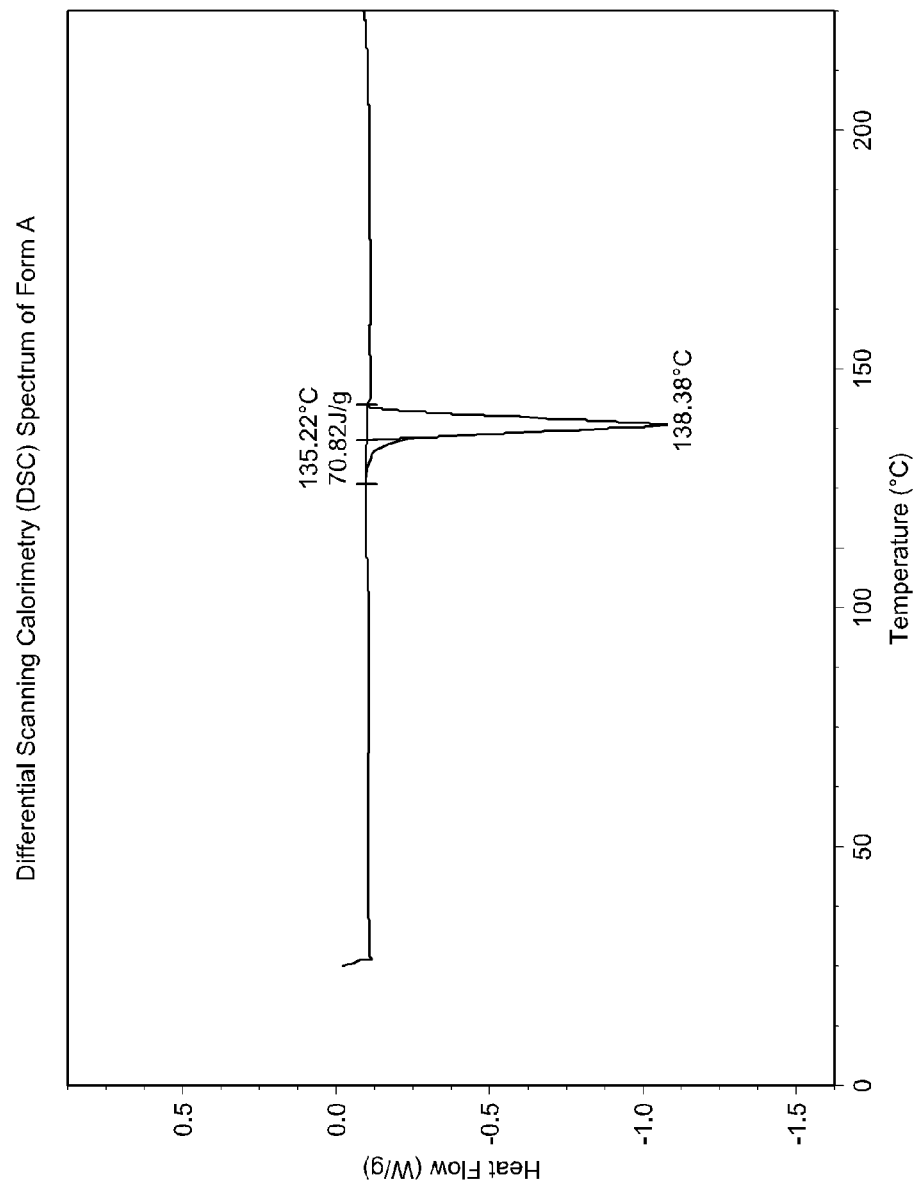
FIG. 2 is a DSC spectrum of Form A.

Peaks with an asterisk (*) are major peaks
Peaks with a double asterisk (**) are secondary peaks In some embodiments, Form A can be characterized by a DSC thermogram as shown in FIG. 2. In some embodiments, Form A can be characterized by a melting point in the range of from about 137° C. to about 139° C. In other embodiments, Form A can be characterized by a melting point of about 138° C. In some embodiments, Form A can be characterized by a melting point of about 138.4° C. In some embodiments, Form A can be characterized by an endotherm in the range of from about 137° C. to about 139° C. In other embodiments, Form A can be characterized by an endotherm of about 138° C. In some embodiments, Form A can be characterized by an endotherm of about 138.4° C.

In some embodiments, Form A can be characterized by a peak at about 130.4 ppm, a peak at about 69.5 ppm, a peak at about 66.9 ppm, and a peak at about 20.6 ppm in a $^{13}$C NMR solid state spectrum.

In some embodiments, Form A can be characterized by a peak at about 172.0 ppm, a peak at about 146.6 ppm, a peak at about 130.4 ppm, a peak at about 104.1 ppm, a peak at about 69.5 ppm, a peak at about 66.9 ppm, and a peak at about 20.6 ppm in a $^{13}$C NMR solid state spectrum.

Figure 3:
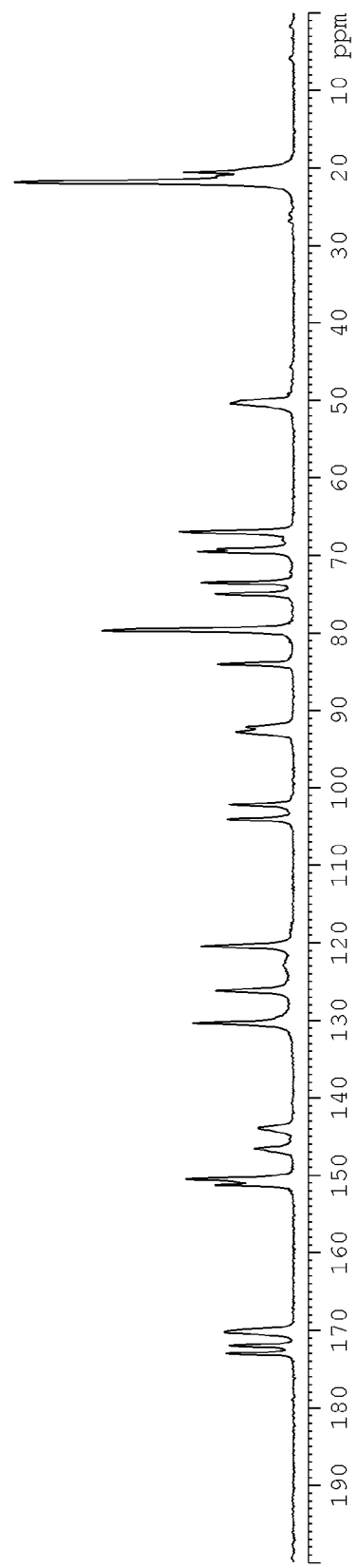
FIG. 3 is a $^{13}$C ssNMR spectrum of Form A.

In some embodiments, Form A can exhibit a $^{13}$C NMR solid state spectrum as shown in FIG. 3.

In some embodiments, Form A can be characterized by one or more peaks in a $^{13}$C NMR solid state spectrum selected from the table below.

| Peak # | v(F1) [ppm] | Intensity [rel] |
|---|---|---|
| 1 | 173.0 | 24.12 |
| 2 | 172.0* | 23.11 |
| 3 | 170.2 | 24.80 |
| 4 | 151.3 | 28.62 |
| 5 | 150.5 | 38.71 |
| 6 | 146.6* | 14.23 |
| 7 | 143.9 | 12.74 |
| 8 | 130.4* | 36.15 |
| 9 | 126.2 | 27.80 |
| 10 | 122.9 | 3.91 |
| 11 | 120.4 | 33.00 |
| 12 | 104.1* | 23.68 |
| 13 | 102.2 | 23.18 |
| 14 | 92.8 | 20.65 |
| 15 | 92.2 | 17.13 |
| 16 | 84.1 | 27.03 |
| 17 | 79.7 | 68.89 |
| 18 | 75.0 | 28.02 |
| 19 | 73.5 | 33.05 |
| 20 | 69.5* | 34.76 |
| 21 | 69.2 | 27.63 |
| 22 | 66.9* | 40.98 |
| 23 | 50.4 | 22.59 |
| 24 | 21.9 | 100.00 |
| 25 | 20.6* | 39.44 |

Peaks with an asterisk (*) are major peaks

Form B

In some embodiments, Compound 1 can be 2'-C-methyluridine-5'-(O-phenyl-N—(S)-1-(isopropoxycarbonyl)ethyl)thiophosphoramidate characterized as Form B.

In some embodiments, Form B can be characterized by one or more peaks in an X-ray powder diffraction pattern, wherein the one or more peaks is selected from a peak in the range of from about 5.5 to about 5.9 degrees, a peak in the range of from about 9.2 to about 9.6 degrees, a peak in the range of from about 16.8 to about 17.2 degrees, and a peak in the range of from about 26.0 to about 26.4 degrees.

In some embodiments, Form B can be characterized by one or more peaks in an X-ray powder diffraction pattern, wherein the one or more peaks is selected from a peak at about 5.7 degrees, a peak at about 9.4 degrees, a peak at about 17.0 degrees, and a peak at about 26.2 degrees.

In some embodiments, Form B can be characterized by a peak at about 5.7 degrees, a peak at about 9.4 degrees, a peak at about 17.0 degrees, and a peak at about 26.2 degrees in an X-ray powder diffraction pattern.

Figure 4:
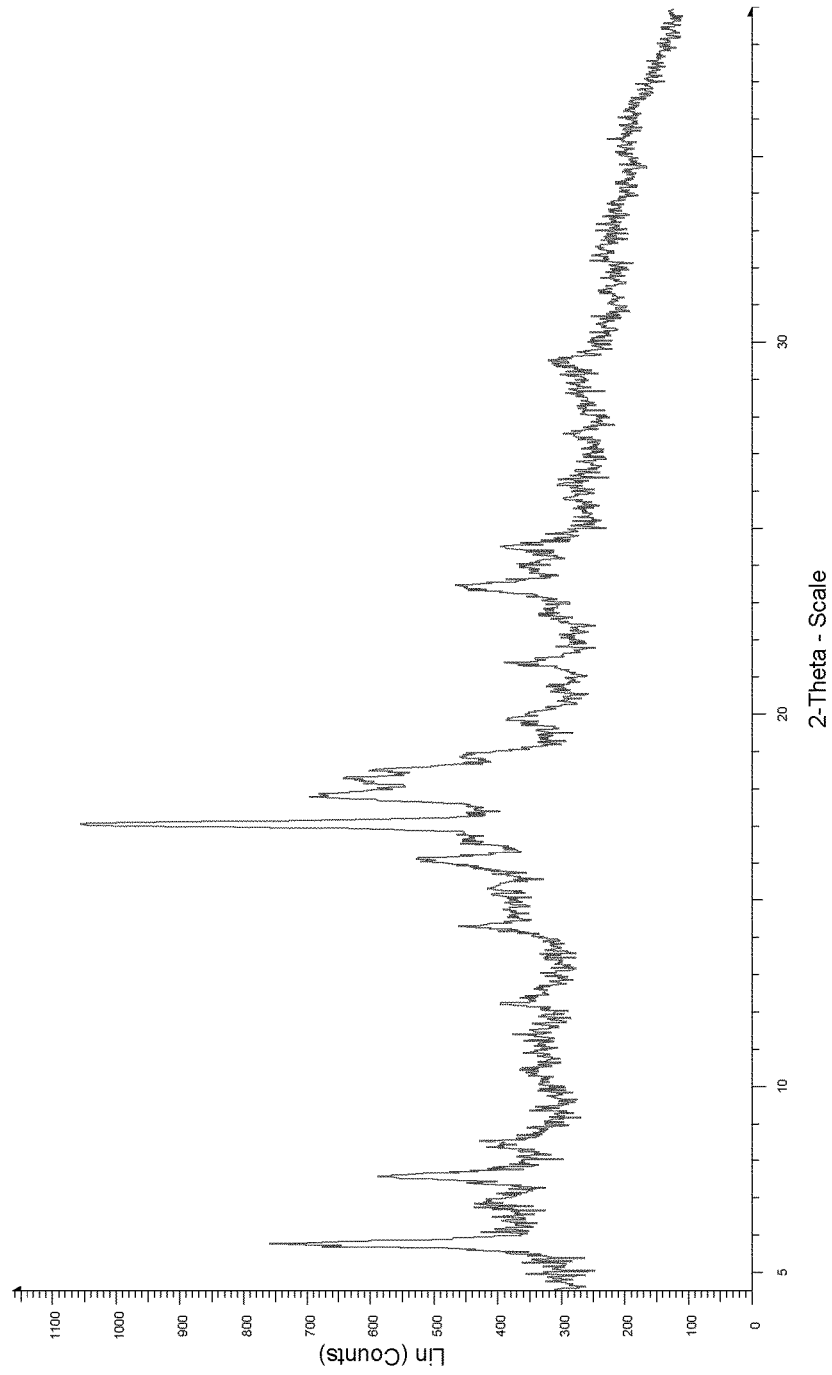
FIG. 4 is an XRPD spectrum of Form B.

In some embodiments, Form B can be characterized by an X-ray diffraction pattern of FIG. 4.

In some embodiments, Form B can be characterized by one or more peaks in an X-ray powder diffraction pattern selected from the table below.

| No. | 2-Theta ° | Intensity % |
|---|---|---|
| 1 | 5.720* | 71.8 |
| 2 | 9.395* | 31.2 |
| 3 | 17.042* | 100.0 |
| 4 | 26.219* | 28.5 |

Peaks with an asterisk (*) are major peaks

In some embodiments, Form B can be characterized by one or more peaks in a $^{13}$C NMR solid state spectrum, wherein the one or more peaks is selected from a peak at about 173.2 ppm, a peak at about 129.9 ppm, a peak at about 118.3 ppm, a peak at about 68.5 ppm, a peak at about 27.1 ppm, or a peak at about 19.5 ppm.

In some embodiments, Form B can be characterized by one or more peaks in a $^{13}$C NMR solid state spectrum, wherein the one or more peaks is selected from a peak at about 173.2 ppm, a peak at about 129.9 ppm, a peak at about 118.3 ppm, a peak at about 72.3 ppm, a peak at about 68.5 ppm, a peak at about 49.2 ppm, a peak at about 27.1 ppm and a peak at about 19.5 ppm. In some embodiments, Form B can be a methyl tert-butyl solvate.

In some embodiments, Form B can be characterized by a peak at about 118.3 ppm, a peak at about 68.5 ppm, and a peak at about 27.1 ppm in a $^{13}$C NMR solid state spectrum.

In some embodiments, Form B can be characterized by a peak at about 173.2 ppm, a peak at about 129.9 ppm, a peak at about 118.3 ppm, a peak at about 68.5 ppm, a peak at about 27.1 ppm, and a peak at about 19.5 ppm in a $^{13}$C NMR solid state spectrum.

Figure 5:
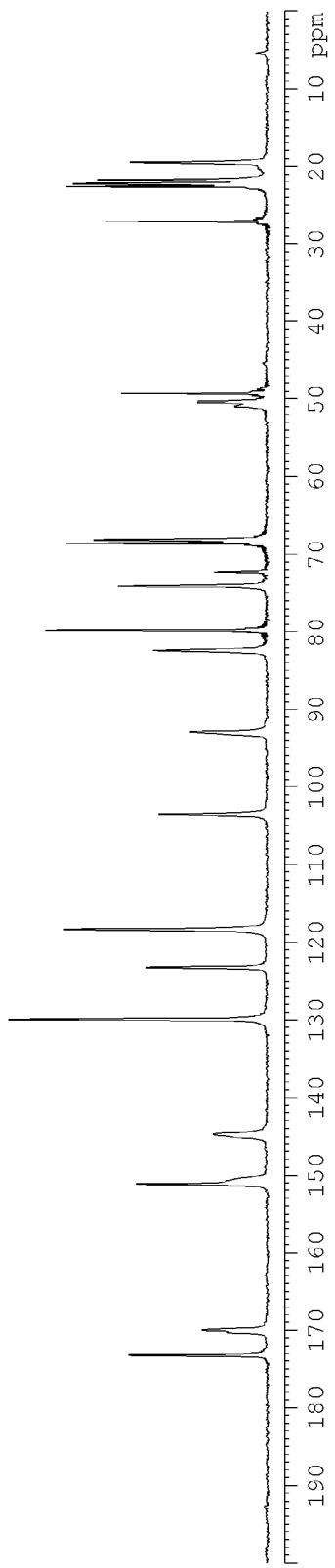
FIG. 5 is a $^{13}$C ssNMR spectrum of Form B.

In some embodiments, Form B can be characterized by a $^{13}$C NMR solid state spectrum of FIG. 5.

In some embodiments, Form B (methyl tert-butyl ether solvate) can be characterized by one or more peaks in a $^{13}$C NMR solid state spectrum selected from the table below.

| Peak | ν(F1) [ppm] | Intensity [rel] |
|---|---|---|
| 1 | 173.2* | 55.0 |
| 2 | 169.9 | 24.91 |
| 3 | 151.1 | 50.46 |
| 4 | 144.7 | 20.81 |
| 5 | 129.9* | 100.00 |
| 6 | 123.3 | 47.74 |
| 7 | 118.3* | 77.98 |
| 8 | 103.5 | 41.84 |
| 9 | 92.8 | 29.78 |
| 10 | 82.4 | 43.94 |
| 11 | 79.8 | 88.11 |
| 12 | 74.1 | 57.28 |
| 13 | 72.3* | 20.83 |
| 14 | 68.5* | 76.94 |
| 15 | 68.1 | 67.80 |
| 16 | 50.9 | 12.62 |
| 17 | 50.3 | 27.03 |
| 18 | 49.2* | 57.83 |
| 19 | 27.1* | 61.90 |
| 20 | 22.6 | 76.64 |
| 21 | 22.2 | 75.51 |
| 22 | 22.0 | 16.01 |
| 23 | 21.7 | 65.44 |
| 24 | 19.5* | 52.58 |

Peaks with an asterisk (*) are major peaks

In some embodiments, Form B can be characterized by one or more peaks in a $^{13}$C NMR solid state spectrum, wherein the one or more peaks is selected from a peak at about 170.3 ppm, a peak at about 150.5 ppm, a peak at about 129.8 ppm, a peak at about 118.2 ppm, a peak at about 79.8 ppm, a peak at about 27.2 ppm, and a peak at about 21.8 ppm.

In other embodiments, Form B can be a cyclohexane solvate.

In some embodiments, Form B can be characterized by a peak at about 150.5 ppm, a peak at about 129.8 ppm, a peak at about 118.2 ppm, and a peak at about 21.8 ppm in a $^{13}$C NMR solid state spectrum.

In some embodiments, Form B can be characterized by a peak at about 170.3 ppm, a peak at about 150.5 ppm, a peak at about 129.8 ppm, a peak at about 118.2 ppm, a peak at about 79.8 ppm, a peak at about 27.2 ppm, and a peak at about 21.8 ppm in a $^{13}$C NMR solid state spectrum.

In some embodiments, Form B (cyclohexane solvate) can be characterized by one or more peaks in a 13C NMR solid state spectrum selected from the table below.

| Peak # | ν(F1) [ppm] | Intensity [rel] |
|---|---|---|
| 1 | 172.6 | 20.01 |
| 2 | 170.3* | 26.09 |
| 3 | 150.5* | 39.10 |
| 4 | 146.6 | 15.32 |
| 5 | 144.4 | 12.23 |
| 6 | 129.8* | 31.00 |
| 7 | 126.3 | 25.02 |
| 8 | 122.6 | 15.89 |
| 9 | 120.4 | 26.04 |
| 10 | 118.2* | 30.57 |
| 11 | 104.1 | 18.00 |
| 12 | 102.2 | 17.34 |
| 13 | 92.8 | 19.56 |
| 14 | 84.2 | 16.62 |
| 15 | 79.8* | 53.48 |
| 16 | 75.0 | 22.56 |
| 17 | 73.6 | 20.49 |
| 18 | 69.5 | 21.11 |
| 19 | 68.1 | 19.74 |
| 20 | 66.9 | 21.59 |
| 21 | 64.0 | 13.37 |
| 22 | 50.5 | 20.41 |
| 23 | 40.8 | 12.34 |

-continued

| Peak # | ν(F1) [ppm] | Intensity [rel] |
|---|---|---|
| 24 | 27.2* | 21.00 |
| 25 | 21.8* | 100.00 |
| 26 | 18.6 | 15.87 |

Peaks with an asterisk (*) are major peaks

Form C

In some embodiments, Compound 1 can be 2'-C-methyluridine-5'-(O-phenyl-N—(S)-1-(isopropoxycarbonyl) ethyl)thiophosphoramidate characterized as Form C.

In some embodiments, Form C can be characterized by one or more peaks in an X-ray powder diffraction pattern, wherein the one or more peaks is selected from a peak in the range of from about 4.8 to about 5.2 degrees, a peak in the range of from about 6.4 to about 6.8 degrees, a peak in the range of from about 8.0 to about 8.4 degrees, a peak in the range of from about 9.0 to about 9.4 degrees, a peak in the range of from about 9.4 to about 9.8 degrees, a peak in the range of from about 16.1 to about 16.5 degrees, and a peak in the range of from about 22.1 to about 22.5 degrees.

In some embodiments, Form C can be characterized by one or more peaks in an X-ray powder diffraction pattern, wherein the one or more peaks is selected from a peak at about 5.0 degrees, a peak at about 6.6 degrees, a peak at about 8.2 degrees, a peak at about 9.2 degrees, a peak at about 9.6 degrees, a peak at about 16.3 degrees, and a peak at about 22.3 degrees.

In some embodiments, Form C can be characterized by a peak at about 5.0 degrees, a peak at about 6.6 degrees, a peak at about 8.2 degrees, and a peak at about 22.3 degrees in an X-ray powder diffraction pattern.

In some embodiments, Form C can be characterized by a peak at about 5.0 degrees, a peak at about 6.6 degrees, a peak at about 8.2 degrees, a peak at about 9.2 degrees, a peak at about 9.6 degrees, a peak at about 16.3 degrees, and a peak at about 22.3 degrees in an X-ray powder diffraction pattern.

Figure 6:
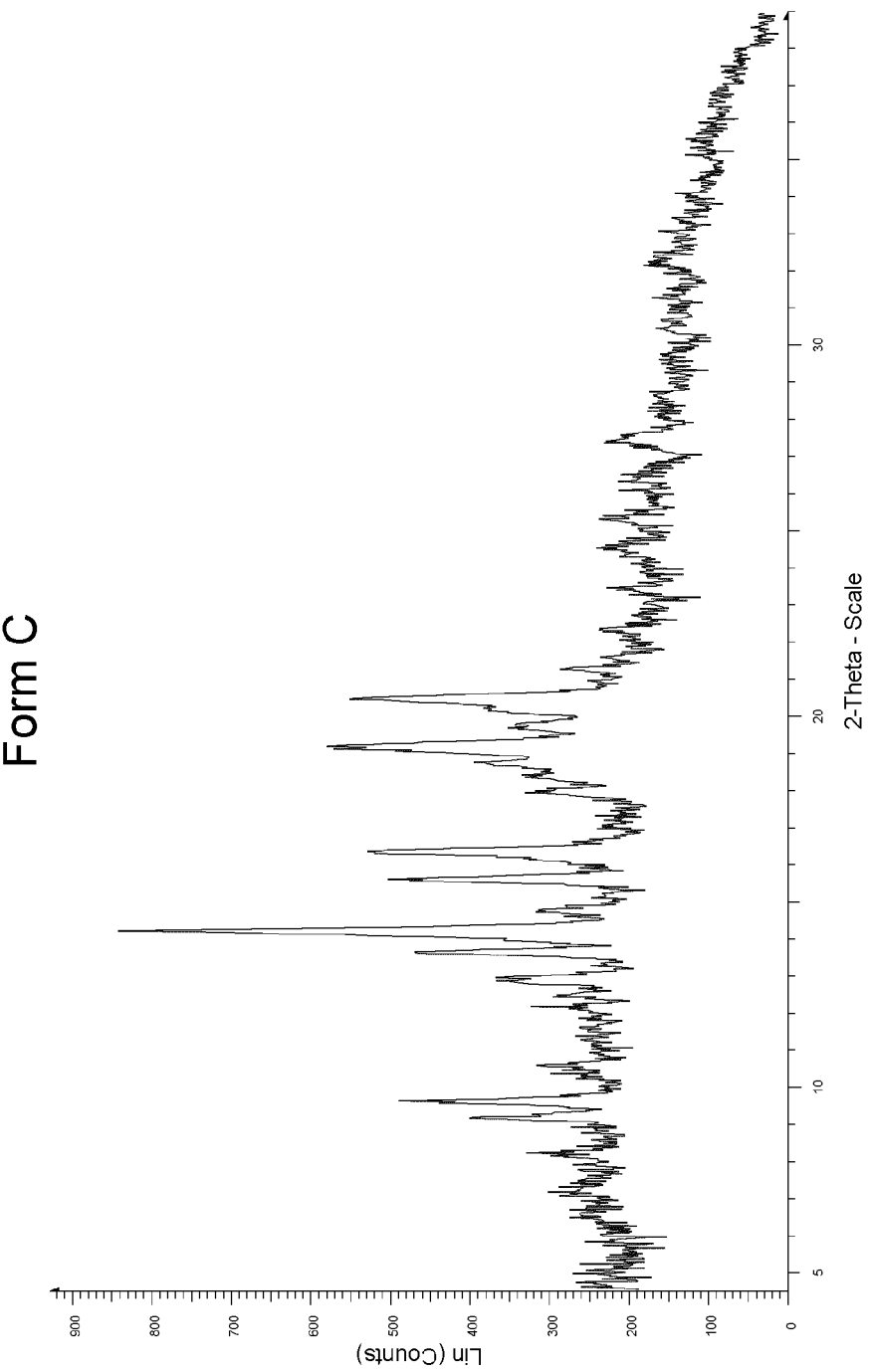
FIG. 6 is an XRPD spectrum of Form C.

In some embodiments, Form C can be characterized by an X-ray powder diffraction pattern of FIG. 6.

In some embodiments, Form C can be characterized by one or more peaks in an X-ray powder diffraction pattern selected from the table below.

| No. | 2-Theta ° | Intensity % |
|---|---|---|
| 1 | 4.980* | 27.4 |
| 2 | 6.573* | 31.0 |
| 3 | 8.174* | 39.0 |
| 4 | 9.151** | 47.4 |
| 5 | 9.585** | 56.2 |
| 6 | 16.337** | 62.7 |
| 7 | 22.340* | 28.1 |

Peaks with an asterisk (*) are major peaks
Peaks with a double asterisk (**) are secondary peaks In some embodiments, Form C can be characterized by one or more peaks in a $^{13}$C NMR solid state spectrum, wherein the one or more peaks is selected from a peak at about 173.7 ppm, a peak at about 151.9 ppm, a peak at about 103.2 ppm, a peak at about 83.3 ppm, a peak at about 80.8 ppm, a peak at about 73.3 ppm, a peak at about 25.1 ppm, and a peak at about 20.1 ppm.

In some embodiments, Form C can be characterized by one or more peaks in a $^{13}$C NMR solid state spectrum, wherein the one or more peaks is selected from a peak at about 173.7 ppm, a peak at about 151.9 ppm, a peak at about 103.2 ppm, a peak at about 83.3 ppm, a peak at about 80.8 ppm, a peak at about 73.3 ppm, a peak at about 63.8 ppm, a peak at about 25.1 ppm, and a peak at about 20.1 ppm.

In some embodiments, Form C can be characterized by a peak at about 173.7 ppm, a peak at about 83.3 ppm, a peak at about 80.8 ppm, and a peak at about 25.1 ppm in a $^{13}$C NMR solid state spectrum.

In some embodiments, Form C can be characterized by a peak at about 173.7 ppm, a peak at about 151.9 ppm, a peak at about 103.2 ppm, a peak at about 83.3 ppm, a peak at about 80.8 ppm, a peak at about 73.3 ppm, a peak at about 25.1 ppm, and a peak at about 20.1 ppm in a $^{13}$C NMR solid state spectrum.

Figure 7:
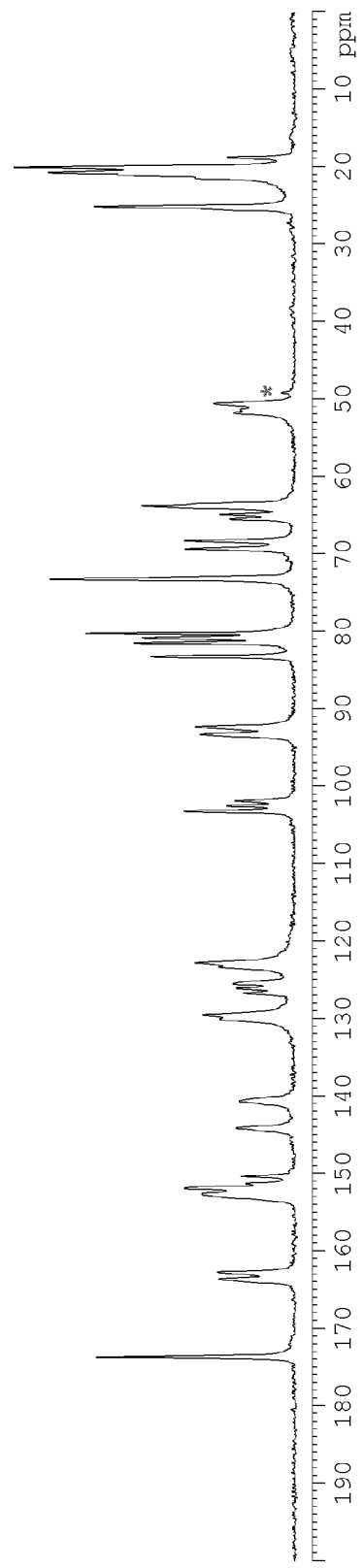
FIG. 7 is a $^{13}$C ssNMR spectrum of Form C.

In some embodiments, Form C can be characterized by a $^{13}$C NMR solid state spectrum of FIG. 7.

In some embodiments, Form C can be characterized by one or more peaks in a $^{13}$C NMR solid state spectrum selected from the table below.

| Peak | ν(F1) [ppm] | Intensity [rel] |
|---|---|---|
| 1 | 173.7* | 72.2 |
| 2 | 163.6 | 27.15 |
| 3 | 162.7 | 27.66 |
| 4 | 152.6 | 33.02 |
| 5 | 151.9* | 39.39 |
| 6 | 151.3 | 17.72 |
| 7 | 150.4 | 19.06 |
| 8 | 144.1 | 20.92 |
| 9 | 140.7 | 19.90 |
| 10 | 129.6 | 32.86 |
| 11 | 126.7 | 18.14 |
| 12 | 126.1 | 20.87 |
| 13 | 125.5 | 22.15 |
| 14 | 123.3 | 27.16 |
| 15 | 122.8 | 35.54 |
| 16 | 103.2* | 40.00 |
| 17 | 102.5 | 24.12 |
| 18 | 101.9 | 21.60 |
| 19 | 93.3 | 34.02 |
| 20 | 92.4 | 35.66 |
| 21 | 83.3* | 51.71 |
| 22 | 81.5 | 57.50 |
| 23 | 80.8* | 54.60 |
| 24 | 80.3 | 75.92 |
| 25 | 73.3* | 88.51 |
| 26 | 69.4 | 39.18 |
| 27 | 68.3 | 39.61 |
| 28 | 65.5 | 23.22 |
| 29 | 64.9 | 26.70 |
| 30 | 63.8* | 54.98 |
| 31 | 51.8 | 21.78 |
| 32 | 50.6 | 28.73 |
| 33 | 25.1* | 71.94 |
| 34 | 20.8 | 88.14 |
| 35 | 20.1* | 100.00 |
| 36 | 18.8 | 24.24 |

Peaks with an asterisk (*) are major peaks

Form D

In some embodiments, Compound 1 can be 2'-C-methyluridine-5'-(O-phenyl-N—(S)-1-(isopropoxycarbonyl) ethyl)thiophosphoramidate characterized as Form D.

In some embodiments, Form D can be characterized by one or more peaks in an X-ray powder diffraction pattern, wherein the one or more peaks is selected from a peak in the range of from about 7.9 to about 8.3 degrees, a peak in the range of from about 13.2 to about 13.6 degrees, a peak in the range of from about 14.2 to about 14.6 degrees, a peak in the range of from about 17.0 to about 17.4 degrees, a peak in the range of from about 29.4 to about 29.8 degrees, and a peak in the range of from about 34.8 to about 35.2 degrees.

In some embodiments, Form D can be characterized by one or more peaks in an X-ray powder diffraction pattern, wherein the one or more peaks is selected from a peak at about 8.1 degrees, a peak at about 13.4 degrees, a peak at about 14.4 degrees, a peak at about 17.2 degrees, a peak at about 29.6 degrees, and a peak at about 35.0 degrees.

In some embodiments, Form D can be characterized by a peak at about 8.1 degrees, a peak at about 13.4 degrees, a peak at about 29.6 degrees, and a peak at about 35.0 degrees in an X-ray powder diffraction pattern.

In some embodiments, Form D can be characterized by a peak at about 8.1 degrees, a peak at about 13.4 degrees, a peak at about 14.4 degrees, a peak at about 17.2 degrees, a peak at about 29.6 degrees, and a peak at about 35.0 degrees in an X-ray powder diffraction pattern.

Figure 8:
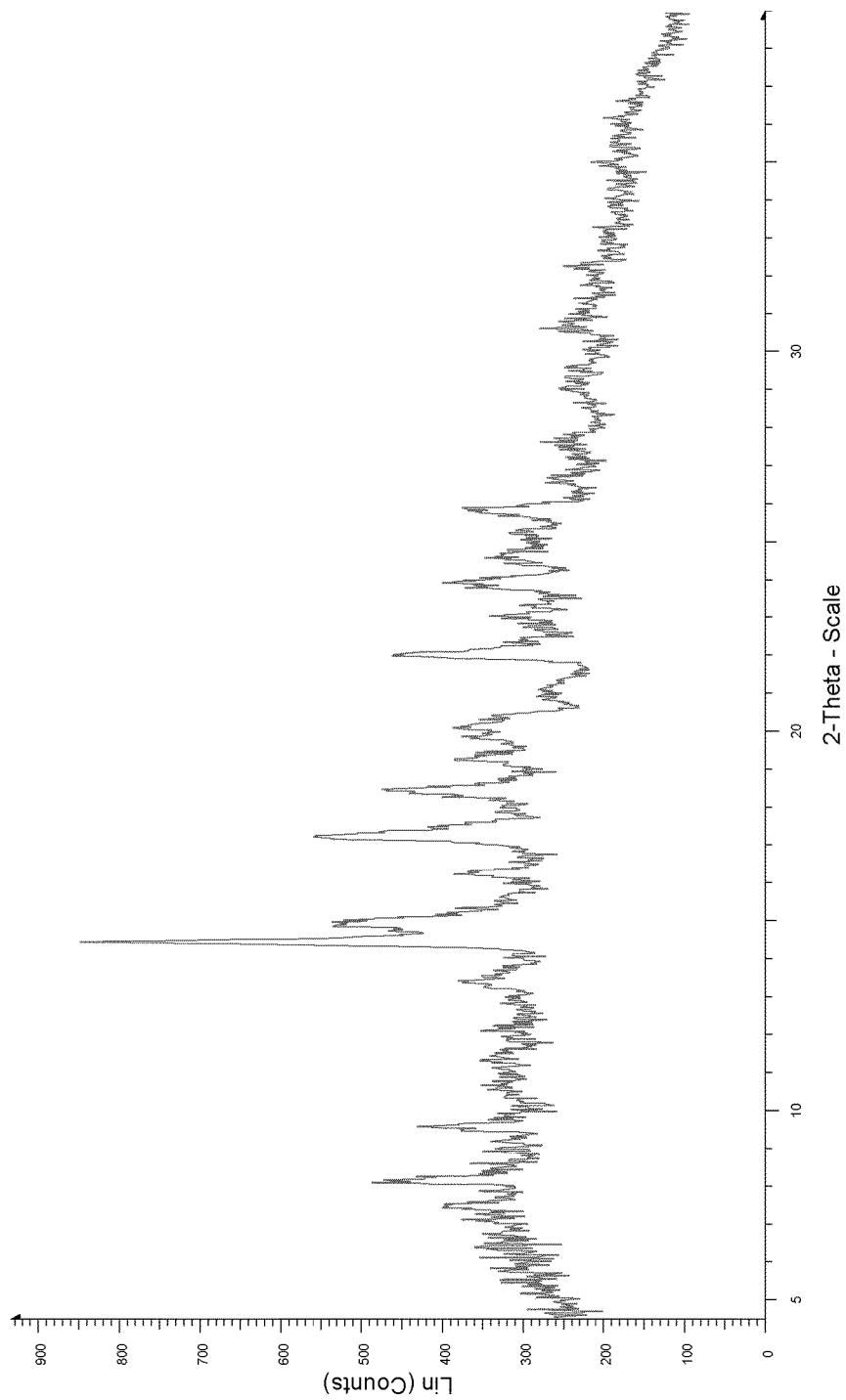
FIG. 8 is an XRPD spectrum of Form D.

In some embodiments, Form D can be characterized by an X-ray powder diffraction pattern of FIG. 8.

In some embodiments, Form D can be characterized by one or more peaks in an X-ray powder diffraction pattern selected from the table below.

| No. | 2-Theta ° | Intensity % |
|---|---|---|
| 1 | 8.105* | 55.6 |
| 2 | 13.357* | 44.1 |
| 3 | 14.424** | 100.0 |
| 4 | 17.215** | 66.0 |
| 5 | 29.590* | 29.1 |
| 6 | 35.019* | 25.3 |

Peaks with an asterisk (*) are major peaks
Peaks with a double asterisk (**) are secondary peaks In some embodiments, Form D can be characterized by one or more peaks in a $^{13}$C NMR solid state spectrum, wherein the one or more peaks is selected from a peak at about 139.1 ppm, a peak at about 125.3 ppm, a peak at about 120.8 ppm, a peak at about 105.2 ppm, a peak at about 72.8 ppm, a peak at about 67.5 ppm, and a peak at about 63.0 ppm.

In some embodiments, Form D can be characterized by a peak at about 125.3 ppm, a peak at about 105.2 ppm, a peak at about 72.8 ppm, and a peak at about 67.5 ppm in a $^{13}$C NMR solid state spectrum.

In some embodiments, Form D can be characterized by a peak at about 139.1 ppm, a peak at about 125.3 ppm, a peak at about 120.8 ppm, a peak at about 105.2 ppm, a peak at about 72.8 ppm, a peak at about 67.5 ppm, and a peak at about 63.0 ppm in a $^{13}$C NMR solid state spectrum.

Figure 9:
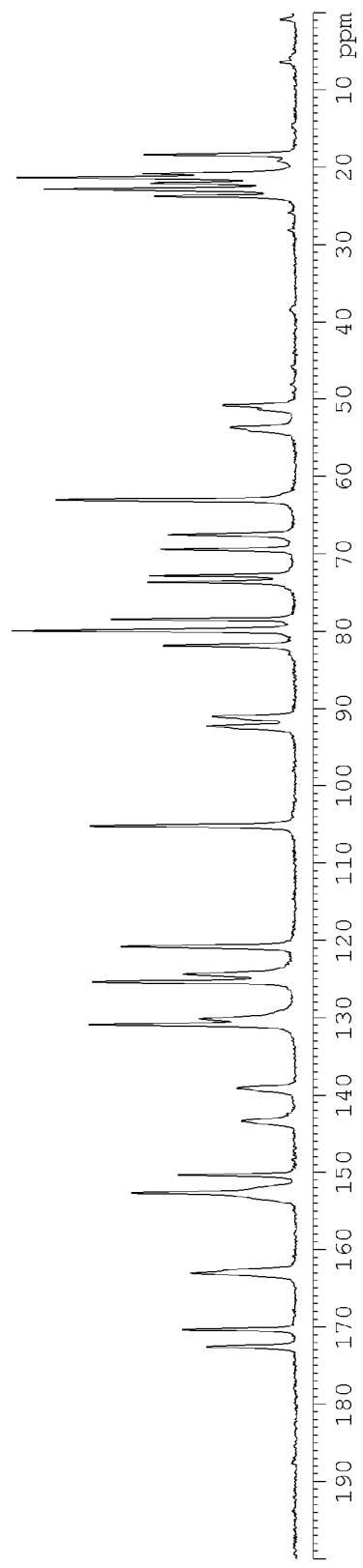
FIG. 9 is a $^{13}$C ssNMR spectrum of Form D.
Figure 10:
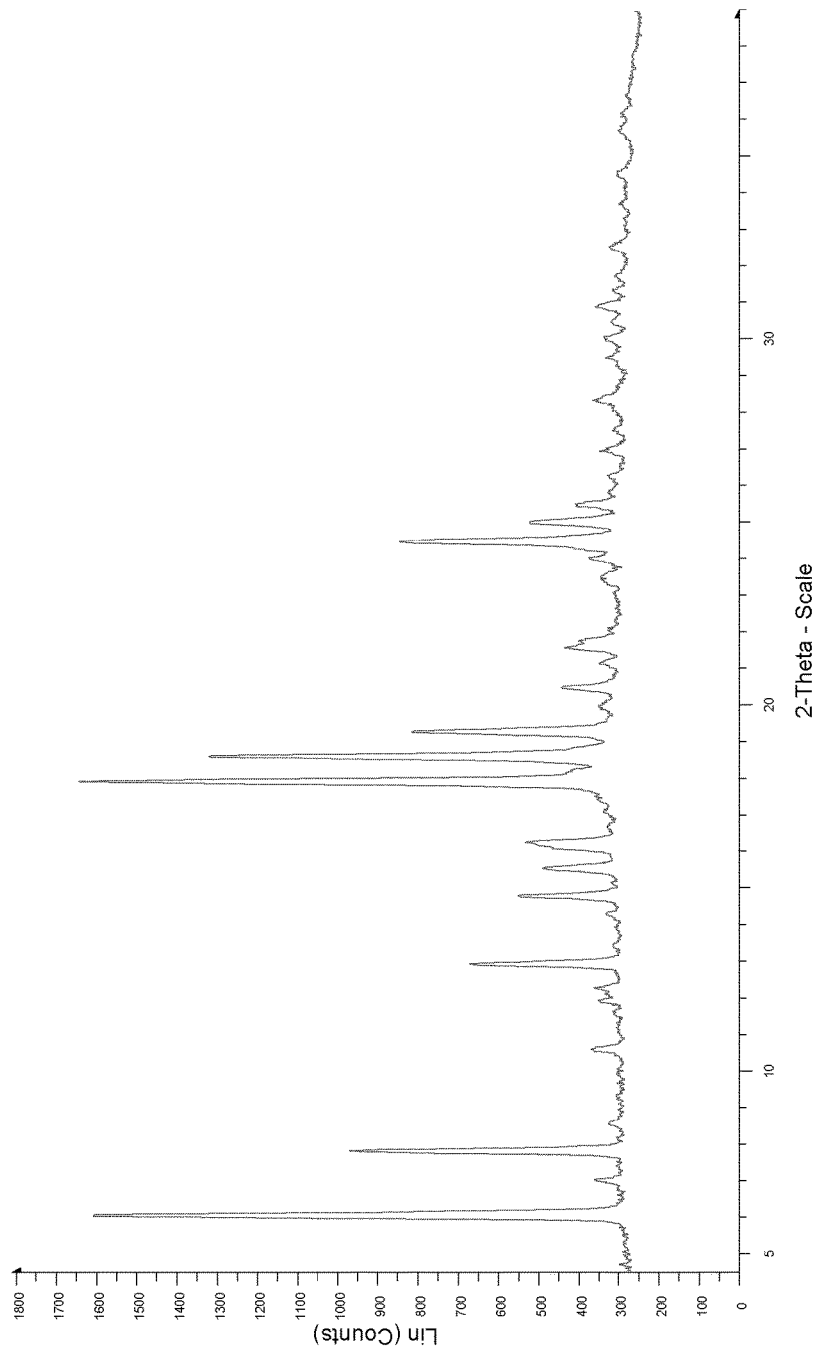
FIG. 10 is an XRPD spectrum of a mixture of Form A and Form E.
Figure 11:
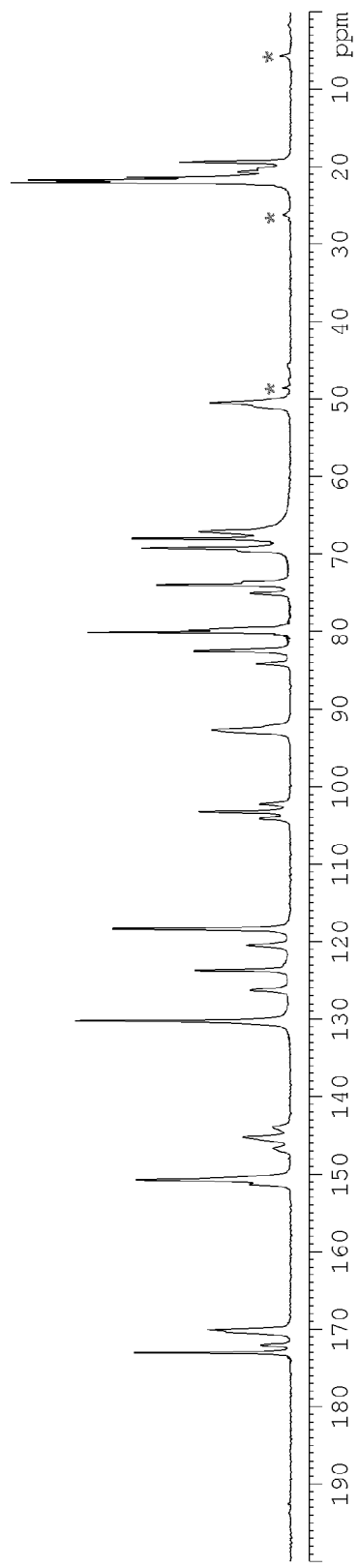
FIG. 11 is a $^{13}$C ssNMR spectrum of a mixture of Form A and Form E.
Figure 12:
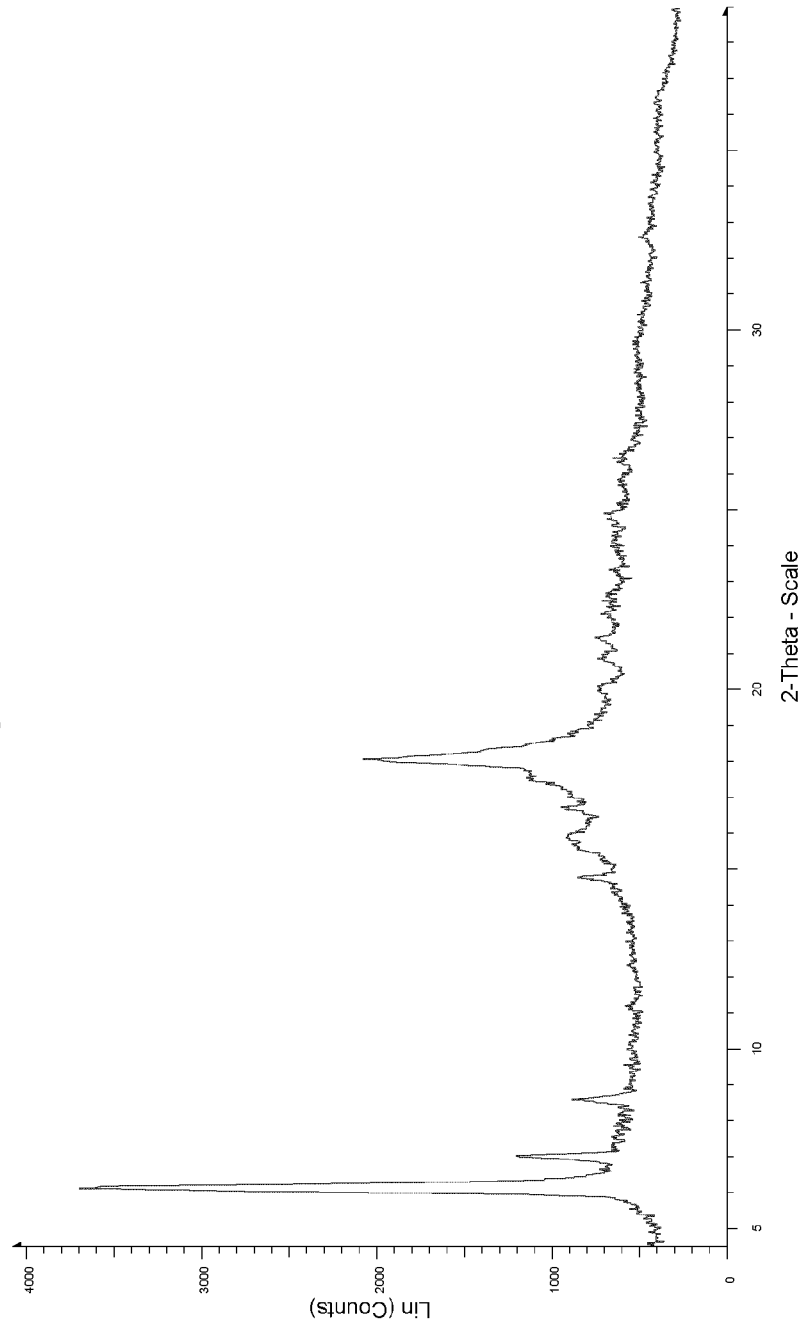
FIG. 12 is an XRPD spectrum of a mixture of Form A and Form F.
Figure 13:
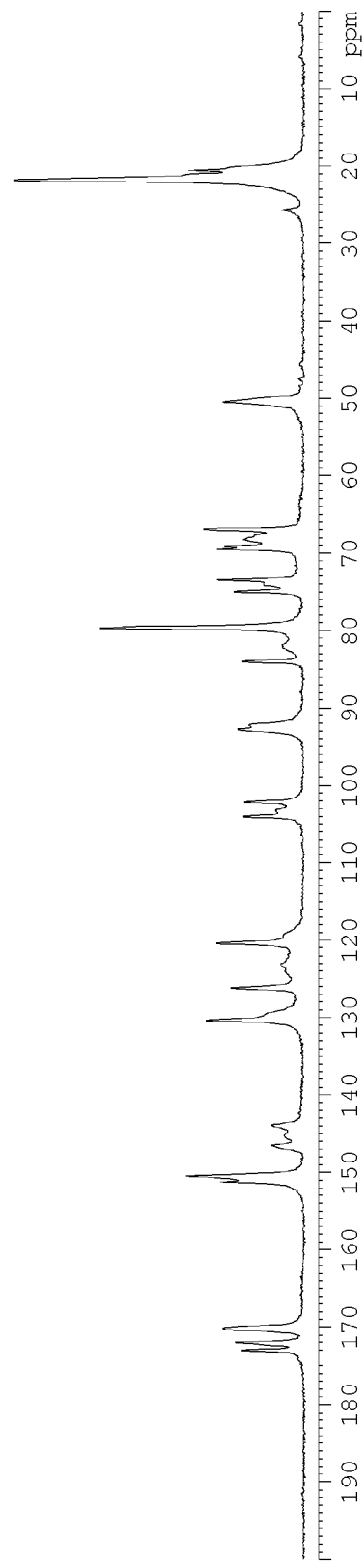
FIG. 13 is a $^{13}$C ssNMR spectrum of a mixture of Form A and Form F.

In some embodiments, Form D can be characterized by a $^{13}$C NMR solid state spectrum of FIG. 9.

In some embodiments, Form D can be characterized by one or more peaks in a $^{13}$C NMR solid state spectrum selected from the table below.

| Peak # | v(F1) [ppm] | Intensity [rel] |
|---|---|---|
| 1 | 172.5 | 31.47 |
| 2 | 170.3 | 39.91 |
| 3 | 163.0 | 36.97 |
| 4 | 152.7 | 57.96 |
| 5 | 150.4 | 41.72 |
| 6 | 143.3 | 19.06 |
| 7 | 139.1* | 20.55 |
| 8 | 130.9 | 74.16 |
| 9 | 130.2 | 33.92 |
| 10 | 125.3* | 71.51 |
| 11 | 124.4 | 39.60 |
| 12 | 120.8* | 61.60 |
| 13 | 105.2* | 73.13 |
| 14 | 92.3 | 31.47 |
| 15 | 91.0 | 29.46 |
| 16 | 81.8 | 47.28 |
| 17 | 79.9 | 100.00 |
| 18 | 78.5 | 65.96 |
| 19 | 73.6 | 52.41 |
| 20 | 72.8* | 51.48 |
| 21 | 69.4 | 48.17 |
| 22 | 67.5* | 45.52 |
| 23 | 63.0* | 84.89 |
| 24 | 53.6 | 23.06 |
| 25 | 50.8 | 25.81 |
| 26 | 23.7 | 50.37 |
| 27 | 22.8 | 89.54 |
| 28 | 22.0 | 51.17 |
| 29 | 21.3 | 98.72 |
| 30 | 20.8 | 54.41 |
| 31 | 18.3 | 54.61 |

Peaks with an asterisk (*) are major peaks

Form E

In some embodiments, Compound 1 can be 2'-C-methyluridine-5'-(O-phenyl-N—(S)-1-(isopropoxycarbonyl)ethyl)thiophosphoramidate characterized as Form E.

In some embodiments, Form E can be characterized by one or more peaks in an X-ray powder diffraction pattern, wherein the one or more peaks is selected from a peak in the range of from about 7.6 to about 8.0 degrees, a peak in the range of from about 10.4 to about 10.8 degrees, a peak in the range of from about 12.7 to about 13.1 degrees, a peak in the range of from about 21.4 to about 21.8 degrees, a peak in the range of from about 24.3 to about 24.7 degrees, and a peak in the range of from about 24.8 to about 25.2 degrees.

In some embodiments, Compound 1 can be 2'-C-methyluridine-5'-(O-phenyl-N—(S)-1-(isopropoxycarbonyl)ethyl)thiophosphoramidate characterized as Form E.

In some embodiments, Form E can be characterized by one or more peaks in an X-ray powder diffraction pattern, wherein the one or more peaks is selected from a peak in the range of from about 7.6 to about 8.0 degrees, a peak in the range of from about 12.7 to about 13.1 degrees, a peak in the range of from about 21.4 to about 21.8 degrees, and a peak in the range of from about 24.8 to about 25.2 degrees.

In some embodiments, Form E can be characterized by one or more peaks in an X-ray powder diffraction pattern, wherein the one or more peaks is selected from a peak at about 7.8 degrees, a peak at about 10.6 degrees, a peak at about 12.9 degrees, a peak at about 21.6 degrees, a peak at about 24.5 degrees, and a peak at about 25.0 degrees.

In some embodiments, Form E can be characterized by a peak at about 7.8 degrees, a peak at about 10.6 degrees, a peak at about 12.9 degrees, a peak at about 21.6 degrees, a peak at about 24.5 degrees, and a peak at about 25.0 degrees in an X-ray powder diffraction pattern.

In some embodiments, Form E can be characterized by one or more peaks in an X-ray powder diffraction pattern, wherein the one or more peaks is selected from a peak from about 7.6 to about 8.0 degrees, a peak from about 10.4 to about 10.8 degrees, a peak from about 12.7 to about 13.1 degrees, a peak from about 24.3 to about 24.7 degrees, and a peak from about 24.8 to about 25.2 degrees.

In some embodiments, Form E can be characterized by one or more peaks in an X-ray powder diffraction pattern, wherein the one or more peaks is selected from a peak at about 7.8 degrees, a peak at about 10.6 degrees, a peak at about 12.9 degrees, a peak at about 24.5 degrees, and a peak at about 25.0 degrees.

In some embodiments, Form E can be characterized by a peak at about 7.8 degrees, a peak at about 12.9 degrees, and a peak at about 25.0 degrees in an X-ray powder diffraction pattern.

In some embodiments, Form E can be characterized by a peak at about 7.8 degrees, a peak at about 12.9 degrees, a peak at about 21.6 degrees and a peak at about 25.0 degrees in an X-ray powder diffraction pattern.

In some embodiments, Form E can be characterized by a peak at about 7.8 degrees, a peak at about 10.6 degrees, a peak at about 12.9 degrees, a peak at about 24.5 degrees, and a peak at about 25.0 degrees in an X-ray powder diffraction pattern.

In some embodiments, Form E can be characterized by one or more peaks in an X-ray powder diffraction pattern selected from the table below.

| No. | 2-Theta ° | Intensity % |
|---|---|---|
| 1 | 7.765* | 58.9 |
| 2 | 10.563** | 22.3 |
| 3 | 12.901* | 40.7 |
| 4 | 21.571* | 26.4 |
| 5 | 24.466** | 51.4 |
| 6 | 25.016* | 31.6 |

Peaks with an asterisk (*) are major peaks
Peaks with a double asterisk (**) are secondary peaks In some embodiments, Form E can be characterized by one or more peaks in a $^{13}$C NMR solid state spectrum, wherein the one or more peaks is selected from a peak at about 173.0 ppm, a peak at about 150.7 ppm, a peak at about 130.2 ppm, a peak at about 118.3 ppm, a peak at about 73.9 ppm, a peak at about 67.0 ppm, and a peak at about 22.0 ppm.

In some embodiments, Form E can be characterized by one or more peaks in a $^{13}$C NMR solid state spectrum, wherein the one or more peaks is selected from a peak at about 173.0 ppm, a peak at about 150.7 ppm, a peak at about 130.2 ppm, a peak at about 118.3 ppm, a peak at about 73.9 ppm, a peak at about 68.0 ppm, a peak at about 67.0 ppm, and a peak at about 22.0 ppm.

In some embodiments, Form E can be characterized by a peak at about 130.2 ppm, a peak at about 118.3 ppm, a peak at about 73.9 ppm, and a peak at about 67.0 ppm in a $^{13}$C NMR solid state spectrum.

In some embodiments, Form E can be characterized by a peak at about 173.0 ppm, a peak at about 150.7 ppm, a peak at about 130.2 ppm, a peak at about 118.3 ppm, a peak at about 73.9 ppm, a peak at about 67.0 ppm, and a peak at about 22.0 ppm in a $^{13}$C NMR solid state spectrum.

In some embodiments, Form E can be characterized by one or more peaks in a $^{13}$C NMR solid state spectrum, wherein the one or more peaks is selected from a peak at about 173.0 ppm, a peak at about 150.7 ppm, a peak at about 118.3 ppm, or a peak at about 73.9 ppm. In some embodiments, Form E can be characterized by a peak at about 118.3 ppm, and a peak at about 73.9 ppm in a $^{13}$C NMR solid state spectrum. In some embodiments, Form E can be characterized by a peak at about 173.0 ppm, a peak at about 150.7 ppm, a peak at about 118.3 ppm, and a peak at about 73.9 ppm in a $^{13}$C NMR solid state spectrum.

In some embodiments, Form E can be characterized by one or more peaks in a $^{13}$C NMR solid state spectrum selected from the table below.

| Peak # | v(F1) [ppm] | Intensity [rel] |
|---|---|---|
| 1 | 173.0* | 56.27 |
| 2 | 172.1 | 10.64 |
| 3 | 170.1 | 29.76 |
| 4 | 151.3 | 14.75 |
| 5 | 150.7* | 55.30 |
| 6 | 146.7 | 6.43 |
| 7 | 145.2 | 17.07 |
| 8 | 144.0 | 6.43 |
| 9 | 130.2* | 78.40 |
| 10 | 126.2 | 14.42 |
| 11 | 123.7 | 34.51 |
| 12 | 120.5 | 15.84 |
| 13 | 118.3* | 65.27 |
| 14 | 104.1 | 11.22 |
| 15 | 103.2 | 33.55 |
| 16 | 102.2 | 11.20 |
| 17 | 92.7 | 28.19 |
| 18 | 84.1 | 12.31 |
| 19 | 82.4 | 35.17 |
| 20 | 80.1 | 73.44 |
| 21 | 79.8 | 36.49 |
| 22 | 75.0 | 14.45 |
| 23 | 73.9* | 48.37 |
| 24 | 69.2 | 53.62 |
| 25 | 68.0* | 59.07 |
| 26 | 67.0* | 32.83 |
| 27 | 50.4 | 28.84 |
| 28 | 22.0* | 100.00 |
| 29 | 21.7 | 93.59 |
| 30 | 21.4 | 58.58 |
| 31 | 20.6 | 18.91 |
| 32 | 19.4 | 40.73 |

Peaks with an asterisk (*) are major peaks

Form F

In some embodiments, Compound 1 can be 2'-C-methyluridine-5'-(O-phenyl-N—(S)-1-(isopropoxycarbonyl)ethyl)thiophosphoramidate characterized as Form F.

In some embodiments, Form F can be characterized by one or more peaks in an X-ray powder diffraction pattern, wherein the one or more peaks is selected from a peak in the range of from about 5.8 to about 6.2 degrees, a peak in the range of from about 6.8 to about 7.2 degrees, a peak in the range of from about 17.3 to about 17.7 degrees, and a peak in the range of from about 17.8 to about 18.2 degrees.

In some embodiments, Form F can be characterized by one or more peaks in an X-ray powder diffraction pattern, wherein the one or more peaks is selected from a peak at about 6.0 degrees, a peak at about 7.0 degrees, a peak at about 17.5 degrees, and a peak at about 18.0 degrees.

In some embodiments, Form F can be characterized by a peak at about 7.8 degrees, a peak at about 12.9 degrees, a peak at about 21.6 degrees, and a peak at about 25.0 degrees in an X-ray powder diffraction pattern.

In some embodiments, Form F can be characterized by a peak at about 6.0 degrees, a peak at about 7.0 degrees, a peak at about 17.5 degrees, and a peak at about 18.0 degrees in an X-ray powder diffraction pattern.

In some embodiments, Form F can be characterized by one or more peaks in an X-ray powder diffraction pattern selected from the table below.

| No. | 2-Theta ° | Intensity % |
|---|---|---|
| 1 | 6.090* | 100.0 |
| 2 | 6.970* | 32.4 |
| 3 | 17.538* | 30.7 |
| 4 | 18.048* | 56.0 |

Peaks with an asterisk (*) are major peaks

In some embodiments, Form F can be characterized by one or more peaks in a $^{13}C$ NMR solid state spectrum, wherein the one or more peaks is selected from a peak at about 170.2 ppm, a peak at about 150.5 ppm, a peak at about 130.4 ppm, a peak at about 79.7 ppm, a peak at about 73.5 ppm, a peak at about 66.9 ppm, a peak at about 21.8 ppm, and a peak at about 20.6 ppm.

In some embodiments, Form F can be characterized by one or more peaks in a $^{13}C$ NMR solid state spectrum, wherein the one or more peaks is selected from a peak at about 170.2 ppm, a peak at about 150.5 ppm, a peak at about 130.4 ppm, a peak at about 79.7 ppm, a peak at about 73.5 ppm, a peak at about 68.2 ppm, a peak at about 66.9 ppm, a peak at about 25.7 ppm, a peak at about 21.8 ppm, and a peak at about 20.6 ppm.

In some embodiments, Form F can be characterized by a peak at about 130.4 ppm, a peak at about 73.5 ppm, a peak at about 66.9 ppm, and a peak at about 20.6 ppm in a $^{13}C$ NMR solid state spectrum. In still a further embodiment, Form F can be characterized by a peak at about 6.1 degrees in an X-ray powder diffraction pattern.

In some embodiments, Form F can be characterized by a peak at about 170.2 ppm, a peak at about 150.5 ppm, a peak at about 130.4 ppm, a peak at about 79.7 ppm, a peak at about 73.5 ppm, a peak at about 66.9 ppm, a peak at about 21.8 ppm, and a peak at about 20.6 ppm in a $^{13}C$ NMR solid state spectrum.

In some embodiments, Form F can be characterized by one or more peaks in a $^{13}C$ NMR solid state spectrum, wherein the one or more peaks is selected from a peak at about 170.2 ppm, a peak at about 150.5 ppm, a peak at about 79.7 ppm, a peak at about 73.5 ppm, or a peak at about 21.8 ppm. In some embodiments, Form F can be characterized by a peak at about 73.5 ppm in a $^{13}C$ NMR solid state spectrum. In some embodiments, Form F can be characterized by a peak at about 170.2 ppm, a peak at about 150.5 ppm, a peak at about 79.7 ppm, a peak at about 73.5 ppm, and a peak at about 21.8 ppm in a $^{13}C$ NMR solid state spectrum.

In some embodiments, Form F can be characterized by one or more peaks in a $^{13}C$ NMR solid state spectrum selected from the table below.

| Peak # | ν(F1) [ppm] | Intensity [rel] |
|---|---|---|
| 1 | 173.0 | 21.53 |
| 2 | 172.0 | 24.07 |
| 3 | 170.2* | 27.88 |
| 4 | 151.3 | 28.85 |
| 5 | 150.5* | 40.71 |
| 6 | 146.6 | 11.13 |
| 7 | 145.2 | 6.82 |
| 8 | 143.9 | 11.03 |
| 9 | 130.4* | 33.74 |
| 10 | 126.2 | 25.38 |
| 11 | 123.1 | 8.05 |
| 12 | 120.4 | 29.96 |
| 13 | 104.0 | 20.89 |
| 14 | 103.2 | 9.89 |
| 15 | 102.2 | 20.47 |
| 16 | 92.8 | 22.77 |
| 17 | 92.2 | 18.97 |
| 18 | 84.0 | 21.12 |
| 19 | 81.9 | 7.45 |
| 20 | 79.7* | 71.06 |
| 21 | 75.0 | 24.15 |
| 22 | 73.5* | 30.33 |
| 23 | 69.5 | 29.78 |
| 24 | 69.2 | 27.71 |
| 25 | 68.2* | 20.78 |
| 26 | 66.9* | 34.82 |
| 27 | 50.4 | 28.03 |
| 28 | 25.7* | 7.70 |
| 29 | 21.8* | 100.00 |
| 30 | 20.6* | 39.64 |

Peaks with an asterisk (*) are major peaks

Form G

In some embodiments, Compound 1 can be 2'-C-methyluridine-5'-(O-phenyl-N—(S)-1-(isopropoxycarbonyl)ethyl)thiophosphoramidate characterized as Form G.

In some embodiments, Form G can be characterized by one or more peaks in an X-ray powder diffraction pattern, wherein the one or more peaks is selected from a peak in the range of from about 5.7 to about 6.1 degrees, a peak in the range of from about 7.3 to about 7.7 degrees, a peak in the range of from about 7.6 to about 8.0 degrees, a peak in the range of from about 12.3 to about 12.7 degrees, a peak in the range of from about 17.5 to about 17.9 degrees, and a peak in the range of from about 18.0 to about 18.4 degrees.

In some embodiments, Form G can be characterized by one or more peaks in an X-ray powder diffraction pattern, wherein the one or more peaks is selected from a peak in the range of from about 5.7 to about 6.1 degrees, a peak in the range of from about 7.3 to about 7.7 degrees, a peak in the range of from about 7.6 to about 8.0 degrees and a peak in the range of from about 17.5 to about 17.9 degrees.

In some embodiments, Form G can be characterized by one or more peaks in an X-ray powder diffraction pattern, wherein the one or more peaks is selected from a peak at about 5.9 degrees, a peak at about 7.5 degrees, a peak at about 7.8 degrees, a peak at about 12.5 degrees, a peak at about 17.7 degrees, and a peak at about 18.2 degrees.

In some embodiments, Form G can be characterized by a peak at about 5.9 degrees, a peak at about 7.5 degrees, a peak at about 7.8 degrees, and a peak at about 17.7 degrees in an X-ray powder diffraction pattern.

In some embodiments, Form G can be characterized by a peak at about 5.9 degrees, a peak at about 7.5 degrees, a peak at about 7.8 degrees, a peak at about 12.5 degrees, a peak at about 17.7 degrees, and a peak at about 18.2 degrees in an X-ray powder diffraction pattern.

Figure 14:
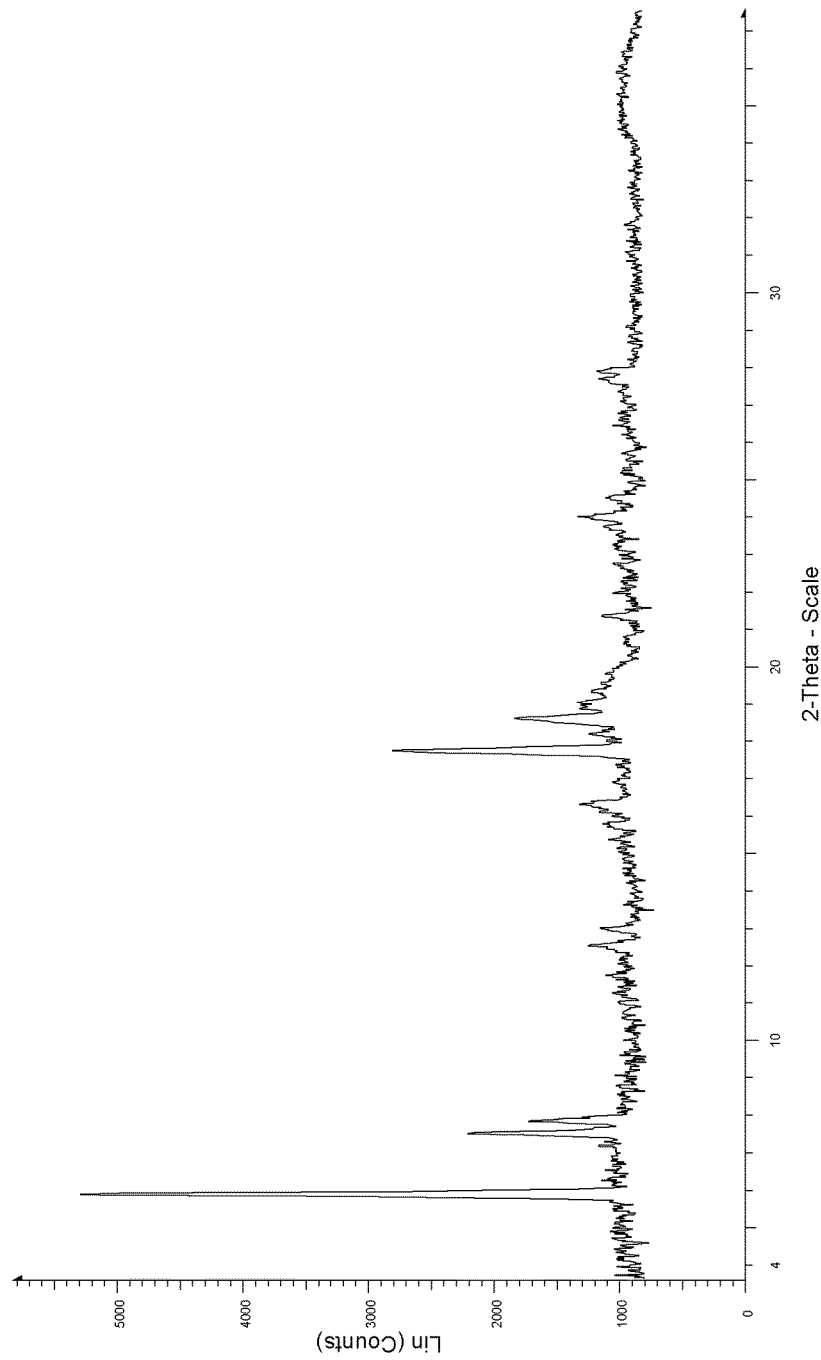
FIG. 14 is an XRPD spectrum of Form G.

In some embodiments, Form G can be characterized by an X-ray powder diffraction pattern of FIG. 14.

In some embodiments, Form G can be characterized by one or more peaks in an X-ray powder diffraction pattern selected from the table below.

| No. | 2-Theta ° | Intensity % |
|---|---|---|
| 1 | 5.857* | 100.0 |
| 2 | 7.498* | 41.6 |
| 3 | 7.835* | 32.1 |
| 4 | 12.522** | 23.5 |

| No. | 2-Theta ° | Intensity % |
|---|---|---|
| 5 | 17.733* | 53.0 |
| 6 | 18.193** | 23.5 |

Peaks with an asterisk (*) are major peaks
Peaks with a double asterisk (**) are secondary peaks In some embodiments, Form G can be characterized by one or more peaks in a $^{13}$C NMR solid state spectrum, wherein the one or more peaks is selected from a peak at about 172.9 ppm, a peak at about 150.8 ppm, a peak at about 130.4 ppm, a peak at about 119.6 ppm, a peak at about 118.7 ppm, a peak at about 83.1 ppm, a peak at about 69.0 ppm, and a peak at about 20.4 ppm.

In some embodiments, Form G can be characterized by one or more peaks in a $^{13}$C NMR solid state spectrum, wherein the one or more peaks is selected from a peak at about 172.9 ppm, a peak at about 150.8 ppm, a peak at about 130.4 ppm, a peak at about 119.6 ppm, a peak at about 118.7 ppm, a peak at about 83.1 ppm, a peak at about 69.0 ppm, a peak at about 54.2 ppm, and a peak at about 20.4 ppm.

In some embodiments, Form G can be characterized by a peak at about 119.6 ppm, a peak at about 118.7 ppm, a peak at about 83.1 ppm, and a peak at about 69.0 ppm in a $^{13}$C NMR solid state spectrum.

In some embodiments, Form G can be characterized by a peak at about 172.9 ppm, a peak at about 150.8 ppm, a peak at about 130.4 ppm, a peak at about 119.6 ppm, a peak at about 118.7 ppm, a peak at about 83.1 ppm, a peak at about 69.0 ppm, and a peak at about 20.4 ppm in a $^{13}$C NMR solid state spectrum.

Figure 15:
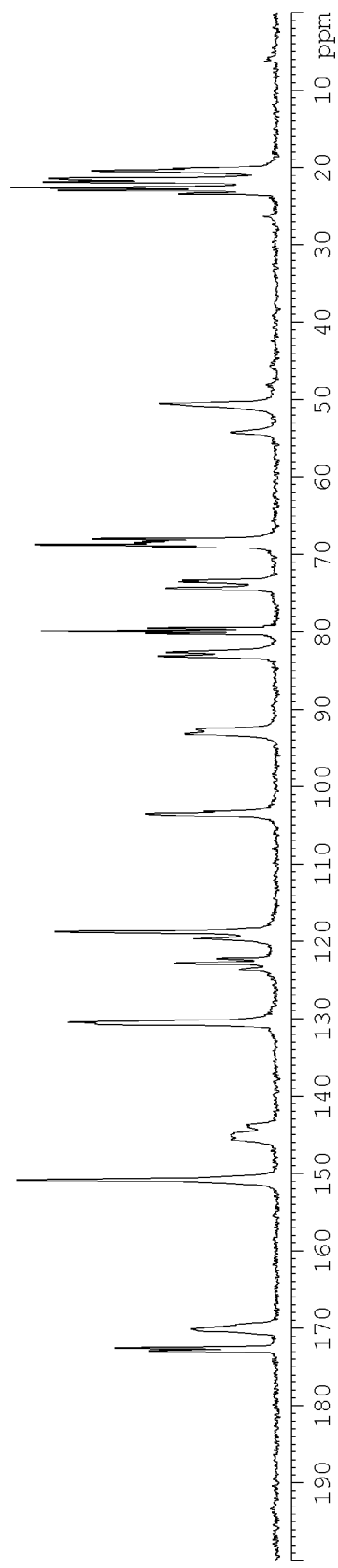
FIG. 15 is a $^{13}$C ssNMR spectrum of Form G.

In some embodiments, Form G can be characterized by a $^{13}$C NMR solid state spectrum of FIG. 15.

In some embodiments, Form G can be characterized by one or more peaks in a $^{13}$C NMR solid state spectrum selected from the table below.

| Peak | v(F1) [ppm] | Intensity [rel] |
|---|---|---|
| 1 | 172.9* | 47.8 |
| 2 | 172.5 | 60.77 |
| 3 | 170.1 | 31.87 |
| 4 | 150.8* | 97.73 |
| 5 | 145.6 | 17.22 |
| 6 | 143.7 | 10.94 |
| 7 | 130.4* | 78.80 |
| 8 | 123.6 | 13.92 |
| 9 | 122.8 | 39.28 |
| 10 | 122.2 | 22.62 |
| 11 | 119.6* | 30.97 |
| 12 | 118.7* | 83.25 |
| 13 | 103.6 | 49.34 |
| 14 | 103.2 | 27.56 |
| 15 | 93.1 | 34.63 |
| 16 | 92.6 | 30.12 |
| 17 | 83.1* | 44.78 |
| 18 | 82.6 | 41.59 |
| 19 | 80.2 | 49.48 |
| 20 | 79.9 | 89.47 |
| 21 | 79.5 | 48.95 |
| 22 | 74.4 | 42.00 |
| 23 | 73.5 | 36.87 |
| 24 | 73.3 | 36.16 |
| 25 | 69.0* | 46.99 |
| 26 | 68.8 | 93.22 |
| 27 | 68.5 | 53.49 |
| 28 | 68.3 | 50.90 |
| 29 | 68.0 | 70.75 |
| 30 | 54.2* | 17.40 |
| 31 | 50.5 | 44.46 |
| 32 | 23.4 | 36.90 |
| 33 | 22.9 | 82.85 |
| 34 | 22.6 | 100.00 |
| 35 | 21.8 | 87.94 |
| 36 | 21.4 | 85.89 |
| 37 | 20.4* | 70.1 |
| 38 | 20.1 | 39.2 |

Peaks with an asterisk (*) are major peaks

Form H

In some embodiments, Compound 1 can be 2'-C-methyluridine-5'-(O-phenyl-N—(S)-1-(isopropoxycarbonyl)ethyl)thiophosphoramidate characterized as Form H.

In some embodiments, Form H can be characterized by one or more peaks in an X-ray powder diffraction pattern, wherein the one or more peaks is selected from a peak in the range of from about 7.9 to about 8.3 degrees, a peak in the range of from about 13.8 to about 14.2 degrees, a peak in the range of from about 17.0 to about 17.4 degrees, and a peak in the range of from about 19.9 to about 20.3 degrees.

In some embodiments, Form H can be characterized by one or more peaks in an X-ray powder diffraction pattern, wherein the one or more peaks is selected from a peak at about 8.1 degrees, a peak at about 14.0 degrees, a peak at about 17.2 degrees, and a peak at about 20.1 degrees.

In some embodiments, Form H can be characterized by a peak at about 8.1 degrees, a peak at about 14.0 degrees, a peak at about 17.2 degrees, and a peak at about 20.1 degrees in an X-ray powder diffraction pattern.

Figure 16:
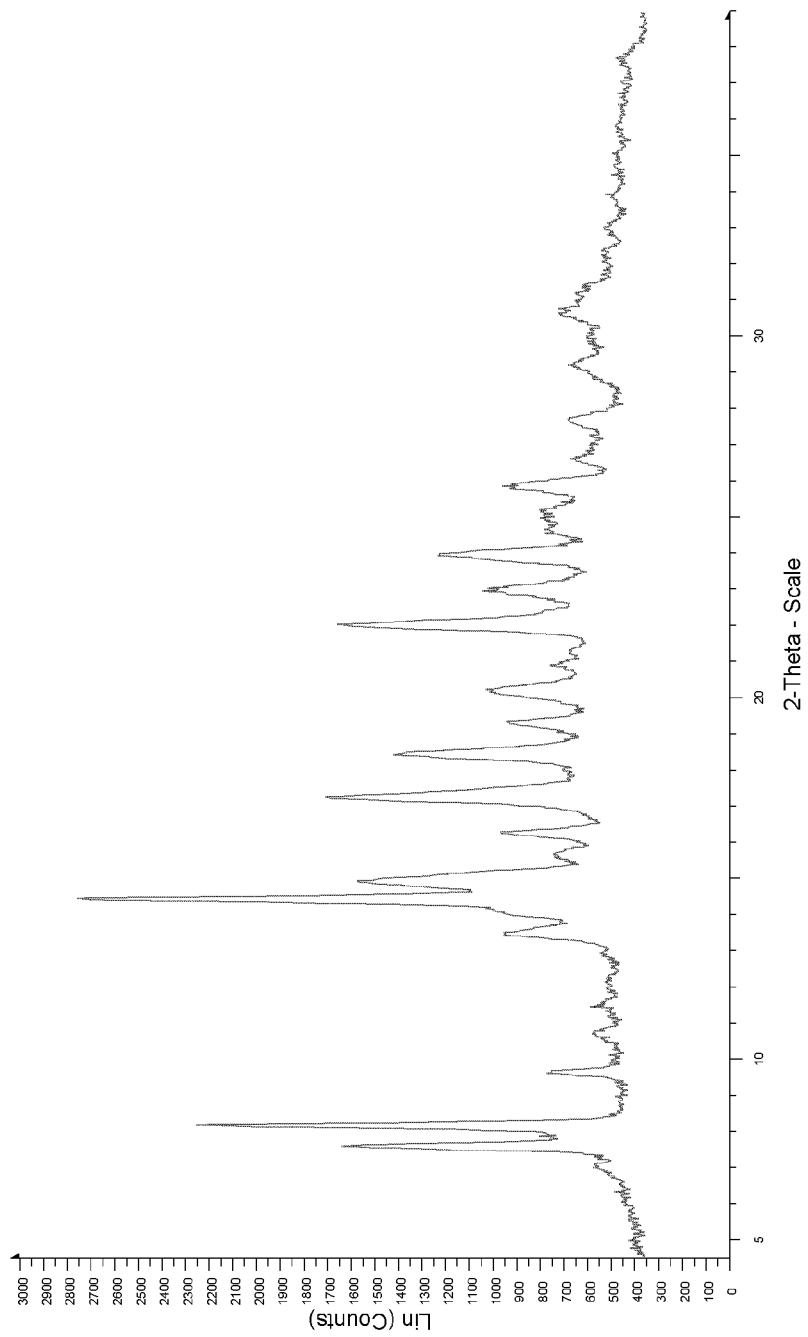
FIG. 16 is an XRPD spectrum of Form H.

In some embodiments, Form H can be characterized by an X-ray powder diffraction pattern of FIG. 16.

In some embodiments, Form H can be characterized by one or more peaks in an X-ray powder diffraction pattern selected from the table below.

| No. | 2-Theta ° | Intensity % |
|---|---|---|
| 1 | 8.132* | 81.7 |
| 2 | 14.020* | 34.6 |
| 3 | 17.226* | 61.7 |
| 4 | 20.902* | 27.3 |

Peaks with an asterisk (*) are major peaks

In some embodiments, Form H can be characterized by one or more peaks in a $^{13}$C NMR solid state spectrum, wherein the one or more peaks is selected from a peak at about 173.4 ppm, a peak at about 153.4 ppm, a peak at about 152.2 ppm, a peak at about 129.8 ppm, a peak at about 119.8 ppm, a peak at about 104.6 ppm, a peak at about 79.4 ppm, and a peak at about 20.6 ppm.

In some embodiments, Form H can be characterized by one or more peaks in a $^{13}$C NMR solid state spectrum, wherein the one or more peaks is selected from a peak at about 173.4 ppm, a peak at about 153.4 ppm, a peak at about 152.2 ppm, a peak at about 129.8 ppm, a peak at about 119.8 ppm, a peak at about 104.6 ppm, a peak at about 79.4 ppm, a peak at about 20.6 ppm, and a peak at about 2.2 ppm.

In some embodiments, Form H can be characterized by a peak at about 173.4 ppm, a peak at about 153.4 ppm, a peak at about 119.8 ppm, and a peak at about 104.6 ppm in a $^{13}$C NMR solid state spectrum.

In some embodiments, Form H can be characterized by a peak at about 173.4 ppm, a peak at about 153.4 ppm, a peak at about 152.2 ppm, a peak at about 129.8 ppm, a peak at about 119.8 ppm, a peak at about 104.6 ppm, a peak at about 79.4 ppm, and a peak at about 20.6 ppm in a $^{13}$C NMR solid state spectrum.

Figure 17:
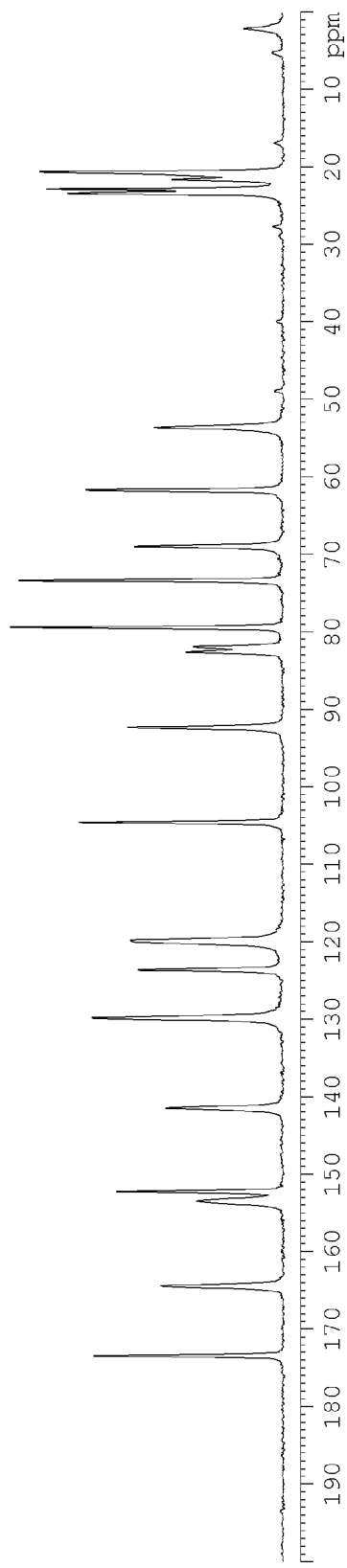
FIG. 17 is a $^{13}$C ssNMR spectrum of Form H.

In some embodiments, Form H can be characterized by a $^{13}$C NMR solid state spectrum of FIG. 17.

In some embodiments, Form H can be characterized by one or more peaks in a $^{13}$C NMR solid state spectrum selected from the table below.

| Peak | ν(F1) [ppm] | Intensity [rel] |
| --- | --- | --- |
| 1 | 173.4* | 70.7 |
| 2 | 164.4 | 44.87 |
| 3 | 153.4* | 31.83 |
| 4 | 152.2* | 61.17 |
| 5 | 141.4 | 42.94 |
| 6 | 129.8* | 70.37 |
| 7 | 123.6 | 53.72 |
| 8 | 119.8* | 55.92 |
| 9 | 104.6* | 76.16 |
| 10 | 92.3 | 56.76 |
| 11 | 82.6 | 35.67 |
| 12 | 81.9 | 32.74 |
| 13 | 79.4* | 100.00 |
| 14 | 73.4 | 96.98 |
| 15 | 68.9 | 54.71 |
| 16 | 61.7 | 73.15 |
| 17 | 53.6 | 47.24 |
| 18 | 23.4 | 79.96 |
| 19 | 22.9 | 86.96 |
| 20 | 21.6 | 41.15 |
| 21 | 20.6* | 90.05 |
| 22 | 2.2* | 14.59 |

Peaks with an asterisk (*) are major peaks

Form I

In some embodiments, Compound 1 can be 2'-C-methyluridine-5'-(O-phenyl-N—(S)-1-(isopropoxycarbonyl) ethyl)thiophosphoramidate characterized as Form I.

In some embodiments, Form I can be characterized by one or more peaks in an X-ray powder diffraction pattern, wherein the one or more peaks is selected from a peak in the range of from about 6.2 to about 6.6 degrees, a peak in the range of from about 9.1 to about 9.5 degrees, a peak in the range of from about 10.6 to about 11.0 degrees, and a peak in the range of from about 11.6 to about 12.0 degrees.

In some embodiments, Form I can be characterized by one or more peaks in an X-ray powder diffraction pattern, wherein the one or more peaks is selected from a peak at about 6.4 degrees, a peak at about 9.3 degrees, a peak at about 10.8 degrees, and a peak at about 11.8 degrees.

In some embodiments, Form I can be characterized by a peak at about 6.4 degrees, a peak at about 9.3 degrees, a peak at about 10.8 degrees, and a peak at about 11.8 degrees in an X-ray powder diffraction pattern.

Figure 18:
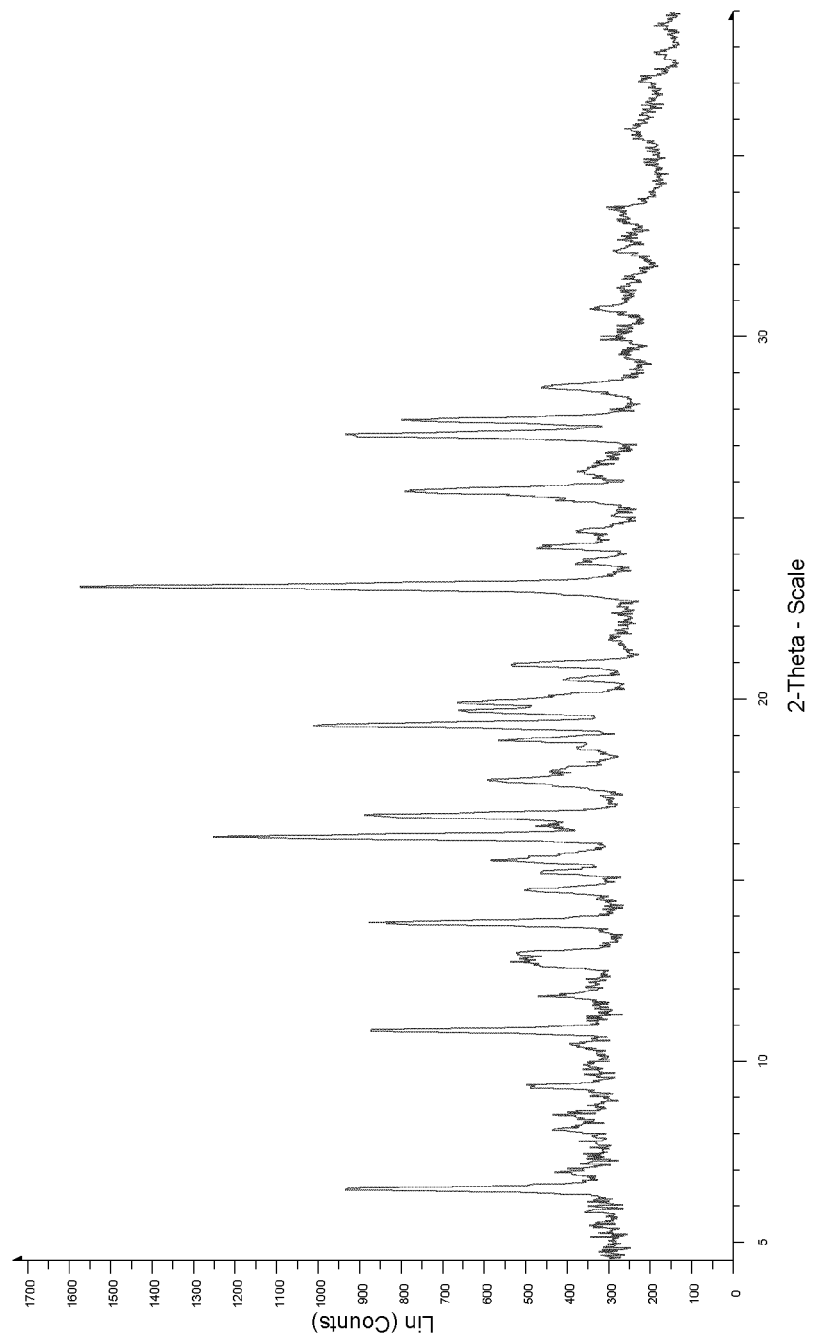
FIG. 18 is an XRPD spectrum of Form I.

In some embodiments, Form I can be characterized by an X-ray powder diffraction pattern of FIG. 18.

In some embodiments, Form I can be characterized by one or more peaks in an X-ray powder diffraction pattern selected from the table below.

| No. | 2-Theta ° | Intensity % |
| --- | --- | --- |
| 1 | 6.434* | 59.2 |
| 2 | 9.283* | 30.8 |
| 3 | 10.831* | 55.3 |
| 4 | 11.794* | 28.3 |

Peaks with an asterisk (*) are major peaks

In some embodiments, Form I can be characterized by one or more peaks in a $^{13}$C NMR solid state spectrum, wherein the one or more peaks is selected from a peak at about 173.0 ppm, a peak at about 152.1 ppm, a peak at about 126.1 ppm, a peak at about 102.7 ppm, a peak at about 74.5 ppm, a peak at about 71.2 ppm, a peak at about 63.3 ppm, and a peak at about 23.3 ppm.

In some embodiments, Form I can be characterized by one or more peaks in a $^{13}$C NMR solid state spectrum, wherein the one or more peaks is selected from a peak at about 173.1 ppm, a peak at about 168.6 ppm, a peak at about 152.1 ppm, a peak at about 123.6 ppm, a peak at about 102.6 ppm, a peak at about 71.4 ppm, a peak at about 63.5 ppm, a peak at about 61.9 ppm, a peak at about 22.4 ppm, and a peak at about 15.5 ppm. In some embodiments, Form I can be an ethyl acetate solvate.

In some embodiments, Form I (ethyl acetate solvate) can be characterized by one or more peaks in a $^{13}$C NMR solid state spectrum selected from the table below.

| Peak | ν(F1) [ppm] | Intensity [rel] |
| --- | --- | --- |
| 1 | 174.2 | 27.6 |
| 2 | 173.1* | 34.33 |
| 3 | 170.3 | 20.24 |
| 4 | 168.6* | 20.76 |
| 5 | 152.1* | 41.55 |
| 6 | 151.1 | 35.37 |
| 7 | 144.9 | 20.96 |
| 8 | 143.6 | 18.23 |
| 9 | 129.4 | 12.59 |
| 10 | 126.1 | 23.63 |
| 11 | 123.6* | 24.98 |
| 12 | 119.3 | 10.42 |
| 13 | 102.6* | 56.41 |
| 14 | 93.2 | 22.66 |
| 15 | 91.1 | 23.83 |
| 16 | 81.7 | 36.81 |
| 17 | 80.6 | 41.38 |
| 18 | 79.6 | 68.17 |
| 19 | 74.3 | 34.18 |
| 20 | 73.2 | 33.47 |
| 21 | 71.4* | 32.36 |
| 22 | 69.3 | 33.35 |
| 23 | 68.7 | 34.79 |
| 24 | 63.5* | 32.91 |
| 25 | 61.9* | 21.88 |
| 26 | 51.3 | 22.60 |
| 27 | 50.5 | 21.35 |
| 28 | 22.4* | 100.00 |
| 29 | 20.1 | 52.23 |
| 30 | 15.5* | 16.24 |

Peaks with an asterisk (*) are major peaks

In some embodiments, Form I can be characterized by one or more peaks in a $^{13}$C NMR solid state spectrum, wherein the one or more peaks is selected from a peak at about 173.0 ppm, a peak at about 168.4 ppm, a peak at about 152.1 ppm, a peak at about 126.1 ppm, a peak at about 102.7 ppm, a peak at about 74.5 ppm, a peak at about 71.2 ppm, a peak at about 63.3 ppm, and a peak at about 23.3 ppm. In some embodiments, Form I can be an isopropyl acetate solvate.

In some embodiments, Form I can be characterized by a peak at about 102.7 ppm, a peak at about 74.5 ppm, a peak at about 71.2 ppm, and a peak at about 63.3 ppm in a $^{13}$C NMR solid state spectrum.

In some embodiments, Form I can be characterized by a peak at about 173.0 ppm, a peak at about 152.1 ppm, a peak at about 126.1 ppm, a peak at about 102.7 ppm, a peak at about 74.5 ppm, a peak at about 71.2 ppm, a peak at about 63.3 ppm, and a peak at about 23.3 ppm in a $^{13}$C NMR solid state spectrum.

Figure 19:
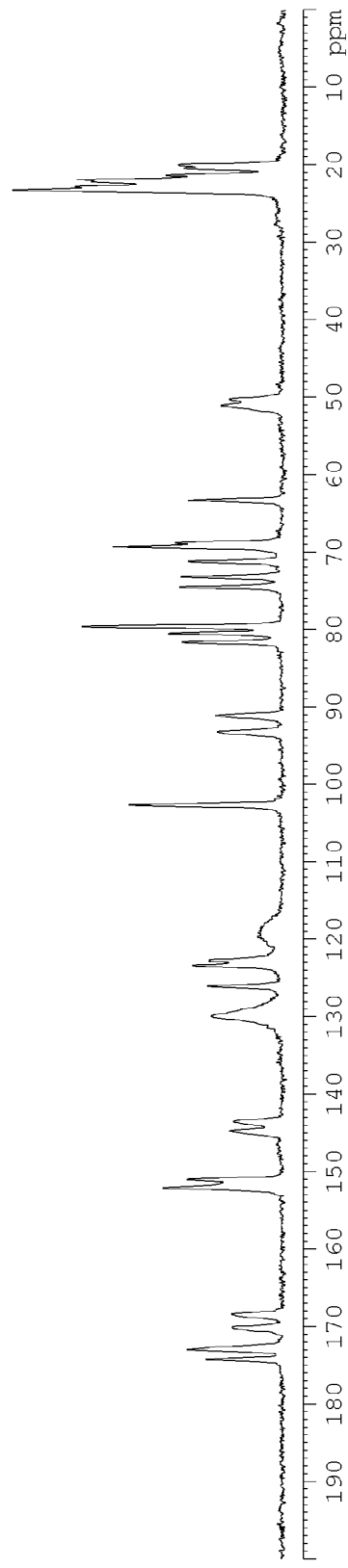
FIG. 19 is a $^{13}$C ssNMR spectrum of Form I.

In some embodiments, Form I can be characterized by a $^{13}$C NMR solid state spectrum of FIG. 19.

In some embodiments, Form I (isopropyl acetate solvate) can be characterized by one or more peaks in a $^{13}$C NMR solid state spectrum selected from the table below.

| Peak | ν(F1) [ppm] | Intensity [rel] |
|---|---|---|
| 1 | 174.2 | 28.4 |
| 2 | 173.0* | 35.35 |
| 3 | 170.1 | 18.49 |
| 4 | 168.4* | 18.99 |
| 5 | 152.1* | 44.16 |
| 6 | 151.0 | 35.26 |
| 7 | 144.8 | 19.59 |
| 8 | 143.5 | 18.22 |
| 9 | 129.9 | 26.35 |
| 10 | 126.1* | 27.72 |
| 11 | 123.4 | 33.24 |
| 12 | 122.8 | 27.21 |
| 13 | 119.6 | 9.23 |
| 14 | 102.7* | 56.58 |
| 15 | 93.2 | 23.93 |
| 16 | 91.1 | 24.94 |
| 17 | 81.6 | 37.12 |
| 18 | 80.5 | 42.31 |
| 19 | 79.6 | 73.82 |
| 20 | 74.5* | 37.87 |
| 21 | 73.2 | 37.91 |
| 22 | 71.2* | 34.86 |
| 23 | 69.3 | 62.97 |
| 24 | 68.8 | 39.70 |
| 25 | 63.3* | 34.57 |
| 26 | 51.1 | 22.87 |
| 27 | 50.3 | 19.47 |
| 28 | 23.3* | 100.00 |
| 29 | 22.8 | 76.24 |
| 30 | 21.9 | 75.98 |
| 31 | 21.4 | 42.76 |
| 32 | 20.4 | 36.17 |
| 33 | 20.0 | 38.34 |

Peaks with an asterisk (*) are major peaks

Form J

In some embodiments, Compound 1 can be 2'-C-methyluridine-5'-(O-phenyl-N—(S)-1-(isopropoxycarbonyl)ethyl)thiophosphoramidate characterized as Form J.

In some embodiments, Form J can be characterized by one or more peaks in an X-ray powder diffraction pattern, wherein the one or more peaks is selected from a peak in the range of from about 5.9 to about 6.3 degrees, a peak in the range of from about 7.3 to about 7.7 degrees, a peak in the range of from about 11.9 to about 12.3 degrees, a peak in the range of from about 13.1 to about 13.5 degrees, a peak in the range of from about 13.8 to about 14.2 degrees, a peak in the range of from about 18.3 to about 18.7 degrees, a peak in the range of from about 22.4 to about 22.8 degrees, a peak in the range of from about 33.0 to about 33.4 degrees, a peak in the range of from about 33.8 to about 34.2 degrees, and a peak in the range of from about 35.1 to about 35.5 degrees.

In some embodiments, Form J can be characterized by one or more peaks in an X-ray powder diffraction pattern, wherein the one or more peaks is selected from a peak in the range of from about 5.9 to about 6.3 degrees, a peak in the range of from about 7.3 to about 7.7 degrees, a peak in the range of from about 11.9 to about 12.3 degrees, a peak in the range of from about 13.1 to about 13.5 degrees, a peak in the range of from about 13.8 to about 14.2 degrees and a peak in the range of from about 18.3 to about 18.7 degrees.

In some embodiments, Form J can be characterized by one or more peaks in an X-ray powder diffraction pattern, wherein the one or more peaks is selected from a peak at about 6.1 degrees, a peak at about 7.5 degrees, a peak at about 12.1 degrees, a peak at about 13.3 degrees, a peak at about 14.0 degrees, a peak at about 18.5 degrees, a peak at about 22.6 degrees, a peak at about 33.2 degrees, a peak at about 34.0 degrees, and a peak at about 35.3 degrees.

In some embodiments, Form J can be characterized by one or more peaks in an X-ray powder diffraction pattern, wherein the one or more peaks is selected from a peak at about 6.1 degrees, a peak at about 7.5 degrees, a peak at about 12.1 degrees, a peak at about 13.3 degrees, a peak at about 14.0 degrees, and a peak at about 18.5 degrees.

In some embodiments, Form J can be characterized by one or more peaks in an X-ray powder diffraction pattern, wherein the one or more peaks is selected from a peak at about 6.1 degrees, a peak at about 7.5 degrees, a peak at about 12.1 degrees, a peak at about 13.3 degrees, a peak at about 14.0 degrees, a peak at about 18.5 degrees, a peak at about 22.6 degrees, a peak at about 33.2 degrees, a peak at about 34.0 degrees, and a peak at about 35.3 degrees.

Figure 20:
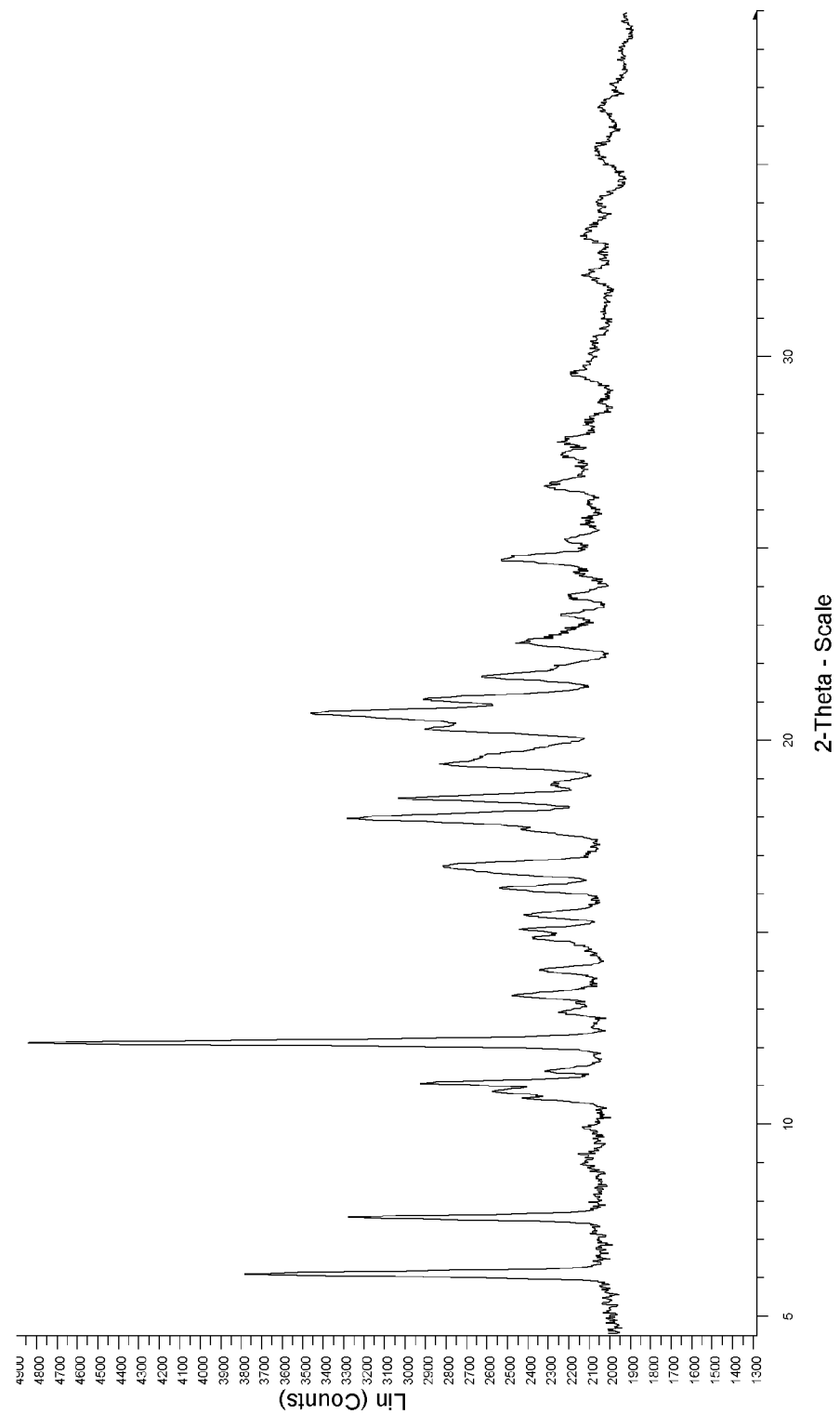
FIG. 20 is an XRPD spectrum of Form J.

In some embodiments, Form J can be characterized by an X-ray powder diffraction pattern of FIG. 20.

In some embodiments, Form J can be characterized by one or more XRPD peaks selected from the table below.

| No. | 2-Theta ° | Intensity % |
|---|---|---|
| 1 | 6.1* | 69.2 |
| 2 | 7.5* | 54.4 |
| 3 | 9.0 | 21.2 |
| 4 | 9.9 | 21.2 |
| 5 | 10.8 | 34.0 |
| 6 | 11.1 | 44.2 |
| 7 | 11.4 | 26.5 |
| 8 | 12.1* | 100.0 |
| 9 | 12.9 | 24.6 |
| 10 | 13.3* | 31.2 |
| 11 | 14.0* | 27.2 |
| 12 | 14.8 | 28.3 |
| 13 | 15.1 | 30.2 |
| 14 | 15.4 | 29.5 |
| 15 | 16.1 | 33.0 |
| 16 | 16.7 | 41.0 |
| 17 | 17.6 | 29.8 |
| 18 | 18.0 | 54.6 |
| 19 | 18.5* | 47.3 |
| 20 | 18.9 | 25.6 |
| 21 | 19.4 | 41.6 |
| 22 | 19.6 | 35.8 |
| 23 | 20.3 | 43.5 |
| 24 | 20.7 | 59.8 |
| 25 | 21.1 | 43.8 |
| 26 | 21.7 | 35.5 |
| 27 | 22.6** | 30.1 |
| 28 | 22.3 | 24.3 |
| 29 | 23.8 | 23.1 |
| 30 | 24.7 | 32.7 |
| 31 | 25.2 | 23.7 |
| 32 | 25.7 | 20.8 |
| 33 | 26.6 | 26.7 |
| 34 | 27.5 | 24.3 |
| 35 | 27.8 | 23.6 |
| 36 | 28.3 | 20.7 |

-continued

| No. | 2-Theta ° | Intensity % |
|---|---|---|
| 37 | 29.6 | 22.9 |
| 38 | 32.2 | 20.3 |
| 39 | 33.2** | 21.5 |
| 40 | 34.0** | 19.2 |
| 41 | 35.3** | 19.3 |
| 42 | 35.4 | 19.4 |
| 43 | 36.5 | 19.0 |

Figure 21:
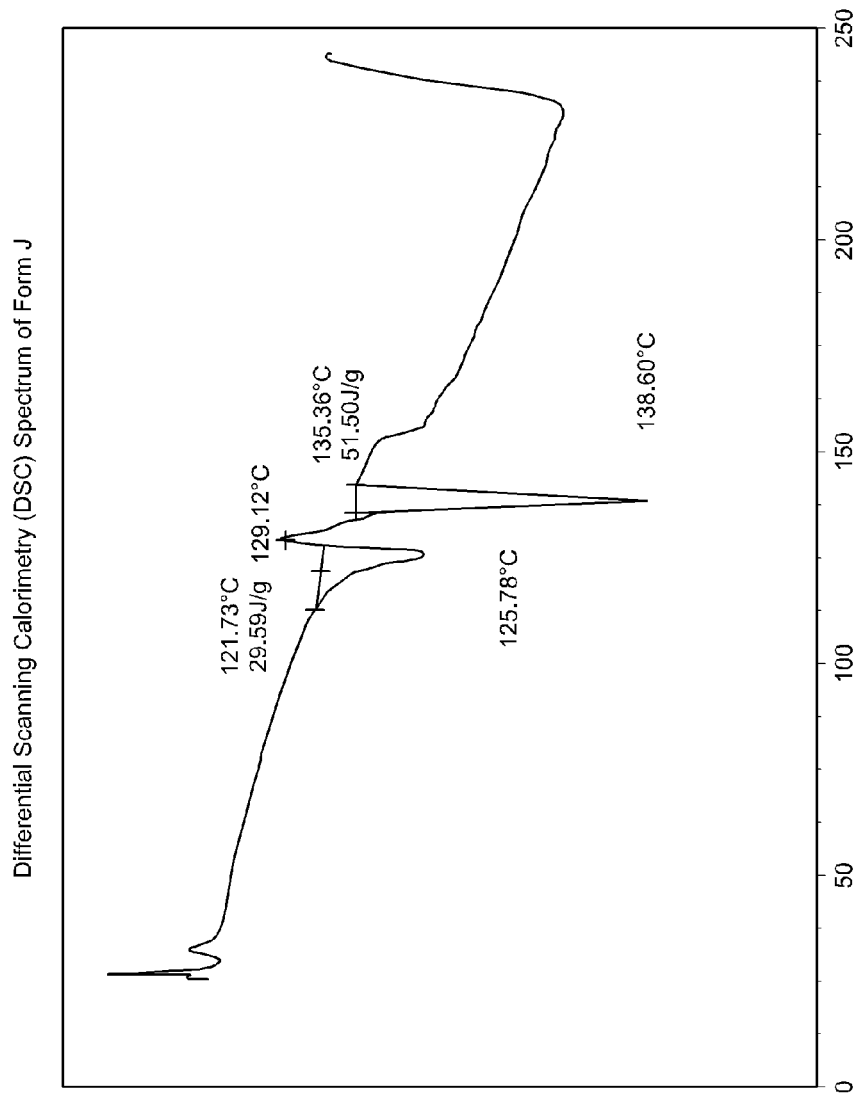
FIG. 21 is a DSC spectrum of Form J.

Peaks with an asterisk (*) are major peaks
Peaks with a double asterisk (**) are secondary peaks In some embodiments, Form J can be characterized by a DSC thermogram as shown in FIG. 21. In some embodiments, Form J can be characterized by a DSC thermogram showing a first endotherm in the range of about 121° C. to about 127° C. (for example, at about 126° C.). In some embodiments, Form J can be characterized by a DSC thermogram showing an exotherm in the range of about 127° C. to about 132° C. (for example, at about 129° C.). In some embodiments, Form J can be characterized by a DSC thermogram showing a second endotherm in the range of about 135° C. to about 142° C. (for example, at about 138° C.). In some embodiments, Form J can be characterized by a DSC thermogram showing a first melting temperature in the range of about 121° C. to about 127° C. (for example, at about 126° C.). In some embodiments, Form J can be characterized by a DSC thermogram showing a recrystallization at a temperature in the range of about 127° C. to about 132° C. (for example, at about 129° C.). In some embodiments, Form J can be characterized by a DSC thermogram showing a second melting temperature in the range of about 135° C. to about 142° C. (for example, at about 138° C.). In some embodiments, Form J can be characterized by a melting temperature in the range of about 121° C. to about 127° C. (for example, at about 126° C.).

In some embodiments, Form J can be characterized by one or more peaks in a $^{13}$C NMR solid state spectrum, wherein the one or more peaks is selected from a peak at about 175.6 ppm, a peak at about 141.4 ppm, a peak at about 127.8 ppm, a peak at about 123.4 ppm, a peak at about 103.1 ppm, a peak at about 83.5 ppm, a peak at about 81.1 ppm, a peak at about 62.2 ppm, a peak at about 25.6 ppm, and a peak at about 19.6 ppm.

In some embodiments, Form J can be characterized by a peak at about 83.5 ppm, a peak at about 81.1 ppm, a peak at about 62.2 ppm, and a peak at about 25.6 ppm in a $^{13}$C NMR solid state spectrum.

In some embodiments, Form J can be characterized by a peak at about 175.6 ppm, a peak at about 141.4 ppm, a peak at about 127.8 ppm, a peak at about 123.4 ppm, a peak at about 103.1 ppm, a peak at about 83.5 ppm, a peak at about 81.1 ppm, a peak at about 62.2 ppm, a peak at about 25.6 ppm, and a peak at about 19.6 ppm in a $^{13}$C NMR solid state spectrum.

Figure 22:
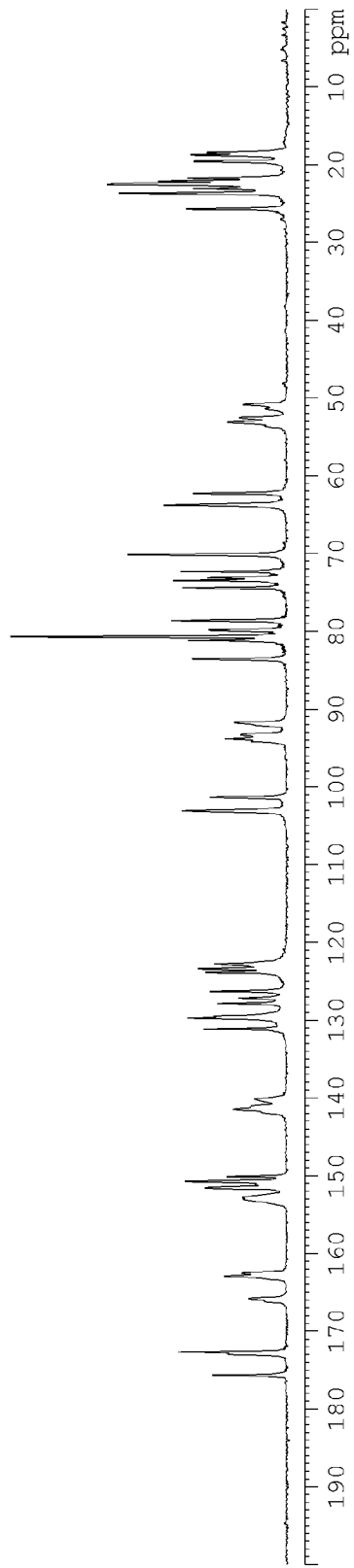
FIG. 22 is a $^{13}$C ssNMR spectrum of Form J.

In some embodiments, Form J can be characterized by a $^{13}$C NMR solid state spectrum of FIG. 22.

In some embodiments, Form J can be characterized by one or more peaks in a $^{13}$C NMR solid state spectrum selected from the table below.

| Peak | v(F1) [ppm] | Intensity [rel] |
|---|---|---|
| 1 | 175.6* | 26.8 |
| 2 | 172.6 | 39.76 |
| 3 | 165.8 | 13.72 |
| 4 | 162.9 | 22.43 |
| 5 | 162.5 | 16.16 |
| 6 | 153.0 | 15.82 |
| 7 | 152.8 | 15.88 |
| 8 | 151.5 | 29.40 |
| 9 | 151.1 | 11.45 |
| 10 | 150.7 | 36.85 |
| 11 | 150.1 | 21.71 |
| 12 | 141.4* | 19.34 |
| 13 | 140.1 | 11.81 |
| 14 | 131.1 | 29.77 |
| 15 | 129.7 | 35.60 |
| 16 | 129.5 | 26.33 |
| 17 | 127.8* | 25.20 |
| 18 | 127.1 | 17.58 |
| 19 | 126.3 | 27.54 |
| 20 | 123.8 | 29.09 |
| 21 | 123.4* | 32.43 |
| 22 | 122.8 | 26.21 |
| 23 | 103.1* | 37.64 |
| 24 | 101.3 | 27.86 |
| 25 | 93.8 | 22.55 |
| 26 | 93.3 | 16.53 |
| 27 | 91.7 | 18.80 |
| 28 | 83.5* | 35.20 |
| 29 | 81.1* | 35.52 |
| 30 | 80.7 | 100.00 |
| 31 | 79.8 | 28.76 |
| 32 | 78.6 | 42.08 |
| 33 | 74.4 | 37.67 |
| 34 | 73.4 | 41.04 |
| 35 | 73.1 | 28.84 |
| 36 | 72.3 | 39.74 |
| 37 | 70.1 | 57.8 |
| 38 | 63.7 | 44.0 |
| 39 | 62.2* | 33.4 |
| 40 | 53.1 | 21.6 |
| 41 | 52.5 | 16.9 |
| 42 | 50.8 | 15.9 |
| 43 | 25.6* | 36.7 |
| 44 | 23.7 | 60.6 |
| 45 | 23.0 | 34.4 |
| 46 | 22.5 | 64.4 |
| 47 | 22.1 | 46.4 |
| 48 | 21.7 | 36.1 |
| 49 | 19.6* | 34.5 |
| 50 | 18.8 | 34.8 |
| 51 | 18.4 | 29.1 |

Peaks with an asterisk (*) are major peaks

Form K

In some embodiments, Compound 1 can be 2'-C-methyluridine-5'-(O-phenyl-N—(S)-1-(isopropoxycarbonyl)ethyl)thiophosphoramidate characterized as Form K.

In some embodiments, Form K can be characterized by one or more peaks in an X-ray powder diffraction pattern, wherein the one or more peaks is selected from a peak in the range of from about 22.4 to about 22.8 degrees, a peak in the range of from about 27.1 to about 27.5 degrees, a peak in the range of from about 28.1 to about 28.5 degrees, and a peak in the range of from about 31.0 to about 31.4 degrees.

In some embodiments, Form K can be characterized by one or more peaks in an X-ray powder diffraction pattern, wherein the one or more peaks is selected from a peak at about 22.6 degrees, a peak at about 27.3 degrees, a peak at about 28.3 degrees, and a peak at about 31.2 degrees.

In some embodiments, Form K can be characterized by a peak at about 22.6 degrees, a peak at about 27.3 degrees, a peak at about 28.3 degrees, and a peak at about 31.2 degrees in an X-ray powder diffraction pattern.

Figure 23:
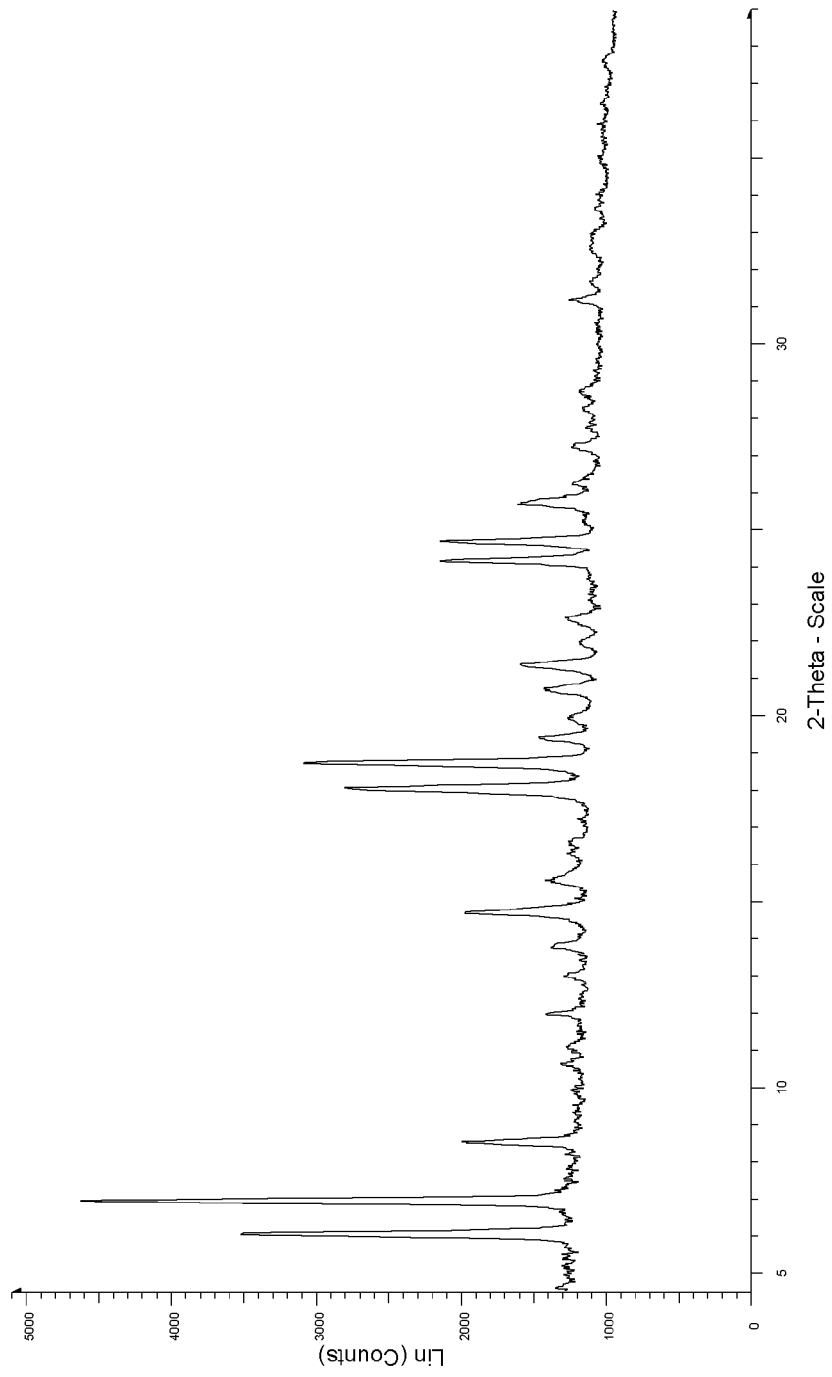
FIG. 23 is an XRPD spectrum of Form K.

In some embodiments, Form K can be characterized by an X-ray powder diffraction pattern of FIG. 23.

In some embodiments, Form K can be characterized by one or more XRPD peaks selected from the table below.

| No. | 2-Theta ° | Intensity % |
|---|---|---|
| 1 | 22.620* | 27.5 |
| 2 | 27.257* | 26.7 |
| 3 | 28.272* | 25.0 |
| 4 | 31.216* | 27.0 |

Peaks with an asterisk (*) are major peaks

In some embodiments, Form K can be characterized by one or more peaks in a $^{13}$C NMR solid state spectrum, wherein the one or more peaks is selected from a peak at about 173.9 ppm, a peak at about 173.4 ppm, a peak at about 151.8 ppm, a peak at about 150.5 ppm, a peak at about 101.9 ppm, a peak at about 92.0 ppm, a peak at about 73.5 ppm, a peak at about 22.1 ppm, and a peak at about 20.4 ppm.

In some embodiments, Form K can be characterized by one or more peaks in a $^{13}$C NMR solid state spectrum, wherein the one or more peaks is selected from a peak at about 173.9 ppm, a peak at about 173.4 ppm, a peak at about 151.8 ppm, a peak at about 150.5 ppm, a peak at about 101.9 ppm, a peak at about 92.0 ppm, a peak at about 80.4 ppm, a peak at about 73.5 ppm, a peak at about 22.1 ppm, and a peak at about 20.4 ppm.

In some embodiments, Form K can be characterized by a peak at about 173.9 ppm, a peak at about 173.4 ppm, a peak at about 101.9 ppm, and a peak at about 92.0 ppm in a $^{13}$C NMR solid state spectrum.

In some embodiments, Form K can be characterized by a peak at about 173.9 ppm, a peak at about 173.4 ppm, a peak at about 151.8 ppm, a peak at about 150.5 ppm, a peak at about 101.9 ppm, a peak at about 92.0 ppm, a peak at about 73.5 ppm, a peak at about 22.1 ppm, and a peak at about 20.4 ppm in a $^{13}$C NMR solid state spectrum.

Figure 24:
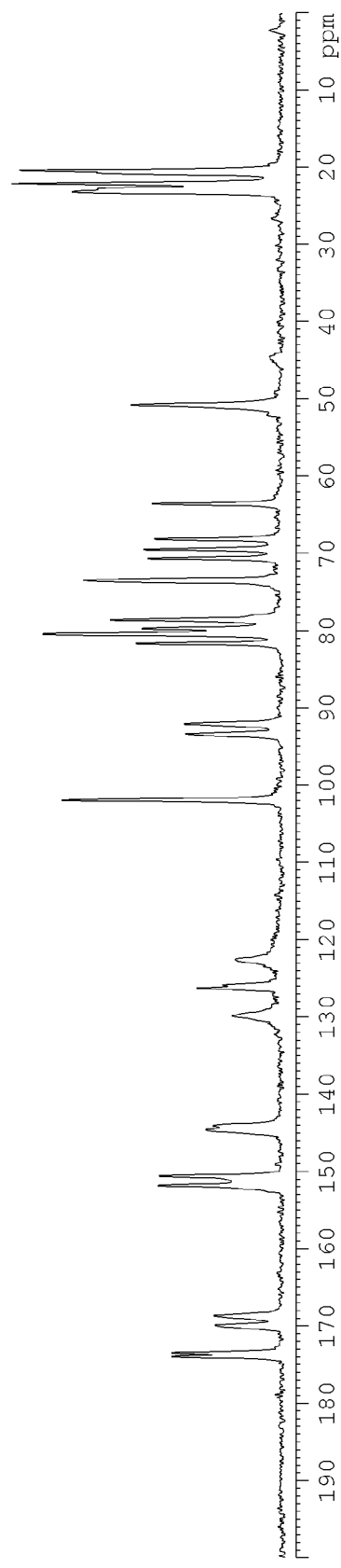
FIG. 24 is a $^{13}$C ssNMR spectrum of Form K.

In some embodiments, Form K can be characterized by a $^{13}$C NMR solid state spectrum of FIG. 24.

In some embodiments, Form K can be characterized by one or more peaks in a $^{13}$C NMR solid state spectrum selected from the table below.

| Peak | ν(F1) [ppm] | Intensity [rel] |
|---|---|---|
| 1 | 173.9* | 40.0 |
| 2 | 173.4* | 39.97 |
| 3 | 169.9 | 23.72 |
| 4 | 168.7 | 24.10 |
| 5 | 151.8* | 45.42 |
| 6 | 150.5* | 44.95 |
| 7 | 144.6 | 27.19 |
| 8 | 144.1 | 24.43 |
| 9 | 129.8 | 17.44 |
| 10 | 126.2 | 30.54 |
| 11 | 125.8 | 20.97 |
| 12 | 122.5 | 16.21 |
| 13 | 101.9* | 81.01 |
| 14 | 93.4 | 34.58 |
| 15 | 92.0* | 35.25 |
| 16 | 81.6 | 54.04 |
| 17 | 80.4* | 88.61 |
| 18 | 79.7 | 51.32 |
| 19 | 78.6 | 62.92 |
| 20 | 73.5* | 72.84 |
| 21 | 70.6 | 49.15 |
| 22 | 69.5 | 50.72 |
| 23 | 68.1 | 46.78 |
| 24 | 63.6 | 47.15 |
| 25 | 50.8 | 55.38 |
| 26 | 23.2 | 76.97 |
| 27 | 22.8 | 67.52 |
| 28 | 22.1* | 100.00 |
| 29 | 20.7 | 68.21 |
| 30 | 20.4* | 97.77 |

Peaks with an asterisk (*) are major peaks

Form L

In some embodiments, Compound 1 can be 2'-C-methyluridine-5'-(O-phenyl-N—(S)-1-(isopropoxycarbonyl)ethyl)thiophosphoramidate characterized as Form L.

In some embodiments, Form L can be characterized by one or more peaks in an X-ray powder diffraction pattern, wherein the one or more peaks is selected from a peak in the range of from about 5.5 to about 5.9 degrees, a peak in the range of from about 5.8 to about 6.2 degrees, a peak in the range of from about 15.0 to about 15.4 degrees, and a peak in the range of from about 15.9 to about 16.3 degrees.

In some embodiments, Form L can be characterized by one or more peaks in an X-ray powder diffraction pattern, wherein the one or more peaks is selected from a peak at about 5.7 degrees, a peak at about 6.0 degrees, a peak at about 15.2 degrees, and a peak at about 16.1 degrees.

In some embodiments, Form L can be characterized by a peak at about 5.7 degrees, a peak at about 6.0 degrees, a peak at about 15.2 degrees, and a peak at about 16.1 degrees in an X-ray powder diffraction pattern.

Figure 25:
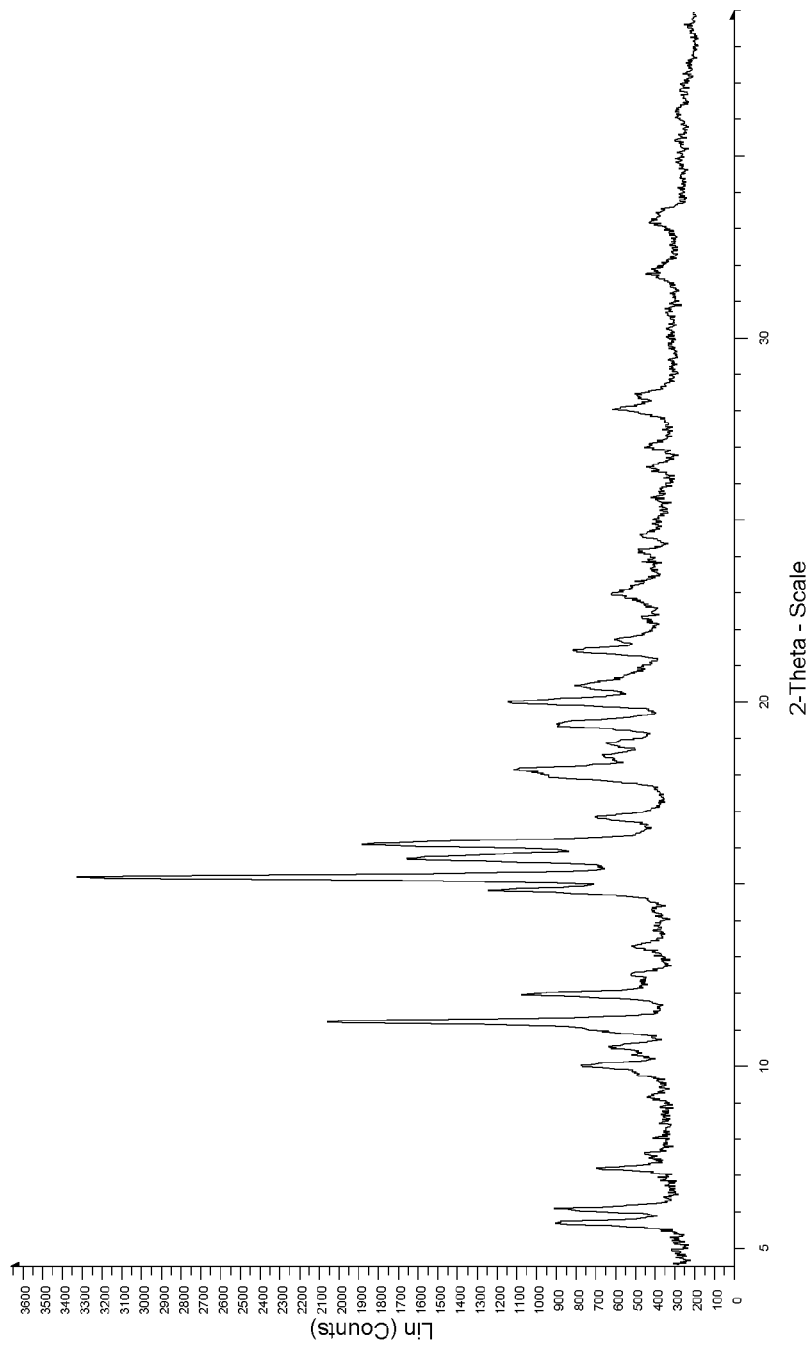
FIG. 25 is an XRPD spectrum of Form L.

In some embodiments, Form L can be characterized by an X-ray powder diffraction pattern of FIG. 25.

In some embodiments, Form L can be characterized by one or more XRPD peaks selected from the table below.

| No. | 2-Theta ° | Intensity % |
|---|---|---|
| 1 | 5.662* | 27.0 |
| 2 | 6.036* | 27.2 |
| 3 | 15.174* | 100.0 |
| 4 | 16.102* | 56.5 |

Peaks with an asterisk (*) are major peaks

In some embodiments, Form L can be characterized by one or more peaks in a $^{13}$C NMR solid state spectrum, wherein the one or more peaks is selected from a peak at about 173.2 ppm, a peak at about 151.4 ppm, a peak at about 140.9 ppm, a peak at about 118.5 ppm, a peak at about 81.5 ppm, a peak at about 80.1 ppm, a peak at about 73.4 ppm, a peak at about 61.6 ppm, and a peak at about 20.9 ppm.

In some embodiments, Form L can be characterized by one or more peaks in a $^{13}$C NMR solid state spectrum, wherein the one or more peaks is selected from a peak at about 173.2 ppm, a peak at about 151.4 ppm, a peak at about 140.9 ppm, a peak at about 118.5 ppm, a peak at about 81.5 ppm, a peak at about 80.1 ppm, a peak at about 73.4 ppm, a peak at about 61.6 ppm, a peak at about 20.9 ppm, and a peak at about 1.6 ppm.

In some embodiments, Form L can be characterized by a peak at about 81.5 ppm, a peak at about 80.1 ppm, a peak at about 61.6 ppm, and a peak at about 20.9 ppm in a $^{13}$C NMR solid state spectrum.

In some embodiments, Form L can be characterized by a peak at about 173.2 ppm, a peak at about 151.4 ppm, a peak at about 140.9 ppm, a peak at about 118.5 ppm, a peak at about 81.5 ppm, a peak at about 80.1 ppm, a peak at about 73.4 ppm, a peak at about 61.6 ppm, and a peak at about 20.9 ppm in a $^{13}$C NMR solid state spectrum.

Figure 26:
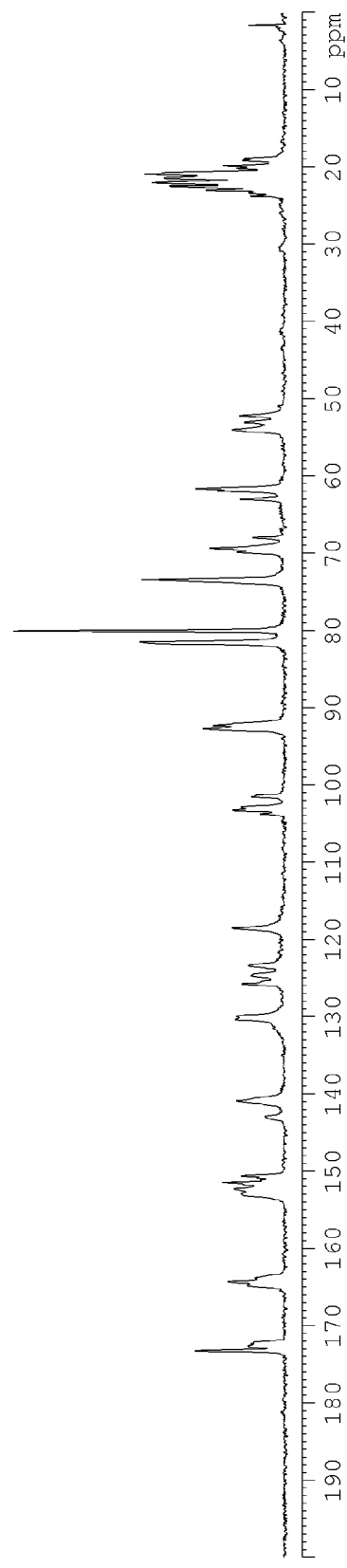
FIG. 26 is a $^{13}$C ssNMR spectrum of Form L.

In some embodiments, Form L can be characterized by a $^{13}$C NMR solid state spectrum of FIG. 26.

In some embodiments, Form L can be characterized by one or more peaks in a $^{13}$C NMR solid state spectrum selected from the table below.

| Peak | v(F1) [ppm] | Intensity [rel] |
|---|---|---|
| 1 | 173.2* | 32.2 |
| 2 | 172.6 | 13.04 |
| 3 | 164.3 | 20.50 |
| 4 | 152.9 | 15.62 |
| 5 | 152.3 | 18.02 |
| 6 | 151.4* | 22.38 |
| 7 | 150.8 | 10.20 |
| 8 | 150.6 | 15.53 |
| 9 | 142.9 | 7.14 |
| 10 | 140.9* | 17.32 |
| 11 | 130.3 | 17.85 |
| 12 | 129.9 | 17.36 |
| 13 | 125.7 | 15.60 |
| 14 | 124.7 | 11.99 |
| 15 | 123.4 | 12.87 |
| 16 | 118.5* | 18.82 |
| 17 | 103.8 | 8.86 |
| 18 | 103.3 | 18.66 |
| 19 | 102.9 | 15.60 |
| 20 | 101.5 | 12.23 |
| 21 | 92.7 | 29.36 |
| 22 | 92.3 | 25.58 |
| 23 | 81.5* | 51.96 |
| 24 | 80.1* | 100.00 |
| 25 | 73.4* | 51.97 |
| 26 | 69.9 | 17.16 |
| 27 | 69.3 | 27.18 |
| 28 | 68.0 | 11.49 |
| 29 | 63.0 | 15.93 |
| 30 | 61.9 | 24.74 |
| 31 | 61.6* | 32.16 |
| 32 | 54.0 | 18.79 |
| 33 | 53.0 | 14.69 |
| 34 | 52.2 | 16.30 |
| 35 | 23.7 | 12.59 |
| 36 | 23.3 | 12.87 |
| 37 | 23.0 | 28.2 |
| 38 | 22.5 | 42.2 |
| 39 | 22.0 | 47.5 |
| 40 | 21.4 | 43.2 |
| 41 | 20.9* | 50.2 |
| 42 | 20.2 | 17.4 |
| 43 | 19.8 | 22.2 |
| 44 | 19.2 | 15.2 |
| 45 | 18.9 | 14.8 |
| 46 | 1.6* | 12.9 |

Peaks with an asterisk (*) are major peaks

Form M

In some embodiments, Compound 1 can be 2'-C-methyluridine-5'-(O-phenyl-N—(S)-1-(isopropoxycarbonyl)ethyl)thiophosphoramidate characterized as Form M.

In some embodiments, Form M can be characterized by one or more peaks in an X-ray powder diffraction pattern, wherein the one or more peaks is selected from a peak in the range of from about 6.1 to about 6.5 degrees, a peak in the range of from about 13.0 to about 13.4 degrees, a peak in the range of from about 22.0 to about 22.4 degrees, and a peak in the range of from about 23.3 to about 23.7 degrees.

In some embodiments, Form M can be characterized by one or more peaks in an X-ray powder diffraction pattern, wherein the one or more peaks is selected from a peak at about 6.3 degrees, a peak at about 13.2 degrees, a peak at about 22.2 degrees, and a peak at about 23.5 degrees.

In some embodiments, Form M can be characterized by a peak at about 6.3 degrees, a peak at about 13.2 degrees, a peak at about 22.2 degrees, and a peak at about 23.5 degrees in an X-ray powder diffraction pattern.

Figure 27:
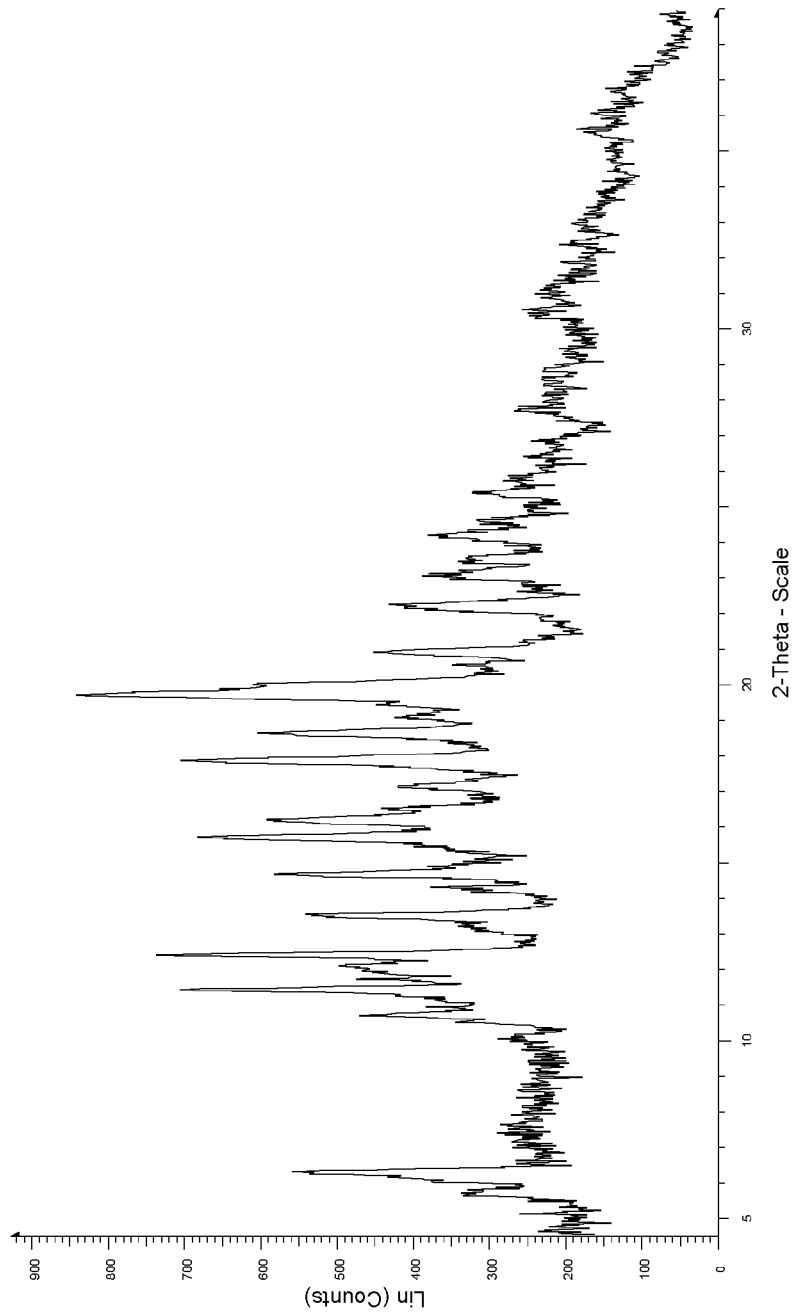
FIG. 27 is an XRPD spectrum of Form M.

In some embodiments, Form M can be characterized by an X-ray powder diffraction pattern of FIG. 27.

In some embodiments, Form M can be characterized by one or more XRPD peaks selected from the table below.

| No. | 2-Theta ° | Intensity % |
|---|---|---|
| 1 | 6.274* | 66.2 |
| 2 | 13.200* | 40.5 |
| 3 | 22.225* | 50.0 |
| 4 | 23.520* | 38.7 |

Peaks with an asterisk (*) are major peaks

In some embodiments, Form M can be characterized by one or more peaks in a $^{13}$C NMR solid state spectrum, wherein the one or more peaks is selected from a peak at about 174.0 ppm, a peak at about 170.5 ppm, a peak at about 129.5 ppm, a peak at about 79.6 ppm, a peak at about 69.7 ppm, a peak at about 63.2 ppm, a peak at about 51.8 ppm, a peak at about 24.0 ppm, and a peak at about 19.5 ppm.

In some embodiments, Form M can be characterized by a peak at about 69.7 ppm, a peak at about 63.2 ppm, a peak at about 51.8 ppm, and a peak at about 24.0 ppm in a $^{13}$C NMR solid state spectrum.

In some embodiments, Form M can be characterized by a peak at about 174.0 ppm, a peak at about 170.5 ppm, a peak at about 129.5 ppm, a peak at about 79.6 ppm, a peak at about 69.7 ppm, a peak at about 63.2 ppm, a peak at about 51.8 ppm, a peak at about 24.0 ppm, and a peak at about 19.5 ppm in a $^{13}$C NMR solid state spectrum.

Figure 28:
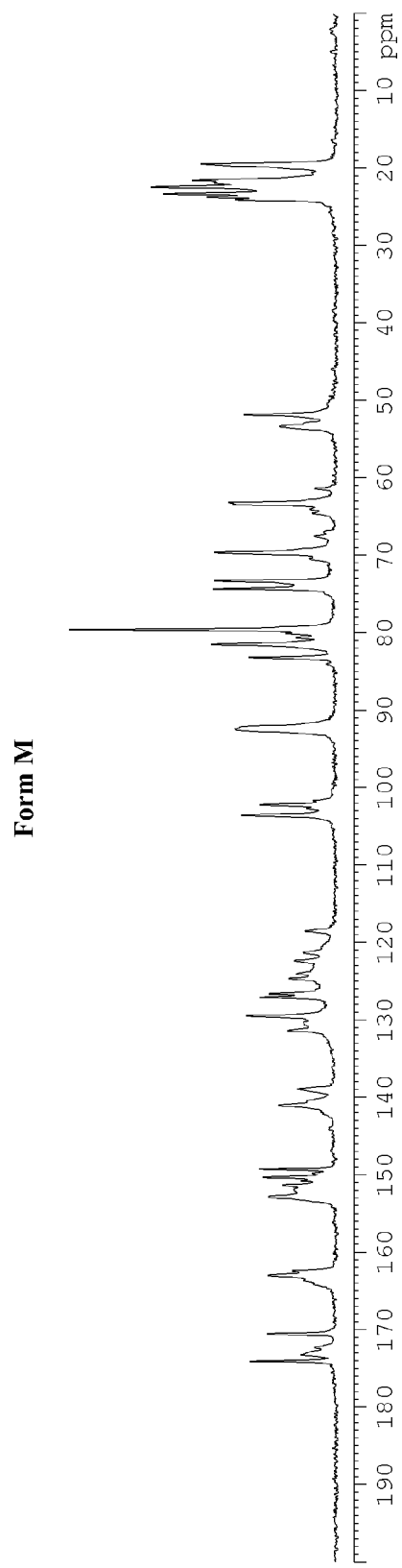
FIG. 28 is a $^{13}$C ssNMR spectrum of Form M.

In some embodiments, Form M can be characterized by a $^{13}$C NMR solid state spectrum of FIG. 28.

In some embodiments, Form M can be characterized by one or more peaks in a $^{13}$C NMR solid state spectrum selected from the table below.

| Peak | v(F1) [ppm] | Intensity [rel] |
|---|---|---|
| 1 | 174.0* | 31.8 |
| 2 | 173.2 | 13.03 |
| 3 | 172.3 | 7.89 |
| 4 | 170.5* | 25.18 |
| 5 | 163.6 | 11.98 |
| 6 | 163.0 | 24.93 |
| 7 | 162.4 | 16.01 |
| 8 | 152.8 | 24.75 |
| 9 | 151.8 | 15.28 |
| 10 | 151.3 | 19.55 |
| 11 | 150.7 | 13.04 |
| 12 | 150.3 | 26.82 |
| 13 | 149.8 | 8.82 |
| 14 | 149.3 | 28.40 |
| 15 | 141.0 | 21.01 |
| 16 | 138.9 | 14.25 |
| 17 | 131.3 | 17.74 |
| 18 | 130.3 | 11.77 |
| 19 | 129.5* | 32.91 |
| 20 | 127.0 | 27.77 |
| 21 | 126.6 | 24.70 |
| 22 | 124.7 | 17.32 |
| 23 | 124.0 | 14.60 |
| 24 | 122.4 | 15.29 |
| 25 | 121.3 | 12.07 |

-continued

| Peak | ν(F1) [ppm] | Intensity [rel] |
|---|---|---|
| 26 | 118.5 | 11.42 |
| 27 | 103.5 | 34.79 |
| 28 | 102.7 | 10.83 |
| 29 | 102.2 | 27.86 |
| 30 | 101.7 | 8.62 |
| 31 | 92.5 | 36.95 |
| 32 | 83.2 | 31.87 |
| 33 | 81.5 | 45.71 |
| 34 | 80.6 | 14.75 |
| 35 | 80.1 | 18.58 |
| 36 | 79.6* | 100.00 |
| 37 | 74.3 | 44.8 |
| 38 | 73.3 | 44.3 |
| 39 | 70.5 | 10.0 |
| 40 | 69.7* | 44.6 |
| 41 | 67.5 | 8.1 |
| 42 | 64.5 | 8.8 |
| 43 | 64.0 | 9.6 |
| 44 | 63.2* | 39.5 |
| 45 | 61.4 | 8.0 |
| 46 | 53.3 | 20.6 |
| 47 | 51.8* | 33.6 |
| 48 | 24.0* | 37.0 |
| 49 | 23.7 | 47.1 |
| 50 | 23.3 | 62.9 |
| 51 | 22.4 | 67.7 |
| 52 | 21.9 | 44.5 |
| 53 | 21.6 | 52.4 |
| 54 | 20.5 | 8.9 |
| 55 | 19.5* | 49.4 |

Peaks with an asterisk (*) are major peaks

Form N

In some embodiments, Compound 1 can be 2'-C-methyluridine-5'-(O-phenyl-N—(S)-1-(isopropoxycarbonyl)ethyl)thiophosphoramidate characterized as Form N.

In some embodiments, Form N can be characterized by one or more peaks in an X-ray powder diffraction pattern, wherein the one or more peaks is selected from a peak in the range of from about 12.2 to about 12.6 degrees, a peak in the range of from about 15.1 to about 15.5 degrees, a peak in the range of from about 16.9 to about 17.3 degrees, and a peak in the range of from about 17.7 to about 18.1 degrees.

In some embodiments, Form N can be characterized by one or more peaks in an X-ray powder diffraction pattern, wherein the one or more peaks is selected from a peak at about 12.4 degrees, a peak at about 15.3 degrees, a peak at about 17.1 degrees, and a peak at about 17.9 degrees.

In some embodiments, Form N can be characterized by a peak at about 12.4 degrees, a peak at about 15.3 degrees, a peak at about 17.1 degrees, and a peak at about 17.9 degrees in an X-ray powder diffraction pattern.

Figure 29:
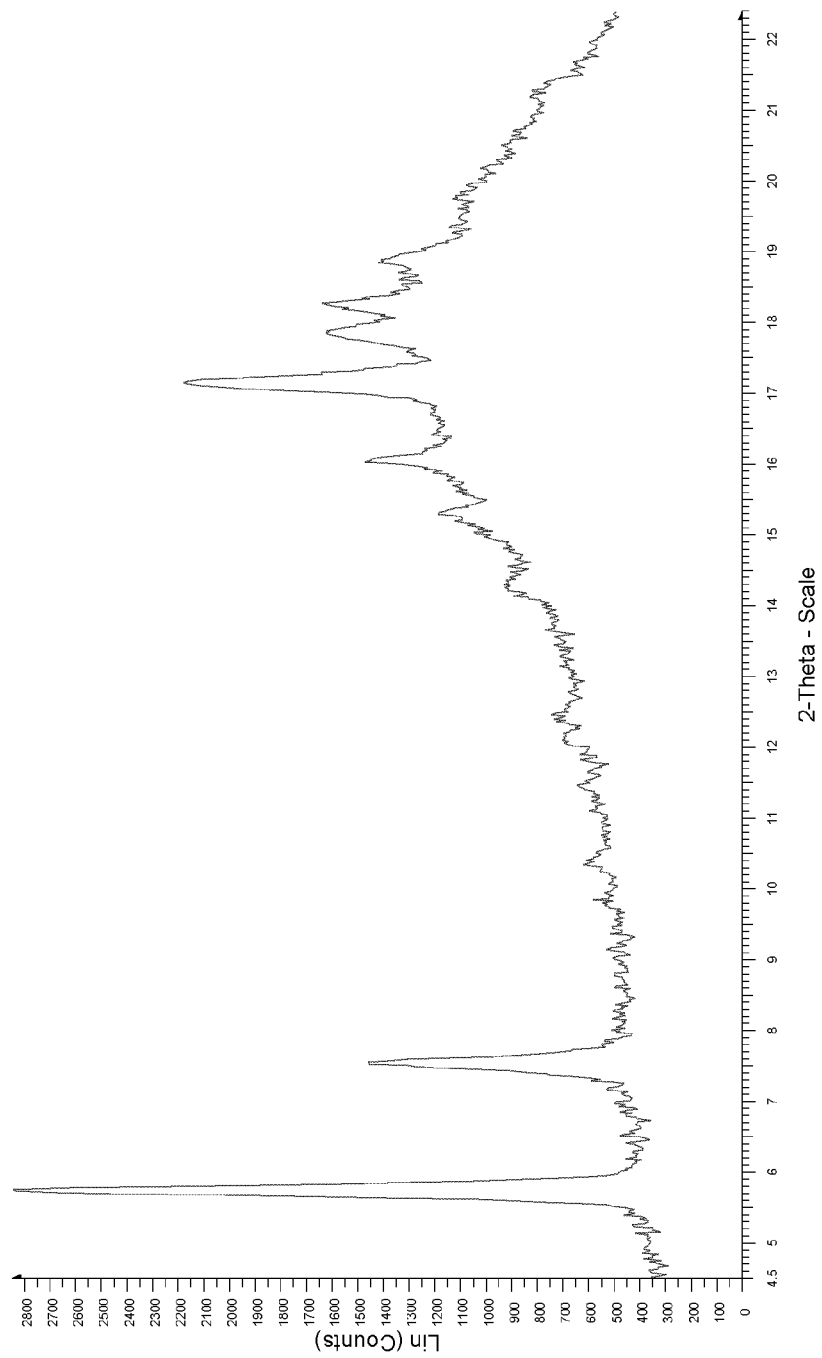
FIG. 29 is an XRPD spectrum of Form N.

In some embodiments, Form N can be characterized by an X-ray powder diffraction pattern of FIG. 29.

In some embodiments, Form N can be characterized by one or more XRPD peaks selected from the table below.

| No. | 2-Theta ° | Intensity % |
|---|---|---|
| 1 | 12.419* | 25.7 |
| 2 | 15.310* | 41.7 |
| 3 | 17.149* | 76.6 |
| 4 | 17.873* | 57.0 |

Peaks with an asterisk (*) are major peaks

In some embodiments, Form N can be characterized by one or more peaks in a $^{13}$C NMR solid state spectrum, wherein the one or more peaks is selected from a peak at about 172.6 ppm, a peak at about 130.4 ppm, a peak at about 129.2 ppm, a peak at about 128.4 ppm, a peak at about 82.2 ppm, a peak at about 74.0 ppm, a peak at about 67.7 ppm, and a peak at about 21.3 ppm.

In some embodiments, Form N can be characterized by one or more peaks in a $^{13}$C NMR solid state spectrum, wherein the one or more peaks is selected from a peak at about 172.6 ppm, a peak at about 130.4 ppm, a peak at about 129.5 ppm, a peak at about 129.2 ppm, a peak at about 128.4 ppm, a peak at about 82.2 ppm, a peak at about 74.0 ppm, a peak at about 67.7 ppm, and a peak at about 21.3 ppm.

In some embodiments, Form N can be characterized by a peak at about 129.2 ppm, a peak at about 128.4 ppm, a peak at about 82.2 ppm, and a peak at about 67.7 ppm in a $^{13}$C NMR solid state spectrum.

In some embodiments, Form N can be characterized by a peak at about 172.6 ppm, a peak at about 130.4 ppm, a peak at about 129.2 ppm, a peak at about 128.4 ppm, a peak at about 82.2 ppm, a peak at about 74.0 ppm, a peak at about 67.7 ppm, and a peak at about 21.3 ppm in a $^{13}$C NMR solid state spectrum.

Figure 30:
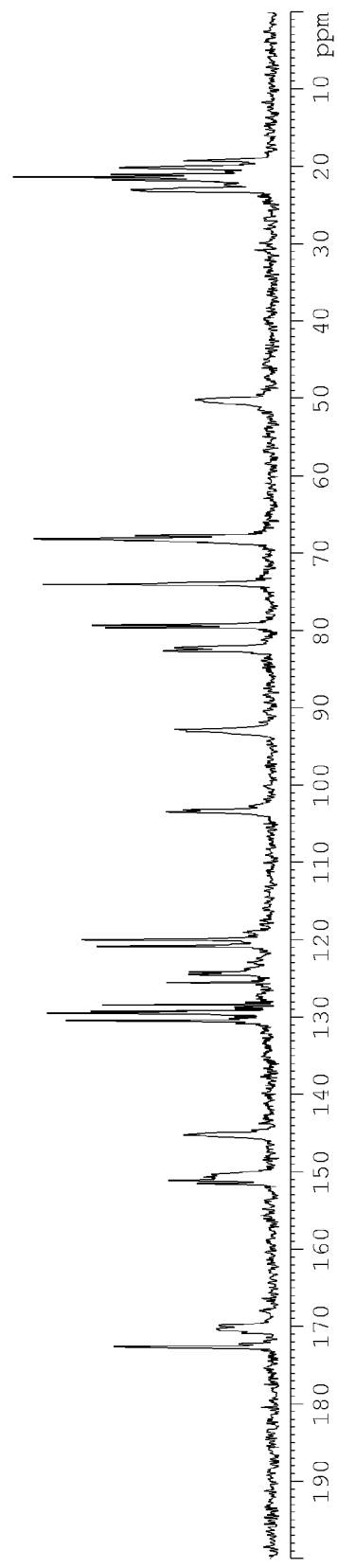
FIG. 30 is a $^{13}$C ssNMR spectrum of Form N.
Figure 31:
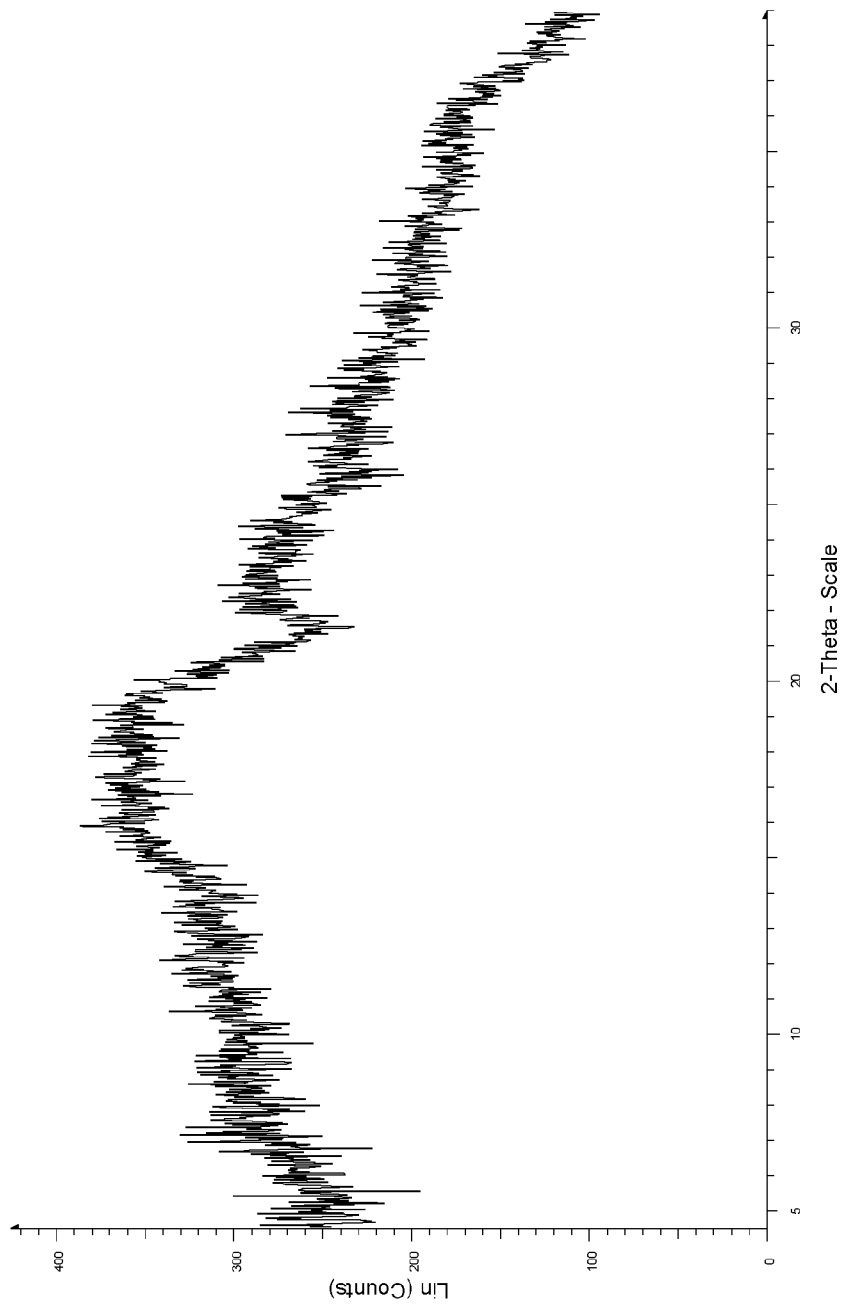
FIG. 31 is an XRPD spectrum of Amorphous Form O.

In some embodiments, Form N can be characterized by a $^{13}$C solid state NMR solid state spectrum of FIG. 30.

In some embodiments, Form N can be characterized by one or more peaks in a $^{13}$C NMR solid state spectrum selected from the table below.

| Peak | ν(F1) [ppm] | Intensity [rel] |
|---|---|---|
| 1 | 172.6* | 60.5 |
| 2 | 170.3 | 21.21 |
| 3 | 169.9 | 20.31 |
| 4 | 151.5 | 28.70 |
| 5 | 151.1 | 40.12 |
| 6 | 150.6 | 26.12 |
| 7 | 145.2 | 33.34 |
| 8 | 130.4* | 78.13 |
| 9 | 129.5* | 87.88 |
| 10 | 129.2* | 70.02 |
| 11 | 128.4* | 64.31 |
| 12 | 125.5 | 40.20 |
| 13 | 124.4 | 31.97 |
| 14 | 124.2 | 31.70 |
| 15 | 120.8 | 66.36 |
| 16 | 120.0 | 74.60 |
| 17 | 103.5 | 40.76 |
| 18 | 103.2 | 33.90 |
| 19 | 92.8 | 37.18 |
| 20 | 82.6 | 41.88 |
| 21 | 82.2* | 37.02 |
| 22 | 79.6 | 64.84 |
| 23 | 79.3 | 68.37 |
| 24 | 74.0* | 88.74 |
| 25 | 68.6 | 28.92 |
| 26 | 68.4 | 57.45 |
| 27 | 68.1 | 92.39 |
| 28 | 67.7* | 51.91 |
| 29 | 50.2 | 29.20 |
| 30 | 23.0 | 54.35 |
| 31 | 22.3 | 18.31 |
| 32 | 21.8 | 60.50 |
| 33 | 21.3* | 100.00 |
| 34 | 21.1 | 61.99 |
| 35 | 20.6 | 18.12 |
| 36 | 20.2 | 58.39 |
| 37 | 19.3 | 34.4 |

Peaks with an asterisk (*) are major peaks

Amorphous Form O

In some embodiments, Compound 1 can be 2'-C-methyluridine-5'-(O-phenyl-N—(S)-1-(isopropoxycarbonyl)ethyl)thiophosphoramidate characterized as Amorphous Form O.

In some embodiments, the Amorphous Form O contains less than about 30% crystallinity. In other embodiments, the Amorphous Form O contains less than about 15% crystallinity. In still other embodiments, the Amorphous Form O contains less than about 1.0% crystallinity. In yet still other embodiments, the Amorphous Form O contains substantially no crystallinity. In some embodiments, the Amorphous Form O is substantially amorphous. In other embodiments, the Amorphous Form O is completely amorphous (i.e., 100% amorphous).

Some embodiments described herein relate to a process for producing Form A that can include:
a) contacting Compound 1 with a first amount of ethyl acetate to form a mixture;
b) heating the mixture until the solids are dissolved;
c) cooling the mixture to allow precipitation of a solid;
d) optionally adding a second amount of ethyl acetate and repeating steps a, b and c; and
e) isolating the solid Form A from said mixture.

In some embodiments, the temperature in step b) can be in the range of from about 55° C. to about 65° C. (for example, about 60° C.).

In some embodiments, the temperature in step c) can be in the range of from about 18° C. to about 24° C. (for example, about 21° C.). In some embodiments, the temperature in step c) can be room temperature (RT).

In some embodiments, the second amount of ethyl acetate in step d) can be approximately equal to the first amount of ethyl acetate used in step a). In other embodiments, the second amount of ethyl acetate in step d) can be up to five times the first amount of ethyl acetate used in step a). In other still other embodiments, the second amount of ethyl acetate in step d) can be less than the first amount of ethyl acetate used in step a). In some embodiments, the first amount of ethyl acetate in step a) can be in the range of from about 1 mL to about 3 mL per gram of Compound 1. In some embodiments, the first amount of ethyl acetate in step a) can be about 2 mL per gram of Compound 1.

In some embodiments, steps a, b and c can be repeated at least one time. In other embodiments, steps a, b and c can be repeated at least 2 times. In some embodiments, steps a, b and c can be repeated one time.

In some embodiments, Form A can be isolated from the mixture by filtration.

Other embodiments described herein relate to a process for producing Form J, that can include
a) contacting Amorphous Form O with ethanol to form a mixture; and
b) isolating Form J from said mixture.

In some embodiments, the mixture can be stirred at room temperature for about 12 hours before isolating Form J. In some embodiments, the mixture can be stirred at a temperature in the range of about 20° C. to about 30° C. for about 12 hours before isolating Form J.

In some embodiments, about 100 mg of Amorphous Form O can be contacted with an amount of ethanol in the range of from about 100 µL to about 200 µL of ethanol. In other embodiments, about 100 mg of Amorphous Form O can be contacted with about 150 µL of ethanol. In some embodiments, the ethanol can be HPLC grade ethanol.

In some embodiments, Form J can be isolated from the mixture by filtration.

Still other embodiments described herein relate to a process for producing a solvated solid form of Compound 1, that can include
a) contacting Compound 1 with a solvent to form a mixture; and
b) isolating the solvated solid form of Compound 1 from said mixture.

In some embodiments, the solvated solid form of Compound 1 can be isolated from the mixture by a method selected from filtration and evaporation.

In some embodiments, the solvent can be MTBE, cyclohexane, nitromethane, acetonitrile, dioxane, THF, dichloromethane, ethyl acetate, isopropyl acetate, chloroform, chlorobenzene, 1,2-dichloroethane, 1,2,3-trichloroethane, or toluene.

In some embodiments, the solvent can be MTBE or cyclohexane and the solvated solid form can be Form B. In other embodiments, the solvent can be nitromethane and the solvated solid form can be Form C. In still other embodiments, the solvent can be dioxane and the solvated solid form can be Form E. In yet still other embodiments, the solvent can be THF and the solvated solid form can be Form F. In some embodiments, the solvent can be dichloromethane and the solvated solid form can be Form G. In other embodiments, the solvent can be acetonitrile and the solvated solid form can be Form H or Form L. In still other embodiments, the solvent can be ethyl acetate or isopropyl acetate and the solvated solid form can be Form I. In yet still other embodiments, the solvent can be chloroform, chlorobenzene, 1,2-dichloroethane or 1,2,3-trichloroethane and the solvated solid form can be Form K. In some embodiments, the solvent can be toluene and the solvated solid form can be Form N.

In some embodiments, the mixture can be sonicated before isolating the solvated solid form.

In some embodiments, the amount of solvent added in step a) above is in the range of from about 0.5 mL to about 10 mL per gram of Compound 1. In some embodiments, the amount of solvent added in step a) above is about 0.83 mL per gram of Compound 1. In other embodiments, the amount of solvent added in step a) above is about 1.0 mL per gram of Compound 1. In still other embodiments, the amount of solvent added in step a) above is about 1.5 mL per gram of Compound 1. In yet still other embodiments, the amount of solvent added in step a) above is about 1.9 mL per gram of Compound 1. In some embodiments, the amount of solvent added in step a) above is about 2.0 mL per gram of Compound 1. In other embodiments, the amount of solvent added in step a) above is about 2.5 mL per gram of Compound 1. In still other embodiments, the amount of solvent added in step a) above is about 3.3 mL per gram of Compound 1. In yet still other embodiments, the amount of solvent added in step a) above is about 4.0 mL per gram of Compound 1. In some embodiments, the amount of solvent added in step a) above is about 5.0 mL per gram of Compound 1. In other embodiments, the amount of solvent added in step a) above is about 6.1 mL per gram of Compound 1. In still other embodiments, the amount of solvent added in step a) above is about 10.0 mL per gram of Compound 1.

In some embodiments, the process further can include removing the solvent from the solvated solid form of Compound 1, including one or more of those described herein, to provide a desolvated solid form of Compound 1. In some embodiments, the desolvated solid form of Compound 1 can be Form D. In other embodiments, the desolvated solid form of Compound 1 can be Form M.

Uses, Formulation and Administration

Pharmaceutically acceptable compositions

Some embodiments described herein generally relate to a pharmaceutical composition that can include one or more solid forms of Compound 1 as described herein, and optionally comprise a pharmaceutically acceptable carrier, adjuvant or vehicle.

Other embodiments described herein relate to a pharmaceutical composition that can include one or more solid forms of Compound 1, and one or more additional agent(s). In some embodiments, the one or more additional agent(s) can be selected from Pegylated interferon-alpha-2a (brand name PEGASYS®) and ribavirin, Pegylated interferon-alpha-2b (brand name PEG-INTRON®) and ribavirin, a HCV protease inhibitor, a HCV polymerase inhibitor, and a NS5A inhibitor.

In some embodiments, the one or more agents can be selected from an interferon, ribavirin, a HCV protease inhibitor, a HCV polymerase inhibitor, a NS5A inhibitor, an antiviral compound, a compound of Formula (BB) and a compound of Formula (DD), or a pharmaceutically acceptable salt any of the aforementioned compounds.

In some embodiments, the one or more agents can be selected from Compounds 1000-1066 and 8001-8012, or a pharmaceutically acceptable salt of any of the aforementioned compounds.

In some embodiments, including those embodiments described previously, the pharmaceutical composition can include a single diastereomer of Compound 1, or a pharmaceutically acceptable salt thereof, (for example, a single diastereomer is present in the pharmaceutical composition at a concentration of greater than 99% compared to the total concentration of the diastereomers of Compound 1). In other embodiments, the pharmaceutical composition can include a mixture of diastereomers of Compound 1, or a pharmaceutically acceptable salt thereof. For example, the pharmaceutical composition can include a concentration of one diastereomer of >50%, ≥60%, ≥70%, ≥80%, ≥90%, ≥95%, or ≥98%, as compared to the total concentration of diastereomers of Compound 1. In some embodiments, the pharmaceutical composition includes a 1:1 mixture of two diastereomers of Compound 1, or a pharmaceutically acceptable salt thereof.

The term "pharmaceutical composition" refers to a mixture of one or more compounds or forms disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid and salicylic acid. Pharmaceutical compositions will generally be tailored to the specific intended route of administration.

The term "physiologically acceptable" defines a carrier, diluent or excipient that does not abrogate the biological activity and properties of the compound.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes will be targeted to and taken up selectively by the organ.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

Uses of the Solid Forms and Pharmaceutically Acceptable Compositions

Some embodiments disclosed herein relate to a method of treating and/or ameliorating a disease or condition that can include administering to a subject an effective amount of one or more solid forms of Compound 1 as described herein, or a pharmaceutically acceptable salt thereof, or a pharmaceutical composition that includes one or more solid forms of Compound 1 as described herein.

Some embodiments disclosed herein relates to a method of ameliorating or treating a viral infection that can include administering to a subject suffering from the viral infection an effective amount of one or more solid forms of Compound 1 as described herein, or a pharmaceutically acceptable salt thereof, or a pharmaceutical composition that includes one or more solid forms of Compound 1 as described herein. Other embodiments described herein relate to the use of an effective amount of one or more solid forms of Compound 1 as described herein in the preparation of a medicament for ameliorating or treating a viral infection. Still other embodiments described herein relate to one or more solid forms of Compound 1 as described herein, or a pharmaceutically acceptable salt thereof, or a pharmaceutical composition that includes one or more solid forms of Compound 1 as described herein, that can be used for ameliorating and/or treating a viral infection by administering an effective amount of said compound(s). In some embodiments, the viral infection can be a hepatitis C viral (HCV) infection.

Some embodiments disclosed herein relate to methods of ameliorating and/or treating a viral infection that can include contacting a cell infected with the virus with an effective amount of one or more solid forms of Compound 1 as described herein, or a pharmaceutically acceptable salt thereof, or a pharmaceutical composition that includes one or more solid forms of Compound 1 as described herein. Other embodiments described herein relate to using one or more compounds described herein, or a pharmaceutically acceptable salt of a compound described herein, in the manufacture of a medicament for ameliorating and/or treating a viral infection that can include contacting a cell infected with the virus with an effective amount of said compound(s). Still other embodiments described herein relate to one or more compounds described herein, or a pharmaceutically acceptable salt of a compound described herein, that can be used for ameliorating and/or treating a viral infection by contacting a cell infected with the virus with an effective amount of said compound(s). In some embodiments, the compound can be one or more solid forms of Compound 1 as described herein, or a pharmaceutically acceptable salt thereof, or a pharmaceutical composition that includes one or more solid forms of Compound 1 as described herein. In other embodiments, the compound can be a mono-, di- and/or tri-phosphate of one or more solid forms of Compound 1 as described herein, or a pharmaceutically acceptable salt thereof, or a pharmaceutical composition that includes one or more solid forms of Compound 1 as described herein. In some embodiments, the virus can be a HCV virus.

Some embodiments disclosed herein relate to methods of inhibiting replication of a virus that can include contacting a cell infected with the virus with an effective amount of one or more compounds described herein, or a pharmaceutically acceptable salt of a compound described herein, or a pharmaceutical composition that includes one or more compounds described herein, or a pharmaceutically acceptable salt thereof. Other embodiments described herein relate to using one or more compounds described herein, or a pharmaceutically acceptable salt of a compound described herein, in the manufacture of a medicament for inhibiting replication of a virus that can include contacting a cell infected with the virus with an effective amount of said compound(s). Still other embodiments described herein relate to a compound described herein, or a pharmaceutically acceptable salt of a compound described herein, that can be used for inhibiting replication of a virus by contacting a cell infected with the virus with an effective amount of said compound(s). In some embodiments, the compound can be one or more solid forms of Compound 1 as described herein, or a pharmaceutically acceptable salt thereof, or a pharmaceutical composition that includes one or more solid forms of Compound 1 as described herein. In other embodiments, the compound can be a mono-, di- and/or tri-phosphate of one or more solid forms of Compound 1 as described herein, or a pharmaceutically acceptable salt thereof, or a pharmaceutical composition that includes one or more solid forms of Compound 1 as described herein. In some embodiments, the virus can be a HCV virus.

In some embodiments, one or more solid forms of Compound 1 as described herein, or a pharmaceutically acceptable salt thereof, or a pharmaceutical composition that includes one or more solid forms of Compound 1 as described herein, can inhibit an RNA dependent RNA polymerase. In some embodiments, one or more solid forms of Compound 1 as described herein, or a pharmaceutically acceptable salt thereof, or a pharmaceutical composition that includes one or more solid forms of Compound 1 as described herein, can inhibit a HCV polymerase (for example, NS5B polymerase). Some embodiments described herein relate to a method for inhibiting NS5B polymerase activity of a virus that can include contacting a cell (such as a cell infected with HCV) with an effective amount of a compound described herein, whereby inhibiting the NS5B polymerase activity of the virus (for example, HCV). Other embodiments described herein relate to the use of an effective amount of a compound as described as described herein for preparing a medicament for inhibiting NS5B polymerase activity of a virus, such as the NS5B polymerase activity of a hepatitis C virus. Still other embodiments described herein relate to a compound described herein, or a pharmaceutically acceptable salt of a compound described herein, that can be used for inhibiting NS5B polymerase activity that can include contacting a cell (such as a cell infected with HCV) an effective amount of said compound(s). In some embodiments, the compound can be one or more solid forms of Compound 1 as described herein, or a pharmaceutically acceptable salt thereof, or a pharmaceutical composition that includes one or more solid forms of Compound 1 as described herein. In other embodiments, the compound can be a mono-, di- and/or tri-phosphate of one or more solid forms of Compound 1 as described herein, or a pharmaceutically acceptable salt thereof, or a pharmaceutical composition that includes one or more solid forms of Compound 1 as described herein. In some embodiments, the virus can be a HCV virus.

HCV is an enveloped positive strand RNA virus in the Flaviviridae family. There are various nonstructural proteins of HCV, such as NS2, NS3, NS4A, NS4B, NS5A, and NS5B. NS5B is believed to be an RNA-dependent RNA polymerase involved in the replication of HCV RNA.

Some embodiments described herein relate to a method of treating HCV infection in a subject suffering from a HCV infection that can include administering to the subject an effective amount of one or more solid forms of Compound 1 as described herein, or a pharmaceutically acceptable salt thereof, or a pharmaceutical composition that includes one or more solid forms of Compound 1 as described herein. Other embodiments described herein relate to the use of an effective amount of a compound as described as described herein for preparing a medicament for treating HCV infection in a subject suffering from a HCV infection. Still other embodiments described herein relate to a compound described herein, or a pharmaceutically acceptable salt of a compound described herein, that can be used for treating HCV infection in a subject suffering from a HCV infection that can include administering an effective amount of said compound(s).

There are a variety of genotypes of HCV, and a variety of subtypes within each genotype. For example, at present it is known that there are eleven (numbered 1 through 11) main genotypes of HCV, although others have classified the genotypes as 6 main genotypes. Each of these genotypes is further subdivided into subtypes (1a-1c; 2a-2c; 3a-3b; 4a-4e; 5a; 6a; 7a-7b; 8a-8b; 9a; 10a; and 11a). In some embodiments, an effective amount of one or more solid forms of Compound 1 as described herein, or a pharmaceutically acceptable salt thereof, or a pharmaceutical composition that includes one or more solid forms of Compound 1 as described herein, can be effective to treat at least one genotype of HCV. In some embodiments, a compound described herein (for example, one or more solid forms of Compound 1 as described herein, or a pharmaceutically acceptable salt thereof, or a pharmaceutical composition that includes one or more solid forms of Compound 1 as described herein) can be effective to treat all 11 genotypes of HCV. In some embodiments, a compound described herein (for example, one or more solid forms of Compound 1 as described herein, or a pharmaceutically acceptable salt thereof, or a pharmaceutical composition that includes one or more solid forms of Compound 1 as described herein) can be effective to treat 3 or more, 5 or more, 7 or more of 9 more genotypes of HCV. In some embodiments, one or more solid forms of Compound 1 as described herein, or a pharmaceutically acceptable salt thereof, or a pharmaceutical composition that includes one or more solid forms of Compound 1 as described herein is more effective against a larger number of HCV genotypes than the standard of care. In some embodiments, one or more solid forms of Compound 1 as described herein, or a pharmaceutically acceptable salt thereof, or a pharmaceutical composition that includes one or more solid forms of Compound 1 as described herein, is more effective against a particular HCV genotype than the standard of care (such as genotype 1, 2, 3, 4, 5 and/or 6).

Various indicators for determining the effectiveness of a method for treating a HCV infection are known to those skilled in the art. Example of suitable indicators include, but are not limited to, a reduction in viral load, a reduction in viral replication, a reduction in time to seroreversion (virus undetectable in patient serum), an increase in the rate of sustained viral response to therapy, a reduction of morbidity or mortality in clinical outcomes, a reduction in the rate of liver function decrease; stasis in liver function; improvement in liver function; reduction in one or more markers of liver dysfunction, including alanine transaminase, aspartate transaminase, total bilirubin, conjugated bilirubin, gamma glutamyl transpeptidase, and/or other indicator of disease response. Similarly, successful therapy with an effective amount of a compound or a pharmaceutical composition described herein (for example, one or more solid forms of Compound 1 as described herein, or a pharmaceutically acceptable salt thereof, or a pharmaceutical composition that includes one or more solid forms of Compound 1 as described herein) can reduce the incidence of liver cancer in HCV patients.

Some embodiments described herein relate to a method of treating a condition selected from liver fibrosis, liver cirrhosis, and liver cancer in a subject suffering from one or more of the aforementioned liver conditions that can include administering to the subject an effective amount of a compound or a pharmaceutical composition described herein (for example, one or more solid forms of Compound 1 as described herein, or a pharmaceutically acceptable salt thereof, or a pharmaceutical composition that includes one or more solid forms of Compound 1 as described herein). One cause of the liver fibrosis, liver cirrhosis, and/or liver cancer can be a HCV infection. Some embodiments described herein relate to a method of increasing liver function in a subject having a HCV infection that can include administering to the subject an effective amount of a compound or a pharmaceutical composition described herein (for example, one or more solid forms of Compound 1 as described herein, or a pharmaceutically acceptable salt thereof, or a pharmaceutical composition that includes one or more solid forms of Compound 1 as described herein). Also contemplated is a method for reducing or eliminating further virus-caused liver damage in a subject having an HCV infection by administering to the subject an effective amount of a compound or a pharmaceutical composition described herein (for example, one or more solid forms of Compound 1 as described herein, or a pharmaceutically acceptable salt thereof, or a pharmaceutical composition that includes one or more solid forms of Compound 1 as described herein). In some embodiments, this method comprises slowing or halting the progression of liver disease. In other embodiments, the course of the disease is reversed, and stasis or improvement in liver function is contemplated.

In some embodiments, an effective amount of one or more solid forms of Compound 1 as described herein, or a pharmaceutically acceptable salt thereof, or a pharmaceutical composition that includes one or more solid forms of Compound 1 as described herein, is an amount that is effective to reduce viral titers undetectable levels, for example, to about 100 to about 500, to about 50 to about 100, to about 10 to about 50, or to about 15 to about 25 international units/mL serum. In some embodiments, an effective amount of one or more solid forms of Compound 1 as described herein, or a pharmaceutically acceptable salt thereof, or a pharmaceutical composition that includes one or more solid forms of Compound 1 as described herein, is an amount that is effective to reduce viral load compared to the viral load before administration of one or more solid forms of Compound 1 as described herein, or a pharmaceutically acceptable salt thereof, or a pharmaceutical composition that includes one or more solid forms of Compound 1 as described herein. For example, wherein the viral load is measured before administration of one or more solid forms of Compound 1 as described herein, or a pharmaceutically acceptable salt thereof, or a pharmaceutical composition that includes one or more solid forms of Compound 1 as described herein, and again after completion of the treatment regime with one or more solid forms of Compound 1 as described herein, or a pharmaceutically acceptable salt thereof, or a pharmaceutical composition that includes one or more solid forms of Compound 1 as described herein (for example, 1 month after completion). In some embodiments, an effective amount of one or more solid forms of Compound 1 as described herein, or a pharmaceutically acceptable salt thereof, or a pharmaceutical composition that includes one or more solid forms of Compound 1 as described herein, can be an amount that is effective to reduce viral load to lower than about 100 genome copies/mL serum. In some embodiments, an effective amount of one or more solid forms of Compound 1 as described herein, or a pharmaceutically acceptable salt thereof, or a pharmaceutical composition that includes one or more solid forms of Compound 1 as described herein, is an amount that is effective to achieve a reduction in viral titer in the serum of the subject in the range of about 1.5-log to about a 2.5-log reduction, about a 3-log to about a 4-log reduction, or a greater than about 5-log reduction compared to the viral load before administration of one or more solid forms of Compound 1 as described herein, or a pharmaceutically acceptable salt thereof, or a pharmaceutical composition that includes one or more solid forms of Compound 1 as described herein. For example, the viral load can be measured before administration of one or more solid forms of Compound 1 as described herein, or a pharmaceutically acceptable salt thereof, or a pharmaceutical composition that includes one or more solid forms of Compound 1 as described herein, and again after completion of the treatment regime with one or more solid forms of Compound 1 as described herein, or a pharmaceutically acceptable salt thereof, or a pharmaceutical composition that includes one or more solid forms of Compound 1 as described herein (for example, 1 month after completion).

In some embodiments, one or more solid forms of Compound 1 as described herein, or a pharmaceutically acceptable salt thereof, or a pharmaceutical composition that includes one or more solid forms of Compound 1 as described herein, can result in at least a 1, 2, 3, 4, 5, 10, 15, 20, 25, 50, 75, 100-fold or more reduction in the replication of HCV relative to pre-treatment levels in a subject, as determined after completion of the treatment regime (for example 1 month after completion). In some embodiments, one or more solid forms of Compound 1 as described herein, or a pharmaceutically acceptable salt thereof, or a pharmaceutical composition that includes one or more solid forms of Compound 1 as described herein, can result in a reduction of the replication of HCV relative to pre-treatment levels in the range of about 2 to about 5 fold, about 10 to about 20 fold, about 15 to about 40 fold, or about 50 to about 100 fold. In some embodiments, one or more solid forms of Compound 1 as described herein, or a pharmaceutically acceptable salt thereof, or a pharmaceutical composition that includes one or more solid forms of Compound 1 as described herein, can result in a reduction of HCV replication in the range of 1 to 1.5 log, 1.5 log to 2 log, 2 log to 2.5 log, 2.5 to 3 log, 3 log to 3.5 log or 3.5 to 4 log more reduction of HCV replication compared to the reduction of HCV reduction achieved by pegylated interferon in combination with ribavirin, administered according to the standard of care, or may achieve the same reduction as that standard of care therapy in a shorter period of time, for example, in one month, two months, or three months, as compared to the reduction achieved after six months of standard of care therapy with ribavirin and pegylated interferon.

In some embodiments, an effective amount of one or more solid forms of Compound 1 as described herein, or a pharmaceutically acceptable salt thereof, or a pharmaceutical composition that includes one or more solid forms of Compound 1 as described herein, is an amount that is effective to achieve a sustained viral response, for example, non-detectable or substantially non-detectable HCV RNA (e.g., less than about 500, less than about 400, less than about 200, or less than about 100 genome copies per milliliter serum) is found in the subject's serum for a period of at least about one month, at least about two months, at least about three months, at least about four months, at least about five months, or at least about six months following cessation of therapy.

In some embodiments, an effective amount one or more solid forms of Compound 1 as described herein, or a pharmaceutically acceptable salt thereof, or a pharmaceutical composition that includes one or more solid forms of Compound 1 as described herein, can reduce a level of a marker of liver fibrosis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the level of the marker in an untreated subject, or to a placebo-treated subject. Methods of measuring serum markers are known to those skilled in the art and include immunological-based methods, e.g., enzyme-linked immunosorbent assays (ELISA), radioimmunoassays, and the like, using antibody specific for a given serum marker. A non-limiting list of examples of markers include measuring the levels of serum alanine aminotransferase (ALT), aspartate aminotransferase (AST), alkaline phosphatase (ALP), gamma-glutamyl transpeptidase (GGT) and total bilirubin (TBIL) using known methods. In general, an ALT level of less than about 45 IU/L (international units/liter), an AST in the range of 10-34 IU/L, ALP in the range of 44-147 IU/L, GGT in the range of 0-51 IU/L, TBIL in the range of 0.3-1.9 mg/dL is considered normal. In some embodiments, an effective amount of one or more solid forms of Compound 1 as described herein, or a pharmaceutically acceptable salt thereof, or a pharmaceutical composition that includes one or more solid forms of Compound 1 as described herein is an amount effective to reduce ALT, AST, ALP, GGT and/or TBIL levels to with what is considered a normal level.

Subjects who are clinically diagnosed with HCV infection include "naïve" subjects (e.g., subjects not previously treated for HCV, particularly those who have not previously received IFN-alpha-based and/or ribavirin-based therapy) and individuals who have failed prior treatment for HCV ("treatment failure" subjects). Treatment failure subjects include "non-responders" (i.e., subjects in whom the HCV titer was not significantly or sufficiently reduced by a previous treatment for HCV (≤0.5 log IU/mL), for example, a previous IFN-alpha monotherapy, a previous IFN-alpha and ribavirin combination therapy, or a previous pegylated IFN-alpha and ribavirin combination therapy); and "relapsers" (i.e., subjects who were previously treated for HCV, for example, who received a previous IFN-alpha monotherapy, a previous IFN-alpha and ribavirin combination therapy, or a previous pegylated IFN-alpha and ribavirin combination therapy, whose HCV titer decreased, and subsequently increased).

In some embodiments, one or more solid forms of Compound 1 as described herein, or a pharmaceutically acceptable salt thereof, or a pharmaceutical composition that includes one or more solid forms of Compound 1 as described herein, can be administered to a treatment failure subject suffering from HCV. In some embodiments, one or more solid forms of Compound 1 as described herein, or a pharmaceutically acceptable salt thereof, or a pharmaceutical composition that includes one or more solid forms of Compound 1 as described herein, can be administered to a non-responder subject suffering from HCV. In some embodiments, one or more solid forms of Compound 1 as described herein, or a pharmaceutically acceptable salt thereof, or a pharmaceutical composition that includes one or more solid forms of Compound 1 as described herein, can be administered to a relapsed subject suffering from HCV.

After a period of time, infectious agents can develop resistance to one or more therapeutic agents. The term "resistance" as used herein refers to a viral strain displaying a delayed, lessened and/or null response to a therapeutic agent(s). For example, after treatment with an antiviral agent, the viral load of a subject infected with a resistant virus may be reduced to a lesser degree compared to the amount in viral load reduction exhibited by a subject infected with a non-resistant strain. In some embodiments, one or more solid forms of Compound 1 as described herein, or a pharmaceutically acceptable salt thereof, or a pharmaceutical composition that includes one or more solid forms of Compound 1 as described herein, can be administered to a subject infected with an HCV strain that is resistant to one or more different anti-HCV agents. In some embodiments, development of resistant HCV strains is delayed when patients are treated with one or more solid forms of Compound 1 as described herein, or a pharmaceutically acceptable salt thereof, or a pharmaceutical composition that includes one or more solid forms of Compound 1 as described herein, compared to the development of HCV strains resistant to other HCV drugs.

In some embodiments, an effective amount of one or more solid forms of Compound 1 as described herein, or a pharmaceutically acceptable salt thereof, or a pharmaceutical composition that includes one or more solid forms of Compound 1 as described herein, can be administered to a subject for whom other anti-HCV medications are contraindicated. For example, administration of pegylated interferon alpha in combination with ribavirin is contraindicated in subjects with hemoglobinopathies (e.g., thalassemia major, sickle-cell anemia) and other subjects at risk from the hematologic side effects of current therapy. In some embodiments, one or more solid forms of Compound 1 as described herein, or a pharmaceutically acceptable salt thereof, or a pharmaceutical composition that includes one or more solid forms of Compound 1 as described herein, can be provided to a subject that is hypersensitive to interferon or ribavirin.

Some subjects being treated for HCV experience a viral load rebound. The term "viral load rebound" as used herein refers to a sustained ≥0.5 log IU/mL increase of viral load above nadir before the end of treatment, where nadir is a ≥0.5 log IU/mL decrease from baseline. In some embodiments, one or more solid forms of Compound 1 as described herein, or a pharmaceutically acceptable salt thereof, or a pharmaceutical composition that includes one or more solid forms of Compound 1 as described herein, can be administered to a subject experiencing viral load rebound, or can prevent such viral load rebound when used to treat the subject.

The standard of care for treating HCV has been associated with several side effects (adverse events). In some embodiments, one or more solid forms of Compound 1 as described herein, or a pharmaceutically acceptable salt thereof, or a pharmaceutical composition that includes one or more solid forms of Compound 1 as described herein, can decrease the number and/or severity of side effects that can be observed in HCV patients being treated with ribavirin and pegylated interferon according to the standard of care. Examples of side effects include, but are not limited to fever, malaise, tachycardia, chills, headache, arthralgias, myalgias, fatigue, apathy, loss of appetite, nausea, vomiting, cognitive changes, asthenia, drowsiness, lack of initiative, irritability, confusion, depression, severe depression, suicidal ideation, anemia, low white blood cell counts, and thinning of hair. In some embodiments, one or more solid forms of Compound 1 as described herein, or a pharmaceutically acceptable salt thereof, or a pharmaceutical composition that includes one or more solid forms of Compound 1 as described herein, can be provided to a subject that discontinued a HCV therapy because of one or more adverse effects or side effects associated with one or more other HCV agents.

Table 1 provides some embodiments of one or more solid forms of Compound 1 as described herein, or a pharmaceutically acceptable salt thereof, or a pharmaceutical composition that includes one or more solid forms of Compound 1 as described herein, compared to the standard of care. Examples include the following: in some embodiments, one or more solid forms of Compound 1 as described herein, or a pharmaceutically acceptable salt thereof, or a pharmaceutical composition that includes one or more solid forms of Compound 1 as described herein, results in a percentage of non-responders that is 10% less than the percentage of non-responders receiving the standard of care; in some embodiments, one or more solid forms of Compound 1 as described herein, or a pharmaceutically acceptable salt thereof, or a pharmaceutical composition that includes one or more solid forms of Compound 1 as described herein, results number of side effects that is in the range of about 10% to about 30% less than compared to the number of side effects experienced by a subject receiving the standard of care; and in some embodiments, one or more solid forms of Compound 1 as described herein, or a pharmaceutically acceptable salt thereof, or a pharmaceutical composition that includes one or more solid forms of Compound 1 as described herein, results a severity of a side effect (such as one of those described herein) that is 25% less than compared to the severity of the same side effect experienced by a subject receiving the standard of care. Methods of quantifying the severity of a side effect are known to those skilled in the art.

TABLE 1

| Percentage of non-responders | Percentage of relapsers | Percentage of resistance | Percentage of viral load rebound | Number of side effects | Severity of side effects |
| --- | --- | --- | --- | --- | --- |
| 10% less | 10% less | 10% less | 10% less | 10% less | 10% less |
| 25% less | 25% less | 25% less | 25% less | 25% less | 25% less |
| 40% less | 40% less | 40% less | 40% less | 40% less | 40% less |
| 50% less | 50% less | 50% less | 50% less | 50% less | 50% less |
| 60% less | 60% less | 60% less | 60% less | 60% less | 60% less |
| 70% less | 70% less | 70% less | 70% less | 70% less | 70% less |
| 80% less | 80% less | 80% less | 80% less | 80% less | 80% less |
| 90% less | 90% less | 90% less | 90% less | 90% less | 90% less |
| about 10% to about 30% less | about 10% to about 30% less | about 10% to about 30% less | about 10% to about 30% less | about 10% to about 30% less | about 10% to about 30% less |
| about 20% to about 50% less | about 20% to about 50% less | about 20% to about 50% less | about 20% to about 50% less | about 20% to about 50% less | about 20% to about 50% less |

TABLE 1-continued

| Percentage of non-responders | Percentage of relapsers | Percentage of resistance | Percentage of viral load rebound | Number of side effects | Severity of side effects |
|---|---|---|---|---|---|
| about 30% to about 70% less | about 30% to about 70% less | about 30% to about 70% less | about 30% to about 70% less | about 30% to about 70% less | about 30% to about 70% less |
| about 20% to about 80% less | about 20% to about 80% less | about 20% to about 80% less | about 20% to about 80% less | about 20% to about 80% less | about 20% to about 80% less |

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

As used herein, the terms "treating," "treatment," "therapeutic," or "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the patient's overall feeling of well-being or appearance.

The term "effective amount" is used to indicate an amount of an active compound, or pharmaceutical agent, that elicits the biological or medicinal response indicated. For example, an effective amount of compound can be the amount needed to prevent, alleviate or ameliorate symptoms of disease or prolong the survival of the subject being treated This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years. In some embodiments, one or more solid forms of Compound 1 as described herein, or a pharmaceutically acceptable salt thereof, or a pharmaceutical composition that includes one or more solid forms of Compound 1 as described herein, can be administered less frequently compared to the frequency of administration of an agent within the standard of care. In some embodiments, one or more solid forms of Compound 1 as described herein, or a pharmaceutically acceptable salt thereof, or a pharmaceutical composition that includes one or more solid forms of Compound 1 as described herein, can be administered one time per day. For example, one or more solid forms of Compound 1 as described herein, or a pharmaceutically acceptable salt thereof, or a pharmaceutical composition that includes one or more solid forms of Compound 1 as described herein, can be administered one time per day to a subject suffering from a HCV infection. In some embodiments, the total time of the treatment regime with one or more solid forms of Compound 1 as described herein, or a pharmaceutically acceptable salt thereof, or a pharmaceutical composition that includes one or more solid forms of Compound 1 as described herein, can less compared to the total time of the treatment regime with the standard of care.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer one or more solid forms of Compound 1 as described herein, or a pharmaceutically acceptable salt thereof, or a pharmaceutical composition that includes one or more solid forms of Compound 1 as described herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

Combination Therapies

In some embodiments, one or more solid forms of Compound 1 as described herein, or a pharmaceutically acceptable salt thereof, or a pharmaceutical composition that includes one or more solid forms of Compound 1 as described herein, can be used in combination with one or more additional agent(s).

Examples of additional agents that can be used in combination with one or more solid forms of Compound 1 as described herein, or a pharmaceutically acceptable salt thereof, or a pharmaceutical composition that includes one or more solid forms of Compound 1 as described herein, include, but are not limited to, agents currently used in a conventional standard of care for treating HCV, HCV protease inhibitors, HCV polymerase inhibitors, NS5A inhibitors, other antiviral compounds, compounds of Formula (BB) (including pharmaceutically acceptable salts and pharmaceutical compositions that can include a compound of Formula (BB), or a pharmaceutically acceptable salt thereof), compounds of Formula (DD) (including pharmaceutically acceptable salts and pharmaceutical compositions that can include a compound of Formula (DD), or a pharmaceutically acceptable salt thereof), and/or combinations thereof. In some embodiments, one or more solid forms of Compound 1 as described herein, or a pharmaceutically acceptable salt thereof, or a pharmaceutical composition that includes one or more solid forms of Compound 1 as described herein, can be used with one, two, three or more additional agents described herein. In some embodiments, one or more solid forms of Compound 1 as described herein, or a pharmaceutically acceptable salt thereof, or a pharmaceutical composition that includes one or more solid forms of Compound 1 as described herein, can be used in combination with an agent(s) currently used in a conventional standard of care therapy. For example, for the treatment of HCV, a compound disclosed herein can be used in combination with Pegylated interferon-alpha-2a (brand name PEGASYS®) and ribavirin, or Pegylated interferon-alpha-2b (brand name PEG-INTRON®) and ribavirin.

In some embodiments, one or more solid forms of Compound 1 as described herein, or a pharmaceutically acceptable salt thereof, or a pharmaceutical composition that includes one or more solid forms of Compound 1 as described herein, can be substituted for an agent currently used in a conventional standard of care therapy. For example, for the treatment of HCV, one or more solid forms of Compound 1 as described herein, or a pharmaceutically acceptable salt thereof, or a pharmaceutical composition that includes one or more solid forms of Compound 1 as described herein, can be used in place of ribavirin.

In some embodiments, one or more solid forms of Compound 1 as described herein, or a pharmaceutically acceptable salt thereof, or a pharmaceutical composition that includes one or more solid forms of Compound 1 as described herein, can be used in combination with an interferon, such as a pegylated interferon. Examples of suitable interferons include, but are not limited to, Pegylated interferon-alpha-2a (brand name PEGASYS®), Pegylated interferon-alpha-2b (brand name PEG-INTRON®), interferon alfacon-1 (brand name INFERGEN®), pegylated interferon lambda and/or a combination thereof.

In some embodiments, one or more solid forms of Compound 1 as described herein, or a pharmaceutically acceptable salt thereof, or a pharmaceutical composition that includes one or more solid forms of Compound 1 as described herein, can be used in combination with a HCV protease inhibitor. A non-limiting list of example HCV protease inhibitors include the following: VX-950 (TELAPREVIR®), MK-5172, ABT-450, BILN-2061, BI-201335, BMS-650032, SCH 503034 (BOCEPREVIR®), GS-9256, GS-9451, IDX-320, ACH-1625, ACH-2684, TMC-435, ITMN-191 (DANOPREVIR®) and/or a combination thereof.

In some embodiments, one or more solid forms of Compound 1 as described herein, or a pharmaceutically acceptable salt thereof, or a pharmaceutical composition that includes one or more solid forms of Compound 1 as described herein, can be used in combination with a HCV polymerase inhibitor. In some embodiments, the HCV polymerase inhibitor can be a nucleoside inhibitor. In other embodiments, the HCV polymerase inhibitor can be a non-nucleoside inhibitor. Examples of suitable nucleoside inhibitors include, but are not limited to, RG7128, PSI-7851, PSI-7977, PSI-352938, PSI-661, 4'-azidouridine (including known prodrugs of 4'-azidouridine), GS-6620, and TMC649128 and/or combinations thereof. A non-limiting list of example nucleoside inhibitors as provided in FIG. 32. Examples of suitable non-nucleoside inhibitors include, but are not limited to, ABT-333, ANA-598, VX-222, HCV-796, BI-207127, GS-9190, PF-00868554 (FILIBUVIR®), VX-497 and/or combinations thereof. A non-limiting list of example non-nucleoside as provided in FIG. 32.

In some embodiments, one or more solid forms of Compound 1 as described herein, or a pharmaceutically acceptable salt thereof, or a pharmaceutical composition that includes one or more solid forms of Compound 1 as described herein, can be used in combination with a NS5A inhibitor. A non-limiting list of example NS5A inhibitors include BMS-790052, GSK-2336805, ACH-3102, PPI-461, ACH-2928, GS-5885, BMS-824393 and/or combinations thereof. A non-limiting list of example NS5A inhibitors as provided in FIG. 32.

In some embodiments, one or more solid forms of Compound 1 as described herein, or a pharmaceutically acceptable salt thereof, or a pharmaceutical composition that includes one or more solid forms of Compound 1 as described herein, can be used in combination with other antiviral compounds. Examples of other antiviral compounds include, but are not limited to, Debio-025, MIR-122 and/or combinations thereof. A non-limiting list of example other antiviral compounds are provided in FIG. 32.

Figure 32:
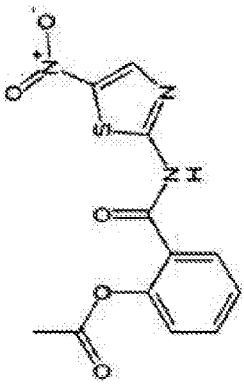
FIG. 32 shows examples of additional agents that can be used to treat HCV.

A non-limiting list of additional agents that can be used in combination with more solid forms of Compound 1 as described herein, or a pharmaceutically acceptable salt thereof, or a pharmaceutical composition that includes one or more solid forms of Compound 1 as described herein, include the following compounds provided in FIG. 32: 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, and 1066.

In some embodiments, one or more solid forms of Compound 1, or a pharmaceutically acceptable salt thereof, or a pharmaceutical composition that includes a compound of Formula (I), or a pharmaceutically acceptable salt thereof, can be used in combination with a compound of Formula (BB), or a pharmaceutically acceptable salt thereof, or a pharmaceutical composition that includes a compound of Formula (BB), or a pharmaceutically acceptable salt thereof (see, U.S. Publication No. 2012/0165286, filed Dec. 20, 2011 the contents of which are incorporated by reference in its entirety):

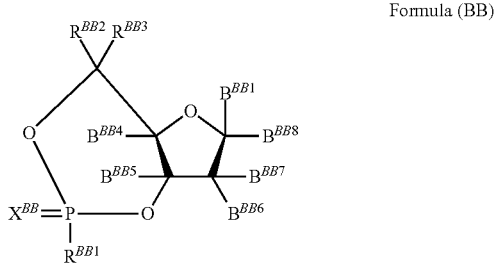

Formula (BB)

wherein $B^{BB1}$ can be an optionally substituted heterocyclic base or an optionally substituted heterocyclic base with a protected amino group; $X^{BB}$ can be O (oxygen) or S (sulfur); $R^{BB1}$ can be selected from $-Z^{BB}-R^{BB9}$, an optionally substituted N-linked amino acid and an optionally substituted N-linked amino acid ester derivative; $Z^{BB}$ can be selected from O (oxygen), S (sulfur) and N($R^{BB10}$); $R^{BB2}$ and $R^{BB3}$ can be independently selected from hydrogen, an optionally substituted $C_{1-6}$ alkyl, an optionally substituted $C_{2-6}$ alkenyl, an optionally substituted $C_{2-6}$ alkynyl, an optionally substituted $C_{1-6}$ haloalkyl and an optionally substituted aryl($C_{1-6}$ alkyl); or $R^{BB2}$ and $R^{BB3}$ can be taken together to form a group selected from an optionally substituted $C_{3-6}$ cycloalkyl, an optionally substituted $C_{3-6}$ cycloalkenyl, an optionally substituted $C_{3-6}$ aryl and an optionally substituted $C_{3-6}$ heteroaryl; $R^{BB4}$ can be selected from hydrogen, halogen, azido, cyano, an optionally substituted $C_{1-6}$ alkyl, an optionally substituted $C_{2-6}$ alkenyl, an optionally substituted $C_{2-6}$ alkynyl and an optionally substituted allenyl; $R^{BB5}$ can be hydrogen or an optionally substituted $C_{1-6}$ alkyl; $R^{BB6}$ can be selected from hydrogen, halogen, azido, amino, cyano, an optionally substituted $C_{1-6}$ alkyl, $-OR^{BB11}$ and $-OC(=O)R^{BB12}$; $R^{BB7}$ can be selected from hydrogen, halogen, azido, cyano, an optionally substituted $C_{1-6}$ alkyl, $-OR^{BB13}$ and $-OC(=O)R^{BB14}$; $R^{BB8}$ can be selected from hydrogen, halogen, azido, cyano, an optionally substituted $C_{1-6}$ alkyl, $-OR^{BB15}$ and $-OC(=O)R^{BB16}$; $R^{BB9}$ can be selected from an optionally substituted alkyl, an optionally substituted alkenyl, an optionally substituted alkynyl, an optionally substituted cycloalkyl, an optionally substituted cycloalkenyl, an optionally substituted aryl, an optionally substituted heteroaryl, an optionally substituted heterocyclyl, an optionally substituted aryl($C_{1-6}$alkyl), an optionally substituted heteroaryl($C_{1-6}$alkyl) and an optionally substituted heterocyclyl($C_{1-6}$alkyl); $R^{BB10}$ can be selected from hydrogen, an optionally substituted alkyl, an optionally substituted alkenyl, an optionally substituted alkynyl, an optionally substituted cycloalkyl, an optionally substituted cycloalkenyl, an optionally substituted aryl, an optionally substituted heteroaryl, an optionally substituted heterocyclyl, an optionally substituted aryl($C_{1-6}$alkyl), an optionally substituted heteroaryl($C_{1-6}$alkyl) and an optionally substituted heterocyclyl($C_{1-6}$alkyl); $R^{BB11}$, $R^{BB13}$ and $R^{BB15}$ can be independently hydrogen or an optionally substituted $C_{1-6}$ alkyl; and $R^{BB12}$, $R^{BB14}$ and $R^{BB16}$ can be independently an optionally substituted $C_{1-6}$ alkyl or an optionally substituted $C_{3-6}$ cycloalkyl. In some embodiments, at least one of $R^{BB2}$ and $R^{BB3}$ is not hydrogen. A non-limiting list of example compounds of Formula (BB) includes the compound numbered 8001-8012 in FIG. 33.

In some embodiments, one or more solid forms of Compound 1 as described herein, or a pharmaceutically acceptable salt thereof, or a pharmaceutical composition that includes one or more solid forms of Compound 1 as described herein, can be used in combination with a compound of Formula (DD), or a pharmaceutically acceptable salt thereof, or a pharmaceutical composition that includes a compound of Formula (DD), or a pharmaceutically acceptable salt thereof (see, U.S. Publication No. 2010/0249068, filed Mar. 19, 2010, the contents of which are incorporated by reference in its entirety):

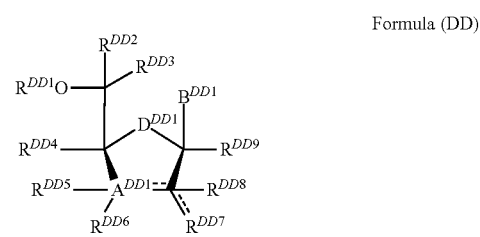

Formula (DD)

wherein each ⚌ can be independently a double or single bond; $A^{DD1}$ can be selected from C (carbon), O (oxygen) and S (sulfur); $B^{DD1}$ can be an optionally substituted heterocyclic base or a derivative thereof; $D^{DD1}$ can be selected from C=CH$_2$, CH$_2$, O (oxygen), S (sulfur), CHF, and CF$_2$; $R^{DD1}$ can be hydrogen, an optionally substituted alkyl, an optionally substituted cycloalkyl, an optionally substituted aralkyl, dialkylaminoalkylene, alkyl-C(=O)—, aryl-C(=O)—, alkoxyalkyl-C(=O)—, aryloxyalkyl-C(=O)—, alkylsulfonyl, arylsulfonyl, aralkylsulfonyl,

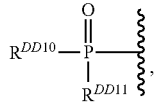

an —O-linked amino acid, diphosphate, triphosphate or derivatives thereof; $R^{DD2}$ and $R^{DD3}$ can be each independently selected from hydrogen, an optionally substituted C$_{1-6}$ alkyl, an optionally substituted C$_{2-6}$ alkenyl, an optionally substituted C$_{2-6}$ alkynyl and an optionally substituted C$_{1-6}$ haloalkyl, provided that at least one of $R^{DD2}$ and $R^{DD3}$ cannot be hydrogen; or $R^{DD2}$ and $R^{DD3}$ are taken together to form a group selected from among C$_{3-6}$ cycloalkyl, C$_{3-6}$ cycloalkenyl, C$_{3-6}$ aryl, and a C$_{3-6}$ heteroaryl; $R^{DD4}$ and $R^{DD9}$ can be independently selected from hydrogen, halogen, —NH$_2$, —NHR$^{DDa1}$, NR$^{DDa1}$R$^{DDb1}$, —OR$^{DDa1}$, —SR$^{DDa1}$, —CN, —NC, —N$_3$, —NO$_2$, —N(R$^{DDc1}$)—NR$^{DDa1}$R$^{DDb1}$, —N(R$^{DDc1}$)—OR$^{DDa1}$, —S—SR$^{DDa1}$, —C(=O)R$^{DDa1}$, —C(=O)OR$^{DDa1}$, —C(=O)NR$^{DDa1}$R$^{DDb1}$, —O—(C=O)R$^{DDa1}$, —O—C(=O)OR$^{DDa1}$, —O—C(=O)NR$^{DDa1}$R$^{DDb1}$, —N(R$^{DDc1}$)—C(=O)NR$^{DDa1}$R$^{DDb1}$, —S(=O)R$^{DDa1}$, S(=O)$_2$R$^{DDa1}$, —O—S(=O)$_2$NR$^{DDa1}$R$^{DDb1}$, —N(R$^{DDc1}$)—S(=O)$_2$NR$^{DDa1}$R$^{DDb1}$, an optionally substituted C$_{1-6}$ alkyl, an optionally substituted C$_{2-6}$ alkenyl, an optionally substituted C$_{2-6}$ alkynyl, an optionally substituted aralkyl and an —O-linked amino acid; $R^{DD5}$, $R^{DD6}$ and $R^{DD7}$ can be independently absent or selected from hydrogen, halogen, —NH$_2$, —NHR$^{DDa1}$, NR$^{DDa1}$R$^{DDb1}$, —OR$^{DDa1}$, —SR$^{DDa1}$, —CN, —NC, —N$_3$, —NO$_2$, —N(R$^{DDc1}$)—NR$^{DDa1}$R$^{DDb1}$, —N(R$^{DDc1}$)—OR$^{DDa1}$, —S—SR$^{DDa1}$, —C(=O)R$^{DDa1}$, —C(=O)OR$^{DDa1}$, —C(=O)NR$^{DDa1}$R$^{DDb1}$, —O—(C=O)R$^{DDa1}$, —O—C(=O)OR$^{DDa1}$, —O—C(=O)NR$^{DDa1}$R$^{DDb1}$, —N(R$^{DDc1}$)—C(=O)NR$^{DDa1}$R$^{DDb1}$, —S(=O)R$^{DDa1}$, S(=O)$_2$R$^{DDa1}$, —O—S(=O)$_2$NR$^{DDa1}$R$^{DDb1}$, —N(R$^{DDc1}$)—S(=O)$_2$NR$^{DDa1}$R$^{DDb1}$, an optionally substituted C$_{1-6}$ alkyl, an optionally substituted C$_{2-6}$ alkenyl, an optionally substituted C$_{2-6}$ alkynyl, an optionally substituted aralkyl and an —O-linked amino acid; or $R^{DD6}$ and $R^{DD7}$ taken together form —O—C(=O)—O—; $R^{DD8}$ can be absent or selected from the group consisting of hydrogen, halogen, —NH$_2$, —NHR$^{DDa1}$, NR$^{DDa1}$R$^{DDb1}$, —OR$^{DDa1}$, —SR$^{DDa1}$, —CN, —NC, —N$_3$, —NO$_2$, —N(R$^{DDc1}$)—NR$^{DDa1}$R$^{DDb1}$, —N(R$^{DDc1}$)—OR$^{DDa1}$, —S—SR$^{DDa1}$, —C(=O)R$^{DDa1}$, —C(=O)OR$^{DDa1}$, —C(=O)NR$^{DDa1}$R$^{DDb1}$, —O—C(=O)OR$^{DDa1}$, —O—C(=O)NR$^{DDa1}$R$^{DDb1}$, —N(R$^{DDc1}$)—C(=O)NR$^{DDa1}$R$^{DDb1}$, —S(=O)R$^{DDa1}$, S(=O)$_2$R$^{DDa1}$, —O—S(=O)$_2$NR$^{DDa1}$R$^{DDb1}$, —N(R$^{DDc1}$)—S(=O)$_2$NR$^{DDa1}$R$^{DDb1}$, an optionally substituted C$_{1-6}$ alkyl, an optionally substituted C$_{2-6}$ alkenyl, an optionally substituted haloalkyl, an optionally substituted hydroxyalkyl and an —O-linked amino acid, or when the bond to $R^{DD7}$ indicated by ⚌ is a double bond, then $R^{DD7}$ is a C$_{2-6}$ alkylidene and $R^{DD8}$ is absent; $R^{DDa1}$, $R^{DDb1}$ and $R^{DDc1}$ can be each independently selected from hydrogen, an optionally substituted alkyl, an optionally substituted alkenyl, an optionally substituted alkynyl, an optionally substituted aryl, an optionally substituted heteroaryl, an optionally substituted aralkyl and an optionally substituted heteroaryl(C$_{1-6}$ alkyl); $R^{DD10}$ can be selected from O$^-$, —OH, an optionally substituted aryloxy or aryl-O—,

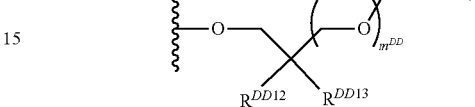

alkyl-C(=O)—O—CH$_2$—O—, alkyl-C(=O)—S—CH$_2$CH$_2$—O— and an —N-linked amino acid; $R^{DD11}$ can be selected from O$^-$, —OH, an optionally substituted aryloxy or aryl-O—,

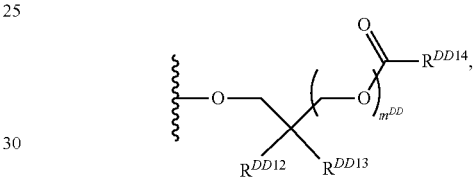

alkyl-C(=O)—O—CH$_2$—O—, alkyl-C(=O)—S—CH$_2$CH$_2$—O— and an —N-linked amino acid; each $R^{DD12}$ and each $R^{DD13}$ can be independently —C≡N or an optionally substituted substituent selected from C$_{1-8}$ organylcarbonyl, C$_{1-8}$ alkoxycarbonyl and C$_{1-8}$ organylaminocarbonyl; each $R^{DD14}$ can be hydrogen or an optionally substituted C$_{1-6}$-alkyl; each m$^{DD}$ can be independently 1 or 2, and if both $R^{DD10}$ and $R^{DD11}$ are

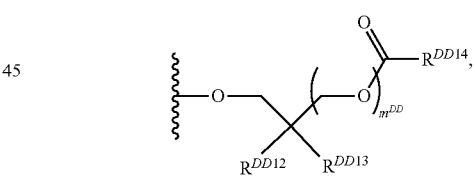

each $R^{DD12}$, each $R^{DD13}$, each $R^{DD14}$ and each m$^{DD}$ can be the same or different. In some embodiments, $R^{DD8}$ can be halogen, —OR$^{DDa1}$, an optionally substituted C$_{1-6}$ alkyl, an optionally substituted C$_{2-6}$ alkenyl, an optionally substituted C$_{2-6}$ alkynyl and an optionally substituted C$_{1-6}$ haloalkyl.

Additional examples of compounds that can be used in combination with one or more solid forms of Compound 1 described herein, or a pharmaceutically acceptable salt thereof, include those described in the following: WO 99/07733 (Boehringer Ingelheim), WO 99/07734 (Boehringer Ingelheim), WO 00/09558 (Boehringer Ingelheim), WO 00/09543 (Boehringer Ingelheim), WO 00/59929 (Boehringer Ingelheim), WO 02/060926 (BMS), WO 2006/039488 (Vertex), WO 2005/077969 (Vertex), WO 2005/035525 (Vertex), WO 2005/028502 (Vertex), WO 2005/007681 (Vertex), WO 2004/092162 (Vertex), WO 2004/092161 (Vertex), WO 2003/035060 (Vertex), WO 03/087092 (Vertex), WO 02/18369 (Vertex), WO 98/17679 (Vertex), WO 03/010140 (Boehringer Ingelheim), WO 03/026587 (Bristol Myers Squibb), WO 02/100846 A1, WO 02/100851 A2, WO 01/85172 AI (GSK), WO 02/098424 A1 (GSK), WO 00/06529 (Merck), WO 02/06246 A1 (Merck), WO 01/47883 (Japan Tobacco), WO 03/000254 (Japan Tobacco), EP 1 256 628 A2 (Agouron), WO 01/90121 A2 (Idenix), WO 02/069903 A2 (Biocryst Pharmaceuticals Inc.), WO 02/057287 A2 (Merck/Isis), WO 02/057425 A2 (Merck/Isis), WO 2010/117635, WO 2010/117977, WO 2010/117704, WO 2010/1200621, WO 2010/096302, WO 2010/017401, WO 2009/102633, WO 2009/102568, WO 2009/102325, WO 2009/102318, WO 2009/020828, WO 2009/020825, WO 2008/144380, WO 2008/021936, WO 2008/021928, WO 2008/021927, WO 2006/133326, WO 2004/014852, WO 2004/014313, WO 2010/096777, WO 2010/065681, WO 2010/065668, WO 2010/065674, WO 2010/062821, WO 2010/099527, WO 2010/096462, WO 2010/091413, WO 2010/094077, WO 2010/111483, WO 2010/120935, WO 2010/126967, WO 2010/132538, WO 2010/122162 and WO 2006/019831 (PTC therapeutics), wherein all the aforementioned are hereby incorporated by reference for the limited purpose of the chemical structures and chemical compounds disclosed therein.

Further examples of compounds that can be used in combination with one or more solid forms of Compound 1 described herein, or a pharmaceutically acceptable salt thereof, include the following: R1626, R1479 (Roche), MK-0608 (Merck), R1656, (Roche-Pharmasset), Valopicitabine (Idenix), JTK-002/003, JTK-109 (Japan Tobacco), GS-7977 (Gilead), EDP-239 (Enanta), PPI-1301 (Presido Pharmaceuticals), (Gao M. et al. Nature, 465, 96-100 (2010)), JTK-853 (Japan Tobacco), RO-5303253 Hoffmann-La Roche), IDX-184 (Idenix Pharmaceuticals), class I interferons (such as alpha-interferons, beta-interferons, delta-interferons, omega-interferons, tau-intefereons, x-interferons, consensus interferons and asialo-interferons), class II interferons (such as gamma-interferons), pegylated interferons, interferon alpha 1A, interferon alpha 1 B, interferon alpha 2A, and interferon alpha 2B, thalidomide, IL-2; hematopoietins, IMPDH inhibitors (for example, Merimepodib (Vertex Pharmaceuticals Inc.)), natural interferon (such as OMNIFERON, Viragen and SUMIFERON, Sumitomo, and a blend of natural interferons), natural interferon alpha (ALFERON, Hemispherx Biopharma, Inc.), interferon alpha n1 from lymphblastoid cells (WELLFERON, Glaxo Wellcome), oral alpha interferon, Peg-interferon, Peg-interferon alpha 2a (PEGASYS, Roche), recombinant interferon alpha 2a (ROFERON, Roche), inhaled interferon alpha 2b (AERX, Aradigm), Peg-interferon alpha 2b (ALBUFERON, Human Genome Sciences/Novartis, PEGINTRON, Schering), recombinant interferon alpha 2b (INTRON A, Schering), pegylated interferon alpha 2b (PEG-INTRON, Schering, VIRAFERONPEG, Schering), interferon beta-1a (REBIF, Serono, Inc. and Pfizer), consensus interferon alpha (INFERGEN, Valeant Pharmaceutical), interferon gamma-1b (ACTIMMUNE, Intermune, Inc.), synthetic thymosin alpha 1 (ZADAXIN, SciClone Pharmaceuticals Inc.), an antisense agent (for example, ISIS-14803), SCH-6, ITMN-B (InterMune), GS9132 (Gilead), ISIS-14803 (ISIS Pharmaceuticals), ribavirin, amantadine, merimepodib, Levovirin, Viramidine, maxamine, *silybum marianum*, interleukine-12, amantadine, ribozyme, thymosin, N-acetyl cysteine and cyclosporin.

Some embodiments described herein relate to a method of ameliorating or treating a viral infection that can include contacting a cell infected with the viral infection with an effective amount of one or more solid forms of Compound 1 as described herein, or a pharmaceutically acceptable salt thereof, in combination with one or more agents selected from an interferon, ribavirin, a HCV protease inhibitor, a HCV polymerase inhibitor, a NS5A inhibitor, an antiviral compound, a mono-, di, and/or tri-phosphate thereof, a compound of Formula (BB), and a compound of Formula (DD), or a pharmaceutically acceptable salt of any of the aforementioned compounds.

Some embodiments described herein relate to a method of ameliorating or treating a viral infection that can include administering to a subject suffering from the viral infection an effective amount of one or more solid forms of Compound 1 as described herein, or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (BB), and a compound of Formula (DD), or a pharmaceutically acceptable salt of any of the aforementioned compounds.

Some embodiments described herein relate to a method of inhibiting viral replication of a virus that can include contacting a cell infected with the virus with an effective amount of one or more solid forms of Compound 1 as described herein, or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (BB), and a compound of Formula (DD), or a pharmaceutically acceptable salt of any of the aforementioned compounds.

Some embodiments described herein relate to the use of a compound described herein, or a pharmaceutically acceptable salt thereof, in the preparation of a medicament for ameliorating or treating a HCV infection, wherein the medicament can be manufactured for use in combination with one or more agents selected from an interferon, ribavirin, a HCV protease inhibitor, a HCV polymerase inhibitor, a NS5A inhibitor, an antiviral compound, a compound of Formula (BB) and a compound of Formula (DD), or a pharmaceutically acceptable salt any of the aforementioned compounds.

Other embodiments described herein relate to the use of a compound described herein, or a pharmaceutically acceptable salt thereof, in the preparation of a medicament for contacting a cell infected with a hepatitis C virus, wherein the medicament can be manufactured for use in combination with one or more agents selected from the group consisting of an interferon, ribavirin, a HCV protease inhibitor, a HCV polymerase inhibitor, a NS5A inhibitor, an antiviral compound, a compound of Formula (BB), and a compound of Formula (DD), or a pharmaceutically acceptable salt any of the aforementioned compounds.

Other embodiments described herein relate to the use of a compound described herein, or a pharmaceutically acceptable salt thereof, in the preparation of a medicament for inhibiting viral replication of a virus (for example, HCV), wherein the medicament can be manufactured for use in combination with one or more agents selected from the group consisting of an interferon, ribavirin, a HCV protease inhibitor, a HCV polymerase inhibitor, a NS5A inhibitor, an antiviral compound, a compound of Formula (BB), and a compound of Formula (DD), or a pharmaceutically acceptable salt any of the aforementioned compounds.

In some embodiments, one or more solid forms of Compound 1 as described herein, or a pharmaceutically acceptable salt thereof, or a pharmaceutical composition that includes one or more solid forms of Compound 1 as described herein, can be administered with one or more additional agent(s) together in a single pharmaceutical composition. In some embodiments, one or more solid forms of Compound 1 as described herein, or a pharmaceutically acceptable salt thereof, or a pharmaceutical composition that includes one or more solid forms of Compound 1 as described herein, can be administered with one or more additional agent(s) as two or more separate pharmaceutical compositions. For example, one or more solid forms of Compound 1 as described herein, or a pharmaceutically acceptable salt thereof, or a pharmaceutical composition that includes one or more solid forms of Compound 1 as described herein, can be administered in one pharmaceutical composition, and at least one of the additional agents can be administered in a second pharmaceutical composition. If there are at least two additional agents, one or more of the additional agents can be in a first pharmaceutical composition that includes one or more solid forms of Compound 1 as described herein, or a pharmaceutically acceptable salt thereof, or a pharmaceutical composition that includes one or more solid forms of Compound 1 as described herein, and at least one of the other additional agent(s) can be in a second pharmaceutical composition.

In some embodiments, one or more solid forms of Compound 1 described herein can be used in combination with VX-950 (TELAPREVIR®) for treating and/or ameliorating HCV, inhibiting NS5B activity of HCV and/or inhibiting replication of HCV. In some embodiments, Form J can be used in combination with VX-950 (TELAPREVIR®) for treating and/or ameliorating HCV, inhibiting NS5B activity of HCV and/or inhibiting replication of HCV. In some embodiments, one or more solid forms of Compound 1 described herein can be used in combination with VX-222 for treating and/or ameliorating HCV, inhibiting NS5B activity of HCV and/or inhibiting replication of HCV. In some embodiments, Form J can be used in combination with VX-222 for treating and/or ameliorating HCV, inhibiting NS5B activity of HCV and/or inhibiting replication of HCV.

The dosing amount(s) and dosing schedule(s) when using one or more solid forms of Compound 1 as described herein, or a pharmaceutically acceptable salt thereof, or a pharmaceutical composition that includes one or more solid forms of Compound 1 as described herein, and one or more additional agents are within the knowledge of those skilled in the art. For example, when performing a conventional standard of care therapy using art-recognized dosing amounts and dosing schedules, one or more solid forms of Compound 1 as described herein, or a pharmaceutically acceptable salt thereof, or a pharmaceutical composition that includes one or more solid forms of Compound 1 as described herein, can be administered in addition to that therapy, or in place of one of the agents of a combination therapy, using effective amounts and dosing protocols as described herein.

The order of administration of one or more solid forms of Compound 1 as described herein, or a pharmaceutically acceptable salt thereof, or a pharmaceutical composition that includes one or more solid forms of Compound 1 as described herein, with one or more additional agent(s) can vary. In some embodiments, one or more solid forms of Compound 1 as described herein, or a pharmaceutically acceptable salt thereof, or a pharmaceutical composition that includes one or more solid forms of Compound 1 as described herein, can be administered prior to all additional agents. In other embodiments, one or more solid forms of Compound 1 as described herein, or a pharmaceutically acceptable salt thereof, or a pharmaceutical composition that includes one or more solid forms of Compound 1 as described herein, can be administered prior to at least one additional agent. In still other embodiments, one or more solid forms of Compound 1 as described herein, or a pharmaceutically acceptable salt thereof, or a pharmaceutical composition that includes one or more solid forms of Compound 1 as described herein, can be administered concomitantly with one or more additional agent(s). In yet still other embodiments, one or more solid forms of Compound 1 as described herein, or a pharmaceutically acceptable salt thereof, or a pharmaceutical composition that includes one or more solid forms of Compound 1 as described herein, can be administered subsequent to the administration of at least one additional agent. In some embodiments, one or more solid forms of Compound 1 as described herein, or a pharmaceutically acceptable salt thereof, or a pharmaceutical composition that includes one or more solid forms of Compound 1 as described herein, can be administered subsequent to the administration of all additional agents.

In some embodiments, the combination of one or more solid forms of Compound 1 as described herein, or a pharmaceutically acceptable salt thereof, or a pharmaceutical composition that includes one or more solid forms of Compound 1 as described herein, in combination with one or more additional agent(s) in FIGS. 32-34 (including pharmaceutically acceptable salts and prodrugs thereof) can result in an additive effect. In some embodiments, the combination one or more solid forms of Compound 1 as described herein, or a pharmaceutically acceptable salt thereof, or a pharmaceutical composition that includes one or more solid forms of Compound 1 as described herein, in combination with one or more additional agent(s) in FIGS. 32-34 (including pharmaceutically acceptable salts and prodrugs thereof) can result in a synergistic effect. In some embodiments, the combination of one or more solid forms of Compound 1 as described herein, or a pharmaceutically acceptable salt thereof, or a pharmaceutical composition that includes one or more solid forms of Compound 1 as described herein, in combination with one or more additional agent(s) in FIGS. 32-34 (including pharmaceutically acceptable salts and prodrugs thereof) can result in a strongly synergistic effect. In some embodiments, the combination of one or more solid forms of Compound 1 as described herein, or a pharmaceutically acceptable salt thereof, or a pharmaceutical composition that includes one or more solid forms of Compound 1 as described herein, in combination with one or more additional agent(s) in FIGS. 32-34 (including pharmaceutically acceptable salts and prodrugs thereof) is not antagonistic.

As used herein, the term "antagonistic" means that the activity of the combination of compounds is less compared to the sum of the activities of the compounds in combination when the activity of each compound is determined individually (i.e. as a single compound). As used herein, the term "synergistic effect" means that the activity of the combination of compounds is greater than the sum of the individual activities of the compounds in the combination when the activity of each compound is determined individually. As used herein, the term "additive effect" means that the activity of the combination of compounds is about equal to the sum of the individual activities of the compound in the combination when the activity of each compound is determined individually.

A potential advantage of utilizing one or more solid forms of Compound 1 as described herein, or a pharmaceutically acceptable salt thereof, or a pharmaceutical composition that includes one or more solid forms of Compound 1 as described herein, in combination with one or more additional agent(s) in FIGS. 32-34 (including pharmaceutically acceptable salts and prodrugs thereof) may be a reduction in the required amount(s) of one or more compounds of FIGS. 32-34 (including pharmaceutically acceptable salts and prodrugs thereof) that is effective in treating a disease condition disclosed herein (for example, HCV), as compared to the amount required to achieve same therapeutic result when one or more compounds of FIGS. 32-34 (including pharmaceutically acceptable salts and prodrugs thereof) are administered without one or more solid forms of Compound 1 as described herein, or a pharmaceutically acceptable salt thereof, or a pharmaceutical composition that includes one or more solid forms of Compound 1 as described herein. For example, the amount of a compound in FIGS. 32-34 (including a pharmaceutically acceptable salt and prodrug thereof), can be less compared to the amount of the compound in FIGS. 32-34 (including a pharmaceutically acceptable salt and prodrug thereof), needed to achieve the same viral load reduction when administered as a monotherapy. Another potential advantage of utilizing one or more solid forms of Compound 1 as described herein, or a pharmaceutically acceptable salt thereof, or a pharmaceutical composition that includes one or more solid forms of Compound 1 as described herein, in combination with one or more additional agent(s) in FIGS. 32-34 (including pharmaceutically acceptable salts and prodrugs thereof) is that the use of two or more compounds having different mechanism of actions can create a higher barrier to the development of resistant viral strains compared to the barrier when a compound is administered as monotherapy.

Additional advantages of utilizing one or more solid forms of Compound 1 as described herein, or a pharmaceutically acceptable salt thereof, or a pharmaceutical composition that includes one or more solid forms of Compound 1 as described herein, in combination with one or more additional agent(s) in FIGS. 32-34 (including pharmaceutically acceptable salts and prodrugs thereof) may include little to no cross resistance between one or more solid forms of Compound 1 as described herein, or a pharmaceutically acceptable salt thereof, or a pharmaceutical composition that includes one or more solid forms of Compound 1 as described herein, and one or more additional agent(s) in FIGS. 32-34 (including pharmaceutically acceptable salts and prodrugs thereof) thereof; different routes for elimination of one or more solid forms of Compound 1 as described herein, or a pharmaceutically acceptable salt thereof, or a pharmaceutical composition that includes one or more solid forms of Compound 1 as described herein, and one or more additional agent(s) in FIGS. 32-34 (including pharmaceutically acceptable salts and prodrugs thereof); little to no overlapping toxicities between one or more solid forms of Compound 1 as described herein, or a pharmaceutically acceptable salt thereof, or a pharmaceutical composition that includes one or more solid forms of Compound 1 as described herein, and one or more additional agent(s) in FIGS. 32-34 (including pharmaceutically acceptable salts and prodrugs thereof); little to no significant effects on cytochrome P450; and/or little to no pharmacokinetic interactions between one or more solid forms of Compound 1 as described herein, or a pharmaceutically acceptable salt thereof, or a pharmaceutical composition that includes one or more solid forms of Compound 1 as described herein, and one or more additional agent(s) in FIGS. 32-34 (including pharmaceutically acceptable salts and prodrugs thereof).

In order that the invention described herein may be more fully understood, the following examples are set forth. It should be understood that these examples are for illustrative purposes only and are not to be construed as limiting this invention in any manner.

EXAMPLES

Methods & Materials
XRPD (X-Ray Powder Diffraction)

Unless otherwise specified, samples were scanned on the Bruker D8 Discover operated at 40 kV, 35 mA. Two frames were registered with an exposure of 120 seconds. Data were integrated over the range of 4.5°-39.0° 2 theta with a step size of 0.02° and merged into one continuous pattern. All XRPD spectra provided herein are measured on a degrees 2-Theta scale.

Differential Scanning Calorimetry (DSC)
The following DSC method was used:
1: Data storage: Off
2: Equilibrate at −20.00° C. or 25.00° C.
3: Modulate +/−1.00° C. every 60 seconds
4: Isothermal for 5.00 min
5: Data storage: On
6: Ramp 2.00-3.00° C./min to 250.00° C.

Solid State Nuclear Magnetic Spectroscopy

Samples were packed into Bruker-Biospin 4 mm $ZrO_2$ rotors (approximately 65 mg or less each depending on sample availability). The rotors were spun inside a Bruker-Biospin 4 mm HFX probe, which was placed in 400 MHz Bruker-Biospin wide bore magnet. Magic angle spinning (MAS) speed of typically 12.5 kHz was used (10.0 kHz if a suspension was characterized instead of a dry powder). The samples were referenced to adamantane at 29.5 ppm. The proton relaxation time was measured using $^1H$ MAS $T_1$ saturation recovery relaxation experiment in order to set up proper recycle delay of the $^{13}C$ cross-polarization (CP) MAS experiment. The CP contact time was set to 2 ms. A CP proton pulse with linear ramp (from 50% to 100%) was employed. The Hartmann-Hahn match was optimized on external reference sample of glycine. SPINAL 64 decoupling was used with the field strength of approximately 90 kHz.

Synthesis of Compound 1 and the Solid Forms of Compound 1

Example 1

Synthesis of 2'-C-methyluridine 5'-(O-phenyl-N—(S)-1-(isopropoxycarbonyl)ethyl)thiophosphoramidate (Compound 1)

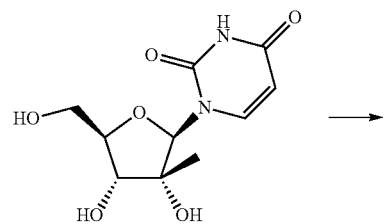

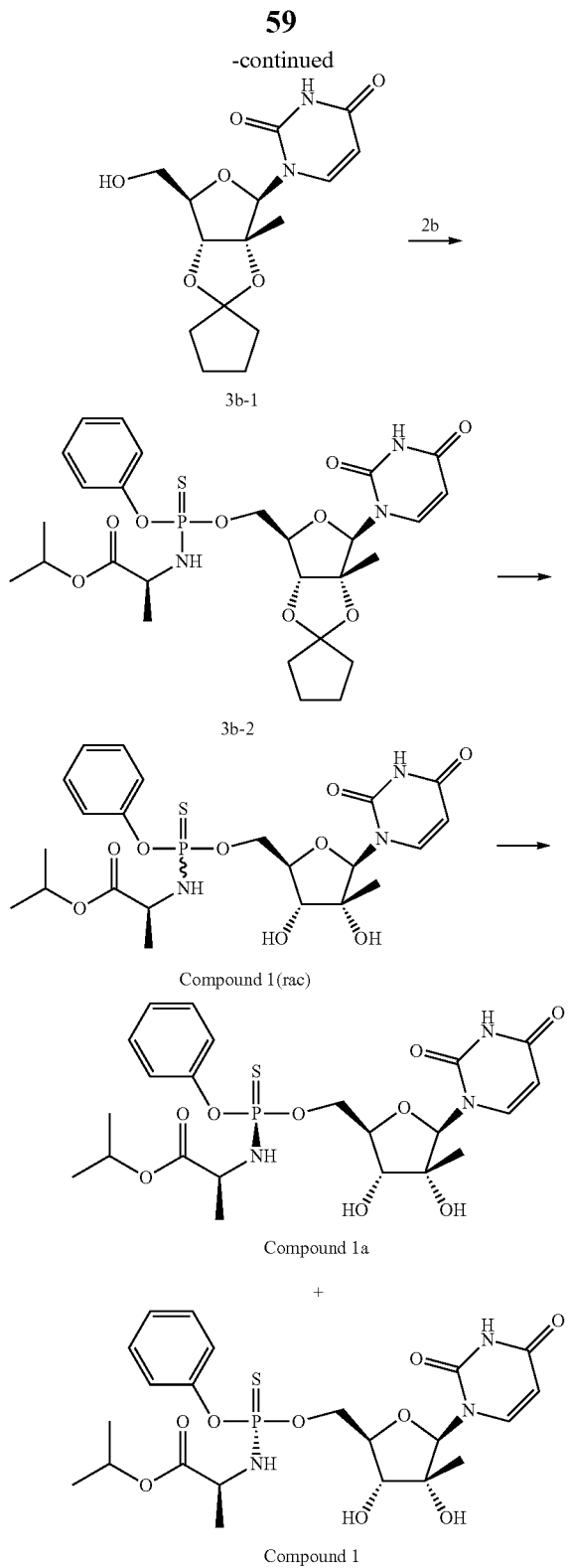

a white solid (14.5 g, 57.7%). $^1$H NMR (CDCl$_3$, 400 MHz) δ8.86 (s, 1H), 7.67 (d, J=8.0 Hz, 1H), 6.06 (s, 1H), 5.73 (d, J=8.0 Hz, 1H), 4.50 (d, J=4.8 Hz, 1H), 4.21 (m, 1H), 4.02-3.86 (m, 2H), 2.17 (m, 1H), 1.98, 1.83, 1.68 (m, 8H), 1.30 (s, 3H).

Step 2: Compound 3b-2—To a suspension of 3b-1 (20 g, 61.7 mmol) in dry CH$_3$CN (100 mL) was added N-methylimidazole (50 mL) and 2b (80 g, 249.2 mmol). The reaction mixture was stirred at 70° C. for 2 h. Solvent was removed and the residue was dissolved in ethyl acetate (500 mL). The solution was washed with brine, dried and evaporated. The residue was purified on a silica gel column (20~50% ethylacetate (EA) in petroleum ether (PE)) to give 3b-2 as a white foam (two isomers, 12.5 g, 33%). $^1$H NMR (CDCl$_3$, 400 MHz) δ8.79-8.92 (m, 1H), 7.55 (m, 1H), 7.34 (m, 2H), 7.20 (m, 3H), 6.09 (d, J=13.6 Hz, 1H), 5.70-5.61 (m, 1H), 5.06-5.01 (m, 1H), 4.38-4.09 (m, 6H), 2.08 (m, 1H), 1.96 (m, 1H), 1.73 (m, 2H), 1.66 (m, 5H), 1.39 (m, 3H), 1.23 (m, 9H); $^{31}$P NMR (CDCl$_3$, 162 MHz) δ67.62, 67.31.

Step 3: Compound 1(rac)—Compound 3b-2 (10 g, 16.4 mmol) was suspended in 100 mL of 80% formic acid and the reaction mixture was stirred at 50° C. for 1.5 hours. Solvent was evaporated and the residue was co-evaporated with toluene to remove traces of acid and water. The residue was purified by RP HPLC (0.5% HCOOH in MeCN and water as mobile phase) to give Compound 1(rac) (a mixture of two P-diastereomers, 5.6 g, 63%). $^1$H NMR (CD$_3$OD, 400 MHz) δ 7.79, 7.87 (2d, J=8.0 Hz, 1H), 7.18-7.38 (m, 5H), 5.98, 6.01 (2s, 1H), 5.59, 5.63 (2d, J=8.0 Hz, 1H), 4.95-5.05 (m, 1H), 4.51-4.56 (m, 1H), 4.30-4.44 (m, 1H), 4.05-4.17 (m, 2H), 3.82-3.87 (m, 1H), 1.34, 1.38 (2d, J=7.2 Hz, 3H), 1.17, 1.25 (2d, J=6.0 Hz, 6H), 1.24, 125 (2s, 3H); $^{31}$P NMR (CD$_3$OD, 162 MHz) δ68.17, 68.40; ESI-LCMS: m/z 544.0 [M+H]$^+$.

Step 4: Separation of Compound 1 and Compound 1a—Compound 1(rac) was separated into its diastereomers by two methods: (a) supercritical fluid chromatography (SFC) and (b) crystallization.

(a) Via SFC: Compound 1(rac) (440 mg, consisting of both Compound 1 and Compound 1a in ~1:1 ratio) was subjected to separation by SFC (chiral PAK AD, 5 um. 250*30 mm using 25% MeOH and 75% CO$_2$ as mobile phase) to give Compound 1a (123.8 mg) and Compound 1 (162.5 mg) as a white solid; Compound 1a: $^1$H NMR (CD$_3$OD, 400 MHz) δ7.87 (d, J=8.4 Hz, 1H), 7.36 (t, J=8.0 Hz, 2H), 7.28 (d, J=8.8 Hz, 2H), 7.19 (t, J=7.6 Hz, 1H), 6.01 (s, 1H), 5.62 (d, J=8.0 Hz, 1H), 5.03-4.97 (m, 1H), 4.56-4.92 (m, 1H), 4.44-4.39 (m, 1H), 4.16-4.13 (m, 1H), 4.10-4.05 (m, 1H), 3.86 (d, J=9.2 Hz, 1H), 1.34 (d, J=7.2 Hz, 3H), 1.25 (d, J=6.4 Hz, 6H), 1.16 (s, 3H); $^{31}$P NMR (CD$_3$OD, 162 MHz) δ68.18; ESI-LCMS: m/z=544 [M+H]$^+$. Compound 1: $^1$H NMR (CD$_3$OD, 400 MHz) δ7.89 (d, J=8.0 Hz, 1H), 7.36 (t, J=8.0 Hz, 2H), 7.30 (d, J=8.4 Hz, 2H), 7.20 (t, J=8.0 Hz, 1H), 5.99 (s, 1H), 5.60 (d, J=8.4 Hz, 1H), 5.03-4.97 (m, 1H), 4.56-4.51 (m, 1H), 4.35-4.30 (m, 1H), 4.14-4.10 (m, 2H), 3.83 (d, J=9.2 Hz, 1H), 1.39 (d, J=7.2 Hz, 3H), 1.25 (d, J=6.4 Hz, 6H), 1.17 (s, 3H); $^{31}$P NMR (CD$_3$OD, 162 MHz) δ68.42; ESI-LCMS: m/z=566 [M+Na]$^+$.

(b) Via Crystallization:

Method 1: Compound 1(rac) as a mixture of diastereomers (1:1, 10 g) was dissolved in 100 mL of dichloromethane (DCM)/ether (1:3). Hexane was added dropwise until the solution became cloudy. The solution was left at (room temperature) RT for 5 h and overnight at −20° C. Precipitated crystals were recrystallized from DCM/ether 1:3 v/v, and one more time from DCM/ether 1:2. Compound 1a (3 g) was obtained as a pure single diastereomer. The mother Step 1: Compound 3b-1—To a suspension of 2'-methyluridine (20 g, 77.52 mmol) in dry CH$_3$CN (200 mL) were added cyclopentanone (20 mL) and trimethylorthoformate (20 mL) followed by p-toluenesulfonic acid monohydrate (7.4 g, 38.76 mmol). The reaction mixture was stirred at 40° C. overnight. The solvent was evaporated. The residue was dissolved in ethyl acetate and washed with brine. The organic layer was dried and evaporated to give pure 3b-1 as liquor after first crystallization was concentrated, and then dissolved in isopropanol. Hexane was added (30% by volume). The clear solution was left overnight at RT to produce a small amount of crystals, which were used as seeds. The mother liquor was evaporated and crystallized 2 times from hexane/isopropanol (4:1) to give 2.3 g of Compound 1.

Method 2: 50 g of Compound 1(rac) was added to 100 mL of DCM and allowed to stir. After brief stirring almost all of the material was dissolved (<100 mg remained suspended). This was filtered and 300 mL of MTBE added while stirring. About 25 mg of Compound 1 was added as seeds and the solution cooled to 3° C. overnight. Significant precipitation was observed. The cold mixture was filtered and the solid washed with 25 mL of MTBE but not filtered dry. The product was dried on a rotvac at 8 torr and 30° C. This material was recrystallized one additional time using the procedure outline above with precipitation being observed upon the addition of 100 mg of the product from the first crystallization as seeds. XRPD indicated that the material recovered was amorphous. Additional solids had precipitated from the supernatant and were collected by filtration. These were then rinsed with 25 mL of MTBE and dried. $^{31}$P NMR showed that this material was Compound 1 with about 4% of Compound 1a.

Example 2

Synthesis of Amorphous Form O 350 mg of Compound 1 was weighed and added to 8 mL of a 1:1 DCM/Methanol (HPLC grade) solution in a vial. The contents were allowed to stir until a clear solution was obtained. This solution was spray dried on a Buchi B-290 Mini with a condenser attached. The resulting spray dried solid was further dried in a vacuum oven at RT overnight to remove any residual solvent. The parameters of the Buchi B-290 Mini are listed below:
Nitrogen flow: 10 L/min;
Nitrogen max pressure: 10 psi;
$CO_2$ max pressure: 15 psi;
Inlet temperature: 95-100° C.;
Outlet temperature: 50° C.;
Aspirator: 100%;
Pump: 30%; and
Nozzle: 1.5

Example 3

Synthesis of Form A

To 1 g of Compound 1 was added 2 mL of ethyl acetate and the mixture was heated to 35° C. and stirred until all solids had dissolved. The mixture was then allowed to cool to room temperature to allow the solids to precipitate out of solution. An additional 2 mL of ethyl acetate was then added to the mixture, and the mixture was again heated to 35° C. until all solids dissolved. The mixture was allowed to cool to allow the solids to precipitate out of solution as above. The solid Form A was then collected by filtration.

Representative XRPD peaks for Form A are shown in the table below. Form A can be identified and/or characterized by one or more of the peaks in the table below.

| No. | 2-Theta ° | Intensity % |
| --- | --- | --- |
| 1 | 7.0* | 91.8 |
| 2 | 8.5* | 100.0 |

-continued

| No. | 2-Theta ° | Intensity % |
| --- | --- | --- |
| 3 | 10.0 | 70.0 |
| 4 | 11.0 | 73.4 |
| 5 | 14.7 | 90.3 |
| 6 | 15.5 | 76.7 |
| 7 | 15.8* | 79.6 |
| 8 | 16.6 | 90.9 |
| 9 | 17.8 | 81.1 |
| 10 | 18.0 | 99.2 |
| 11 | 18.8 | 72.2 |
| 12 | 19.9 | 76.1 |
| 13 | 20.8 | 73.5 |
| 14 | 21.4* | 77.0 |
| 15 | 22.0** | 68.9 |
| 16 | 22.6** | 73.0 |
| 17 | 23.3** | 68.8 |
| 18 | 25.8 | 71.7 |
| 19 | 28.7 | 67.4 |

Peaks with an asterisk (*) are major peaks
Peaks with a double asterisk (**) are secondary peaks Representative peaks from the $^{13}$C NMR solid state spectrum of Form A are shown in the table below. Form A can be identified and/or characterized by one or more of the peaks selected from the table below.

| Peak # | ν(F1) [ppm] | Intensity [rel] |
| --- | --- | --- |
| 1 | 173.0 | 24.12 |
| 2 | 172.0* | 23.11 |
| 3 | 170.2 | 24.80 |
| 4 | 151.3 | 28.62 |
| 5 | 150.5 | 38.71 |
| 6 | 146.6* | 14.23 |
| 7 | 143.9 | 12.74 |
| 8 | 130.4* | 36.15 |
| 9 | 126.2 | 27.80 |
| 10 | 122.9 | 3.91 |
| 11 | 120.4 | 33.00 |
| 12 | 104.1* | 23.68 |
| 13 | 102.2 | 23.18 |
| 14 | 92.8 | 20.65 |
| 15 | 92.2 | 17.13 |
| 16 | 84.1 | 27.03 |
| 17 | 79.7 | 68.89 |
| 18 | 75.0 | 28.02 |
| 19 | 73.5 | 33.05 |
| 20 | 69.5* | 34.76 |
| 21 | 69.2 | 27.63 |
| 22 | 66.9* | 40.98 |
| 23 | 50.4 | 22.59 |
| 24 | 21.9 | 100.00 |
| 25 | 20.6* | 39.44 |

Peaks with an asterisk (*) are major peaks

Example 4

Synthesis of the Form B (methyl tert-butyl ether solvate) and Form B (cyclohexane solvate). Form B (methyl tert-butyl ether solvate) and Form B (cyclohexane solvate) were determined to be isostructural by XRPD analysis.

Example 4a

Synthesis of Form B (Methyl Tert-Butyl Ether Solvate)

To a vial containing 20 mg of Form A was added 200 μL of HPLC grade methyl tert-butyl ether (MTBE). The vial was stirred at an intermediate speed (250 rpm) on a stir plate at RT for 3 weeks. The mixture was filtered through a 0.22 μm PVDF filter to provide Form B (methyl tert-butyl ether solvate).

Representative peaks from the $^{13}C$ NMR solid state spectrum of Form B (methyl tert-butyl ether solvate) are shown in the table below. Form B (methyl tert-butyl ether solvate) can be identified and/or characterized by one or more of the peaks selected from the table below.

| Peak # | v(F1) [ppm] | Intensity [rel] |
|---|---|---|
| 1 | 173.2* | 55.0 |
| 2 | 169.9 | 24.91 |
| 3 | 151.1 | 50.46 |
| 4 | 144.7 | 20.81 |
| 5 | 129.9* | 100.00 |
| 6 | 123.3 | 47.74 |
| 7 | 118.3* | 77.98 |
| 8 | 103.5 | 41.84 |
| 9 | 92.8 | 29.78 |
| 10 | 82.4 | 43.94 |
| 11 | 79.8 | 88.11 |
| 12 | 74.1 | 57.28 |
| 13 | 72.3* | 20.83 |
| 14 | 68.5* | 76.94 |
| 15 | 68.1 | 67.80 |
| 16 | 50.9 | 12.62 |
| 17 | 50.3 | 27.03 |
| 18 | 49.2* | 57.83 |
| 19 | 27.1* | 61.90 |
| 20 | 22.6 | 76.64 |
| 21 | 22.2 | 75.51 |
| 22 | 22.0 | 16.01 |
| 23 | 21.7 | 65.44 |
| 24 | 19.5* | 52.58 |

Peaks with an asterisk (*) are major peaks

Representative peaks from the XRPD spectrum of Form B (methyl tert-butyl ether solvate) are shown in the table below. Form B (methyl tert-butyl ether solvate) can be identified and/or characterized by one or more of the peaks selected from the table below.

| No. | 2-Theta ° | Intensity % |
|---|---|---|
| 1 | 5.720* | 71.8 |
| 2 | 9.395* | 31.2 |
| 3 | 17.042* | 100.0 |
| 4 | 26.219* | 28.5 |

Peaks with an asterisk (*) are major peaks

Example 4b

Synthesis of Form B (Cyclohexane Solvate)

To a vial containing 20 mg of Form A was added 200 μL of HPLC grade cyclohexane. The vial was stirred at an intermediate speed (250 rpm) on a stir plate at RT for 3 weeks. The mixture was filtered through a 0.22 μm PVDF filter to provide Form B (cyclohexane solvate).

Representative peaks from the $^{13}C$ NMR solid state spectrum of Form B (cyclohexane solvate) are shown in the table below. Form B (cyclohexane solvate) can be identified and/or characterized by one or more of the peaks selected from the table below.

| Peak # | v(F1) [ppm] | Intensity [rel] |
|---|---|---|
| 1 | 172.6 | 20.01 |
| 2 | 170.3* | 26.09 |
| 3 | 150.5* | 39.10 |
| 4 | 146.6 | 15.32 |
| 5 | 144.4 | 12.23 |
| 6 | 129.8* | 31.00 |
| 7 | 126.3 | 25.02 |
| 8 | 122.6 | 15.89 |
| 9 | 120.4 | 26.04 |
| 10 | 118.2* | 30.57 |
| 11 | 104.1 | 18.00 |
| 12 | 102.2 | 17.34 |
| 13 | 92.8 | 19.56 |
| 14 | 84.2 | 16.62 |
| 15 | 79.8* | 53.48 |
| 16 | 75.0 | 22.56 |
| 17 | 73.6 | 20.49 |
| 18 | 69.5 | 21.11 |
| 19 | 68.1 | 19.74 |
| 20 | 66.9 | 21.59 |
| 21 | 64.0 | 13.37 |
| 22 | 50.5 | 20.41 |
| 23 | 40.8 | 12.34 |
| 24 | 27.2* | 21.00 |
| 25 | 21.8* | 100.00 |
| 26 | 18.6 | 15.87 |

Peaks with an asterisk (*) are major peaks

Representative peaks from the XRPD spectrum of Form B (cyclohexane solvate) are shown in the table below. Form B (cyclohexane solvate) can be identified and/or characterized by one or more of the peaks selected from the table below.

| No. | 2-Theta ° | Intensity % |
|---|---|---|
| 1 | 5.720* | 71.8 |
| 2 | 9.395* | 31.2 |
| 3 | 17.042* | 100.0 |
| 4 | 26.219* | 28.5 |

Peaks with an asterisk (*) are major peaks

Example 5

Synthesis of Form C (Nitromethane Solvate)

To a vial containing 20 mg of Form A was added 100 μL of HPLC grade nitromethane. The vial was stirred at an intermediate speed (250 rpm) on a stir plate at RT for 3 weeks. The mixture was filtered through a 0.22 μm PVDF filter to provide Form C.

Representative peaks from the $^{13}C$ NMR solid state spectrum of Form C (nitromethane solvate) are shown in the table below. Form C (nitromethane solvate) can be identified and/or characterized by one or more of the peaks selected from the table below.

| Peak # | v(F1) [ppm] | Intensity [rel] |
|---|---|---|
| 1 | 173.7* | 72.2 |
| 2 | 163.6 | 27.15 |
| 3 | 162.7 | 27.66 |
| 4 | 152.6 | 33.02 |
| 5 | 151.9* | 39.39 |
| 6 | 151.3 | 17.72 |
| 7 | 150.4 | 19.06 |

-continued

| Peak # | v(F1) [ppm] | Intensity [rel] |
|---|---|---|
| 8 | 144.1 | 20.92 |
| 9 | 140.7 | 19.90 |
| 10 | 129.6 | 32.86 |
| 11 | 126.7 | 18.14 |
| 12 | 126.1 | 20.87 |
| 13 | 125.5 | 22.15 |
| 14 | 123.3 | 27.16 |
| 15 | 122.8 | 35.54 |
| 16 | 103.2* | 40.00 |
| 17 | 102.5 | 24.12 |
| 18 | 101.9 | 21.60 |
| 19 | 93.3 | 34.02 |
| 20 | 92.4 | 35.66 |
| 21 | 83.3* | 51.71 |
| 22 | 81.5 | 57.50 |
| 23 | 80.8* | 54.60 |
| 24 | 80.3 | 75.92 |
| 25 | 73.3* | 88.51 |
| 26 | 69.4 | 39.18 |
| 27 | 68.3 | 39.61 |
| 28 | 65.5 | 23.22 |
| 29 | 64.9 | 26.70 |
| 30 | 63.8* | 54.98 |
| 31 | 51.8 | 21.78 |
| 32 | 50.6 | 28.73 |
| 33 | 25.1* | 71.94 |
| 34 | 20.8 | 88.14 |
| 35 | 20.1* | 100.00 |
| 36 | 18.8 | 24.24 |

Peaks with an asterisk (*) are major peaks

Representative peaks from the XRPD spectrum of Form C (nitromethane solvate) are shown in the table below. Form C (nitromethane solvate) can be identified and/or characterized by one or more of the peaks selected from the table below.

| No. | 2-Theta ° | Intensity % |
|---|---|---|
| 1 | 4.980* | 27.4 |
| 2 | 6.573* | 31.0 |
| 3 | 8.174* | 39.0 |
| 4 | 9.151** | 47.4 |
| 5 | 9.585** | 56.2 |
| 6 | 16.337** | 62.7 |
| 7 | 22.340* | 28.1 |

Peaks with an asterisk (*) are major peaks
Peaks with a double asterisk (**) are secondary peaks Example 6

Synthesis of Form D (Desolvated Acetonitrile Solvate)

To a vial containing 50 mg of Form A was added 100 μL of HPLC grade acetonitrile (ACN) and stirred at RT until all solids dissolved. The vial was then stirred at an intermediate speed (250 rpm) on a stir plate at 5° C. for 3 weeks. The mixture was filtered through a 0.22 μm PVDF filter, and the isolated solid was dried at RT and atmospheric pressure until the solid was substantially desolvated to provide Form D (desolvated acetonitrile solvate).

Representative peaks from the $^{13}$C NMR solid state spectrum of Form D (desolvated acetonitrile solvate) are shown in the table below. Form D (desolvated acetonitrile solvate) can be identified and/or characterized by one or more of the peaks selected from the table below.

| Peak # | v(F1) [ppm] | Intensity [rel] |
|---|---|---|
| 1 | 172.5 | 31.47 |
| 2 | 170.3 | 39.91 |
| 3 | 163.0 | 36.97 |
| 4 | 152.7 | 57.96 |
| 5 | 150.4 | 41.72 |
| 6 | 143.3 | 19.06 |
| 7 | 139.1* | 20.55 |
| 8 | 130.9 | 74.16 |
| 9 | 130.2 | 33.92 |
| 10 | 125.3* | 71.51 |
| 11 | 124.4 | 39.60 |
| 12 | 120.8* | 61.60 |
| 13 | 105.2* | 73.13 |
| 14 | 92.3 | 31.47 |
| 15 | 91.0 | 29.46 |
| 16 | 81.8 | 47.28 |
| 17 | 79.9 | 100.00 |
| 18 | 78.5 | 65.96 |
| 19 | 73.6 | 52.41 |
| 20 | 72.8* | 51.48 |
| 21 | 69.4 | 48.17 |
| 22 | 67.5* | 45.52 |
| 23 | 63.0* | 84.89 |
| 24 | 53.6 | 23.06 |
| 25 | 50.8 | 25.81 |
| 26 | 23.7 | 50.37 |
| 27 | 22.8 | 89.54 |
| 28 | 22.0 | 51.17 |
| 29 | 21.3 | 98.72 |
| 30 | 20.8 | 54.41 |
| 31 | 18.3 | 54.61 |

Peaks with an asterisk (*) are major peaks

Representative peaks from the XRPD spectrum of Form D (desolvated acetonitrile solvate) are shown in the table below. Form D (desolvated acetonitrile solvate) can be identified and/or characterized by one or more of the peaks selected from the table below.

| No. | 2-Theta ° | Intensity % |
|---|---|---|
| 1 | 8.105* | 55.6 |
| 2 | 13.357* | 44.1 |
| 3 | 14.424** | 100.0 |
| 4 | 17.215** | 66.0 |
| 5 | 29.590* | 29.1 |
| 6 | 35.019* | 25.3 |

Peaks with an asterisk (*) are major peaks
Peaks with a double asterisk (**) are secondary peaks Example 7

Synthesis of a Mixture of Form E (Dioxane Solvate) and Form A

To a vial containing 40 mg of Form A was added 100 μL of HPLC grade dioxane. The vial was stirred at an intermediate speed (250 rpm) on a stir plate at 5° C. for 24 hours. 100 μL of HPLC grade heptane was then added, and the vial was sonicated in a ultrasonicator for 2 minutes. The mixture was then stirred at 5° C. for an additional 3 weeks. The vial was then uncapped and placed in the open air to evaporate the solvent and provide a solid mixture of Form E (dioxane solvate) and Form A.

Representative peaks from the $^{13}$C NMR solid state spectrum of Form E (dioxane solvate) are shown in the table below. Form E (dioxane solvate) can be identified and/or characterized by one or more of the peaks selected from the table below.

| Peak # | ν(F1) [ppm] | Intensity [rel] |
|---|---|---|
| 1 | 173.0* | 56.27 |
| 2 | 172.1 | 10.64 |
| 3 | 170.1 | 29.76 |
| 4 | 151.3 | 14.75 |
| 5 | 150.7* | 55.30 |
| 6 | 146.7 | 6.43 |
| 7 | 145.2 | 17.07 |
| 8 | 144.0 | 6.43 |
| 9 | 130.2* | 78.40 |
| 10 | 126.2 | 14.42 |
| 11 | 123.7 | 34.51 |
| 12 | 120.5 | 15.84 |
| 13 | 118.3* | 65.27 |
| 14 | 104.1 | 11.22 |
| 15 | 103.2 | 33.55 |
| 16 | 102.2 | 11.20 |
| 17 | 92.7 | 28.19 |
| 18 | 84.1 | 12.31 |
| 19 | 82.4 | 35.17 |
| 20 | 80.1 | 73.44 |
| 21 | 79.8 | 36.49 |
| 22 | 75.0 | 14.45 |
| 23 | 73.9* | 48.37 |
| 24 | 69.2 | 53.62 |
| 25 | 68.0* | 59.07 |
| 26 | 67.0* | 32.83 |
| 27 | 50.4 | 28.84 |
| 28 | 22.0* | 100.00 |
| 29 | 21.7 | 93.59 |
| 30 | 21.4 | 58.58 |
| 31 | 20.6 | 18.91 |
| 32 | 19.4 | 40.73 |

Peaks with an asterisk (*) are major peaks

Representative peaks from the XRPD spectrum of Form E (dioxane solvate) are shown in the table below. Form E (dioxane solvate) can be identified and/or characterized by one or more of the peaks selected from the table below.

| No. | 2-Theta ° | Intensity % |
|---|---|---|
| 1 | 7.765* | 58.9 |
| 2 | 10.563** | 22.3 |
| 3 | 12.901* | 40.7 |
| 4 | 21.571* | 26.4 |
| 5 | 24.466** | 51.4 |
| 6 | 25.016* | 31.6 |

Peaks with an asterisk (*) are major peaks
Peaks with a double asterisk (**) are secondary peaks

Example 8

Synthesis of a Mixture of Form F (Tetrahydrofuran Solvate) and Form A

To a vial containing 60 mg of Form A was added 200 μL of HPLC grade tetrahydrofuran (THF). The vial was stirred at an intermediate speed (250 rpm) on a stir plate at RT for 3 weeks. The vial was then uncapped and placed in the open air to evaporate the solvent and provide a solid mixture of Form F (tetrahydrofuran solvate) and Form A.

Representative peaks from the $^{13}$C NMR solid state spectrum of Form F (tetrahydrofuran solvate) are shown in the table below. Form F (tetrahydrofuran solvate) can be identified and/or characterized by one or more of the peaks selected from the table below.

| Peak # | ν(F1) [ppm] | Intensity [rel] |
|---|---|---|
| 1 | 173.0 | 21.53 |
| 2 | 172.0 | 24.07 |
| 3 | 170.2* | 27.88 |
| 4 | 151.3 | 28.85 |
| 5 | 150.5* | 40.71 |
| 6 | 146.6 | 11.13 |
| 7 | 145.2 | 6.82 |
| 8 | 143.9 | 11.03 |
| 9 | 130.4* | 33.74 |
| 10 | 126.2 | 25.38 |
| 11 | 123.1 | 8.05 |
| 12 | 120.4 | 29.96 |
| 13 | 104.0 | 20.89 |
| 14 | 103.2 | 9.89 |
| 15 | 102.2 | 20.47 |
| 16 | 92.8 | 22.77 |
| 17 | 92.2 | 18.97 |
| 18 | 84.0 | 21.12 |
| 19 | 81.9 | 7.45 |
| 20 | 79.7* | 71.06 |
| 21 | 75.0 | 24.15 |
| 22 | 73.5* | 30.33 |
| 23 | 69.5 | 29.78 |
| 24 | 69.2 | 27.71 |
| 25 | 68.2* | 20.78 |
| 26 | 66.9* | 34.82 |
| 27 | 50.4 | 28.03 |
| 28 | 25.7* | 7.70 |
| 29 | 21.8* | 100.00 |
| 30 | 20.6* | 39.64 |

Peaks with an asterisk (*) are major peaks

Representative peaks from the XRPD spectrum of Form F (tetrahydrofuran solvate) are shown in the table below. Form F (tetrahydrofuran solvate) can be identified and/or characterized by one or more of the peaks selected from the table below.

| No. | 2-Theta ° | Intensity % |
|---|---|---|
| 1 | 6.090* | 100.0 |
| 2 | 6.970* | 32.4 |
| 3 | 17.538* | 30.7 |
| 4 | 18.048* | 56.0 |

Peaks with an asterisk (*) are major peaks

Example 9

Synthesis of Form G (Dichloromethane Solvate)

To a vial containing 50 mg of Amorphous Form O was added 50 μL of HPLC grade dichloromethane (DCM). The vial was stirred at an intermediate speed (250 rpm) on a stir plate at RT for 1 hour. An aliquot (~25 μL) was placed in a capillary tube which was then sealed off at both ends. The capillary tube was placed on an XRPD holder and analyzed (an acquisition time of 600 seconds was used for each frame).

Representative peaks from the $^{13}$C NMR solid state spectrum of Form G (dichloromethane solvate) are shown in the table below. Form G (dichloromethane solvate) can be identified and/or characterized by one or more of the peaks selected from the table below.

| Peak # | ν(F1) [ppm] | Intensity [rel] |
|---|---|---|
| 1 | 172.9* | 47.8 |
| 2 | 172.5 | 60.77 |
| 3 | 170.1 | 31.87 |
| 4 | 150.8* | 97.73 |
| 5 | 145.6 | 17.22 |
| 6 | 143.7 | 10.94 |
| 7 | 130.4* | 78.80 |
| 8 | 123.6 | 13.92 |
| 9 | 122.8 | 39.28 |
| 10 | 122.2 | 22.62 |
| 11 | 119.6* | 30.97 |
| 12 | 118.7* | 83.25 |
| 13 | 103.6 | 49.34 |
| 14 | 103.2 | 27.56 |
| 15 | 93.1 | 34.63 |
| 16 | 92.6 | 30.12 |
| 17 | 83.1* | 44.78 |
| 18 | 82.6 | 41.59 |
| 19 | 80.2 | 49.48 |
| 20 | 79.9 | 89.47 |
| 21 | 79.5 | 48.95 |
| 22 | 74.4 | 42.00 |
| 23 | 73.5 | 36.87 |
| 24 | 73.3 | 36.16 |
| 25 | 69.0* | 46.99 |
| 26 | 68.8 | 93.22 |
| 27 | 68.5 | 53.49 |
| 28 | 68.3 | 50.90 |
| 29 | 68.0 | 70.75 |
| 30 | 54.2* | 17.40 |
| 31 | 50.5 | 44.46 |
| 32 | 23.4 | 36.90 |
| 33 | 22.9 | 82.85 |
| 34 | 22.6 | 100.00 |
| 35 | 21.8 | 87.94 |
| 36 | 21.4 | 85.89 |
| 37 | 20.4* | 70.1 |
| 38 | 20.1 | 39.2 |

Peaks with an asterisk (*) are major peaks

Representative peaks from the XRPD spectrum of Form G (dichloromethane solvate) are shown in the table below. Form G (dichloromethane solvate) can be identified and/or characterized by one or more of the peaks selected from the table below.

| No. | 2-Theta ° | Intensity % |
|---|---|---|
| 1 | 5.857* | 100.0 |
| 2 | 7.498* | 41.6 |
| 3 | 7.835* | 32.1 |
| 4 | 12.522** | 23.5 |
| 5 | 17.733* | 53.0 |
| 6 | 18.193** | 23.5 |

Peaks with an asterisk (*) are major peaks
Peaks with a double asterisk (**) are secondary peaks

Example 10

Synthesis of Form H (Acetonitrile Solvate)

To a vial containing 120 mg of Amorphous Form O was added 100 µL of HPLC grade acetonitrile (ACN), and the mixture was stirred at RT until the solids dissolved. The vial was then sonicated in an ultrasonicator for 2 minutes, and the mixture was then stirred at an intermediate speed (250 rpm) on a stir plate at RT for 5 minutes. The mixture was filtered through a 0.22 µm PVDF filter to provide Form H (acetonitrile solvate).

Representative peaks from the $^{13}$C NMR solid state spectrum of Form H (acetonitrile solvate) are shown in the table below. Form H (acetonitrile solvate) can be identified and/or characterized by one or more of the peaks selected from the table below.

| Peak # | ν(F1) [ppm] | Intensity [rel] |
|---|---|---|
| 1 | 173.4* | 70.7 |
| 2 | 164.4 | 44.87 |
| 3 | 153.4* | 31.83 |
| 4 | 152.2* | 61.17 |
| 5 | 141.4 | 42.94 |
| 6 | 129.8* | 70.37 |
| 7 | 123.6 | 53.72 |
| 8 | 119.8* | 55.92 |
| 9 | 104.6* | 76.16 |
| 10 | 92.3 | 56.76 |
| 11 | 82.6 | 35.67 |
| 12 | 81.9 | 32.74 |
| 13 | 79.4* | 100.00 |
| 14 | 73.4 | 96.98 |
| 15 | 68.9 | 54.71 |
| 16 | 61.7 | 73.15 |
| 17 | 53.6 | 47.24 |
| 18 | 23.4 | 79.96 |
| 19 | 22.9 | 86.96 |
| 20 | 21.6 | 41.15 |
| 21 | 20.6* | 90.05 |
| 22 | 2.2* | 14.59 |

Peaks with an asterisk (*) are major peaks

Representative peaks from the XRPD spectrum of Form H (acetonitrile solvate) are shown in the table below. Form H (acetonitrile solvate) can be identified and/or characterized by one or more of the peaks selected from the table below.

| No. | 2-Theta ° | Intensity % |
|---|---|---|
| 1 | 8.132* | 81.7 |
| 2 | 14.020* | 34.6 |
| 3 | 17.226* | 61.7 |
| 4 | 20.902* | 27.3 |

Peaks with an asterisk (*) are major peaks

Example 11

Synthesis of the isostructural Form I (isopropyl acetate solvate) and Form I (ethyl acetate solvate). Form I (isopropyl acetate solvate) and Form I (ethyl acetate solvate) were determined to be isostructural by XRPD analysis.

Example 11a

Synthesis of Form I (Isopropyl Acetate Solvate)

To a vial containing 33 mg of Amorphous Form O was added 200 µL of HPLC grade isopropyl acetate (IPAC). The mixture was then stirred at an intermediate speed (250 rpm) on a stir plate at RT for 2 hours. The mixture was filtered through a 0.22 µm PVDF filter to provide Form I (isopropyl acetate solvate).

Representative peaks from the $^{13}$C NMR solid state spectrum of Form I (isopropyl acetate solvate) are shown in the table below. Form I (isopropyl acetate solvate) can be identified and/or characterized by one or more of the peaks selected from the table below.

| Peak | ν(F1) [ppm] | Intensity [rel] |
|---|---|---|
| 1 | 174.2 | 28.4 |
| 2 | 173.0* | 35.35 |
| 3 | 170.1 | 18.49 |
| 4 | 168.4* | 18.99 |
| 5 | 152.1* | 44.16 |
| 6 | 151.0 | 35.26 |
| 7 | 144.8 | 19.59 |
| 8 | 143.5 | 18.22 |
| 9 | 129.9 | 26.35 |
| 10 | 126.1* | 27.72 |
| 11 | 123.4 | 33.24 |
| 12 | 122.8 | 27.21 |
| 13 | 119.6 | 9.23 |
| 14 | 102.7* | 56.58 |
| 15 | 93.2 | 23.93 |
| 16 | 91.1 | 24.94 |
| 17 | 81.6 | 37.12 |
| 18 | 80.5 | 42.31 |
| 19 | 79.6 | 73.82 |
| 20 | 74.5* | 37.87 |
| 21 | 73.2 | 37.91 |
| 22 | 71.2* | 34.86 |
| 23 | 69.3 | 62.97 |
| 24 | 68.8 | 39.70 |
| 25 | 63.3* | 34.57 |
| 26 | 51.1 | 22.87 |
| 27 | 50.3 | 19.47 |
| 28 | 23.3* | 100.00 |
| 29 | 22.8 | 76.24 |
| 30 | 21.9 | 75.98 |
| 31 | 21.4 | 42.76 |
| 32 | 20.4 | 36.17 |
| 33 | 20.0 | 38.34 |

Peaks with an asterisk (*) are major peaks

Representative peaks from the XRPD spectrum of Form I (isopropyl acetate solvate) are shown in the table below. Form I (isopropyl acetate solvate) can be identified and/or characterized by one or more of the peaks selected from the table below.

| No. | 2-Theta ° | Intensity % |
|---|---|---|
| 1 | 6.434* | 59.2 |
| 2 | 9.283* | 30.8 |
| 3 | 10.831* | 55.3 |
| 4 | 11.794* | 28.3 |

Peaks with an asterisk (*) are major peaks

Example 11b

Synthesis of Form I (Ethyl Acetate Solvate)

To a vial containing 33 mg of Amorphous Form O was added 200 µL of HPLC grade ethyl acetate. The mixture was then stirred at an intermediate speed (250 rpm) on a stir plate at RT for 2 hours. The mixture was filtered through a 0.22 µm PVDF filter to provide Form I (ethyl acetate solvate).

Representative peaks from the $^{13}$C NMR solid state spectrum of Form I (ethyl acetate solvate) are shown in the table below. Form I (ethyl acetate solvate) can be identified and/or characterized by one or more of the peaks selected from the table below.

| Peak | ν(F1) [ppm] | Intensity [rel] |
|---|---|---|
| 1 | 174.2 | 27.6 |
| 2 | 173.1* | 34.33 |
| 3 | 170.3 | 20.24 |
| 4 | 168.6* | 20.76 |
| 5 | 152.1* | 41.55 |
| 6 | 151.1 | 35.37 |
| 7 | 144.9 | 20.96 |
| 8 | 143.6 | 18.23 |
| 9 | 129.4 | 12.59 |
| 10 | 126.1 | 23.63 |
| 11 | 123.6* | 24.98 |
| 12 | 119.3 | 10.42 |
| 13 | 102.6* | 56.41 |
| 14 | 93.2 | 22.66 |
| 15 | 91.1 | 23.83 |
| 16 | 81.7 | 36.81 |
| 17 | 80.6 | 41.38 |
| 18 | 79.6 | 68.17 |
| 19 | 74.3 | 34.18 |
| 20 | 73.2 | 33.47 |
| 21 | 71.4* | 32.36 |
| 22 | 69.3 | 33.35 |
| 23 | 68.7 | 34.79 |
| 24 | 63.5* | 32.91 |
| 25 | 61.9* | 21.88 |
| 26 | 51.3 | 22.60 |
| 27 | 50.5 | 21.35 |
| 28 | 22.4* | 100.00 |
| 29 | 20.1 | 52.23 |
| 30 | 15.5* | 16.24 |

Representative peaks from the XRPD spectrum of Form I (ethyl acetate solvate) are shown in the table below. Form I (ethyl acetate solvate) can be identified and/or characterized by one or more of the peaks selected from the table below.

| No. | 2-Theta ° | Intensity % |
|---|---|---|
| 1 | 6.434* | 59.2 |
| 2 | 9.283* | 30.8 |
| 3 | 10.831* | 55.3 |
| 4 | 11.794* | 28.3 |

Peaks with an asterisk (*) are major peaks

Example 12

Synthesis of Form J

To a vial containing 100 mg of Amorphous Form O was added 150 µL of HPLC grade ethanol. The contents of the vial was stirred at an intermediate speed (250 rpm) on a stir plate at RT overnight. The mixture was filtered through a 0.22 µm PVDF filter to provide Form J.

Representative peaks from the XRPD spectrum of Form J are shown in the table below. Form J can be identified and/or characterized by one or more of the peaks selected from the table below.

| No. | 2-Theta ° | Intensity % |
|---|---|---|
| 1 | 6.1* | 69.2 |
| 2 | 7.5* | 54.4 |
| 3 | 9.0 | 21.2 |
| 4 | 9.9 | 21.2 |
| 5 | 10.8 | 34.0 |
| 6 | 11.1 | 44.2 |

| No. | 2-Theta ° | Intensity % |
|---|---|---|
| 7 | 11.4 | 26.5 |
| 8 | 12.1* | 100.0 |
| 9 | 12.9 | 24.6 |
| 10 | 13.3* | 31.2 |
| 11 | 14.0* | 27.2 |
| 12 | 14.8 | 28.3 |
| 13 | 15.1 | 30.2 |
| 14 | 15.4 | 29.5 |
| 15 | 16.1 | 33.0 |
| 16 | 16.7 | 41.0 |
| 17 | 17.6 | 29.8 |
| 18 | 18.0 | 54.6 |
| 19 | 18.5* | 47.3 |
| 20 | 18.9 | 25.6 |
| 21 | 19.4 | 41.6 |
| 22 | 19.6 | 35.8 |
| 23 | 20.3 | 43.5 |
| 24 | 20.7 | 59.8 |
| 25 | 21.1 | 43.8 |
| 26 | 21.7 | 35.5 |
| 27 | 22.6** | 30.1 |
| 28 | 22.3 | 24.3 |
| 29 | 23.8 | 23.1 |
| 30 | 24.7 | 32.7 |
| 31 | 25.2 | 23.7 |
| 32 | 25.7 | 20.8 |
| 33 | 26.6 | 26.7 |
| 34 | 27.5 | 24.3 |
| 35 | 27.8 | 23.6 |
| 36 | 28.3 | 20.7 |
| 37 | 29.6 | 22.9 |
| 38 | 32.2 | 20.3 |
| 39 | 33.2** | 21.5 |
| 40 | 34.0** | 19.2 |
| 41 | 35.3** | 19.3 |
| 42 | 35.4 | 19.4 |
| 43 | 36.5 | 19.0 |

Peaks with an asterisk (*) are major peaks
Peaks with a double asterisk (**) are secondary peaks Representative peaks from the 13C NMR solid state spectrum of Form J are shown in the table below. Form J can be identified and/or characterized by one or more of the peaks selected from the table below.

| Peak | v(F1) [ppm] | Intensity [rel] |
|---|---|---|
| 1 | 175.6* | 26.8 |
| 2 | 172.6 | 39.76 |
| 3 | 165.8 | 13.72 |
| 4 | 162.9 | 22.43 |
| 5 | 162.5 | 16.16 |
| 6 | 153.0 | 15.82 |
| 7 | 152.8 | 15.88 |
| 8 | 151.5 | 29.40 |
| 9 | 151.1 | 11.45 |
| 10 | 150.7 | 36.85 |
| 11 | 150.1 | 21.71 |
| 12 | 141.4* | 19.34 |
| 13 | 140.1 | 11.81 |
| 14 | 131.1 | 29.77 |
| 15 | 129.7 | 35.60 |
| 16 | 129.5 | 26.33 |
| 17 | 127.8* | 25.20 |
| 18 | 127.1 | 17.58 |
| 19 | 126.3 | 27.54 |
| 20 | 123.8 | 29.09 |
| 21 | 123.4* | 32.43 |
| 22 | 122.8 | 26.21 |
| 23 | 103.1* | 37.64 |
| 24 | 101.3 | 27.86 |
| 25 | 93.8 | 22.55 |
| 26 | 93.3 | 16.53 |
| 27 | 91.7 | 18.80 |
| 28 | 83.5* | 35.20 |
| 29 | 81.1* | 35.52 |
| 30 | 80.7 | 100.00 |
| 31 | 79.8 | 28.76 |
| 32 | 78.6 | 42.08 |
| 33 | 74.4 | 37.67 |
| 34 | 73.4 | 41.04 |
| 35 | 73.1 | 28.84 |
| 36 | 72.3 | 39.74 |
| 37 | 70.1 | 57.8 |
| 38 | 63.7 | 44.0 |
| 39 | 62.2* | 33.4 |
| 40 | 53.1 | 21.6 |
| 41 | 52.5 | 16.9 |
| 42 | 50.8 | 15.9 |
| 43 | 25.6* | 36.7 |
| 44 | 23.7 | 60.6 |
| 45 | 23.0 | 34.4 |
| 46 | 22.5 | 64.4 |
| 47 | 22.1 | 46.4 |
| 48 | 21.7 | 36.1 |
| 49 | 19.6* | 34.5 |
| 50 | 18.8 | 34.8 |
| 51 | 18.4 | 29.1 |

Peaks with an asterisk (*) are major peaks

Example 13

Synthesis of Form K (Chloroform Solvate)

To a vial containing 80 mg of Form J was added 200 μL of HPLC grade chloroform. The vial was sonicated in an ultrasonicator for 1 minute, and the mixture was then stirred at an intermediate speed (250 rpm) on a stir plate at RT overnight. An aliquot (~25 μL) was placed on a holder and analyzed by XRPD.

Representative peaks from the $^{13}$C NMR solid state spectrum of Form K are shown in the table below. Form K can be identified and/or characterized by one or more of the peaks selected from the table below.

| Peak | v(F1) [ppm] | Intensity [rel] |
|---|---|---|
| 1 | 173.9* | 40.0 |
| 2 | 173.4* | 39.97 |
| 3 | 169.9 | 23.72 |
| 4 | 168.7 | 24.10 |
| 5 | 151.8* | 45.42 |
| 6 | 150.5* | 44.95 |
| 7 | 144.6 | 27.19 |
| 8 | 144.1 | 24.43 |
| 9 | 129.8 | 17.44 |
| 10 | 126.2 | 30.54 |
| 11 | 125.8 | 20.97 |
| 12 | 122.5 | 16.21 |
| 13 | 101.9* | 81.01 |
| 14 | 93.4 | 34.58 |
| 15 | 92.0* | 35.25 |
| 16 | 81.6 | 54.04 |
| 17 | 80.4* | 88.61 |
| 18 | 79.7 | 51.32 |
| 19 | 78.6 | 62.92 |
| 20 | 73.5* | 72.84 |
| 21 | 70.6 | 49.15 |
| 22 | 69.5 | 50.72 |
| 23 | 68.1 | 46.78 |
| 24 | 63.6 | 47.15 |
| 25 | 50.8 | 55.38 |

-continued

| Peak | ν(F1) [ppm] | Intensity [rel] |
|---|---|---|
| 26 | 23.2 | 76.97 |
| 27 | 22.8 | 67.52 |
| 28 | 22.1* | 100.00 |
| 29 | 20.7 | 68.21 |
| 30 | 20.4* | 97.77 |

Peaks with an asterisk (*) are major peaks

Representative peaks from the XRPD spectrum of Form K are shown in the table below. Form K can be identified and/or characterized by one or more of the peaks selected from the table below.

| No. | 2-Theta ° | Intensity % |
|---|---|---|
| 1 | 22.620* | 27.5 |
| 2 | 27.257* | 26.7 |
| 3 | 28.272* | 25.0 |
| 4 | 31.216* | 27.0 |

Peaks with an asterisk (*) are major peaks

Example 14

Synthesis of Form L (Acetonitrile Solvate)

To a vial containing 80 mg of Form J was added 150 µL of HPLC grade acetonitrile (ACN). The vial was sonicated in an ultrasonicator for 1 minute, and the mixture was then stirred at an intermediate speed (250 rpm) on a stir plate at RT for 2 days. The resulting solid Form L (acetonitrile solvate) in the mixture was analyzed by XRPD as a suspension without isolation of the solid.

Representative peaks from the $^{13}$C NMR solid state spectrum of Form L (acetonitrile solvate) are shown in the table below. Form L (acetonitrile solvate) can be identified and/or characterized by one or more of the peaks selected from the table below.

| Peak | ν(F1) [ppm] | Intensity [rel] |
|---|---|---|
| 1 | 173.2* | 32.2 |
| 2 | 172.6 | 13.04 |
| 3 | 164.3 | 20.50 |
| 4 | 152.9 | 15.62 |
| 5 | 152.3 | 18.02 |
| 6 | 151.4* | 22.38 |
| 7 | 150.8 | 10.20 |
| 8 | 150.6 | 15.53 |
| 9 | 142.9 | 7.14 |
| 10 | 140.9* | 17.32 |
| 11 | 130.3 | 17.85 |
| 12 | 129.9 | 17.36 |
| 13 | 125.7 | 15.60 |
| 14 | 124.7 | 11.99 |
| 15 | 123.4 | 12.87 |
| 16 | 118.5* | 18.82 |
| 17 | 103.8 | 8.86 |
| 18 | 103.3 | 18.66 |
| 19 | 102.9 | 15.60 |
| 20 | 101.5 | 12.23 |
| 21 | 92.7 | 29.36 |
| 22 | 92.3 | 25.58 |
| 23 | 81.5* | 51.96 |
| 24 | 80.1* | 100.00 |
| 25 | 73.4* | 51.97 |
| 26 | 69.9 | 17.16 |

-continued

| Peak | ν(F1) [ppm] | Intensity [rel] |
|---|---|---|
| 27 | 69.3 | 27.18 |
| 28 | 68.0 | 11.49 |
| 29 | 63.0 | 15.93 |
| 30 | 61.9 | 24.74 |
| 31 | 61.6* | 32.16 |
| 32 | 54.0 | 18.79 |
| 33 | 53.0 | 14.69 |
| 34 | 52.2 | 16.30 |
| 35 | 23.7 | 12.59 |
| 36 | 23.3 | 12.87 |
| 37 | 23.0 | 28.2 |
| 38 | 22.5 | 42.2 |
| 39 | 22.0 | 47.5 |
| 40 | 21.4 | 43.2 |
| 41 | 20.9* | 50.2 |
| 42 | 20.2 | 17.4 |
| 43 | 19.8 | 22.2 |
| 44 | 19.2 | 15.2 |
| 45 | 18.9 | 14.8 |
| 46 | 1.6* | 12.9 |

Representative peaks from the XRPD spectrum of Form L (acetonitrile solvate) are shown in the table below. Form L (acetonitrile solvate) can be identified and/or characterized by one or more of the peaks selected from the table below.

| No. | 2-Theta ° | Intensity % |
|---|---|---|
| 1 | 5.662* | 27.0 |
| 2 | 6.036* | 27.2 |
| 3 | 15.174* | 100.0 |
| 4 | 16.102* | 56.5 |

Peaks with an asterisk (*) are major peaks

Example 15

Synthesis of Form M

Form L, as produced above, was isolated from the mixture and placed in a vacuum overnight until the solid was substantially desolvated, to provide Form M.

Representative peaks from the $^{13}$C NMR solid state spectrum of Form M are shown in the table below. Form M can be identified and/or characterized by one or more of the peaks selected from the table below.

| Peak | ν(F1) [ppm] | Intensity [rel] |
|---|---|---|
| 1 | 174.0* | 31.8 |
| 2 | 173.2 | 13.03 |
| 3 | 172.3 | 7.89 |
| 4 | 170.5* | 25.18 |
| 5 | 163.6 | 11.98 |
| 6 | 163.0 | 24.93 |
| 7 | 162.4 | 16.01 |
| 8 | 152.8 | 24.75 |
| 9 | 151.8 | 15.28 |
| 10 | 151.3 | 19.55 |
| 11 | 150.7 | 13.04 |
| 12 | 150.3 | 26.82 |
| 13 | 149.8 | 8.82 |
| 14 | 149.3 | 28.40 |
| 15 | 141.0 | 21.01 |
| 16 | 138.9 | 14.25 |
| 17 | 131.3 | 17.74 |
| 18 | 130.3 | 11.77 |

-continued

| Peak | ν(F1) [ppm] | Intensity [rel] |
|---|---|---|
| 19 | 129.5* | 32.91 |
| 20 | 127.0 | 27.77 |
| 21 | 126.6 | 24.70 |
| 22 | 124.7 | 17.32 |
| 23 | 124.0 | 14.60 |
| 24 | 122.4 | 15.29 |
| 25 | 121.3 | 12.07 |
| 26 | 118.5 | 11.42 |
| 27 | 103.5 | 34.79 |
| 28 | 102.7 | 10.83 |
| 29 | 102.2 | 27.86 |
| 30 | 101.7 | 8.62 |
| 31 | 92.5 | 36.95 |
| 32 | 83.2 | 31.87 |
| 33 | 81.5 | 45.71 |
| 34 | 80.6 | 14.75 |
| 35 | 80.1 | 18.58 |
| 36 | 79.6* | 100.00 |
| 37 | 74.3 | 44.8 |
| 38 | 73.3 | 44.3 |
| 39 | 70.5 | 10.0 |
| 40 | 69.7* | 44.6 |
| 41 | 67.5 | 8.1 |
| 42 | 64.5 | 8.8 |
| 43 | 64.0 | 9.6 |
| 44 | 63.2* | 39.5 |
| 45 | 61.4 | 8.0 |
| 46 | 53.3 | 20.6 |
| 47 | 51.8* | 33.6 |
| 48 | 24.0* | 37.0 |
| 49 | 23.7 | 47.1 |
| 50 | 23.3 | 62.9 |
| 51 | 22.4 | 67.7 |
| 52 | 21.9 | 44.5 |
| 53 | 21.6 | 52.4 |
| 54 | 20.5 | 8.9 |
| 55 | 19.5* | 49.4 |

Peaks with an asterisk (*) are major peaks

Representative peaks from the XRPD spectrum of Form M are shown in the table below. Form M can be identified and/or characterized by one or more of the peaks selected from the table below.

| No. | 2-Theta ° | Intensity % |
|---|---|---|
| 1 | 6.274* | 66.2 |
| 2 | 13.200* | 40.5 |
| 3 | 22.225* | 50.0 |
| 4 | 23.520* | 38.7 |

Peaks with an asterisk (*) are major peaks

Example 16

Synthesis of Form N (Toluene Solvate)

To a vial containing 50 mg of Amorphous Form O was added 200 μL of HPLC grade toluene. The vial was sonicated in an ultrasonicator for 1 minute, and the mixture was then stirred at an intermediate speed (250 rpm) on a stir plate at RT for 3 days. The resulting solid Form N (toluene solvate) in the mixture was analyzed by XRPD (Bruker D8 Discover; 40 kV, 35 mA; single frame registered with an exposure of 120 seconds) as a suspension without isolation of the solid.

Representative peaks from the $^{13}$C NMR solid state spectrum of Form N (toluene solvate) are shown in the table below. Form N (toluene solvate) can be identified and/or characterized by one or more of the peaks selected from the table below.

| Peak | ν(F1) [ppm] | Intensity [rel] |
|---|---|---|
| 1 | 172.6* | 60.5 |
| 2 | 170.3 | 21.21 |
| 3 | 169.9 | 20.31 |
| 4 | 151.5 | 28.70 |
| 5 | 151.1 | 40.12 |
| 6 | 150.6 | 26.12 |
| 7 | 145.2 | 33.34 |
| 8 | 130.4* | 78.13 |
| 9 | 129.5* | 87.88 |
| 10 | 129.2* | 70.02 |
| 11 | 128.4* | 64.31 |
| 12 | 125.5 | 40.20 |
| 13 | 124.4 | 31.97 |
| 14 | 124.2 | 31.70 |
| 15 | 120.8 | 66.36 |
| 16 | 120.0 | 74.60 |
| 17 | 103.5 | 40.76 |
| 18 | 103.2 | 33.90 |
| 19 | 92.8 | 37.18 |
| 20 | 82.6 | 41.88 |
| 21 | 82.2* | 37.02 |
| 22 | 79.6 | 64.84 |
| 23 | 79.3 | 68.37 |
| 24 | 74.0* | 88.74 |
| 25 | 68.6 | 28.92 |
| 26 | 68.4 | 57.45 |
| 27 | 68.1 | 92.39 |
| 28 | 67.7* | 51.91 |
| 29 | 50.2 | 29.20 |
| 30 | 23.0 | 54.35 |
| 31 | 22.3 | 18.31 |
| 32 | 21.8 | 60.50 |
| 33 | 21.3* | 100.00 |
| 34 | 21.1 | 61.99 |
| 35 | 20.6 | 18.12 |
| 36 | 20.2 | 58.39 |
| 37 | 19.3 | 34.4 |

Peaks with an asterisk (*) are major peaks

Representative peaks from the XRPD spectrum of Form N (toluene solvate) are shown in the table below. Form N (toluene solvate) can be identified and/or characterized by one or more of the peaks selected from the table below.

| No. | 2-Theta ° | Intensity % |
|---|---|---|
| 1 | 12.419* | 25.7 |
| 2 | 15.310* | 41.7 |
| 3 | 17.149* | 76.6 |
| 4 | 17.873* | 57.0 |

Peaks with an asterisk (*) are major peaks

Example 17

HCV Replicon Assay

Cells

Huh-7 cells containing the self-replicating, subgenomic HCV replicon with a stable luciferase (LUC) reporter were cultured in Dulbecco's modified Eagle's medium (DMEM) containing 2 mM L-glutamine and supplemented with 10% heat-inactivated fetal bovine serum (FBS), 1% penicillin-streptomyocin, 1% nonessential amino acids, and 0.5 mg/mL G418.

Determination of Anti-HCV Activity

Determination of 50% inhibitory concentration ($EC_{50}$) of compounds in HCV replicon cells were performed by the following procedure. On the first day, 5,000 HCV replicon cells were plated per well in a 96-well plate. On the following day, test compounds were solubilized in 100% DMSO to 100× the desired final testing concentration. Each compound was then serially diluted (1:3) up to 9 different concentrations. Compounds in 100% DMSO are reduced to 10% DMSO by diluting 1:10 in cell culture media. The compounds were diluted to 10% DMSO with cell culture media, which were used to dose the HCV replicon cells in 96-well format. The final DMSO concentration was 1%. The HCV replicon cells were incubated at 37° C. for 72 hours. At 72 hours, cells were processed when the cells are still subconfluent. Compounds that reduce the LUC signal are determined by Bright-Glo Luciferase Assay (Promega, Madison, Wis.). Percent Inhibition was determined for each compound concentration in relation to the control cells (untreated HCV replicon) to calculate the $EC_{50}$.

Compound 1 was determined to have an $EC_{50}$ of less than 1 μM by the above procedure.

What is claimed is:

1. A polymorphic form of 2'-C-methyluridine-5'(O-phenyl-N-(S)-1-(isopropoxycarbonyl)ethyl)thiophosphoramidate, wherein the polymorphic form is characterized as Form B, Form C, Form D, Form E, Form F, Form G, Form H, Form I, Form K, Form L, Form M, or Form N.

2. Form B of claim 1, wherein the Form B is characterized by one or more peaks in an X-ray powder diffraction pattern, wherein the one or more peaks is selected from a peak from about 5.5 to about 5.9 degrees, a peak from about 9.2 to about 9.6 degrees, a peak from about 16.8 to about 17.2 degrees, and a peak from about 26.0 to about 26.4 degrees.

3. Form C of claim 1, wherein the Form C is characterized by one or more peaks in an X-ray powder diffraction pattern, wherein the one or more peaks is selected from a peak from about 4.8 to about 5.2 degrees, a peak from about 6.4 to about 6.8 degrees, a peak from about 8.0 to about 8.4 degrees, a peak from about 9.0 to about 9.4 degrees, a peak from about 9.4 to about 9.8 degrees, a peak from about 16.1 to about 16.5 degrees, and a peak from about 22.1 to about 22.5 degrees.

4. Form D of claim 1, wherein the Form D is characterized by one or more peaks in an X-ray powder diffraction pattern, wherein the one or more peaks is selected from a peak from about 7.9 to about 8.3 degrees, a peak from about 13.2 to about 13.6 degrees, a peak from about 14.2 to about 14.6 degrees, a peak from about 17.0 to about 17.4 degrees, a peak from about 29.4 to about 29.8 degrees, and a peak from about 34.8 to about 35.2 degrees.

5. Form E of claim 1, wherein the Form E is characterized by one or more peaks in an X-ray powder diffraction pattern, wherein the one or more peaks is selected from a peak from about 7.6 to about 8.0 degrees, a peak from about 10.4 to about 10.8 degrees, a peak from about 12.7 to about 13.1 degrees, a peak from about 24.3 to about 24.7 degrees, and a peak from about 24.8 to about 25.2 degrees.

6. Form F of claim 1, wherein the Form F is characterized by one or more peaks in an X-ray powder diffraction pattern, wherein the one or more peaks is selected from a peak from about 5.9 to about 6.3 degrees, a peak from about 6.8 to about 7.2 degrees, a peak from about 17.3 to about 17.7 degrees, and a peak from about 17.8 to about 18.2 degrees.

7. Form G of claim 1, wherein the Form G is characterized by one or more peaks in an X-ray powder diffraction pattern, wherein the one or more peaks is selected from a peak from about 5.7 to about 6.1 degrees, a peak from about 7.3 to about 7.7 degrees, a peak from about 7.6 to about 8.0 degrees, a peak from about 12.3 to about 12.7 degrees, a peak from about 17.5 to about 17.9 degrees, and a peak from about 18.0 to about 18.4 degrees.

8. Form H of claim 1, wherein the Form H is characterized by one or more peaks in an X-ray powder diffraction pattern, wherein the one or more peaks is selected from a peak from about 7.9 to about 8.3 degrees, a peak from about 13.8 to about 14.2 degrees, a peak from about 17.0 to about 7.4 degrees, and a peak from about 19.9 to about 20.3 degrees.

9. Form I of claim 1, wherein the Form I is characterized by one or more peaks in an X-ray powder diffraction pattern, wherein the one or more peaks is selected from a peak from about 6.2 to about 6.6 degrees, a peak from about 9.1 to about 9.5 degrees, a peak from about 10.6 to about 11.0 degrees, and a peak from about 11.6 to about 12.0 degrees.

10. Form K of claim 1, wherein the Form K is characterized by one or more peaks in an X-ray powder diffraction pattern, wherein the one or more peaks is selected from a peak from about 22.4 to about 22.8 degrees, a peak from about 27.1 to about 27.5 degrees, a peak from about 28.1 to about 28.5 degrees, and a peak from about 31.0 to about 31.4 degrees.

11. Form L of claim 1 wherein the Form L is characterized by one or more peaks in an X-ray powder diffraction pattern, wherein the one or more peaks is selected from a peak from about 5.5 to about 5.9 degrees, a peak from about 5.8 to about 6.2 degrees, a peak from about 15.0 to about 15.4 degrees, and a peak from about 15.9 to about 16.3 degrees.

12. Form M of claim 1, wherein the Form M is characterized by one or more peaks in an X-ray powder diffraction pattern, wherein the one or more peaks is selected from a peak from about 6.1 to about 6.5 degrees, a peak from about 13.0 to about 13.4 degrees, a peak from about 22.0 to about 22.4 degrees, and a peak from about 23.3 to about 23.7 degrees.

13. Form N of claim 1, wherein the Form N is characterized by one or more peaks in an X-ray powder diffraction pattern, wherein the one or more peaks is selected from a peak from about 12.2 to about 12.6 degrees, a peak from about 15.1 to about 15.5 degrees, a peak from about 16.9 to about 17.3 degrees, and a peak from about 17.7 to about 18.1 degrees.

14. Amorphous Form O that contains less than about 15% crystallinity of 2'-C-methyluridine-5'-(O-phenyl-N-(S)-1-(isopropoxycarbonyl)ethyl)thiophosphoramidate.

15. Amorphous Form O of claim 14, wherein the Amorphous Form O contains less than about 1.0% crystallinity.

16. A pharmaceutical composition comprising one or more solid forms of Compound 1 according to claim 1.

17. A method of ameliorating or treating a viral infection in a patient, said method comprising administering to said patient an effective amount of a compound of claim 1, or a pharmaceutically acceptable salt thereof.

18. A method for inhibiting replication of a hepatitis C virus comprising contacting a cell infected with the hepatitis C virus with a compound of claim 1, or a pharmaceutically acceptable salt thereof.

19. A method for ameliorating or treating a HCV infection comprising contacting a cell infected with the hepatitis C virus with a compound of claim 1, or a pharmaceutically acceptable salt thereof.

20. The method of claim 18, further comprising one or more agents selected from the group consisting of an interferon, ribavirin, a HCV protease inhibitor, a HCV polymerase inhibitor, a NS5A inhibitor, an antiviral compound, a compound of Formula (BB) and a compound of Formula (DD), or a pharmaceutically acceptable salt any of the aforementioned compounds, wherein the compound of Formula (BB), or a pharmaceutically acceptable salt thereof, is

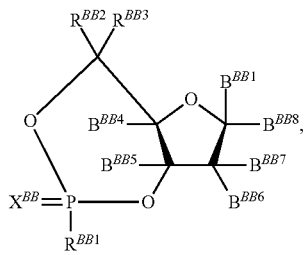

Formula (BB)

wherein $B^{BB1}$ can be an optionally substituted heterocyclic base or an optionally substituted heterocyclic base with a protected amino group; $X^{BB}$ can be O (oxygen) or S (sulfur); $R^{BB1}$ can be selected from $-Z^{BB}-R^{BB9}$, an optionally substituted N-linked amino acid and an optionally substituted N-linked amino acid ester derivative; $Z^{BB}$ can be selected from O (oxygen), S (sulfur) and $N(R^{BB10})$; $R^{BB2}$ and $R^{BB3}$ can be independently selected from hydrogen, an optionally substituted $C_{1-6}$ alkyl, an optionally substituted $C_{2-6}$ alkenyl, an optionally substituted $C_{2-6}$ alkynyl, an optionally substituted $C_{1-6}$ haloalkyl and an optionally substituted aryl($C_{1-6}$ alkyl); or $R^{BB2}$ and $R^{BB3}$ can be taken together to form a group selected from an optionally substituted $C_{3-6}$ cycloalkyl, an optionally substituted $C_{3-6}$ cycloalkenyl, an optionally substituted $C_{3-6}$ aryl and an optionally substituted $C_{3-6}$ heteroaryl; $R^{BB4}$ can be selected from hydrogen, halogen, azido, cyano, an optionally substituted $C_{1-6}$ alkyl, an optionally substituted $C_{2-6}$ alkenyl, an optionally substituted $C_{2-6}$ alkynyl and an optionally substituted allenyl; $R^{BB5}$ can be hydrogen or an optionally substituted $C_{1-6}$ alkyl; $R^{BB6}$ can be selected from hydrogen, halogen, azido, amino, cyano, an optionally substituted $C_{1-6}$ alkyl, $-OR^{BB11}$ and $-OC(=O)R^{BB12}$; $R^{BB7}$ can be selected from hydrogen, halogen, azido, cyano, an optionally substituted $C_{1-6}$ alkyl, $-OR^{BB13}$ and $-OC(=O)R^{BB14}$; $R^{BB8}$ can be selected from hydrogen, halogen, azido, cyano, an optionally substituted $C_{1-6}$ alkyl, $-OR^{BB15}$ and $-OC(=O)R^{BB16}$; $R^{BB9}$ can be selected from an optionally substituted alkyl, an optionally substituted alkenyl, an optionally substituted alkynyl, an optionally substituted cycloalkyl, an optionally substituted cycloalkenyl, an optionally substituted aryl, an optionally substituted heteroaryl, an optionally substituted heterocyclyl, an optionally substituted aryl($C_{1-6}$alkyl), an optionally substituted heteroaryl($C_{1-6}$alkyl) and an optionally substituted heterocyclyl ($C_{1-6}$alkyl); $R^{BB10}$ can be selected from hydrogen, an optionally substituted alkyl, an optionally substituted alkenyl, an optionally substituted alkynyl, an optionally substituted cycloalkyl, an optionally substituted cycloalkenyl, an optionally substituted aryl, an optionally substituted heteroaryl, an optionally substituted heterocyclyl, an optionally substituted aryl($C_{1-6}$alkyl), an optionally substituted heteroaryl($C_{1-6}$alkyl) and an optionally substituted heterocyclyl ($C_{1-6}$alkyl); $R^{BB11}$, $R^{BB13}$ and $R^{BB15}$ can be independently hydrogen or an optionally substituted $C_{1-6}$ alkyl; and $R^{BB12}$, $R^{BB14}$ and $R^{BB16}$ can be independently an optionally substituted $C_{1-6}$ alkyl or an optionally substituted $C_{3-6}$ cycloalkyl, and wherein the compound of Formula (DD), or a pharmaceutically acceptable salt thereof, is

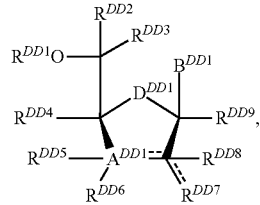

Formula (DD)

wherein each ------ can be independently a double or single bond; $A^{DD1}$ can be selected from C (carbon), O (oxygen) and S (sulfur); $B^{DD1}$ can be an optionally substituted heterocyclic base or a derivative thereof; $D^{DD1}$ can be selected from $C=CH_2$, $CH_2$, O (oxygen), S (sulfur), CHF, and $CF_2$; $R^{DD1}$ can be hydrogen, an optionally substituted alkyl, an optionally substituted cycloalkyl, an optionally substituted aralkyl, dialkylaminoalkylene, alkyl-C(=O)—, aryl-C(=O)—alkoxyalkyl-C(=O)—, aryloxyalkyl-C(=O)—, alkylsulfonyl, arylsulfonyl, aralkylsulfonyl, $$R^{DD10}-\overset{\overset{O}{\|}}{\underset{\underset{R^{DD11}}{|}}{P}}-,$$

an —O-linked amino acid, diphosphate, triphosphate or derivatives thereof; $R^{DD2}$ and $R^{DD3}$ can be each independently selected from hydrogen, an optionally substituted $C_{1-6}$ alkyl, an optionally substituted $C_{2-6}$ alkenyl, an optionally substituted $C_{2-6}$ alkynyl and an optionally substituted $C_{1-6}$ haloalkyl, provided that at least one of $R^{DD2}$ and $R^{DD3}$ cannot be hydrogen; or $R^{DD2}$ and $R^{DD3}$ are taken together to form a group selected from among $C_{3-6}$ cycloalkyl, $C_{3-6}$ cycloalkenyl, $C_{3-6}$ aryl, and a $C_{3-6}$ heteroaryl; $R^{DD4}$ and $R^{DD9}$ can be independently selected from hydrogen, halogen, $-NH_2$, $-NHR^{DDa1}$, $NR^{DDa1}R^{DDb1}$, $-OR^{DDa1}$, $-SR^{DDa1}$, $-CN$, $-NC$, $-N_3$, $-NO_2$, $-N(R^{DDc1})-NR^{DDa1}R^{DDb1}$, $-N(R^{DDc1})-OR^{DDa1}$, $-S-SR^{DDa1}$, $-C(=O)R^{DDa1}$, $-C(=O)OR^{DDa1}$, $-C(=O)NR^{DDa1}R^{DDb1}$, $-O-(C=O)R^{DDa1}$, $-O-C(=O)OR^{DDa1}$, $-O-C(=O)NR^{DDa1}R^{DDb1}$, $-N(R^{DDc1})-C(=O) NR^{DDa1}R^{DDb1}$, $-S(=O)R^{DDa1}$, $S(=O)_2R^{DDa1}$, $-O-S(=O)_2NR^{DDa1}R^{DDb1}$, $-N(R^{DDc1})-S(=O)_2 NR^{DDa1}R^{DDb1}$, an optionally substituted $C_{1-6}$ alkyl, an optionally substituted $C_{2-6}$ alkenyl, an optionally substituted $C_{2-6}$ alkynyl, an optionally substituted aralkyl and an —O-linked amino acid; $R^{DD5}$, $R^{DD6}$ and $R^{DD7}$ can be independently absent or selected from hydrogen, halogen, $-NH_2$, $-NHR^{DDa1}$, $NR^{DDa1}R^{DDb1}$, $-OR^{DDa1}$, $-SR^{DDa1}$, $-CN$, $-NC$, $-N_3$, $-NO_2$, $-N(R^{DDc1})-NR^{DDa1}R^{DDb1}$, $-N(R^{DDc1})-OR^{DDa1}$, $-S-SR^{DDa1}$, $-C(=O)R^{DDa1}$, $-C(=O)OR^{DDa1}$, $-C(=O)NR^{DDa1}R^{DDb1}$, $-O-(C=O)R^{DDa1}$, $-O-C(=O)OR^{DDa1}$, $-O-C(=O) NR^{DDa1}R^{DDb1}$, $-N(R^{DDc1})-C(=O)NR^{DDa1}R^{DDb1}$, $-S(=O)R^{DDa1}$, $S(=O)_2R^{DDa}$, $-O-S(=O)_2 NR^{DDa1}R^{DDb1}$, $-N(R^{DDc1})-S(=O)_2NR^{DDa1}R^{DDb1}$, an optionally substituted $C_{1-6}$ alkyl, an optionally substituted $C_{2-6}$ alkenyl, an optionally substituted $C_{2-6}$ alkynyl, an optionally substituted aralkyl and an —O-linked amino acid; or $R^{DD6}$ and $R^{DD7}$ taken together form $-O-C(=O)-O-$; $R^{DD8}$ can be absent or selected from the group consisting of hydrogen, halogen, $-NH_2$, $-NHR^{DDa1}$, $NR^{DDa1}R^{DDb1}$, $-OR^{DDa1}$, $SR^{DDa1}$, $-CN$, $-NC$, $-N_3$, —NO$_2$, —N(R$^{DDc1}$)—NR$^{DDa1}$R$^{DDb1}$, —N(R$^{DDc1}$)—OR$^{DDa1}$, —S—SR$^{DDa1}$, —C(=O)R$^{DDa1}$, —C(=O)OR$^{DDa1}$, —C(=O)NR$^{DDa1}$R$^{DDb1}$, —O—C(=O)OR$^{DDa1}$, —O—C(=O)NR$^{DDa1}$R$^{DDb1}$, —N(R$^{DDc1}$)—C(=O)NR$^{DDa1}$R$^{DDb1}$, —S(=O)R$^{DDa1}$, S(=O)$_2$R$^{DDa1}$, —O—S(=O)$_2$NR$^{DDa1}$R$^{DDb1}$, —N(R$^{DDc1}$)—S(=O)$_2$NR$^{DDa1}$R$^{DDb1}$, an optionally substituted C$_{1-6}$ alkyl, an optionally substituted C$_{2-6}$ alkenyl, an optionally substituted C$_{26}$ alkynyl, an optionally substituted haloalkyl, an optionally substituted hydroxyalkyl and an —O-linked amino acid, or when the bond to R$^{DD7}$ indicated by ═══ is a double bond, then R$^{DD7}$ is a C$_{2-6}$ alkylidene and R$^{DD8}$ is absent; R$^{DDa1}$, R$^{DDb1}$ and R$^{DDc1}$ can be each independently selected from hydrogen, an optionally substituted alkyl, an optionally substituted alkenyl, an optionally substituted alkynyl, an optionally substituted aryl, an optionally substituted heteroaryl, an optionally substituted aralkyl and an optionally substituted heteroaryl(C$_{1-6}$ alkyl); R$^{DD10}$ can be selected from O$^-$, —OH, an optionally substituted aryloxy or aryl-O—,

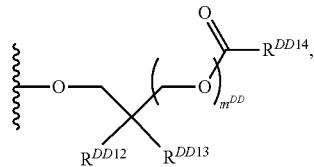

alkyl-C(=O)—O—CH$_2$—O—, alkyl-C(=O)—S—CH$_2$CH$_2$—O— and an —N-linked amino acid; R$^{DD11}$ can be selected from O$^-$, —OH, an optionally substituted aryloxy or aryl-O—,

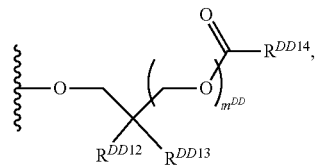

alkyl-C(=O)—O—CH$_2$—O—, alkyl-C(=O)—S—CH$_2$CH$_2$—O— and an —N-linked amino acid; each R$^{DD12}$ and each R$^{DD13}$ can be independently —C≡N or an optionally substituted substituent selected from C$_{1-8}$ organylcarbonyl, C$_{1-8}$ alkoxycarbonyl and C$_{1-8}$ organylaminocarbonyl; each R$^{DD14}$ can be hydrogen or an optionally substituted C$_{1-6}$-alkyl; each m$^{DD}$ can be independently 1 or 2, and if both R$^{DD10}$ and R$^{DD11}$ are

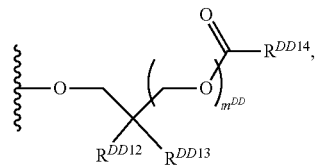

each R$^{DD12}$, each R$^{DD13}$, each R$^{DD14}$ and each m$^{DD}$ can be the same or different.

\* \* \* \* \*